United States Patent
Tao et al.

(10) Patent No.: US 10,766,879 B2
(45) Date of Patent: Sep. 8, 2020

(54) PYRIMIDINE DERIVATIVES AS KINASE INHIBITORS AND THEIR THERAPEUTICAL APPLICATIONS

(71) Applicant: NantBioScience, Inc., Culver City, CA (US)

(72) Inventors: Chunlin Tao, Newport Coast, CA (US); Qinwei Wang, Alhambra, CA (US); Laxman Nallan, Rancho Mission Viejo, CA (US); David Ho, Monterey Park, CA (US); Tulay Polat, Tustin, CA (US); Forrest Arp, Irvine, CA (US); Paul Weingarten, Anaheim, CA (US)

(73) Assignee: NANTBIOSCIENCE, INC., Culver City, CA (US)

( * ) Notice: Subject to any disclaimer, the term of this patent is extended or adjusted under 35 U.S.C. 154(b) by 404 days.

(21) Appl. No.: 15/553,890

(22) PCT Filed: Feb. 27, 2015

(86) PCT No.: PCT/US2015/018085
§ 371 (c)(1),
(2) Date: Aug. 25, 2017

(87) PCT Pub. No.: WO2016/137506
PCT Pub. Date: Sep. 1, 2016

(65) Prior Publication Data
US 2018/0155327 A1    Jun. 7, 2018

(51) Int. Cl.
| | | |
|---|---|---|
| *C07D 403/12* | (2006.01) | |
| *A61K 31/506* | (2006.01) | |
| *A61P 37/00* | (2006.01) | |
| *C07D 401/14* | (2006.01) | |
| *C07D 403/14* | (2006.01) | |
| *C07D 417/14* | (2006.01) | |
| *C07D 487/04* | (2006.01) | |
| *A61P 29/00* | (2006.01) | |
| *A61P 35/00* | (2006.01) | |
| *A61K 31/5377* | (2006.01) | |
| *A61K 45/06* | (2006.01) | |
| *C07D 405/14* | (2006.01) | |

(52) U.S. Cl.
CPC .......... *C07D 403/12* (2013.01); *A61K 31/506* (2013.01); *A61K 31/5377* (2013.01); *A61K 45/06* (2013.01); *A61P 29/00* (2018.01); *A61P 35/00* (2018.01); *A61P 37/00* (2018.01); *C07D 401/14* (2013.01); *C07D 403/14* (2013.01); *C07D 405/14* (2013.01); *C07D 417/14* (2013.01); *C07D 487/04* (2013.01)

(58) Field of Classification Search
None
See application file for complete search history.

(56) References Cited

U.S. PATENT DOCUMENTS

| | | |
|---|---|---|
| 7,468,380 B2 | 12/2008 | Tsuruoka et al. |
| 8,013,153 B2 | 9/2011 | Butler et al. |
| 8,501,756 B2 | 8/2013 | Artman, III et al. |
| 8,901,143 B2 | 12/2014 | Su et al. |
| 2007/0004764 A1 | 1/2007 | Tsuruoka et al. |
| 2010/0305084 A1 | 12/2010 | Castanedo et al. |
| 2011/0053923 A1 | 3/2011 | Foote et al. |
| 2018/0215734 A1 | 8/2018 | Tao et al. |

FOREIGN PATENT DOCUMENTS

| | | | |
|---|---|---|---|
| JP | 2010-524952 A | 7/2010 | |
| JP | 2018-506564 A | 3/2018 | |
| JP | 2018-506565 A | 3/2018 | |
| WO | WO 2008/128231 A1 | 10/2008 | |
| WO | WO 2014/145403 A1 | 9/2014 | |
| WO | WO 2014/183300 A1 | 11/2014 | |
| WO | WO-2014183300 A1 * | 11/2014 | ........... C07D 401/14 |
| WO | WO 2016/137506 A1 | 1/2016 | |
| WO | WO 2016/138527 A1 | 1/2016 | |

OTHER PUBLICATIONS

Anderson 'The process of Structure-based Drug Design' Chemistry and Biology, vol. 10, p. 787-797, 2003.*
Thiel 'Structure-aided drug design's next generation' Nature Biology, 22(5), p. 513-519, 2004.*
U.S. Appl. No. 15/553,870, office action dated Aug. 13, 2018.
Japanese Patent Application No. 545365/2017, Office Action (dated Jun. 26, 2018).
Japanese Patent Application No. 545369/2017, Office Action (dated Jun. 26, 2018).
International Patent Application No, PCT/US2016/020095, International Search Report (dated Jul. 12. 2016).
International Patent Application No. PCT/US2015/018085, International Search Report (dated May 20, 2015).

* cited by examiner

*Primary Examiner* — Jared Barsky
(74) *Attorney, Agent, or Firm* — Mintz, Levin, Cohn, Ferris, Glovsky and Popeo, P.C.

(57) ABSTRACT

The present invention provides antitumor agents comprising substituted pyrimidine derivatives and pharmaceutically-acceptable formulations thereof, methods for making novel compounds and methods for using the compounds. The compounds and compositions in accordance with the invention have utility in treatment of a variety of diseases and have kinase inhibitory activities.

9 Claims, No Drawings

PYRIMIDINE DERIVATIVES AS KINASE INHIBITORS AND THEIR THERAPEUTICAL APPLICATIONS

CROSS-REFERENCE TO RELATED APPLICATIONS

This patent application is the national phase entry of International Patent Application No. PCT/US2015/018085, filed Feb. 27, 2015, which is hereby incorporated by reference in its entirety.

STATEMENT REGARDING FEDERALLY SPONSORED RESEARCH AND DEVELOPMENT

This invention was made without Government support.

INCORPORATION-BY-REFERENCE OF MATERIAL SUBMITTED ELECTRONICALLY

None

STATEMENT REGARDING PRIOR DISCLOSURES BY THE INVENTOR OR A JOINT INVENTOR

There have been no prior disclosures of this invention.

FIELD OF THE INVENTION

The present invention relates generally to the use of compounds to treat a variety of disorders, diseases and pathologic conditions and more specifically to the use of substituted pyrimidine derivatives to modulate protein kinases and for treating protein kinase-mediated diseases.

BACKGROUND OF THE INVENTION

Protein kinases constitute a large family of structurally related enzymes that are responsible for the control of a variety of signal transduction processes within the cell. Protein kinases, containing a similar 250-300 amino acid catalytic domain, catalyze the phosphorylation of target protein substrates.

The kinases may be categorized into families by the substrates in the phosphorylate (e.g., protein-tyrosine, protein-serine/threonine, lipids, etc.). Tyrosine phosphorylation is a central event in the regulation of a variety of biological processes such as cell proliferation, migration, differentiation and survival. Several families of receptor and non-receptor tyrosine kinases control these events by catalyzing the transfer of phosphate from ATP to a tyrosine residue of specific cell protein targets. Sequence motifs have been identified that generally correspond to each of these kinase families [Hanks et al., FASEB J., (1995), 9, 576-596; Knighton et al., Science, (1991), 253, 407-414; Garcia-Bustos et al., EMBO J., (1994), 13:2352-2361). Examples of kinases in the protein kinase family include, without limitation, abl, Akt, bcr-abl, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, Tie, Tie-2, TRK, Yes, and Zap70.

Studies indicated that protein kinases play a central role in the regulation and maintenance of a wide variety of cellular processes and cellular function. For example, kinase activity acts as molecular switches regulating cell proliferation, activation, and/or differentiation. Uncontrolled or excessive kinase activity has been observed in many disease states including benign and malignant proliferation disorders as well as diseases resulting from inappropriate activation of the immune system (autoimmune disorders), allograft rejection, and graft vs host disease.

It is reported that many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. In addition, endothelial cell specific receptor PTKs, such as VEGF-2 and Tie-2, mediate the angiogenic process and are involved in supporting the progression of cancers and other diseases involving uncontrolled vascularization. Accordingly, there has been a substantial effort in medicinal chemistry to find protein kinase inhibitors that are effective as therapeutic agents.

Many cancers are characterized by disruptions in cellular signaling pathways that lead to uncontrolled growth and proliferation of cancerous cells. Receptor tyrosine kinases (RTKs) play a crucial role in these signaling pathways, transmitting extracellular molecular signals into cytoplasm and/or nucleus of a cell. RTKs are transmembrane proteins that generally include an extracellular ligand-binding domain, a membrane-spanning domain and a catalytic cytoplasmic tyrosine kinase domain. The binding of ligand to the extracellular portion is believed to promote dimerization, resulting in trans-phosphorylation and activation of the intracellular tyrosine kinase domain (Schlessinger et al. Neuron 1992; 9:383-391).

Considering the lack of currently available treatment options for the majority of the conditions associated with protein kinases, there is still a great need for new therapeutic agents that inhibit these protein targets.

SUMMARY OF THE INVENTION

Accordingly, it is an objective of the present invention to provide an antitumor agent comprising a substituted pyrimidine derivatives as described in formula (I), pharmaceutically-acceptable formulations thereof, methods for making novel compounds and compositions for using the compounds. The compounds and compositions comprising the compounds in formula (I) have utility in treatment of a variety of diseases.

The combination therapy described herein may be provided by the preparation of the substituted pyrimidine derivatives of formula (I) and the other therapeutic agent as separate pharmaceutical formulations followed by the administration thereof to a patient simultaneously, semi-simultaneously, separately or over regular intervals.

The present invention provides methods of use for certain chemical compounds such as kinase inhibitors for treatment of various diseases, disorders, and pathologies, for example, cancer, and vascular disorders, such as myocardial infarction (MI), stroke, or ischemia. The compounds described in this invention may block the enzymatic activity of some or many of the members of the FGFR kinase family, in addition to blocking the activity of other receptor and non-receptor kinase. Such compounds may be beneficial for treatment of the diseases where disorders affect cell motility, adhesion, and cell cycle progression, and in addition, diseases with related hypoxic conditions, osteoporosis and conditions, which result from or are related to increases in vascular permeability, inflammation or respiratory distress, tumor growth, invasion, angiogenesis, metastases and apoptosis.

DETAILED DESCRIPTION OF THE INVENTION

The present invention is related to compounds having general Formula (I)

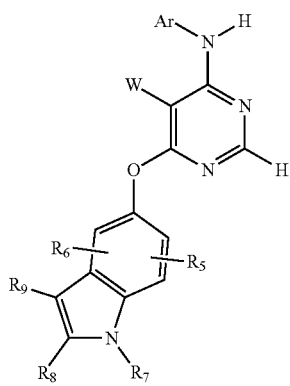

or a pharmaceutically acceptable salt thereof, wherein:

W is selected from: F, Cl, Br, I, CN, C1-C4 alkyl, C1-C6 alkoxy, C2-C6 alkenyl, CF3, CF2H, CFH2, C2-C6 alkynyl, CON(R1)R2.

R1 and R2 represent hydrogen, alkyl, cycloalkyl, alkenyl, alkynyl, alkylthio, aryl, arylalkyl.

Ar represents heteroaryl or aryl, each of which is substituted with from 0 to 4 substituents independently chosen from:

(1) halogen, hydroxy, amino, amide, cyano, —COOH, —SO$_2$NH$_2$, oxo, nitro and alkoxycarbonyl; and
(2) NR1
(3) groups of the formula (Ia):

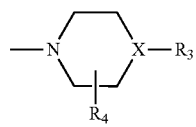

wherein:

R$_4$ represents hydrogen, C$_1$-C$_4$ alkyl, oxo;

X is CH, when R$_3$ is hydrogen; or X—R$_3$ is O; or X is N, R$_3$ represents groups of hydrogen, C$_1$-C$_6$ alkyl, C$_2$-C$_6$ alkenyl, C$_2$-C$_6$ alkynyl, C$_3$-C$_{10}$ aryl or heteroaryl, (C$_3$-C$_7$cycloalkyl)C$_1$-C$_4$ alkyl, C$_1$-C$_6$ haloalkyl, C$_1$-C$_6$ alkoxy, C$_1$-C$_6$ alkylthio, C$_2$-C$_6$ alkanoyl, C$_1$-C$_6$ alkoxycarbonyl, C$_2$-C$_6$ alkanoyloxy, mono- and di-(C$_3$-C$_8$ cycloalkyl) aminoC$_0$-C$_4$alkyl, (4- to 7-membered heterocycle)C$_0$-C$_4$alkyl, C$_1$-C$_6$ alkylsulfonyl, mono- and di-(C$_1$-C$_6$ alkyl) sulfonamido, and mono- and di-(C$_1$-C$_6$ alkyl)aminocarbonyl, each of which is substituted with from 0 to 4 substituents independently chosen from halogen, hydroxy, cyano, amino, —COOH and oxo.

R$_5$ and R$_6$ are independently selected from: hydrogen, F, Cl, Br, CN, C$_1$-C$_4$ alkyl, C$_1$-C$_6$ alkoxy.

R$_7$, R$_8$ and R$_9$ are independently selected from Hydrogene, C$_1$-C$_4$ alkyl, C$_2$-C$_6$ alkenyl, C$_2$-C$_6$ alkynyl, C$_3$-C$_{10}$ aryl or heteroaryl, C$_1$-C$_6$ alkoxy, C$_1$-C$_6$ alkylthio, C$_2$-C$_6$ alkanoyl, C$_1$-C$_6$ alkoxycarbonyl, C$_2$-C$_6$ alkanoyloxy.

The term "halo" or "halogen" refers to fluorine, chlorine, bromine or iodine.

The term "alkyl" herein alone or as part of another group refers to a monovalent alkane (hydrocarbon) derived radical containing from 1 to 12 carbon atoms unless otherwise defined. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, dimethylpentyl, octyl, 2,2,4-trimethylpentyl, nonyl, decyl, undecyl, dodecyl, and the like. Exemplary substituents include but are not limited to one or more of the following groups: alkyl, aryl, halo (such as F, Cl, Br, I), haloalkyl (such as CCl$_3$ or CF$_3$), alkoxy, alkylthio, hydroxy, carboxy (—COOH), alkyloxycarbonyl (—C(O)R), alkylcarbonyloxy (—OCOR), amino (—NH$_2$), carbamoyl (—NHCOOR— or —OCONHR—), urea (—NHCONHR—) or thiol (—SH). In some preferred embodiments of the present invention, alkyl groups are substituted with, for example, amino, heterocycloalkyl, such as morpholine, piperazine, piperidine, azetidine, hydroxyl, methoxy, or heteroaryl groups such as pyrrolidine, The term 'cycloalkyl" herein alone or as part of another group refers to fully saturated and partially unsaturated hydrocarbon rings of 3 to 9, preferably 3 to 7 carbon atoms. The examples include cyclopropyl, cyclobutyl, cyclopentyl and cyclohexyl, and like. Further, a cycloalkyl may be substituted. A substituted cycloalkyl refers to such rings having one, two, or three substituents, selected from the group consisting of halo, alkyl, substituted alkyl, alkenyl, alkynyl, nitro, cyano, oxo (=O), hydroxy, alkoxy, thioalkyl, —CO$_2$H, —C(=O)H, CO$_2$-alkyl, —C(=O)alkyl, keto, =N—OH, =N—O-alkyl, aryl, heteroaryl, heterocyclo, —NR'R", —C(=O)NR'R", —CO$_2$NR'R", —C(=O)NR'R", —NR'CO$_2$R", —NR'C(=O)R", —SO$_2$NR'R", and —NR'SO$_2$R", wherein each of R' and R" are independently selected from hydrogen, alkyl, substituted alkyl, and cycloalkyl, or R' and R" together form a heterocyclo or heteroaryl ring.

The term 'alkenyl" herein alone or as part of another group refers to a hydrocarbon radical straight, branched or cyclic containing from 2 to 12 carbon atoms and at least one carbon to carbon double bond. Examples of such groups include the vinyl, allyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, and like. Alkenyl groups may also be substituted at any available point of attachment. Exemplary substituents for alkenyl groups include those listed above for alkyl groups, and especially include C3 to C7 cycloalkyl groups such as cyclopropyl, cyclopentyl and cyclohexyl, which may be further substituted with, for example, amino, oxo, hydroxyl, etc.

The term "alkynyl" refers to straight or branched chain alkyne groups, which have one or more unsaturated carbon-carbon bonds, at least one of which is a triple bond. Alkynyl groups include C2-C8 alkynyl, C$_2$-C$_6$ alkynyl and C$_2$-C$_4$ alkynyl groups, which have from 2 to 8, 2 to 6 or 2 to 4 carbon atoms, respectively. Illustrative of the alkynyl group include ethenyl, propenyl, isopropenyl, butenyl, isobutenyl, pentenyl, and hexenyl. Alkynyl groups may also be substituted at any available point of attachment. Exemplary substituents for alkynyl groups include those listed above for alkyl groups such as amino, alkylamino, etc. The numbers in the subscript after the symbol "C" define the number of carbon atoms a particular group can contain.

The term "alkoxy" alone or as part of another group denotes an alkyl group as described above bonded through an oxygen linkage (—O—). Preferred alkoxy groups have from 1 to 8 carbon atoms. Examples of such groups include the methoxy, ethoxy, n-propoxy, isopropoxy, n-butoxy, isobutoxy, sec-butoxy, tert-butoxy, n-pentyloxy, isopentyloxy, n-hexyloxy, cyclohexyloxy, n-heptyloxy, n-octyloxy and 2-ethylhexyloxy.

The term "alkylthio" refers to an alkyl group as described above attached via a sulfur bridge. Preferred alkoxy and alkylthio groups are those in which an alkyl group is attached via the heteroatom bridge. Preferred alkylthio groups have from 1 to 8 carbon atoms. Examples of such groups include the methylthio, ethylthio, n-propythiol, n-butylthiol, and like.

The term "oxo," as used herein, refers to a keto (C=O) group. An oxo group that is a substituent of a nonaromatic carbon atom results in a conversion of —CH$_2$— to —C(=O)—.

The term "alkoxycarbonyl" herein alone or as part of another group denotes an alkoxy group bonded through a carbonyl group. An alkoxycarbonyl radical is represented by the formula: —C(O)OR, where the R group is a straight or branched $C_1$-$C_6$ alkyl group, cycloalkyl, aryl, or heteroaryl.

The term "arylalkyl" herein alone or as part of another group denotes an aromatic ring bonded through an alkyl group (such as benzyl) as described above.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 20 atoms therein, with alternating (resonating) double bonds between adjacent carbon atoms or suitable heteroatoms. Aryl groups may optionally be substituted with one or more groups including, but not limited to halogen such as I, Br, F, or Cl; alkyl, such as methyl, ethyl, propyl, alkoxy, such as methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl S(O)m (m=0, 1, 2), or thiol.

The term "aromatic" refers to a cyclically conjugated molecular entity with a stability, due to delocalization, significantly greater than that of a hypothetical localized structure, such as the Kekule structure.

The term "amino" herein alone or as part of another group refers to —NH$_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives.

The term "alkylsulfonyl" refers to groups of the formula (SO$_2$)-alkyl, in which the sulfur atom is the point of attachment. Preferably, alkylsulfonyl groups include $C_1$-$C_6$ alkylsulfonyl groups, which have from 1 to 6 carbon atoms. Methylsulfonyl is one representative alkylsulfonyl group.

The term "heteroatom" refers to any atom other than carbon, for example, N, O, or S.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom.

The term "heterocycle" or "heterocycloalkyl" herein alone or as part of another group refers to a cycloalkyl group (nonaromatic) in which one of the carbon atoms in the ring is replaced by a heteroatom selected from O, S or N. The "heterocycle" has from 1 to 3 fused, pendant or spiro rings, at least one of which is a heterocyclic ring (i.e., one or more ring atoms is a heteroatom, with the remaining ring atoms being carbon). The heterocyclic ring may be optionally substituted which means that the heterocyclic ring may be substituted at one or more substitutable ring positions by one or more groups independently selected from alkyl (preferably lower alkyl), heterocycloalkyl, heteroaryl, alkoxy (preferably lower alkoxy), nitro, monoalkylamino (preferably a lower alkylamino), dialkylamino (preferably a alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy; lower alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. A heterocyclic group may generally be linked via any ring or substituent atom, provided that a stable compound results. N-linked heterocyclic groups are linked via a component nitrogen atom.

Typically, a heterocyclic ring comprises 1-4 heteroatoms; within certain embodiments each heterocyclic ring has 1 or 2 heteroatoms per ring. Each heterocyclic ring generally contains from 3 to 8 ring members (rings having from to 7 ring members are recited in certain embodiments), and heterocycles comprising fused, pendant or spiro rings typically contain from 9 to 14 ring members which consists of carbon atoms and contains one, two, or three heteroatoms selected from nitrogen, oxygen and/or sulfur.

Examples of "heterocycle" or "heterocycloalkyl groups include piperazine, piperidine, morpholine, thiomorpholine, pyrrolidine, imidazolidine and thiazolide.

The term "substituent," as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (preferably a carbon or nitrogen atom) that is a ring member.

The term "optionally substituted" as it refers that the aryl or heterocyclyl or other group may be substituted at one or more substitutable positions by one or more groups independently selected from alkyl (preferably lower alkyl), alkoxy (preferably lower alkoxy), nitro, monoalkylamino (preferably with one to six carbons), dialkylamino (preferably with one to six carbons), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy and lower alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Optional substitution is also indicated by the phrase "substituted with from 0 to X substituents," where X is the maximum number of possible substituents. Certain optionally substituted groups are substituted with from 0 to 2, 3 or 4 independently selected substituents.

A dash ("-") that is not between two letters or symbols is used to indicate a point oft attachment for a substituent. For example, —$CONH_2$ is attached through the carbon atom.

A dashed cycle that locates inside of a heterocyle ring is used to indicate a conjugated system. The bonds between two atoms may be single bond or double bond. The term "kinase" refers to any enzyme that catalyzes the addition of phosphate groups to a protein residue; for example, serine and threonine kinases catalyze the addition of phosphate groups to serine and threonine residues.

The term "therapeutically effective amount" refers to the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

The term "pharmaceutically acceptable" refers to the fact that the carrier, diluent or excipient is compatible with the other ingredients of the formulation and not deleterious to the recipient thereof.

The terms "administration of a compound" or "administering a compound" refer to the act of providing a compound of the invention or pharmaceutical composition to the subject in need of treatment.

The term "protected" refers that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., Protective Groups in Organic Synthesis, John Wiley & Sons, New York (1999).

The term "pharmaceutically acceptable salt" of a compound recited herein is an acid or base salt that is suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$-COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol or acetonitrile, is preferred. It will be apparent that each compound of Formula I may, but need not, be formulated as a hydrate, solvate or non-covalent complex. In addition, the various crystal forms and polymorphs are within the scope of the present invention. Also provided herein are prodrugs of the compounds of Formula I.

Preferred W groups of formula (I) are: F, Cl, Br, CN, $CF_3$, $CF_2H$, $CFH_2$, $CH_3$, $OCH_3$, $NH_2$ and the list below:

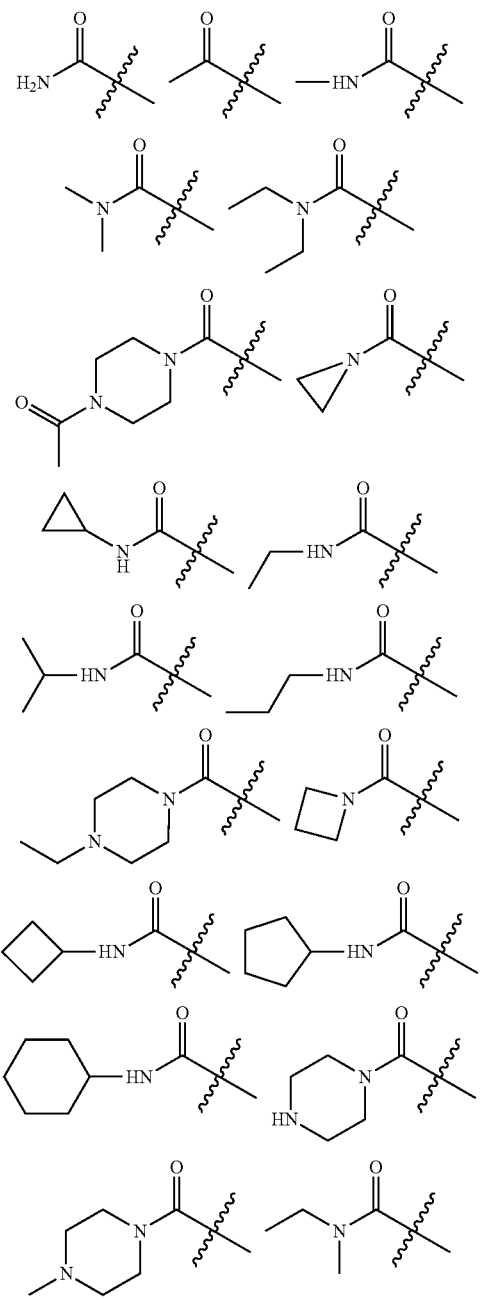

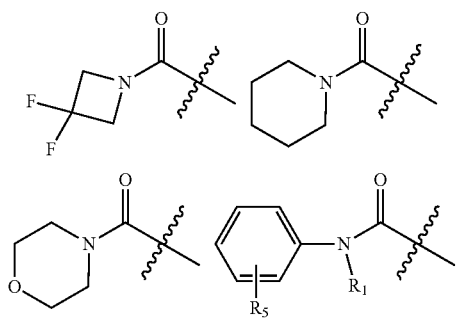
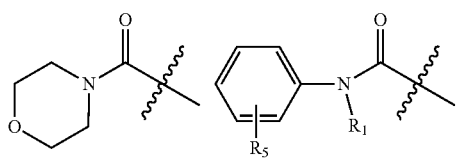
Preferred substituted indole groups of formula (I) are listed below:
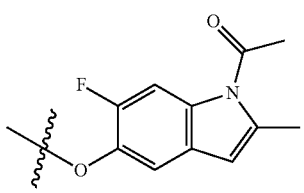
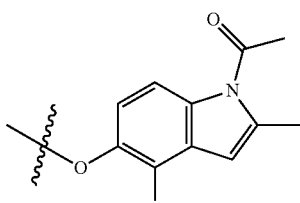
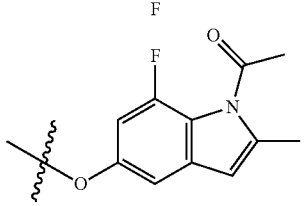
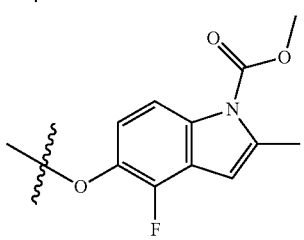
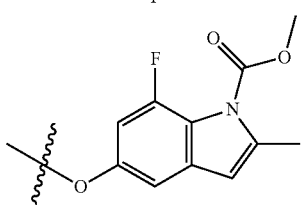
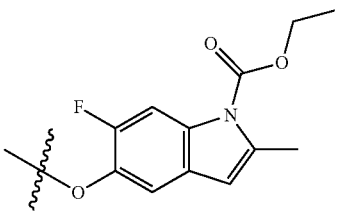
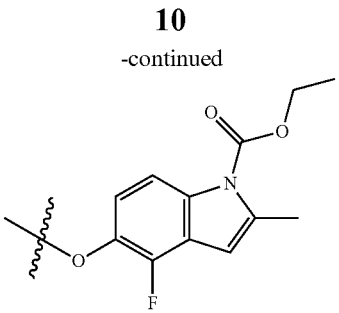
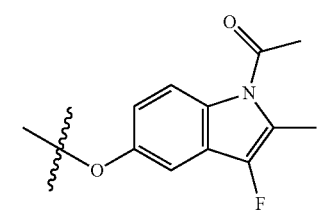
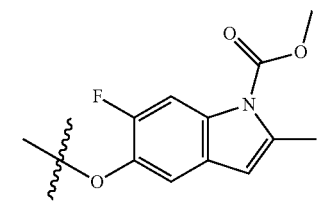
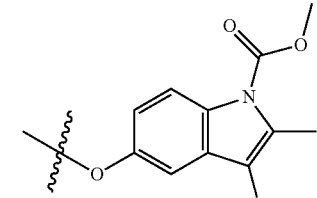
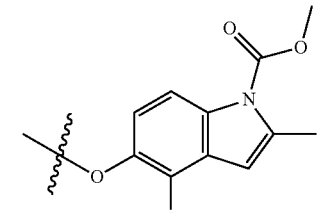
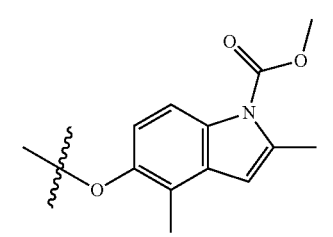
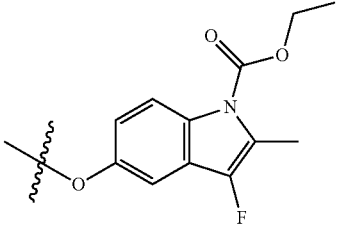

-continued
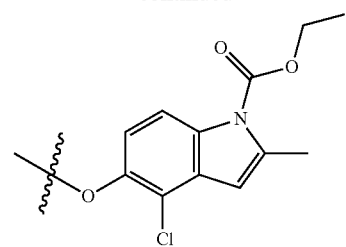
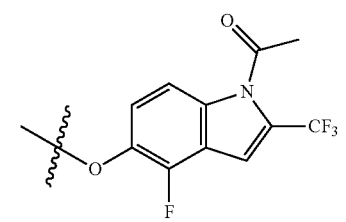
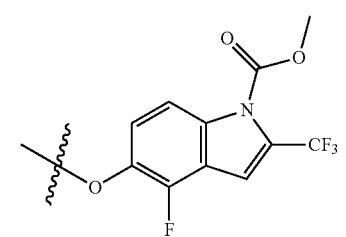
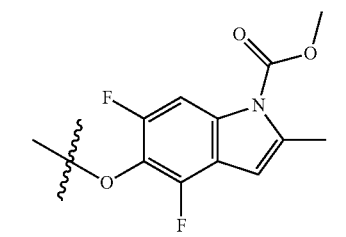
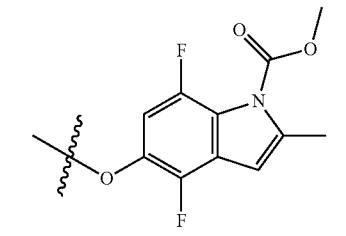
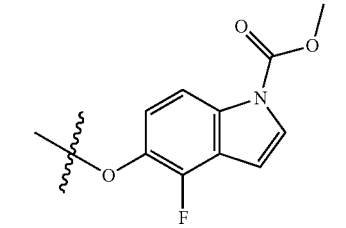
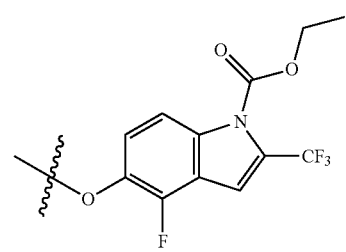
-continued
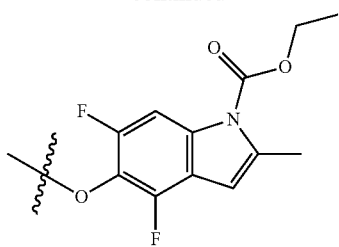
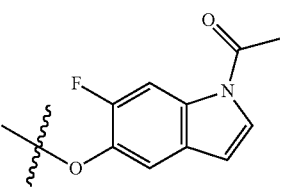
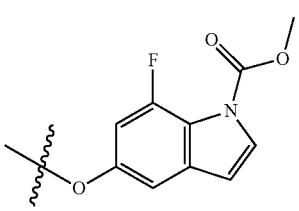
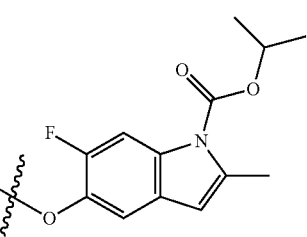
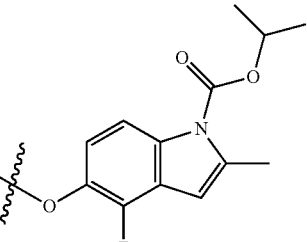
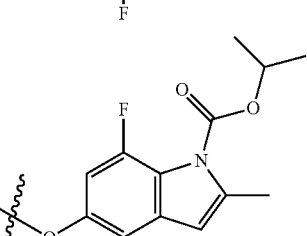
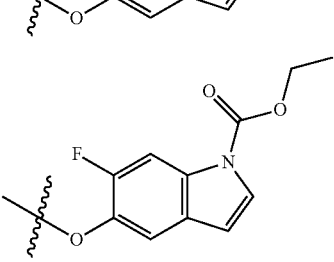

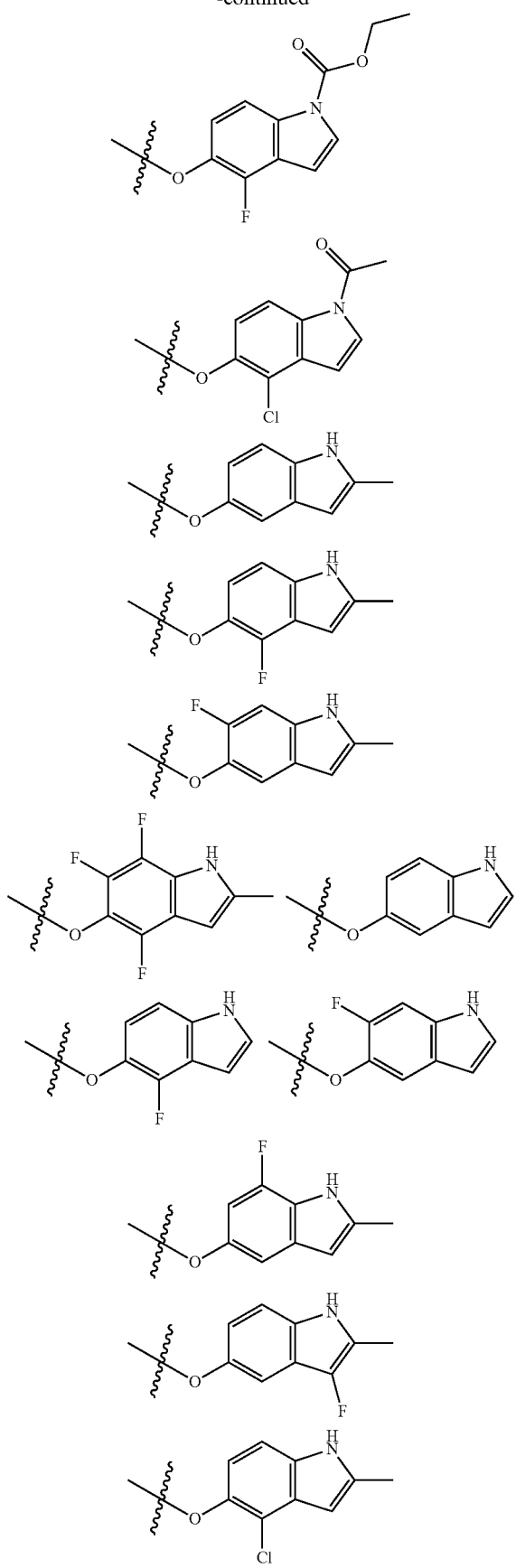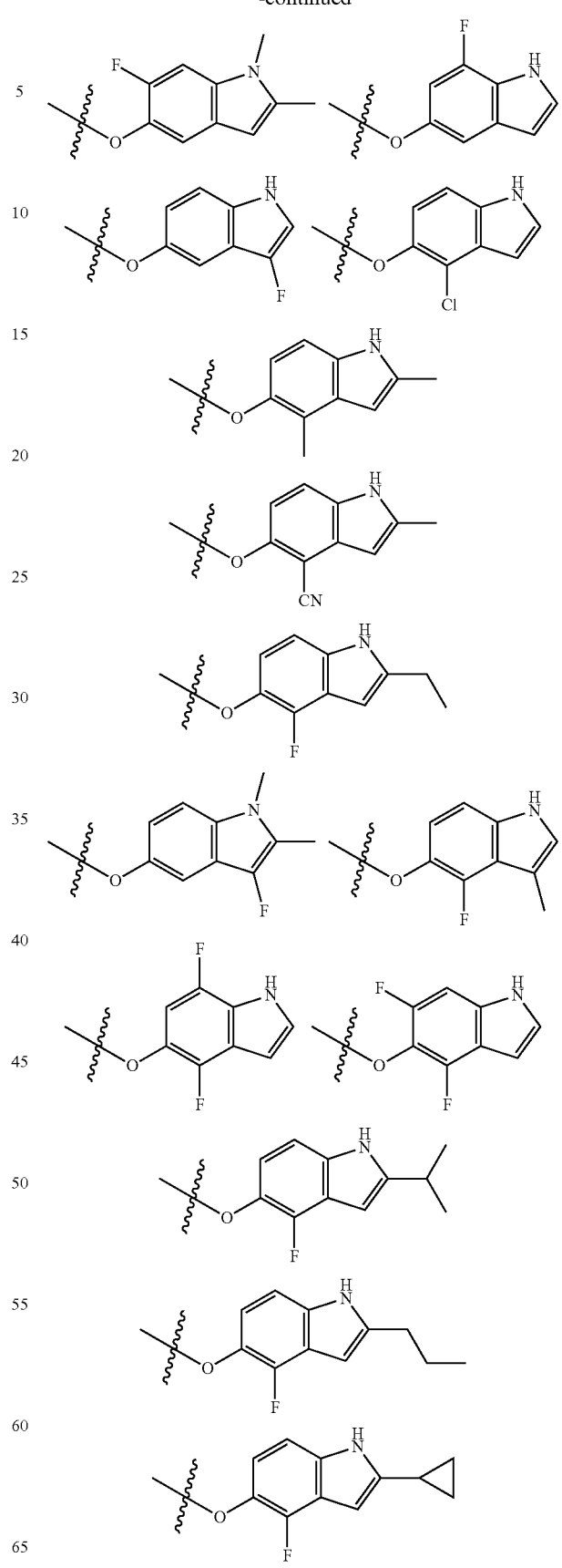

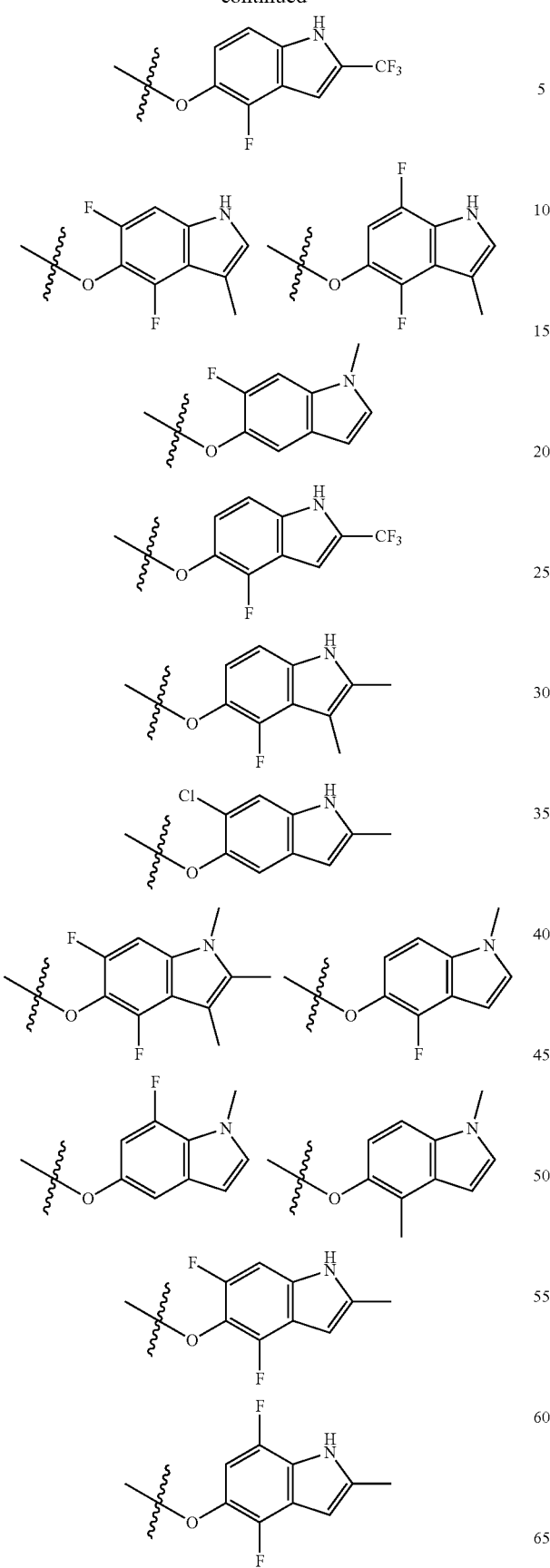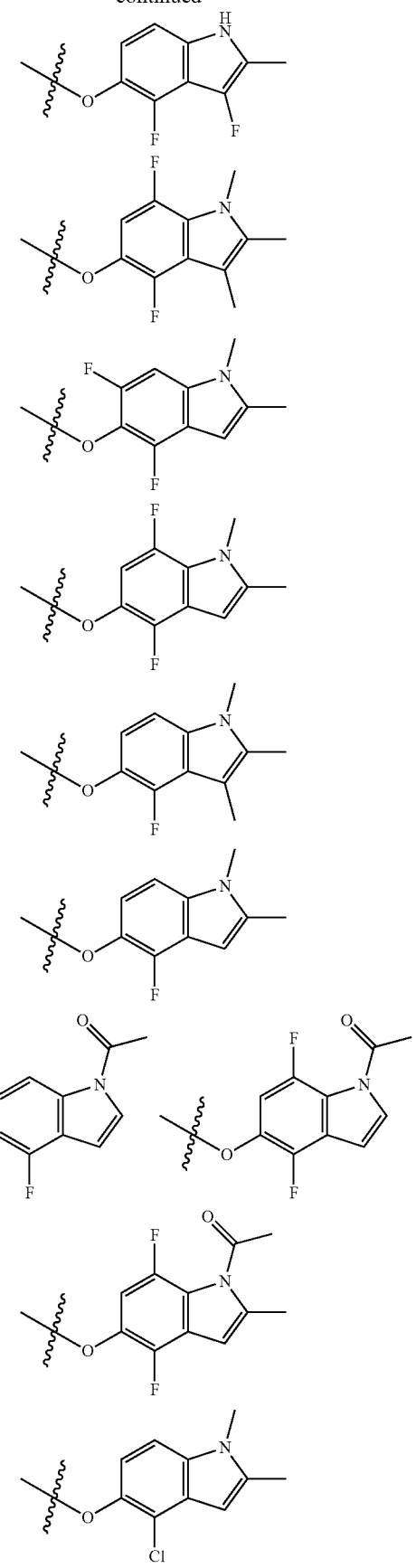

-continued
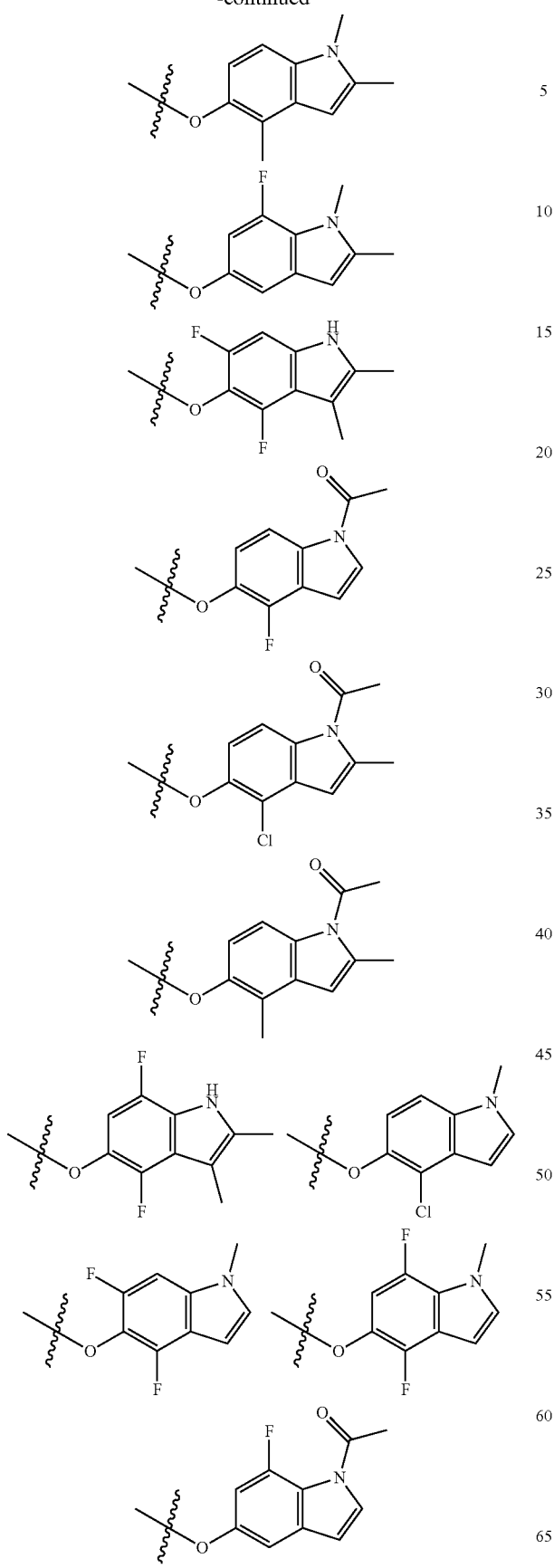
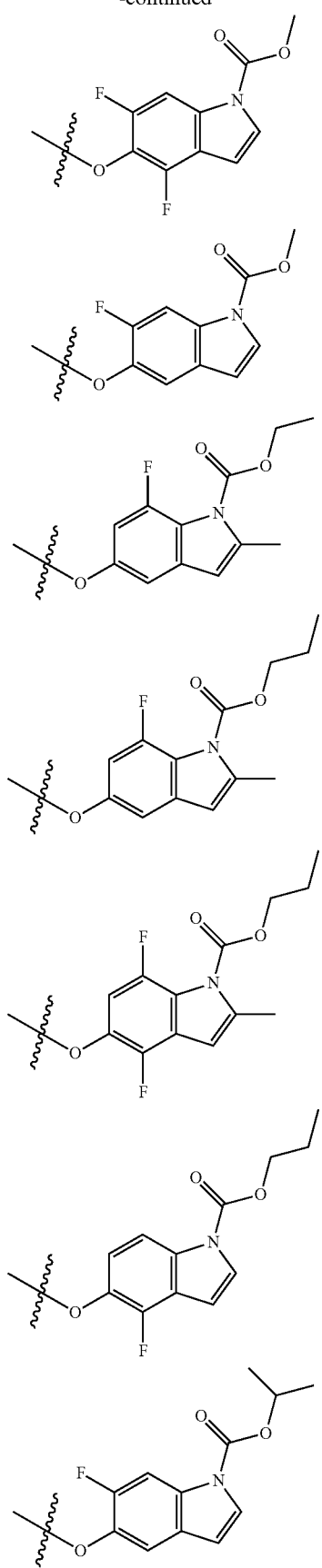

-continued
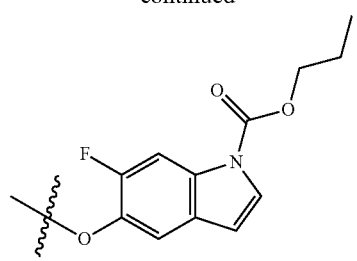
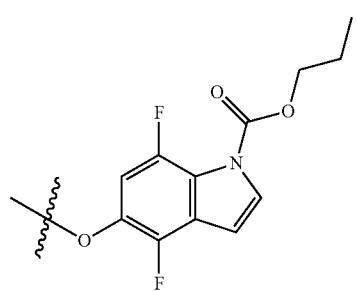 [SMILES: *Oc1cc(F)c2c(ccn2C(=O)OCCC)c1F]
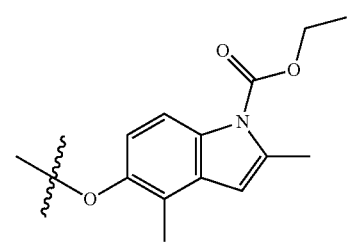
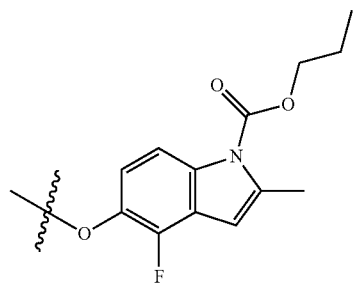
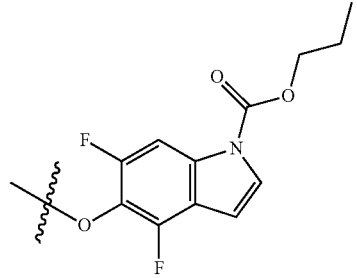
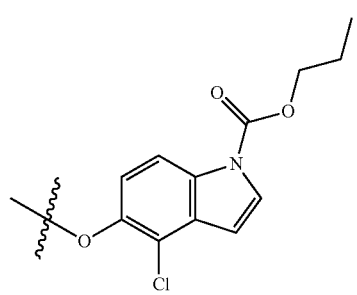
-continued
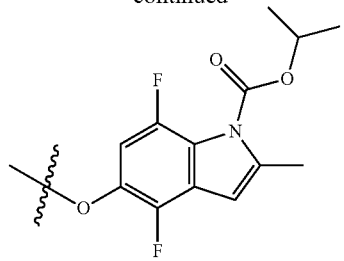
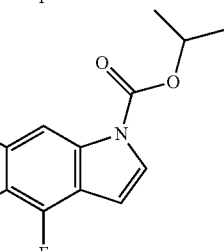
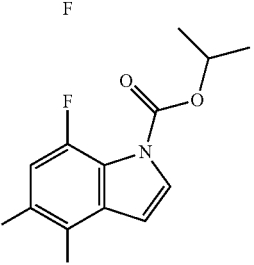
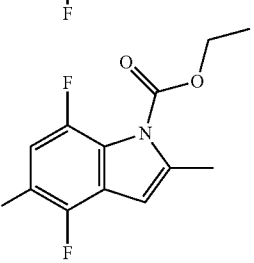
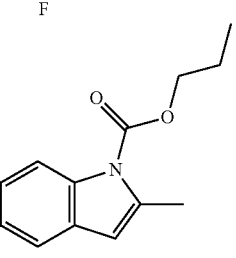
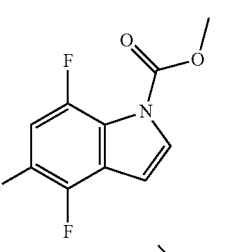
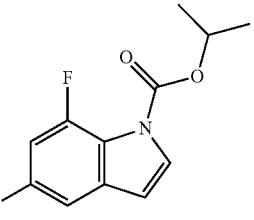

-continued
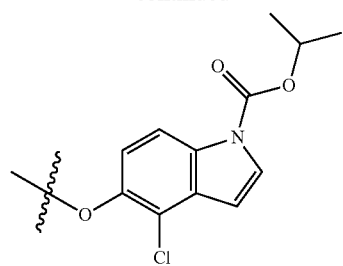
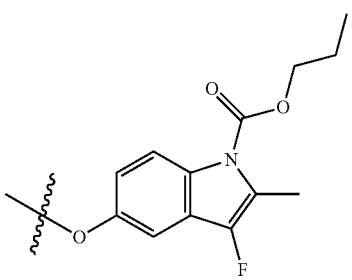
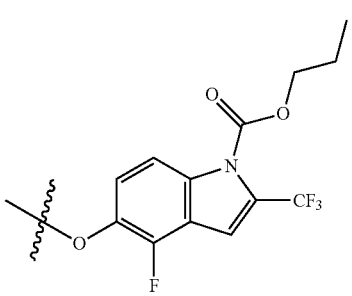
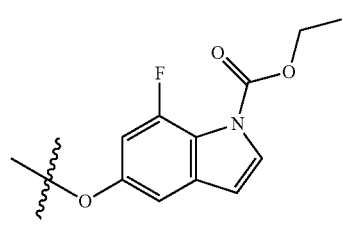
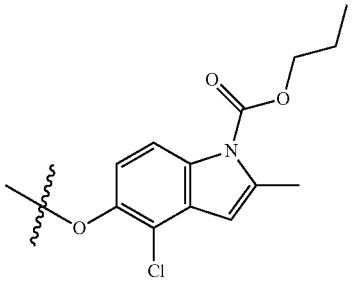
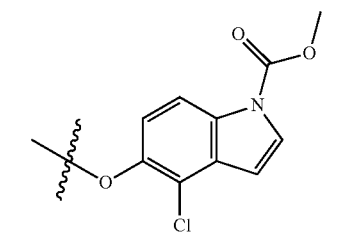
-continued
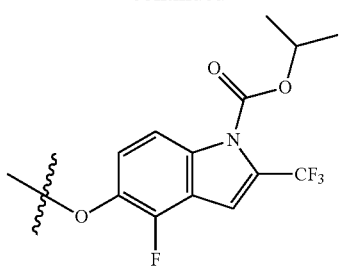
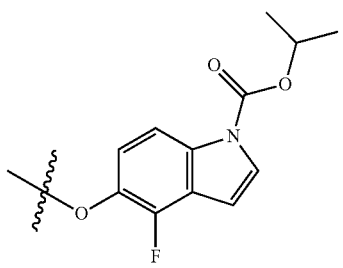 [SMILES: *Oc1cc(F)c2c(ccn2C(=O)OC(C)C)c1F]
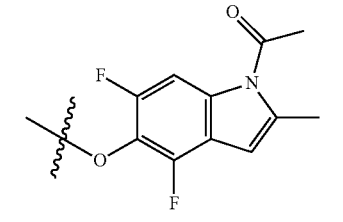
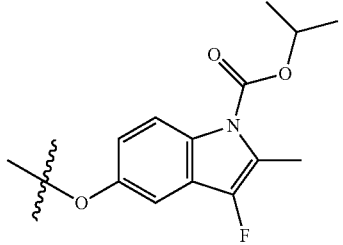
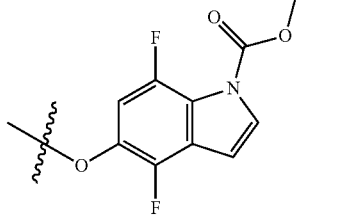
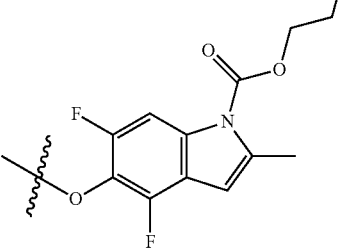

-continued
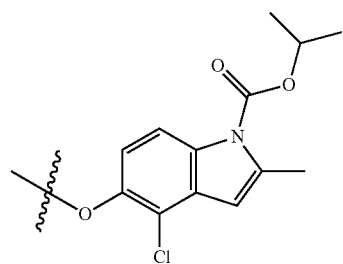
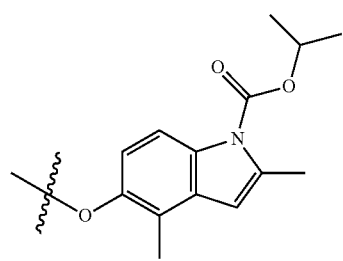
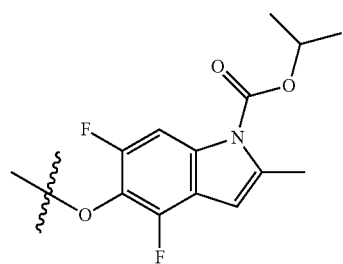
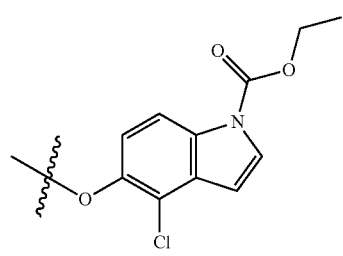
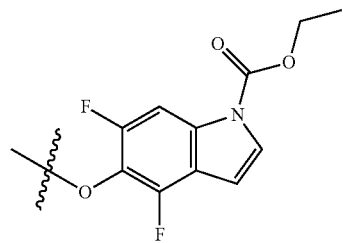
Preferred Ar groups of formula (I) are as below:
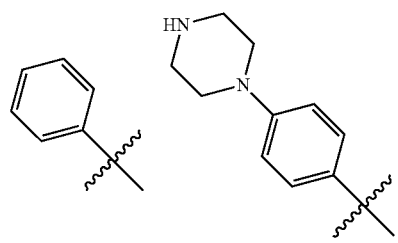
-continued
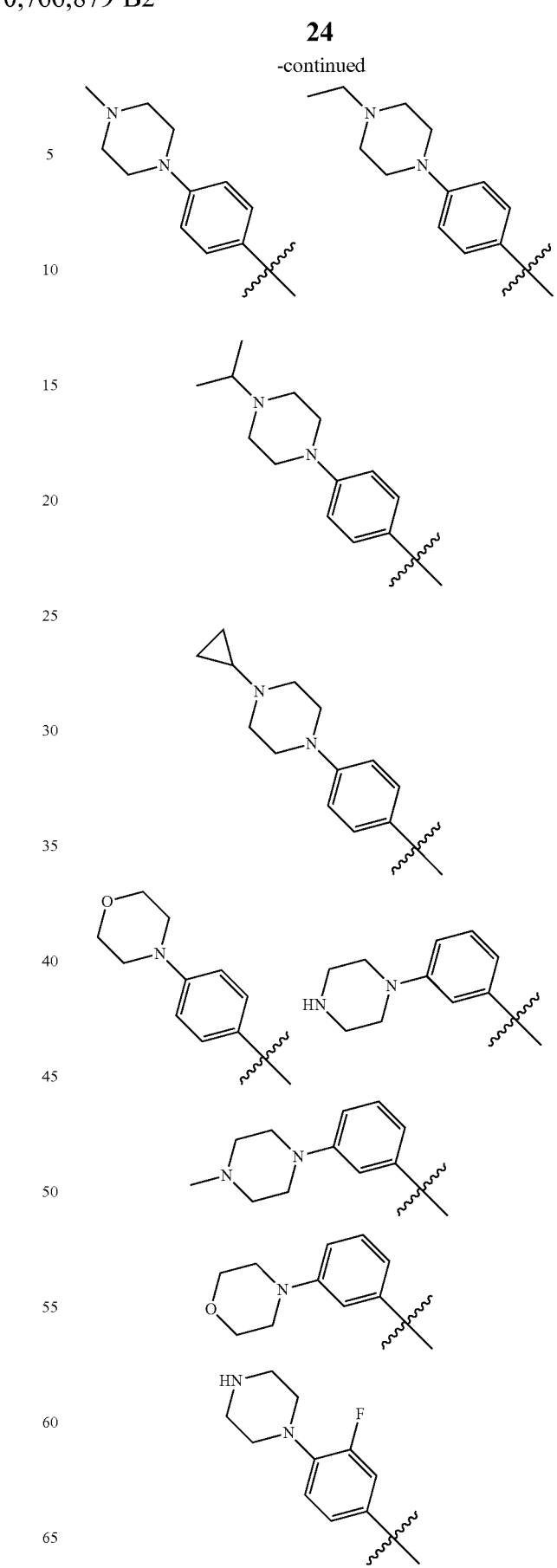

-continued
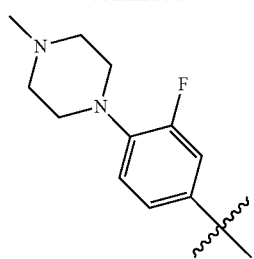
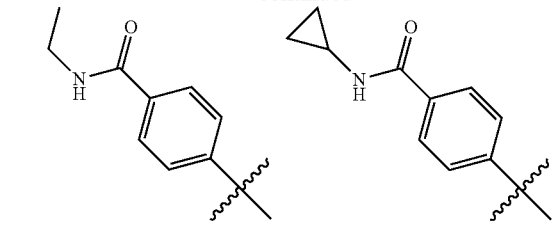
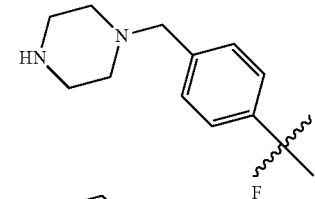
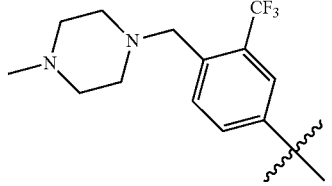
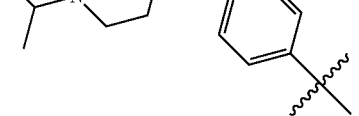
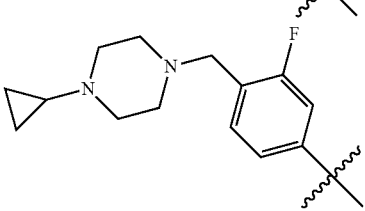

-continued
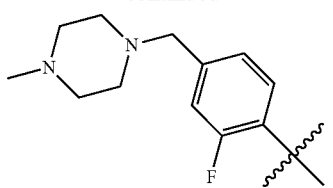
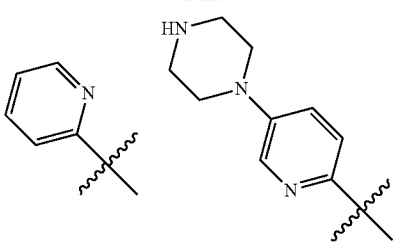
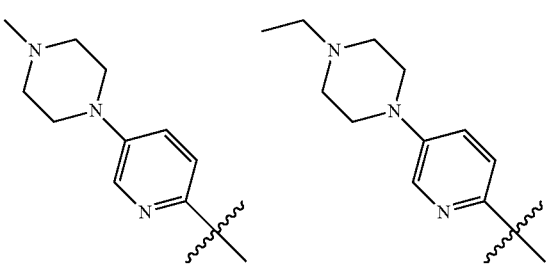
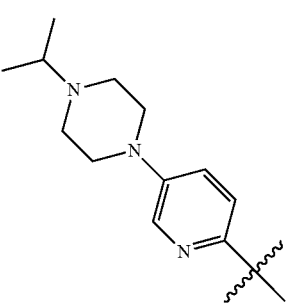
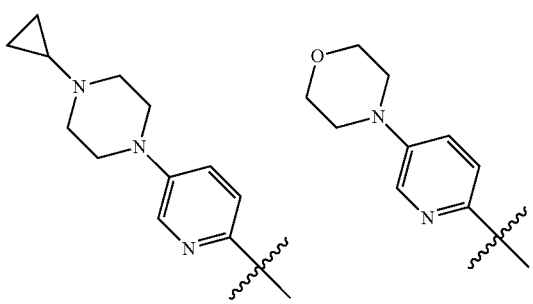
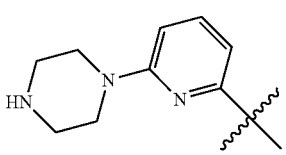
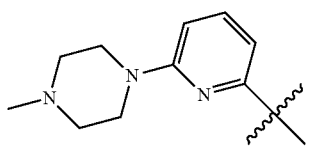
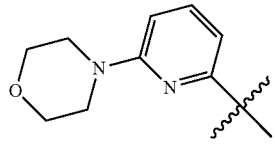

-continued
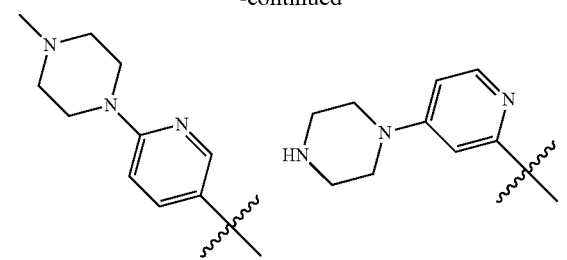
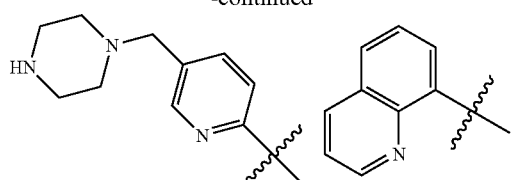
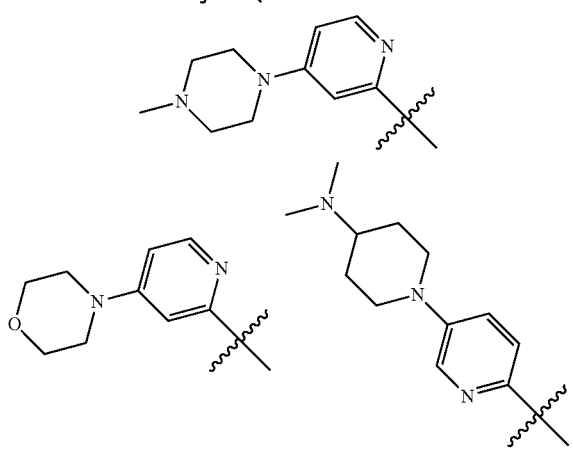
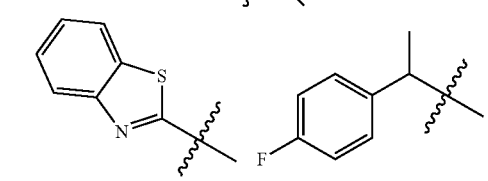
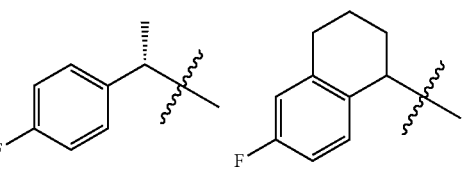
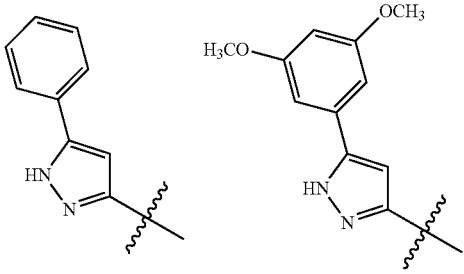
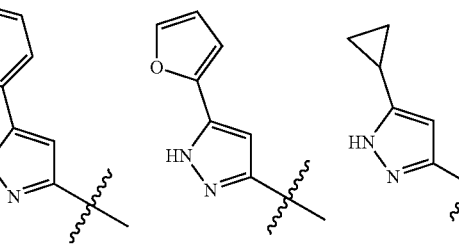
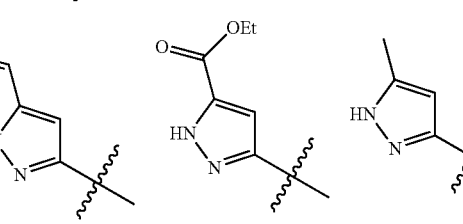
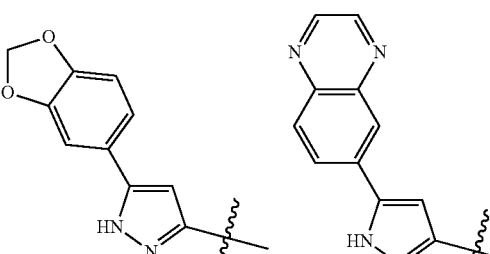
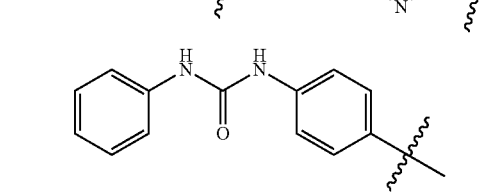

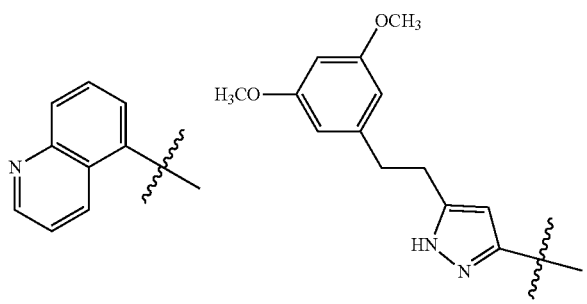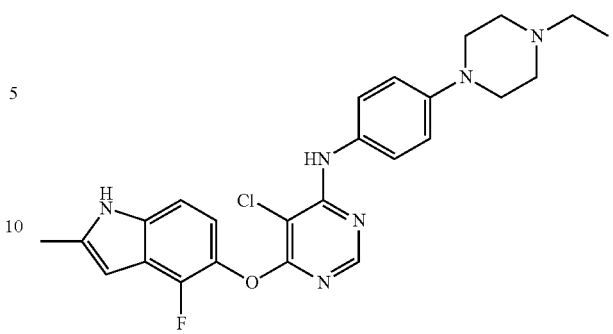
Examples of specific compounds of the present invention are those compounds defined in the following:
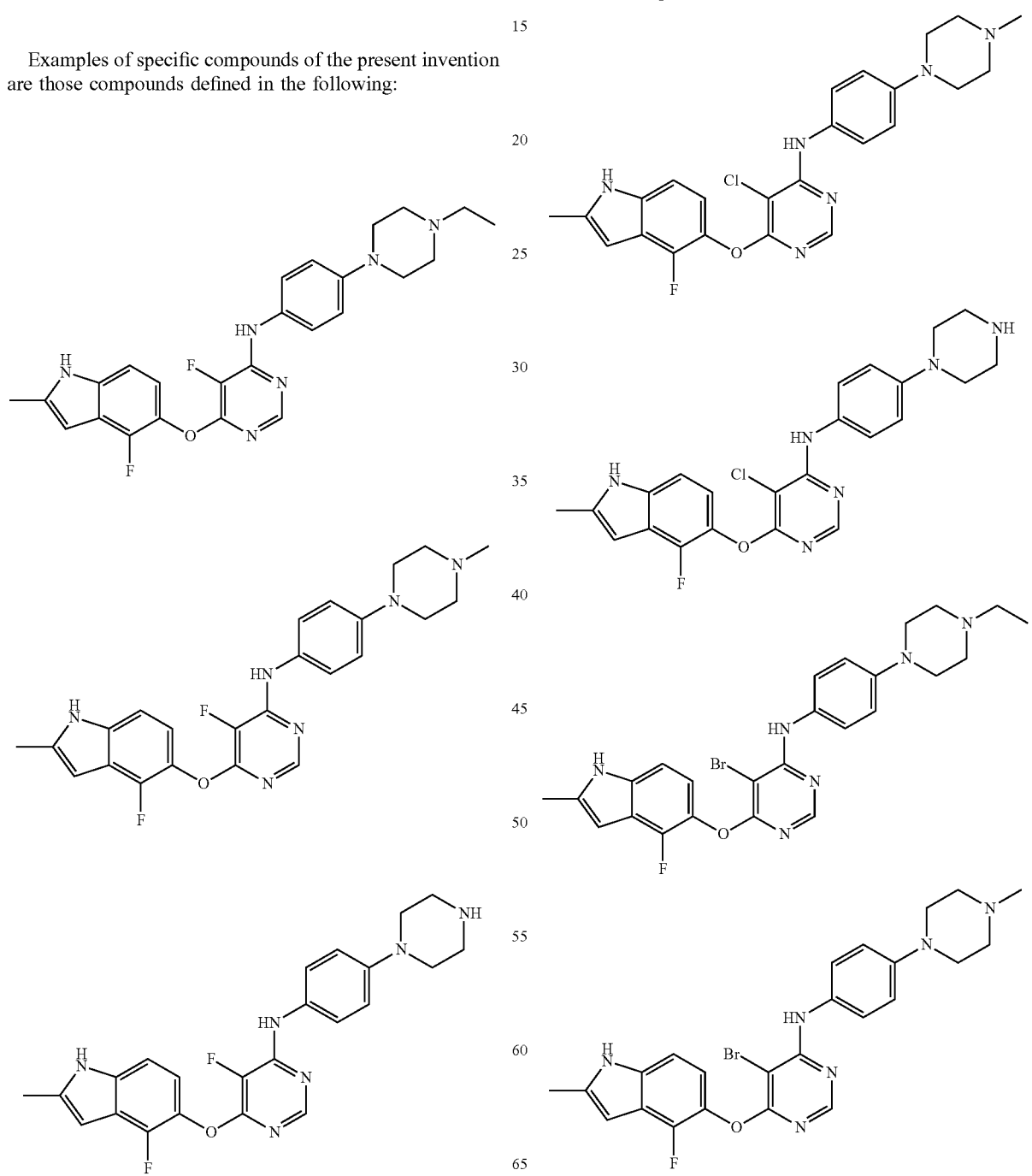

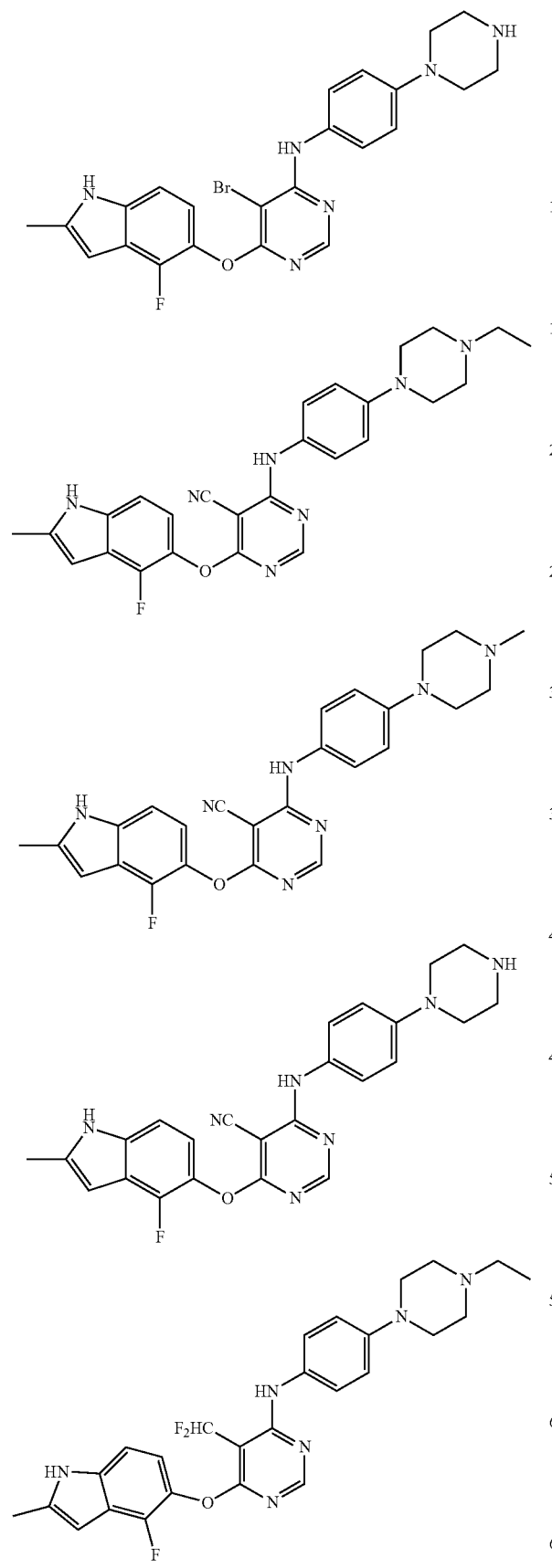
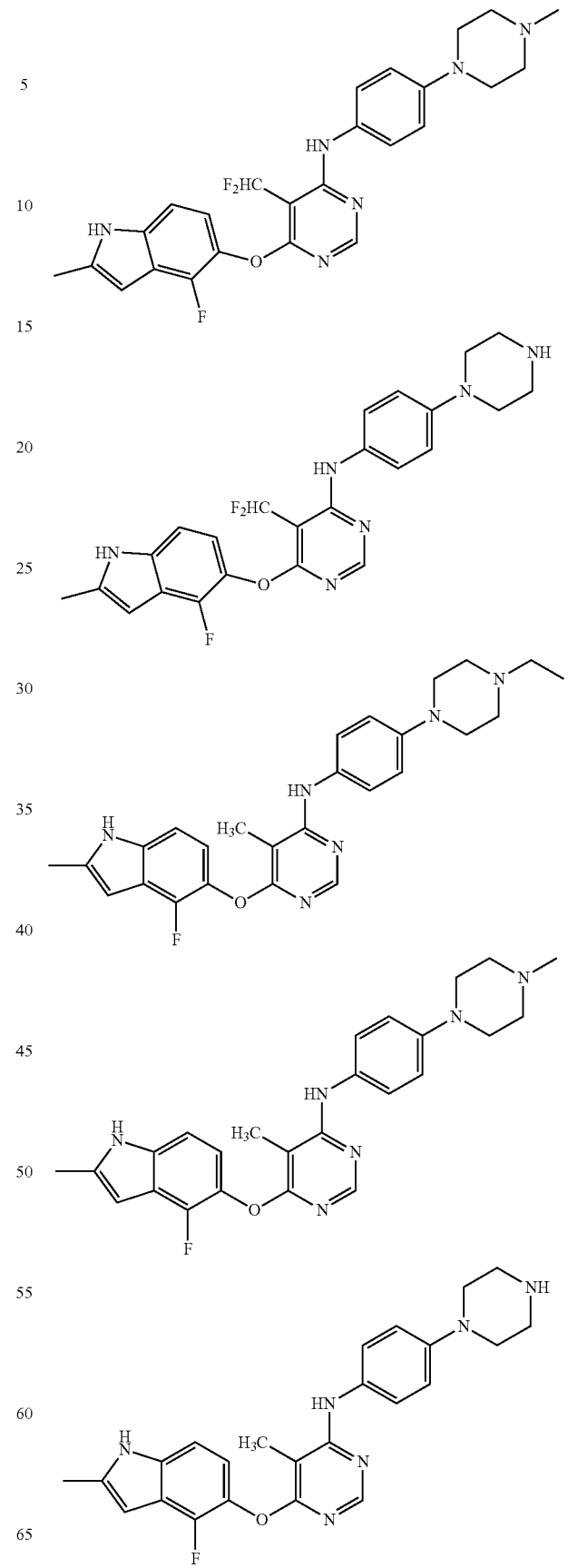

35
-continued
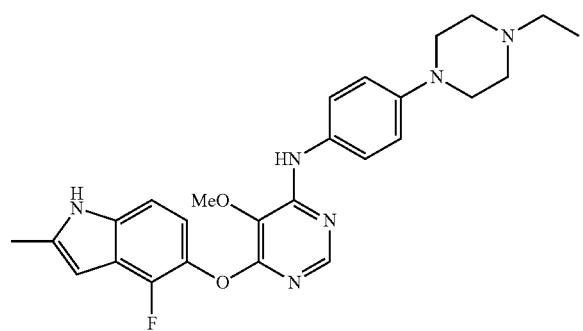
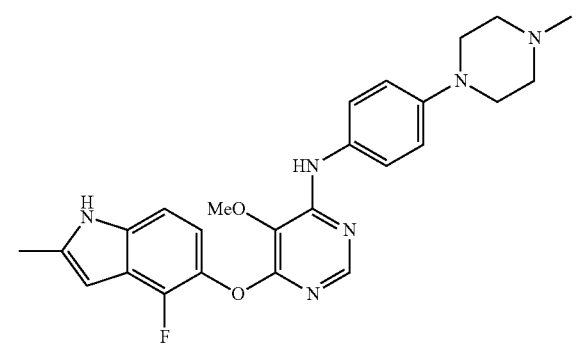
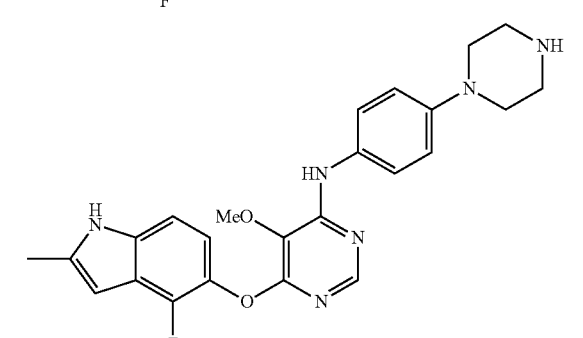
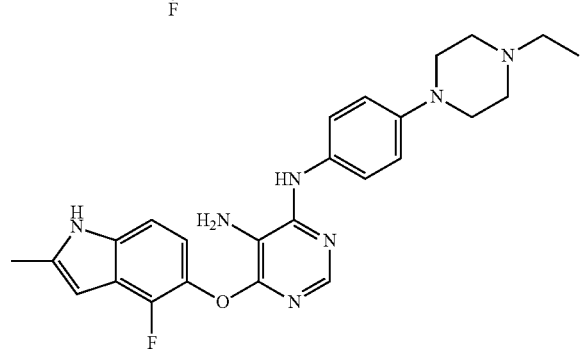
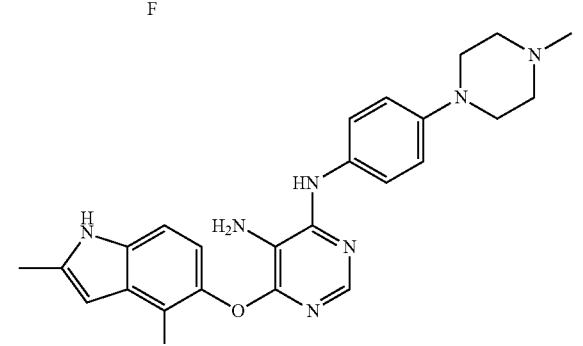
36
-continued
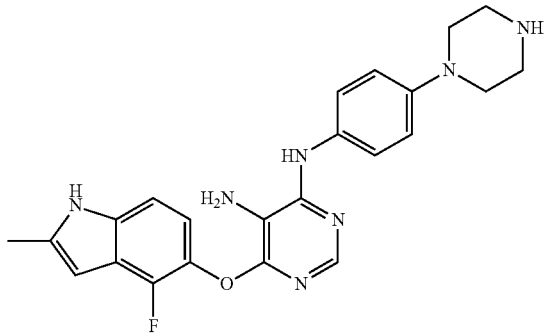
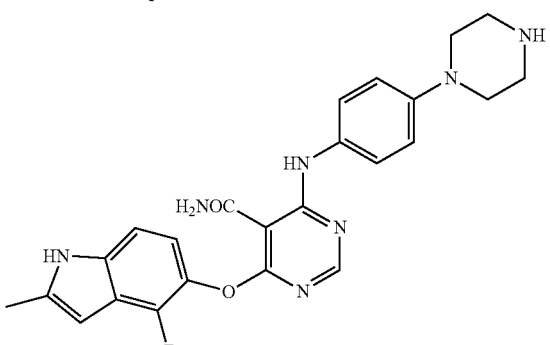
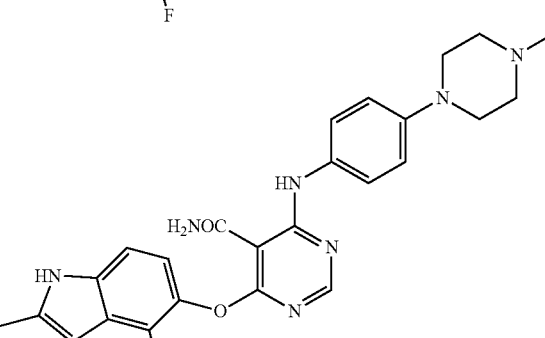
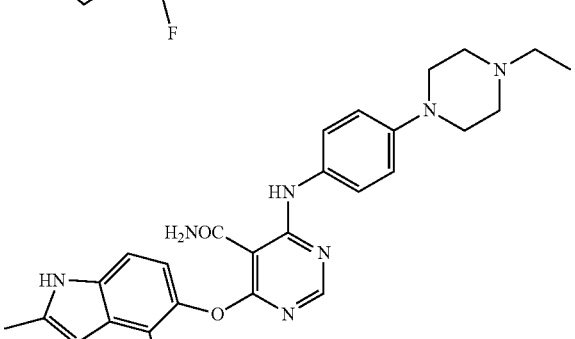
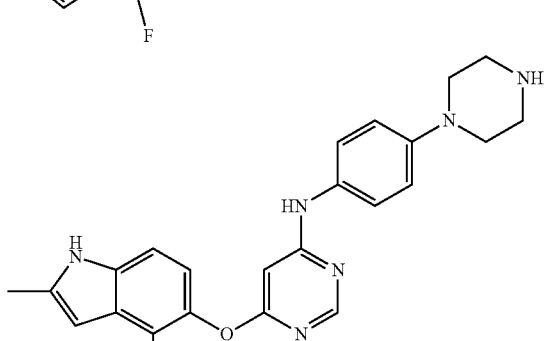

37
-continued
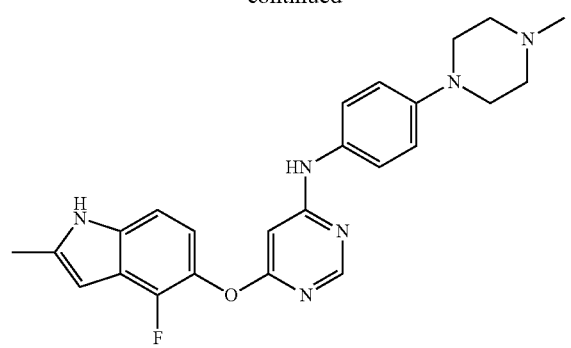
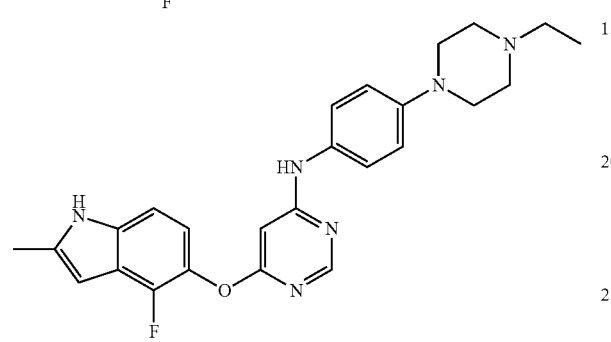
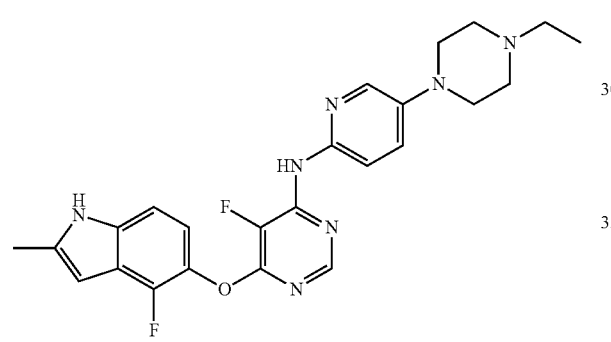
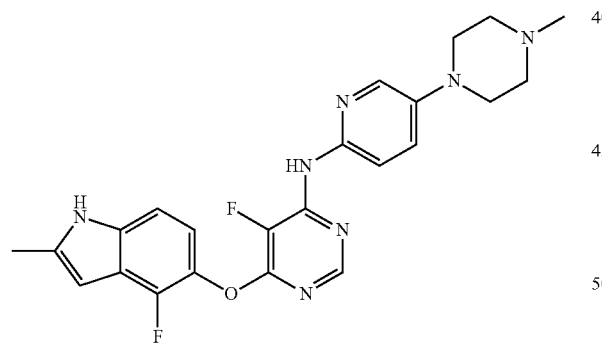
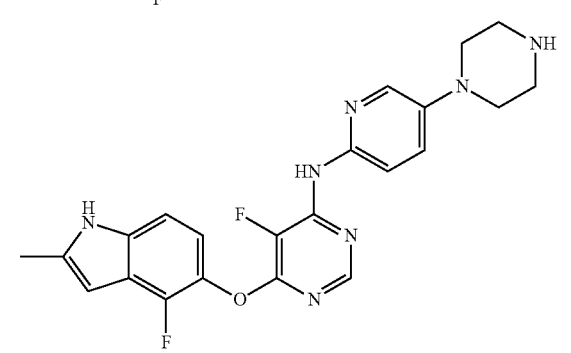
38
-continued
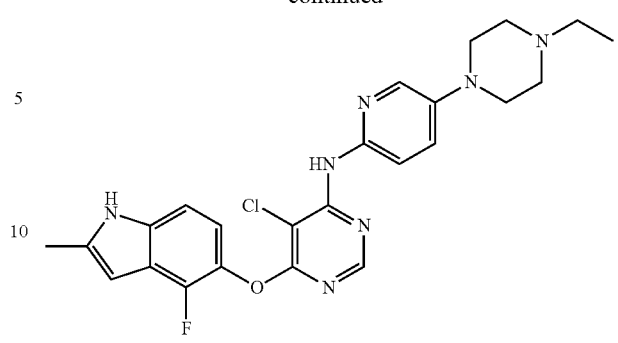
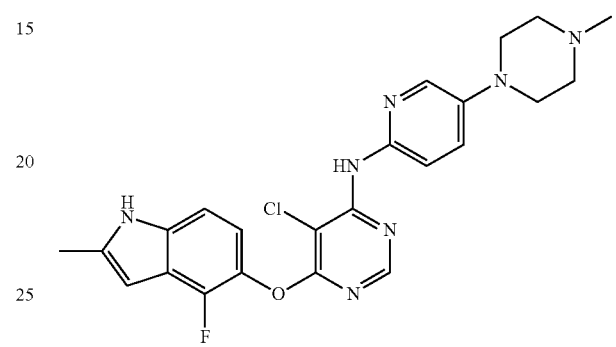
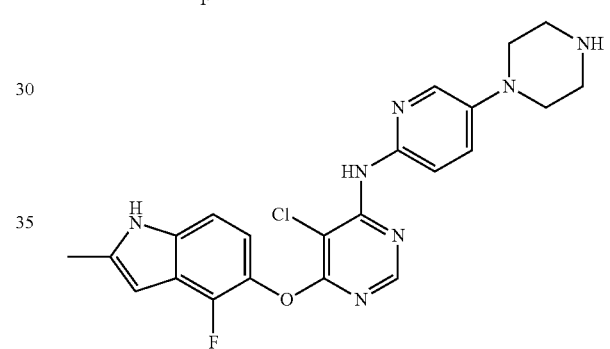
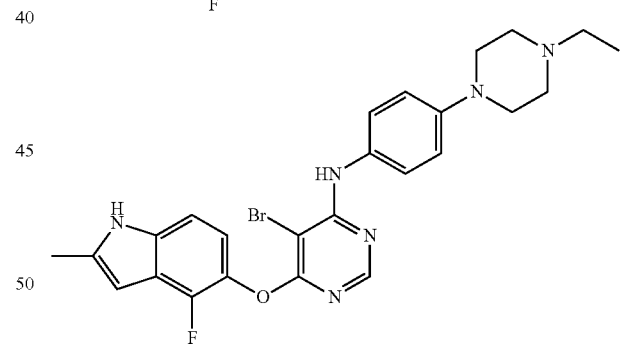
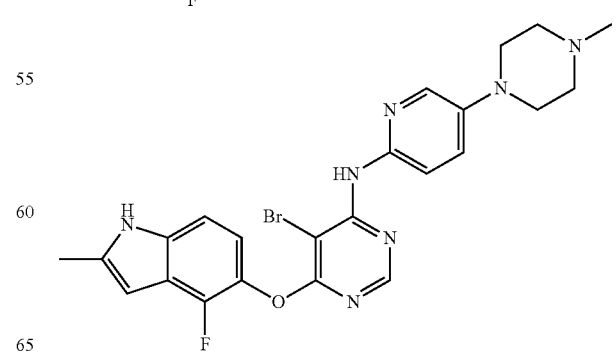

-continued
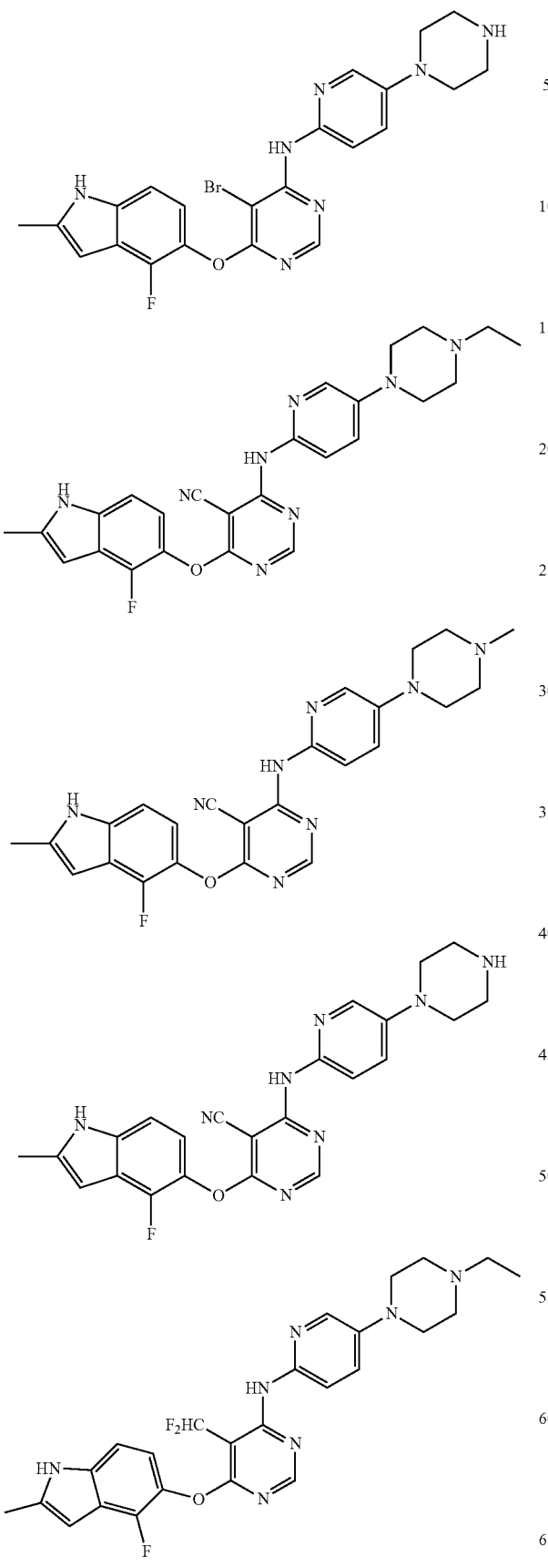
-continued
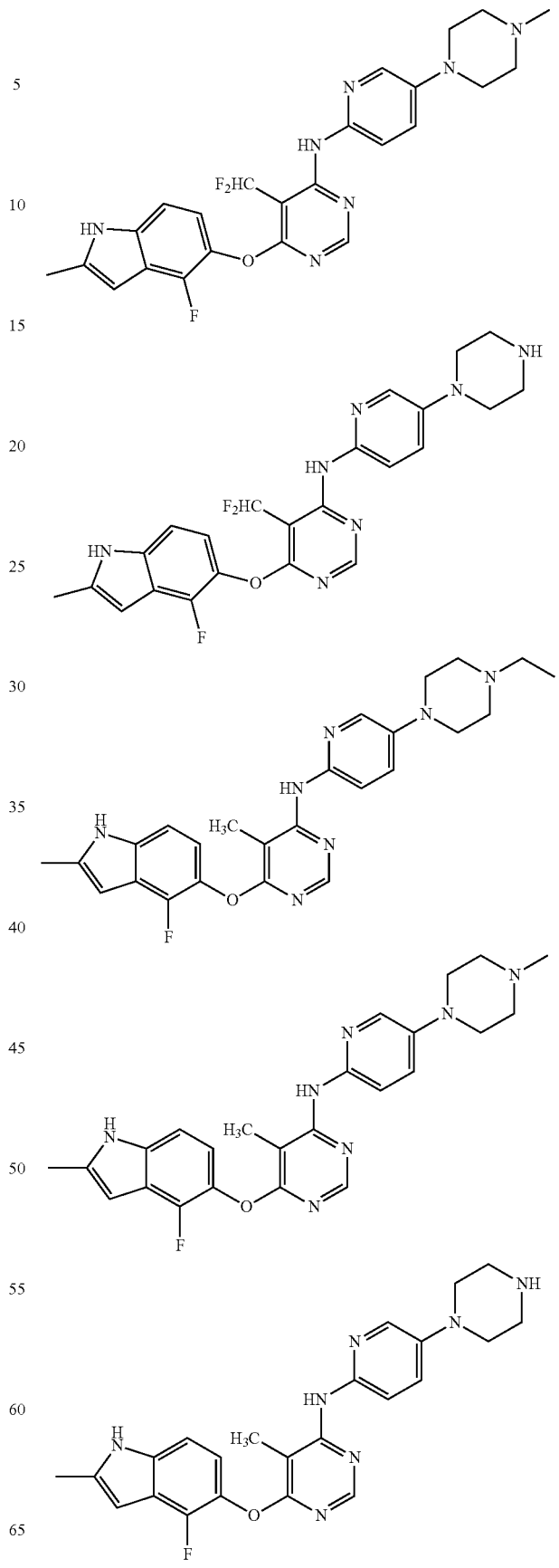

-continued
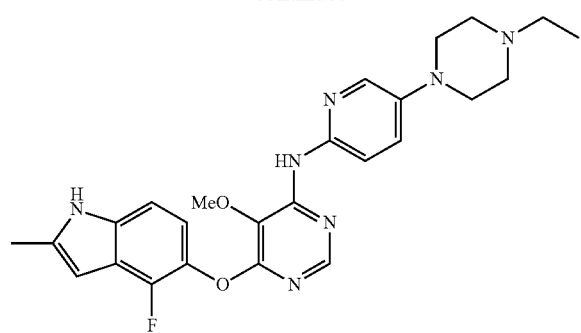
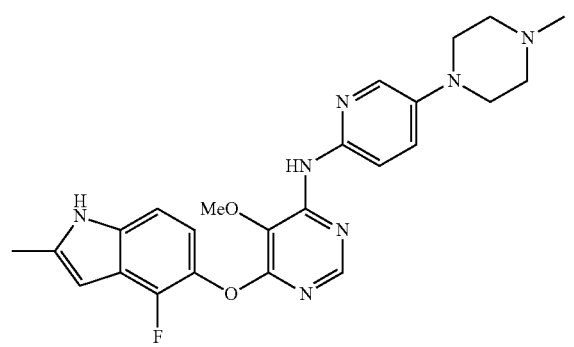
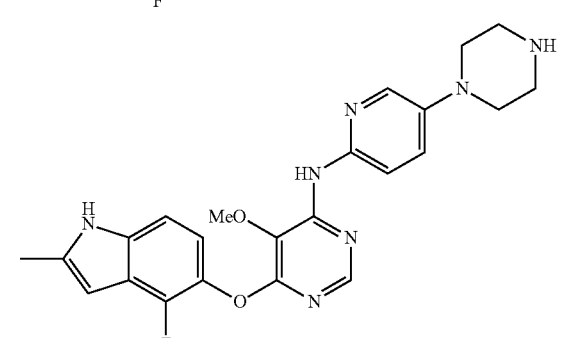
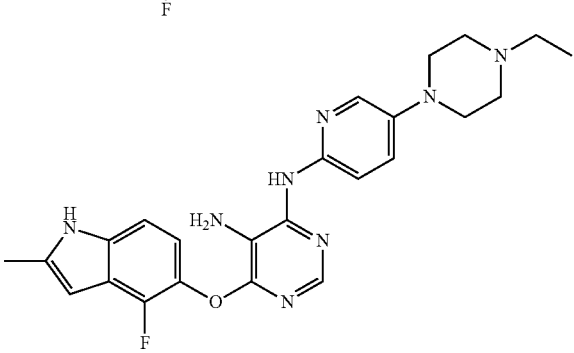
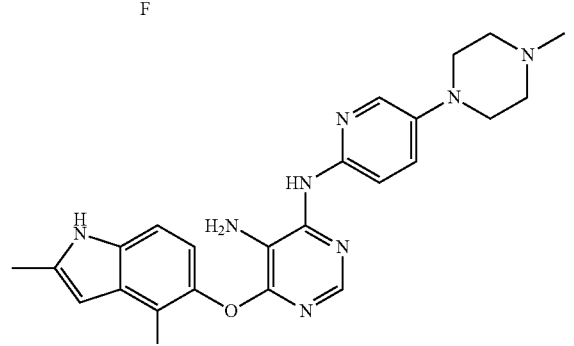
-continued
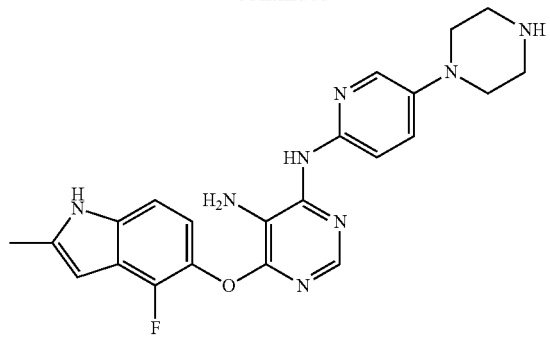
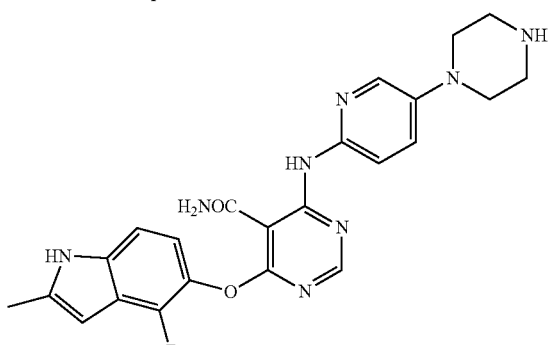
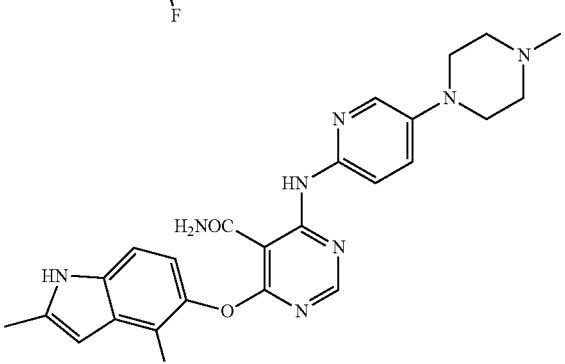
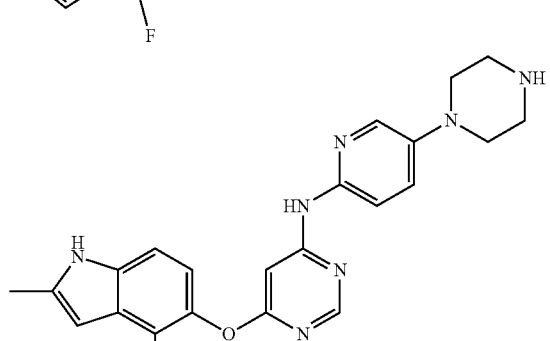

-continued
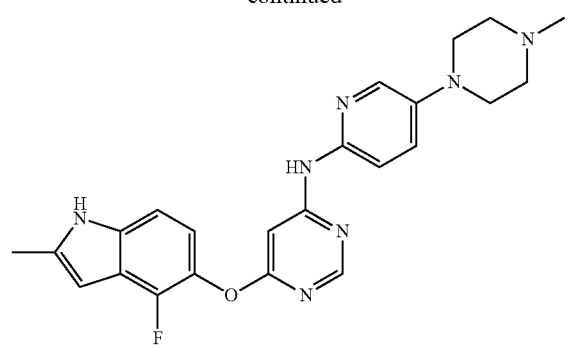
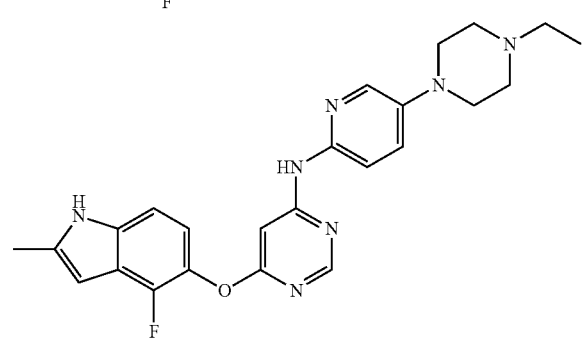
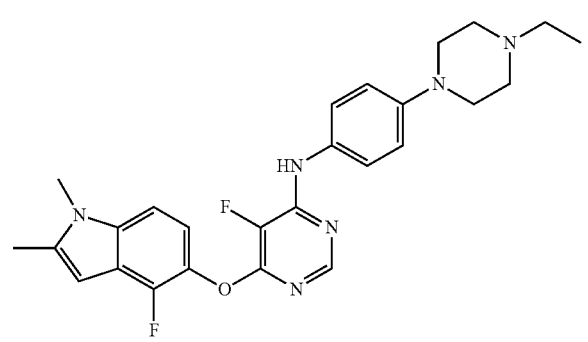
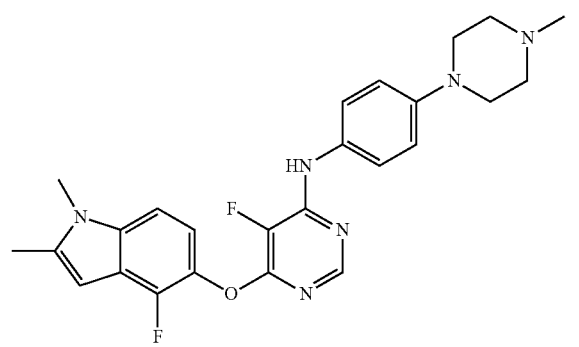
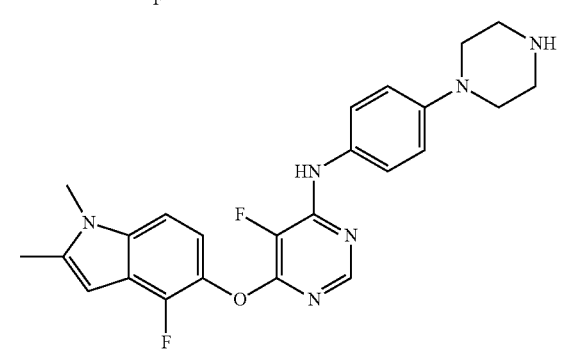
-continued
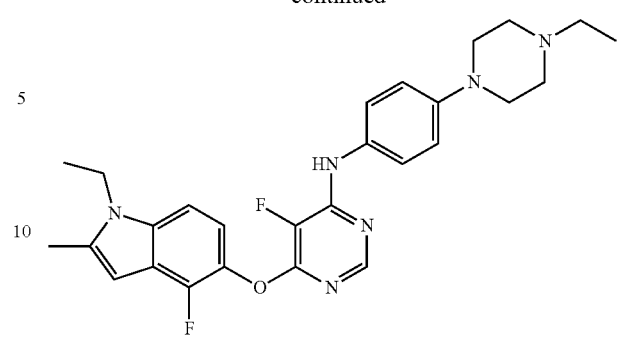
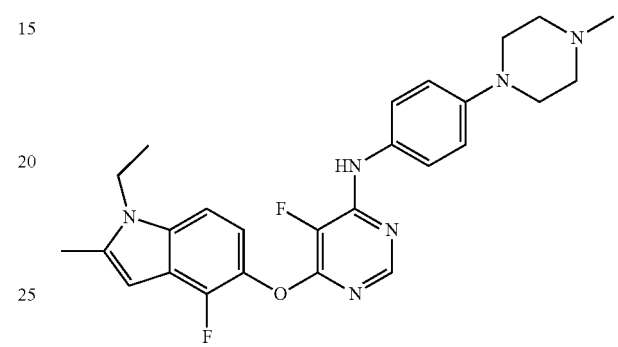
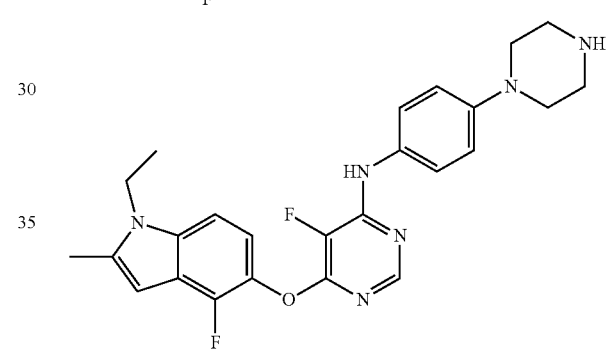
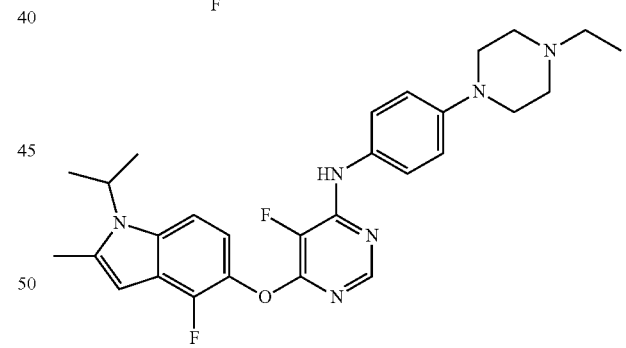
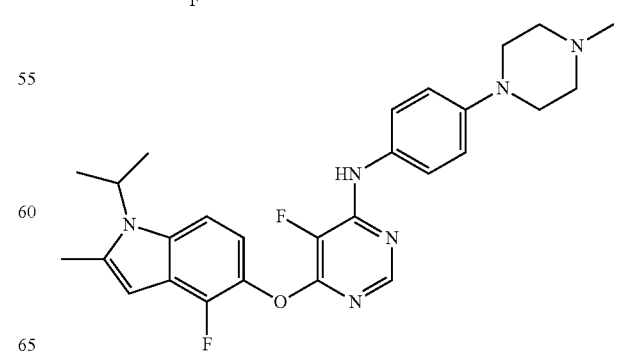

-continued
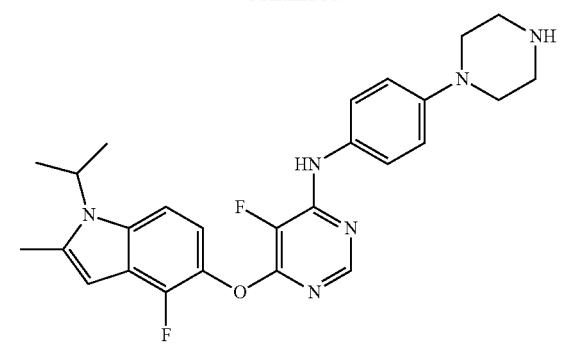
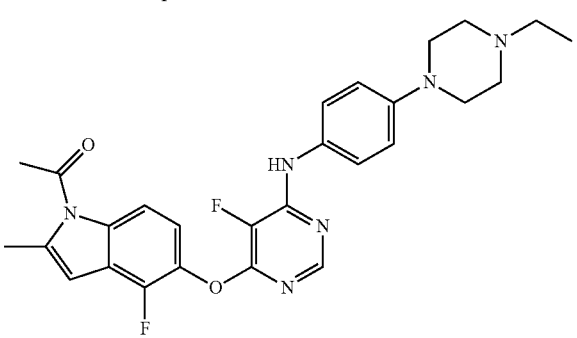
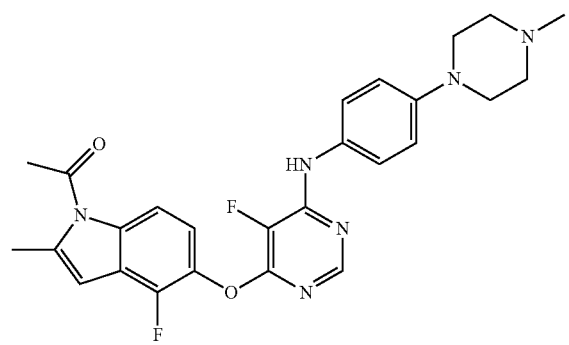
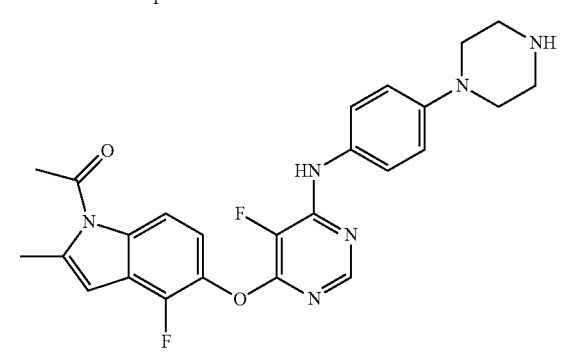
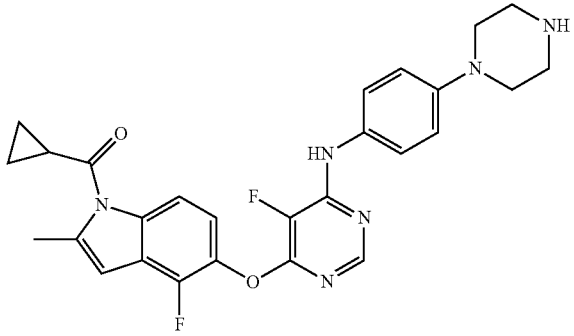
-continued
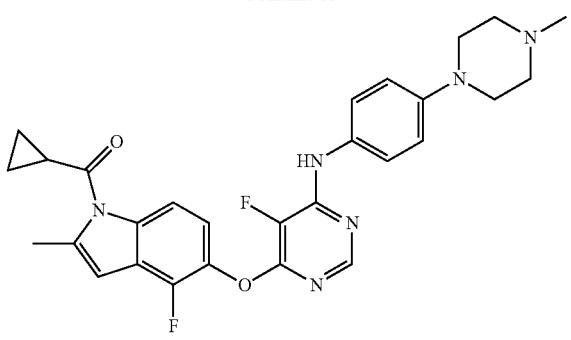
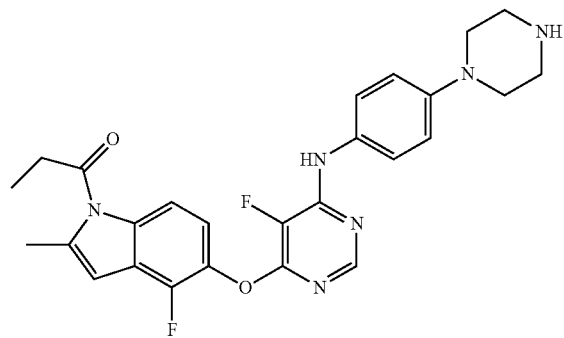
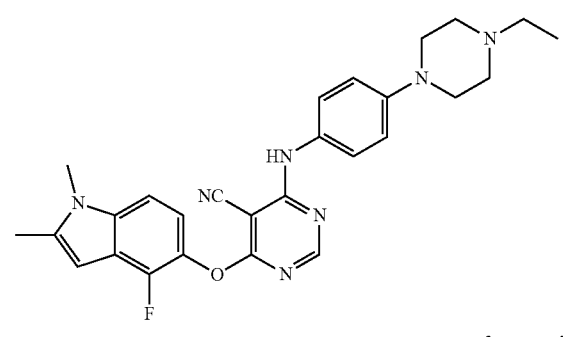
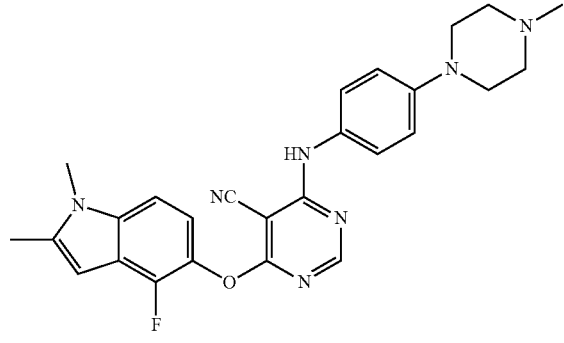
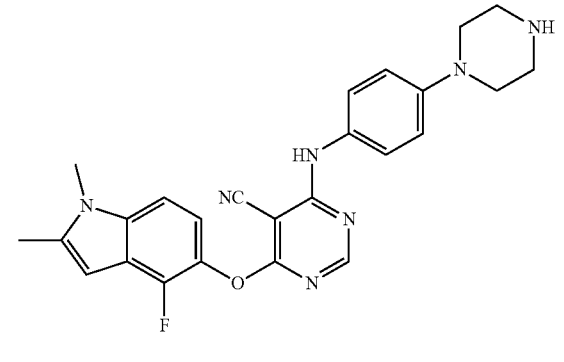

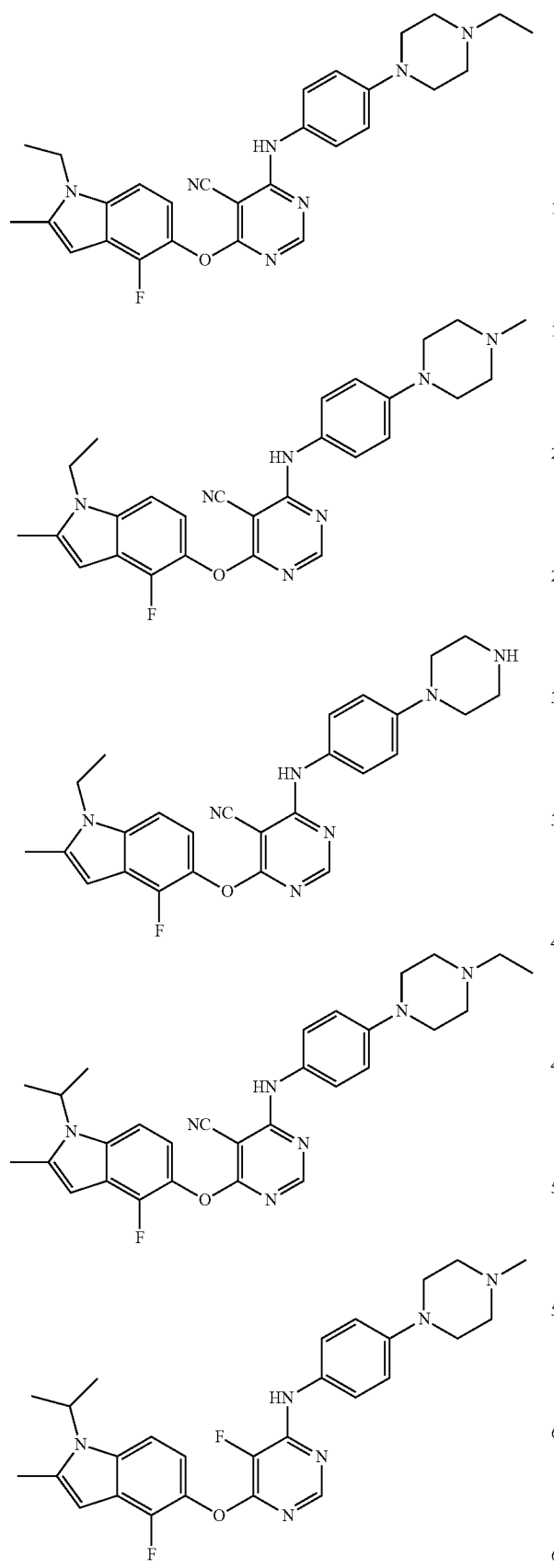

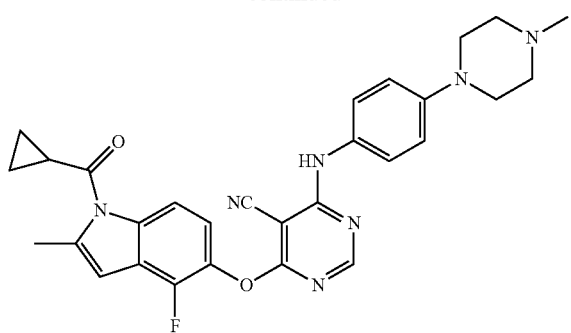 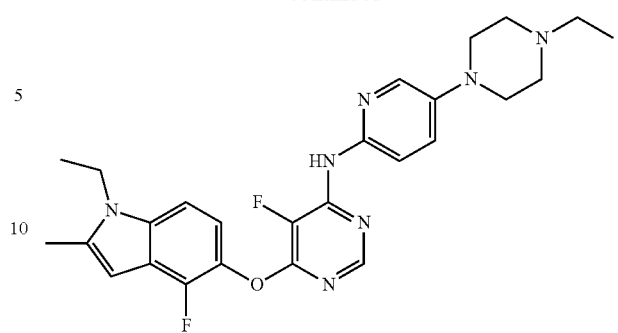
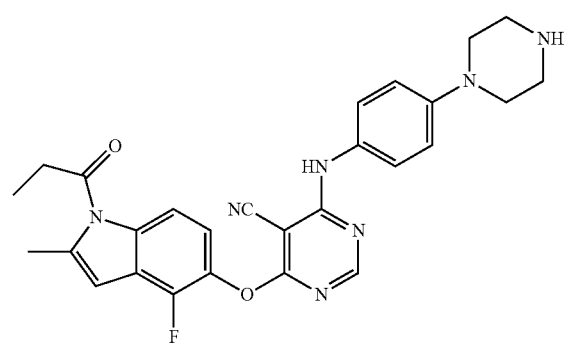 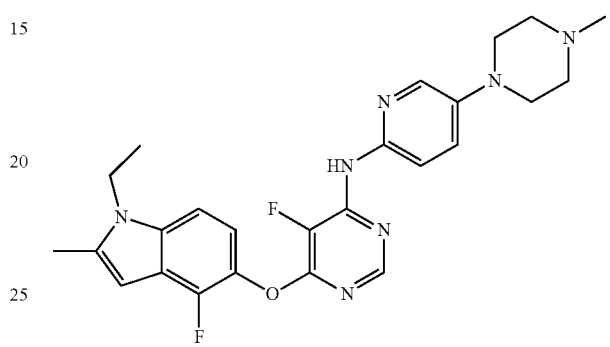
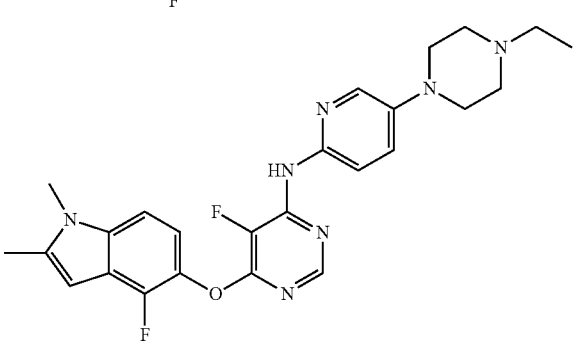 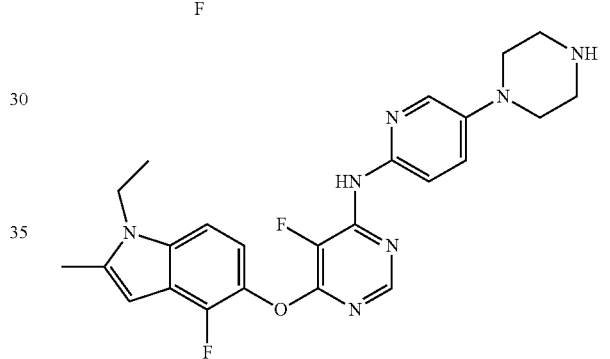
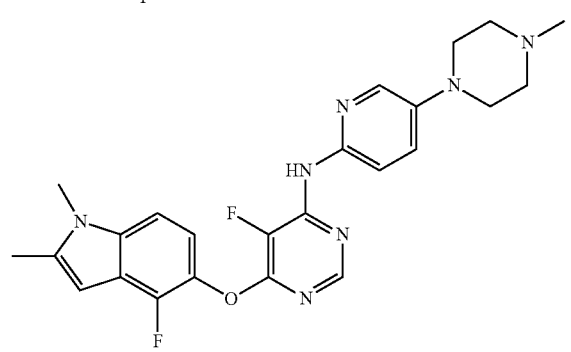 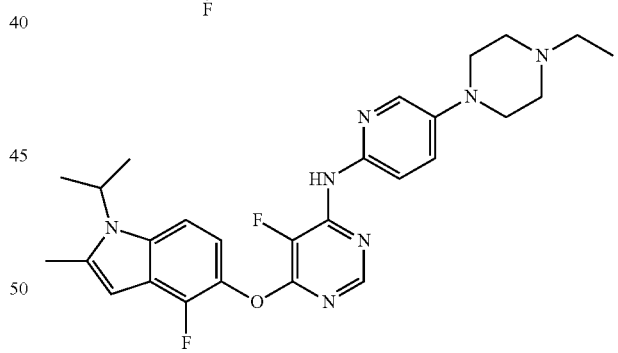
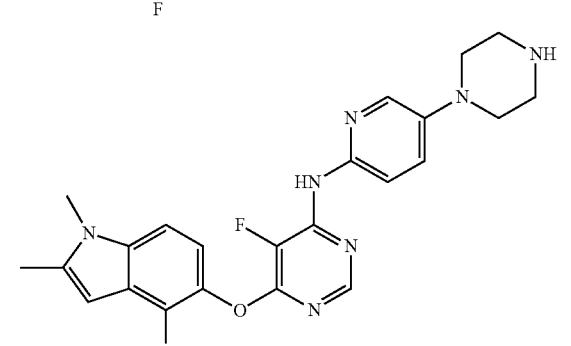 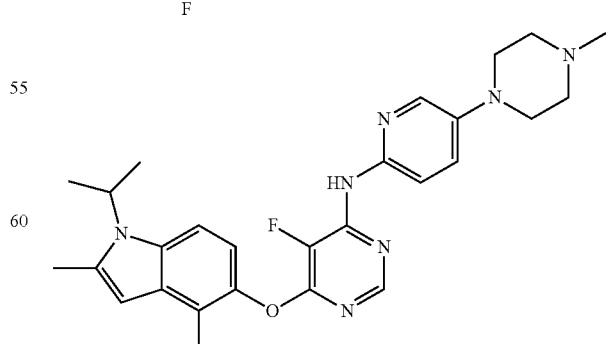

51
-continued
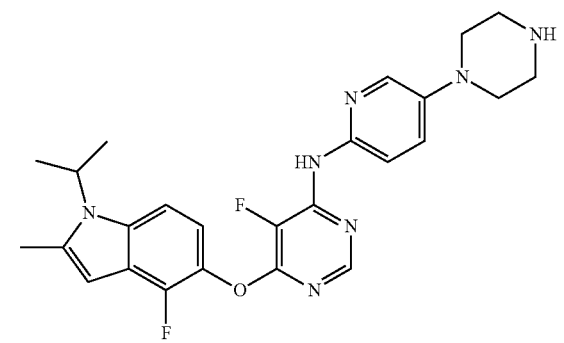
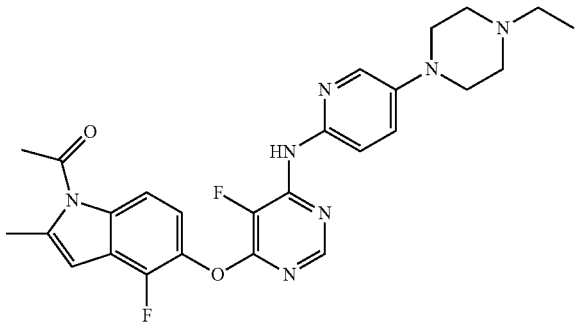
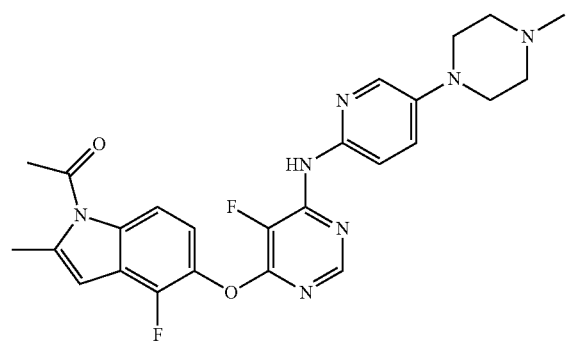
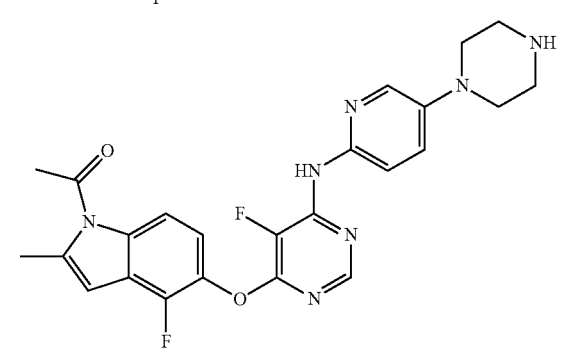
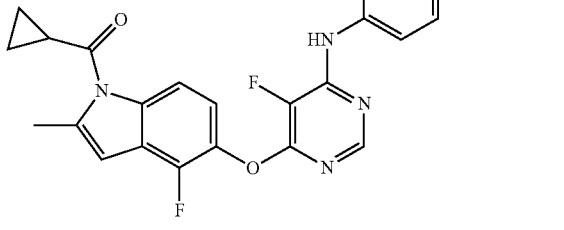
52
-continued
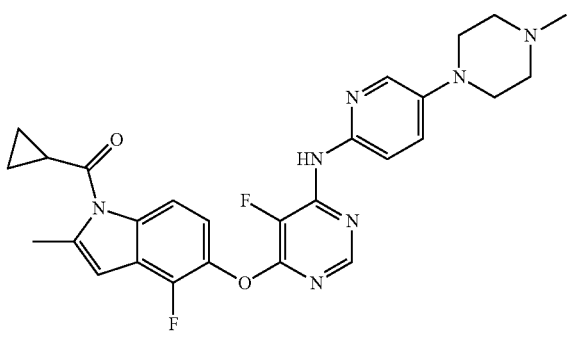
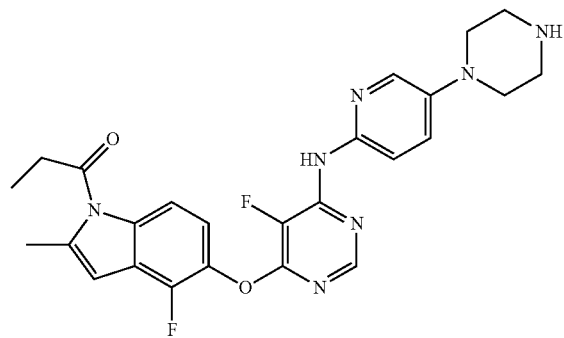 [SMILES: CCC(=O)n1c(C)cc2c(F)c(Oc3ncnc(Nc4ccc(N5CCNCC5)cn4)c3C#N)cc(F)c21]
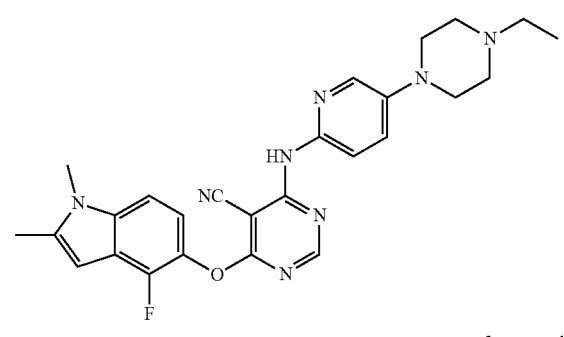
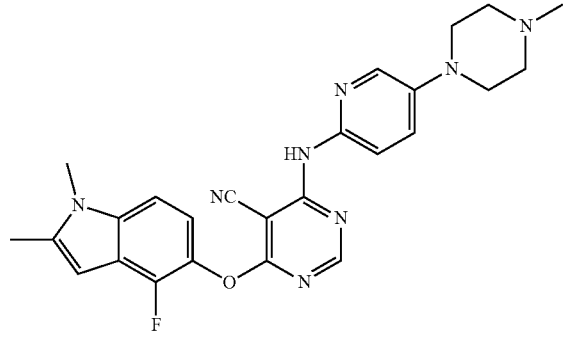
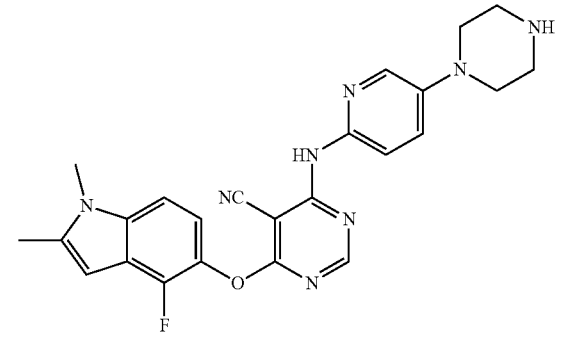

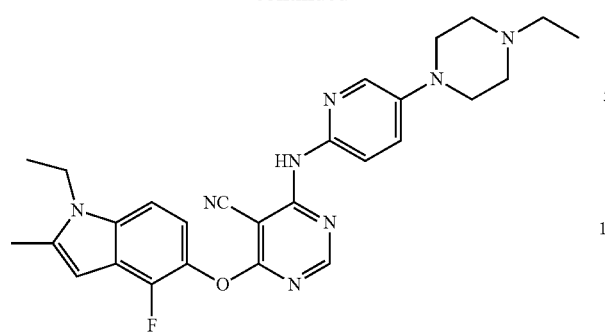
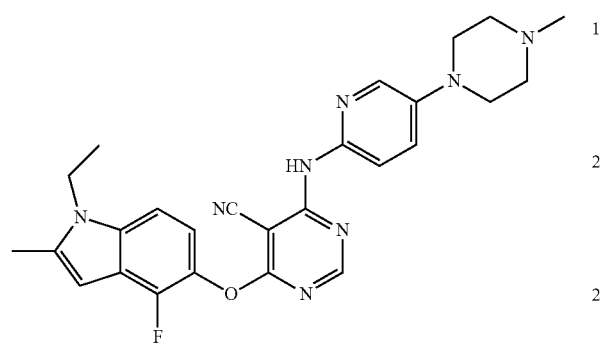
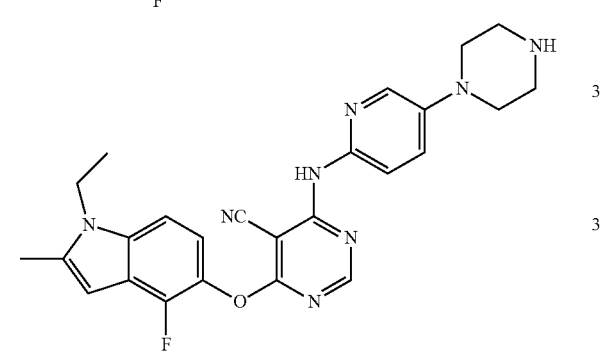
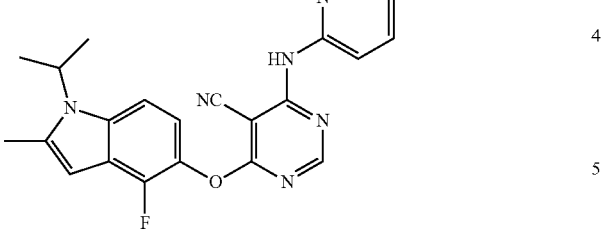
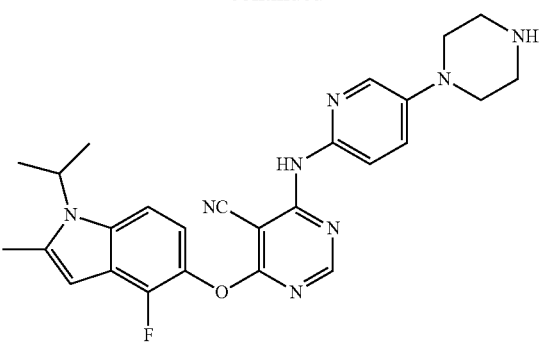
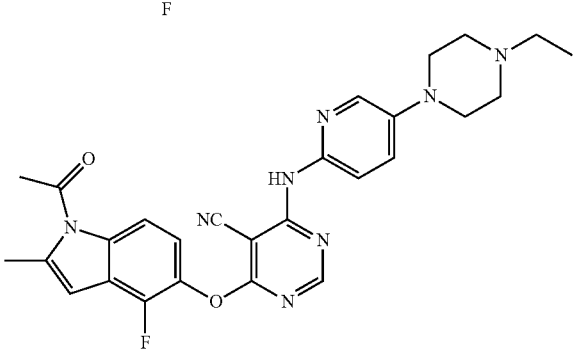
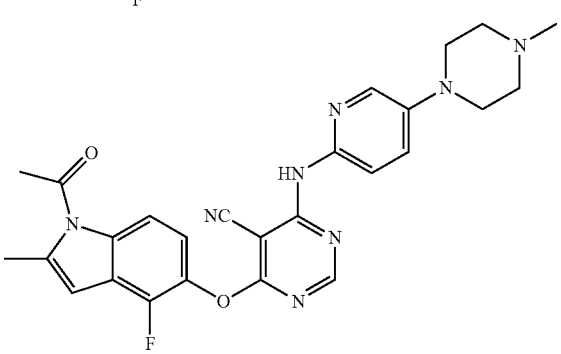
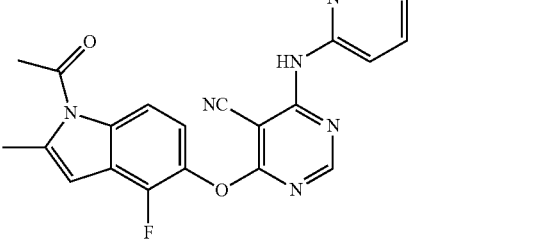

55
-continued
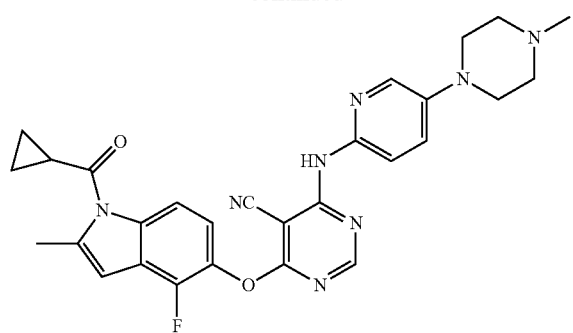
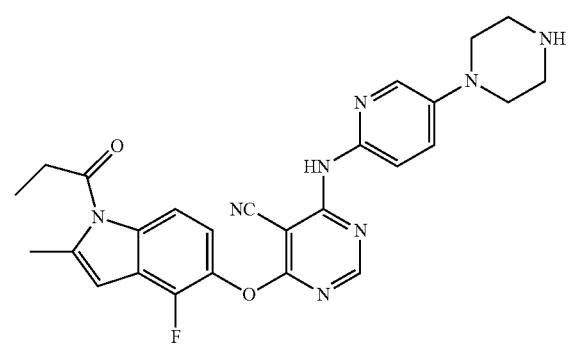
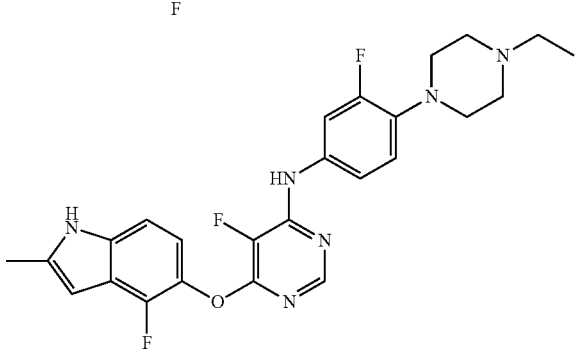
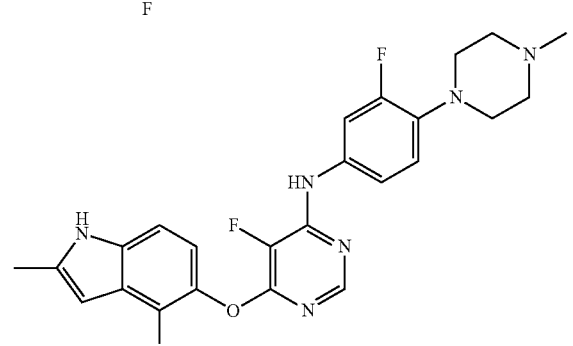
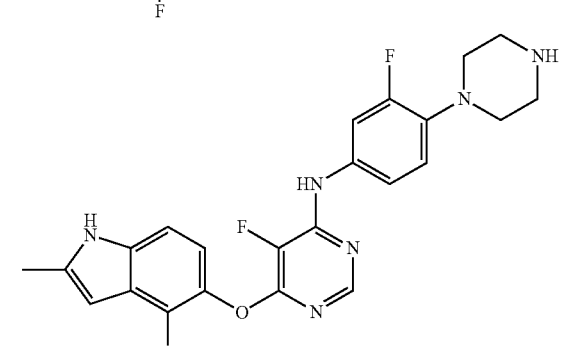
56
-continued
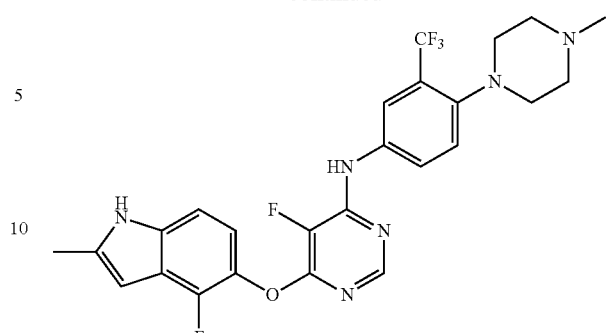
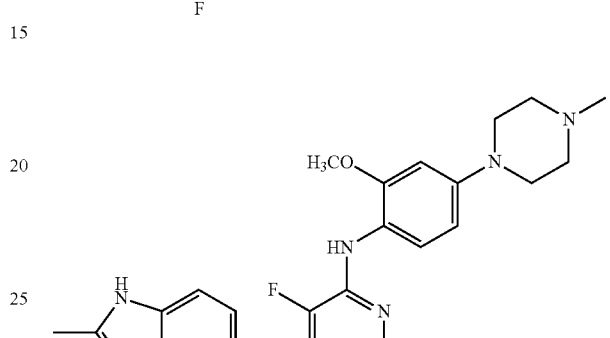
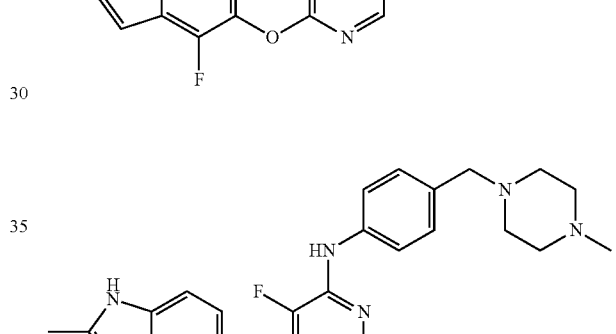
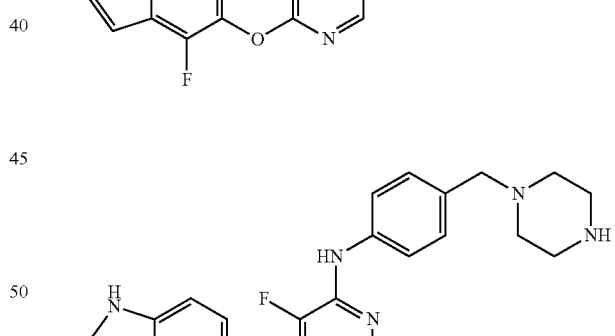
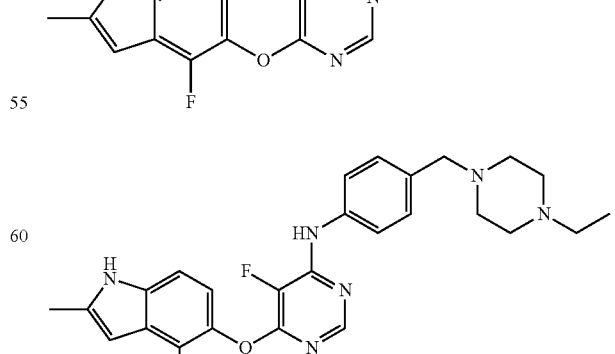

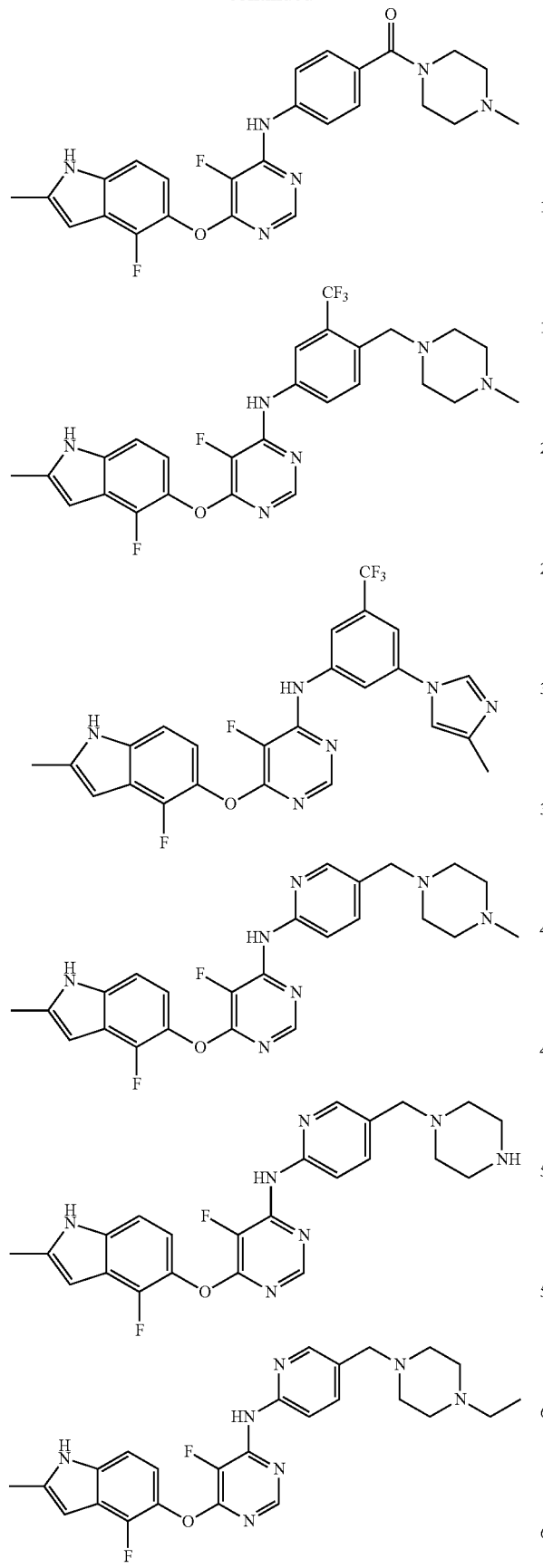
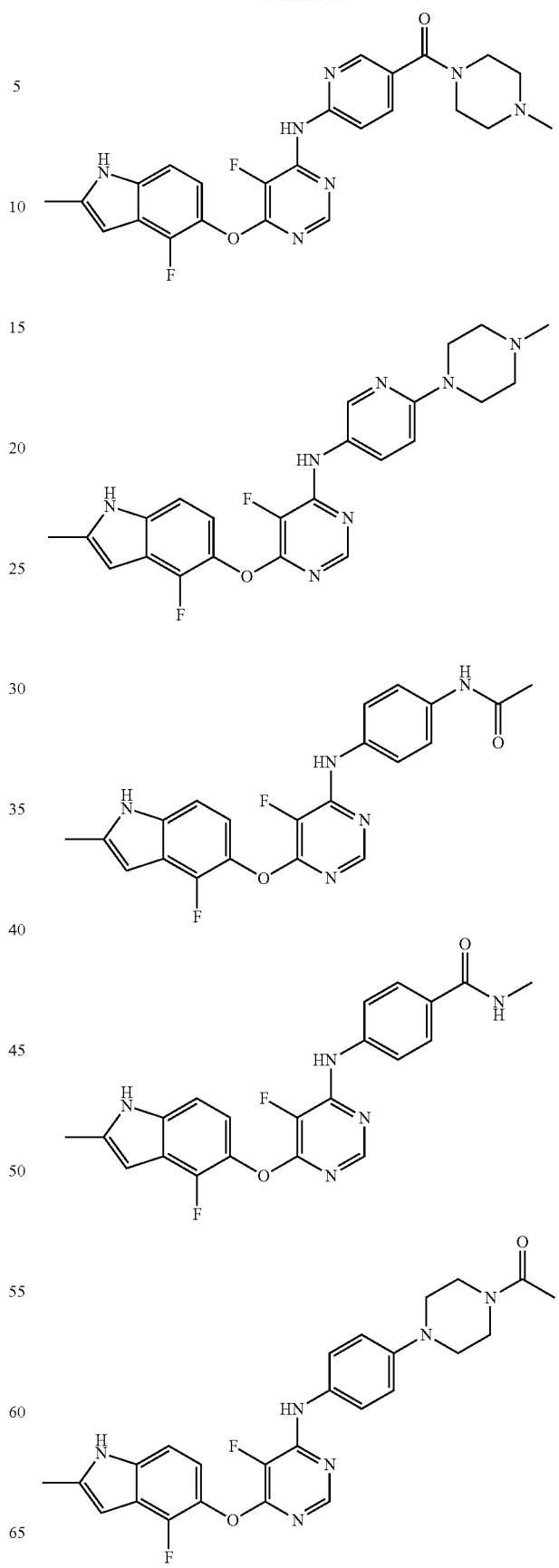

-continued
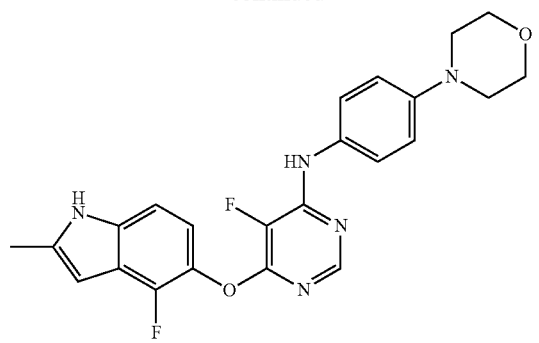
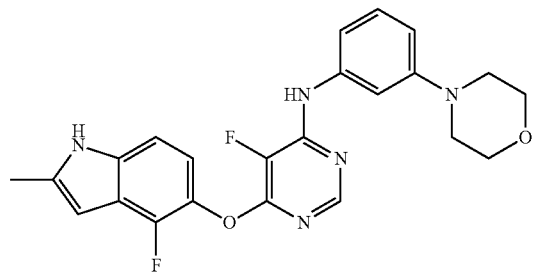
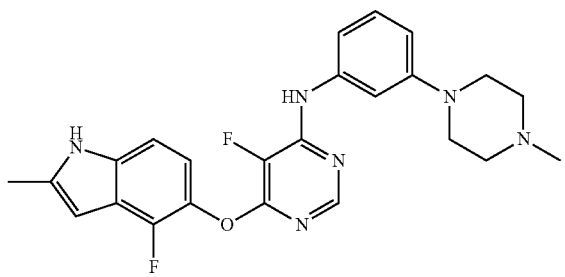
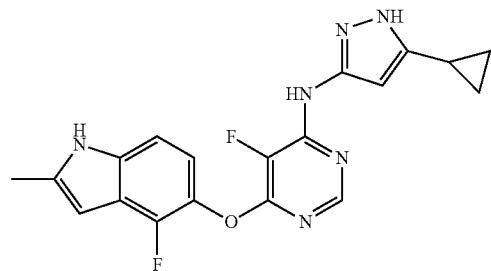
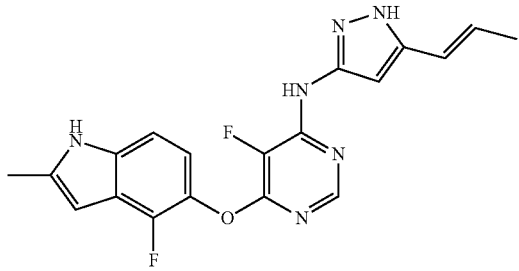
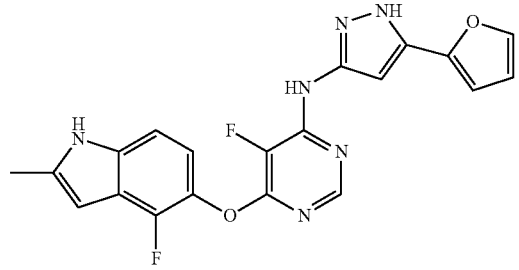
-continued
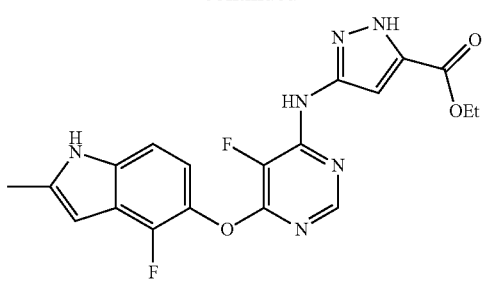
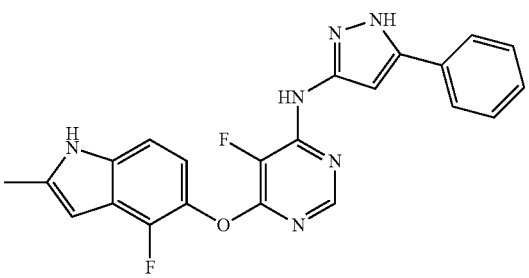
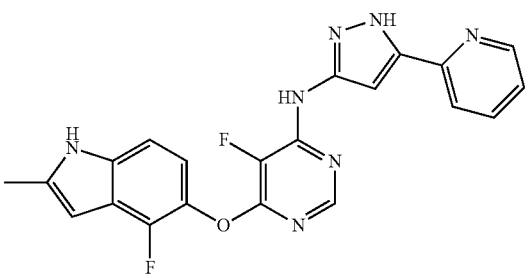
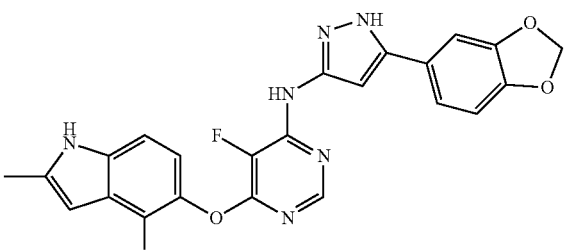
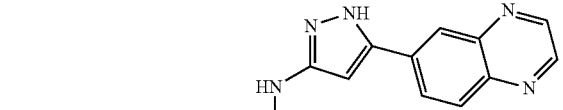
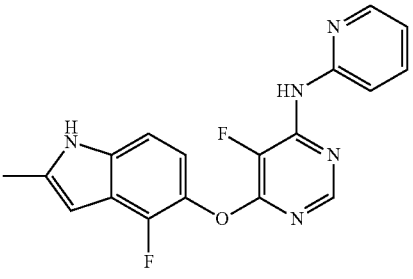

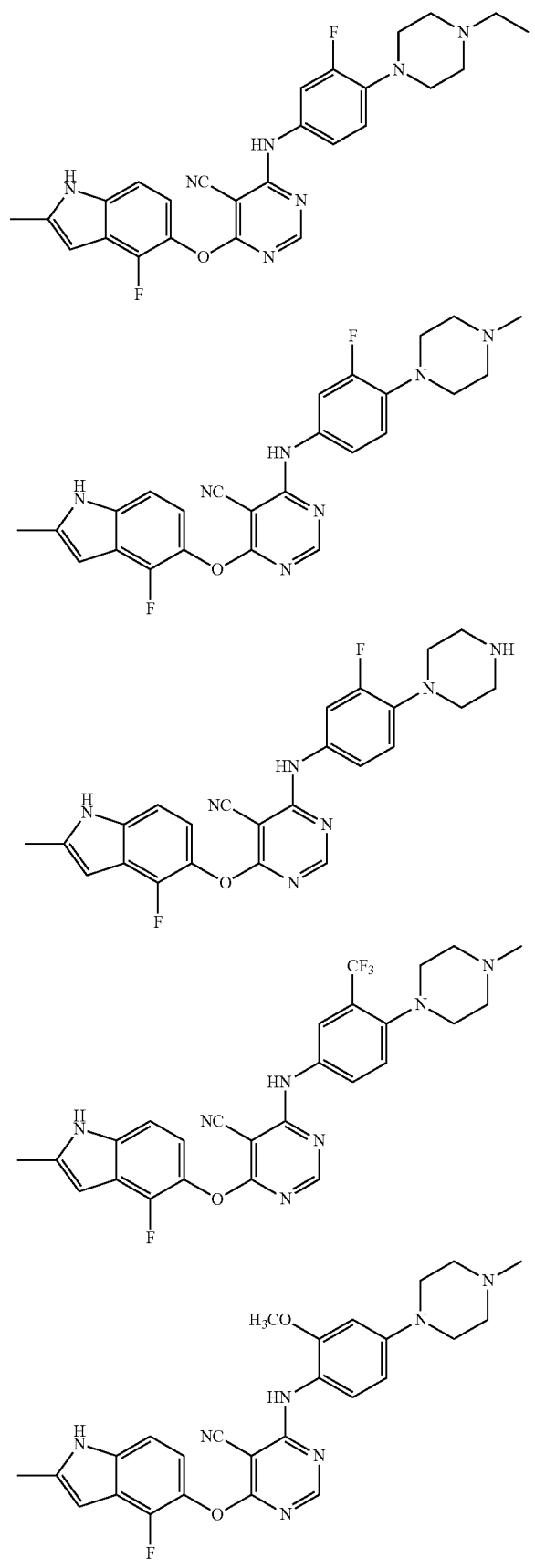
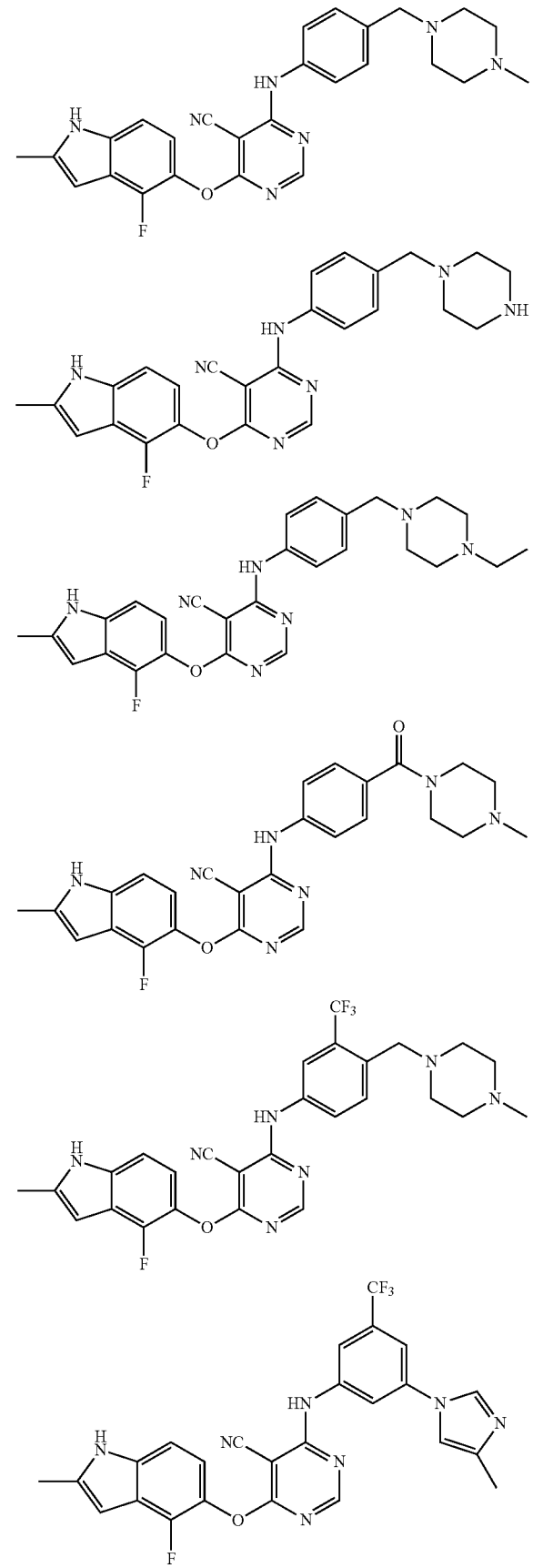

63
-continued
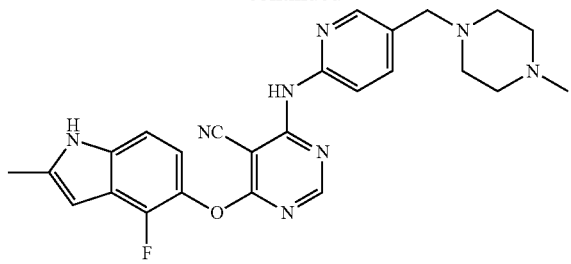
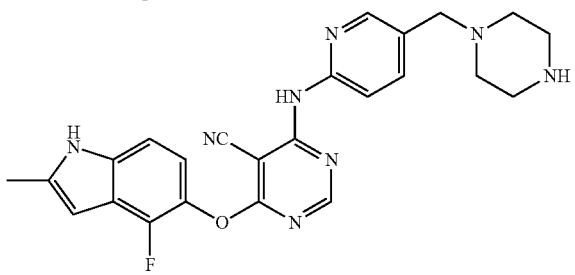
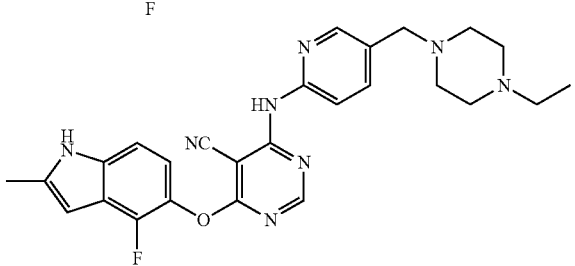
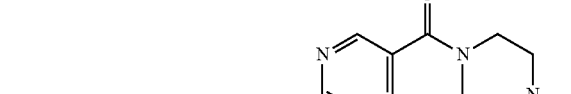
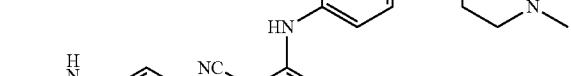
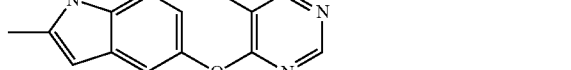
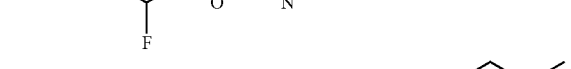

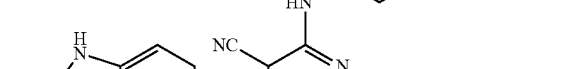

64
-continued
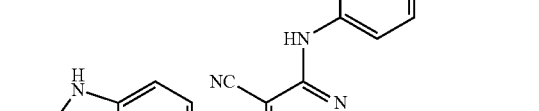
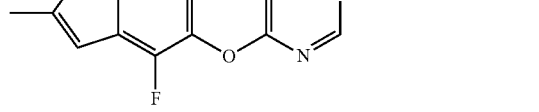
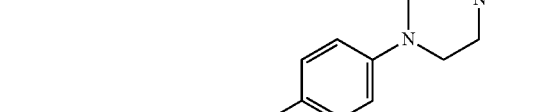
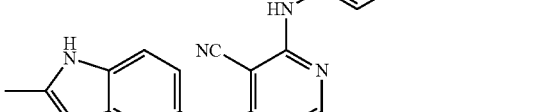
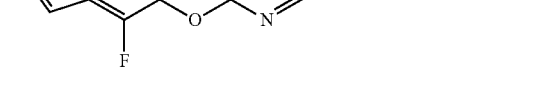
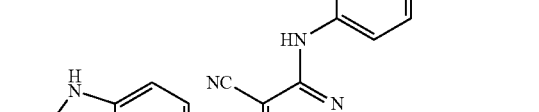
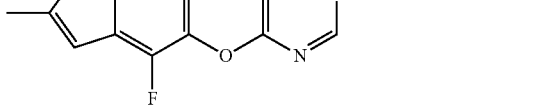
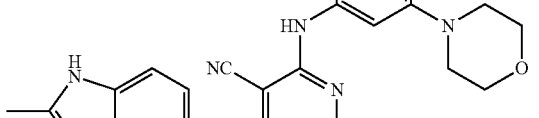
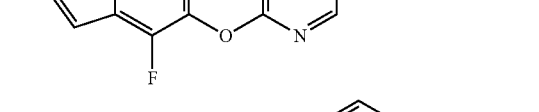

-continued
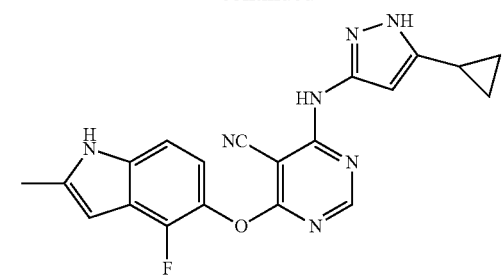
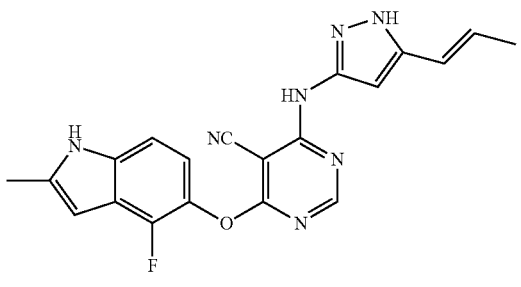
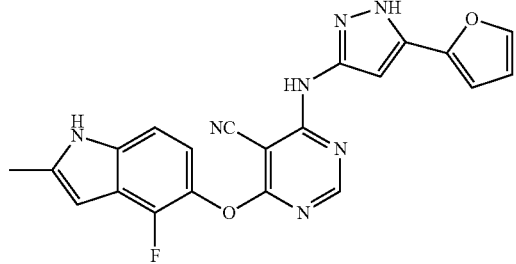
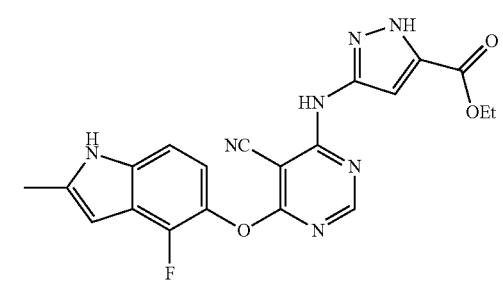
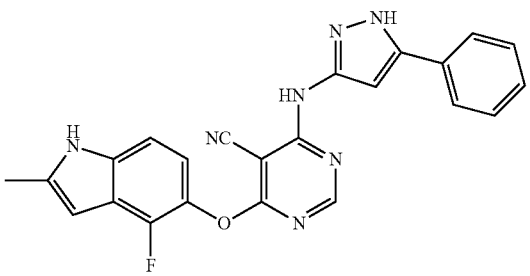
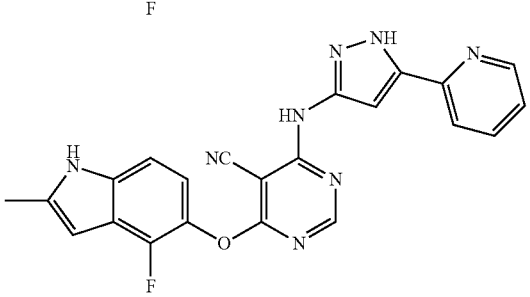
-continued
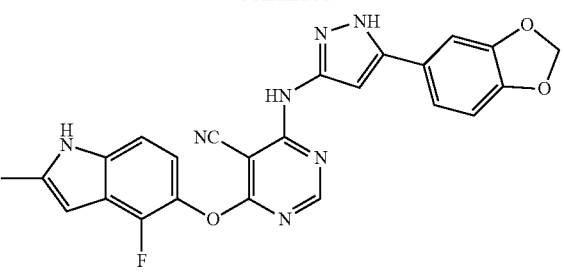
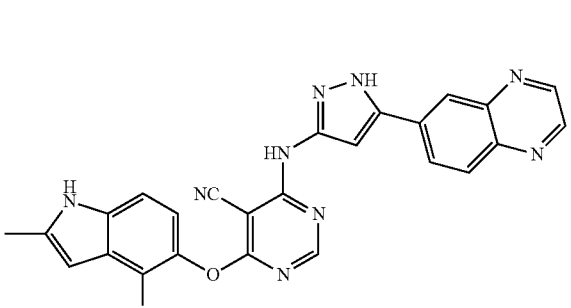
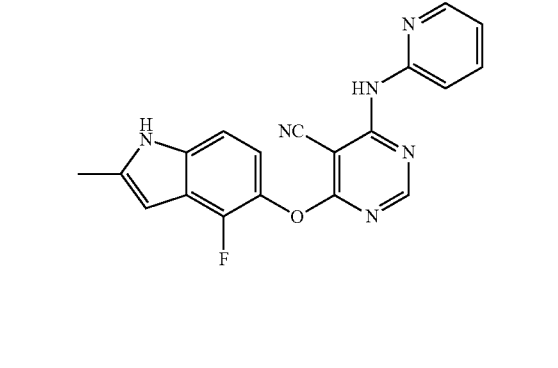
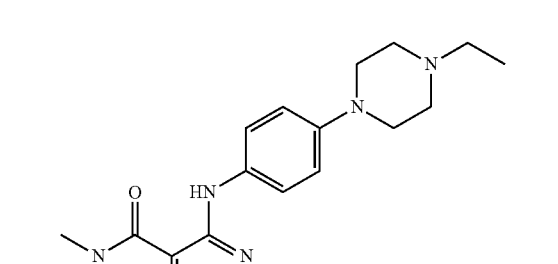
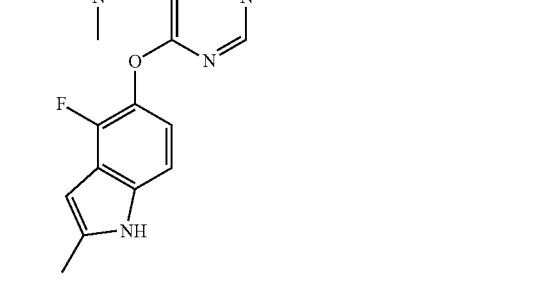

67
-continued
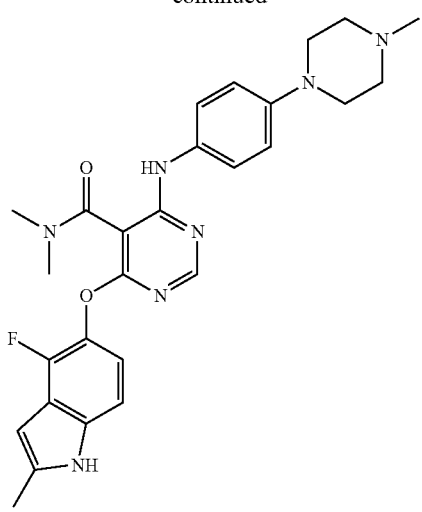
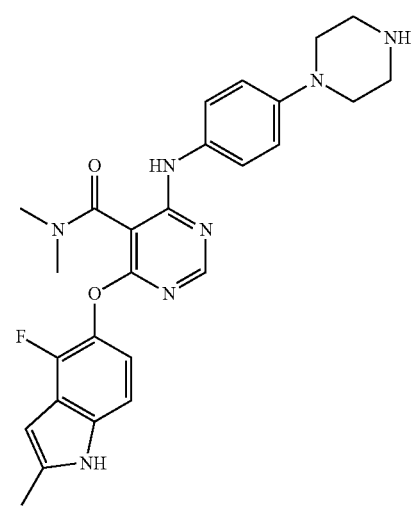
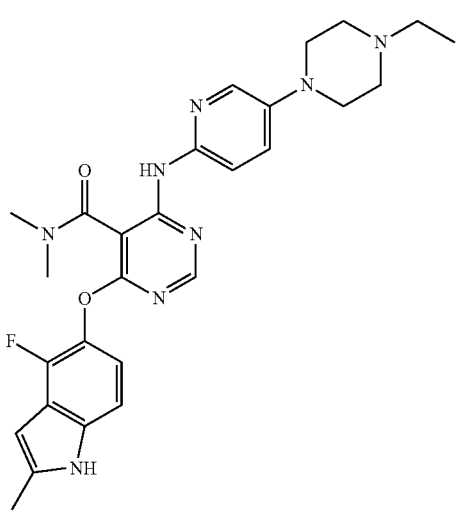
68
-continued
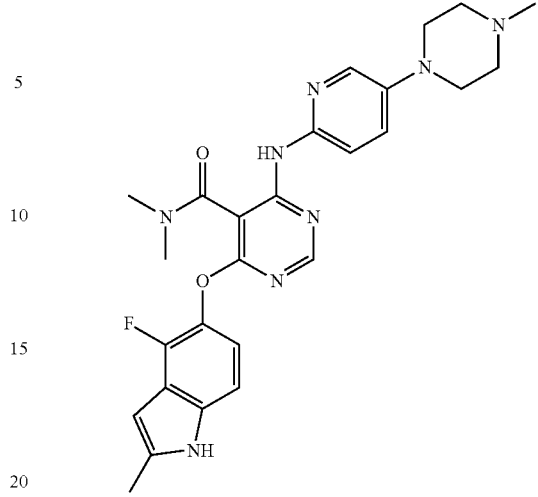
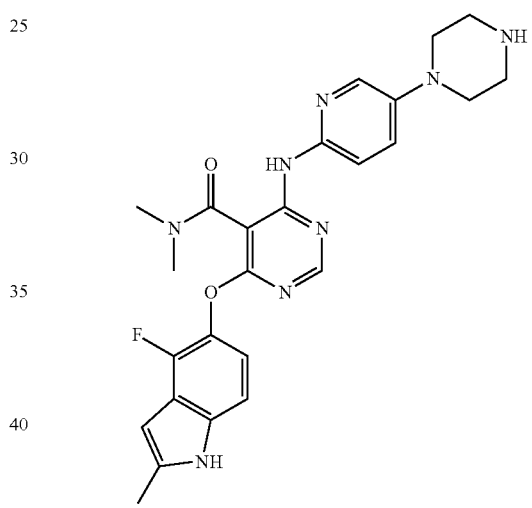
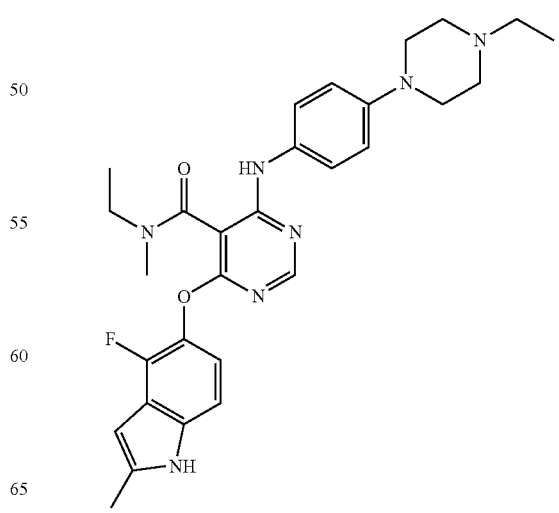

69
-continued
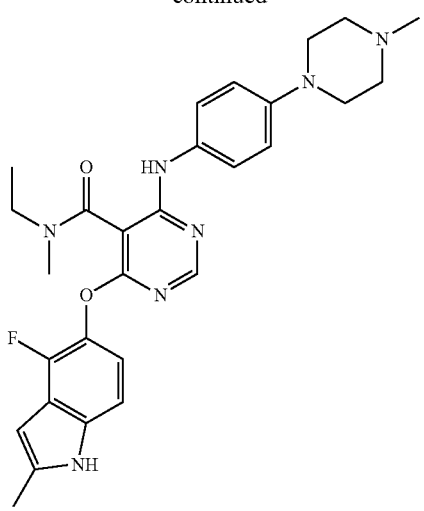
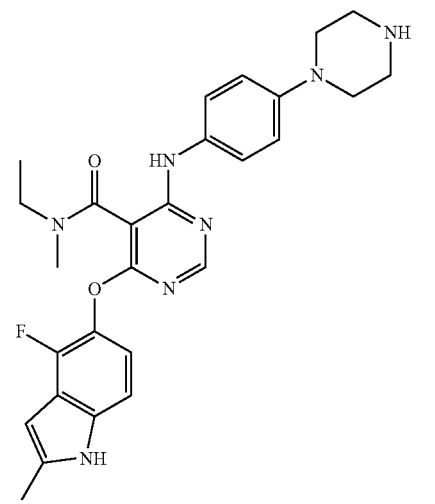
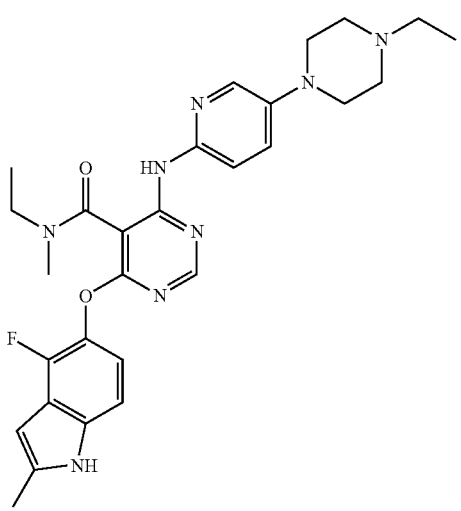
70
-continued
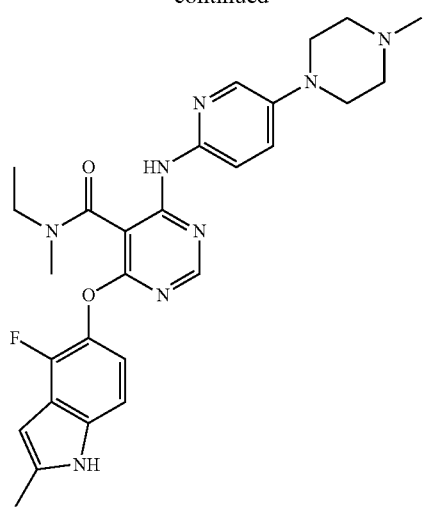
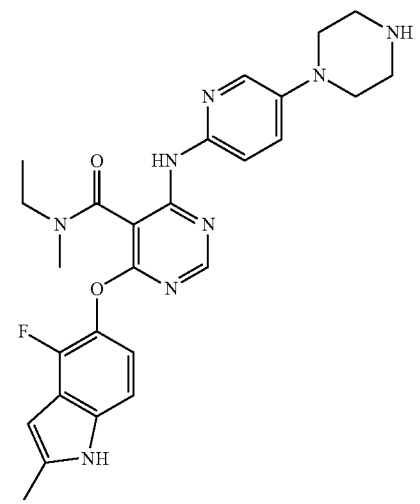
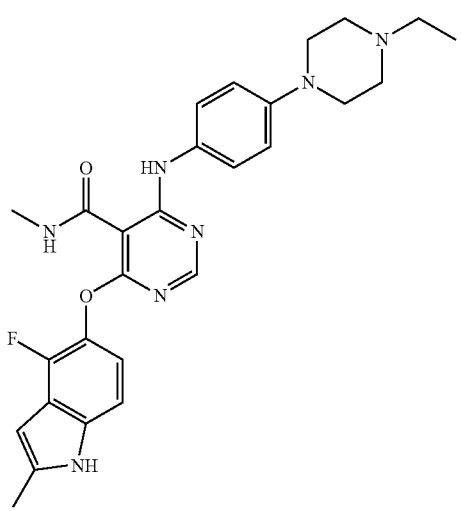

-continued
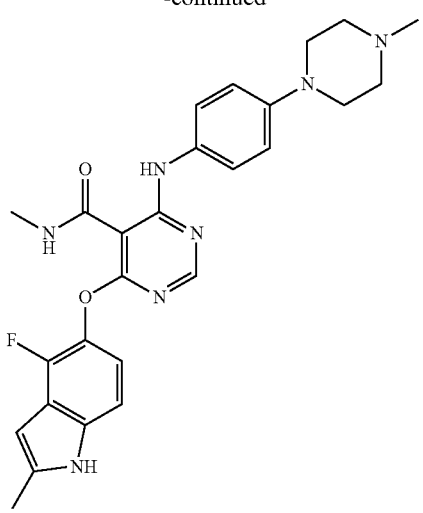
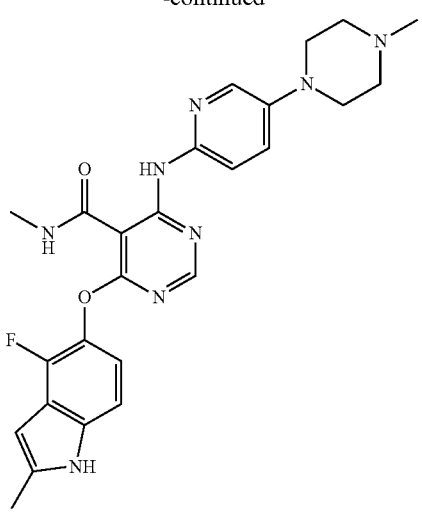
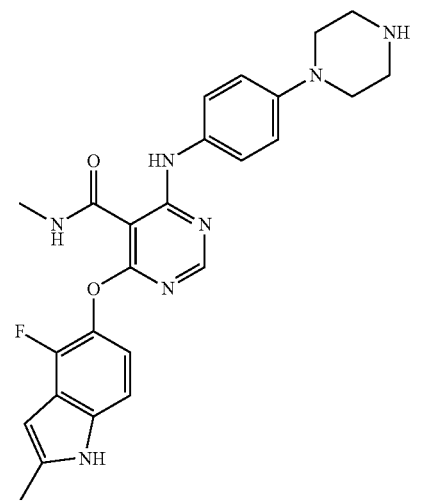
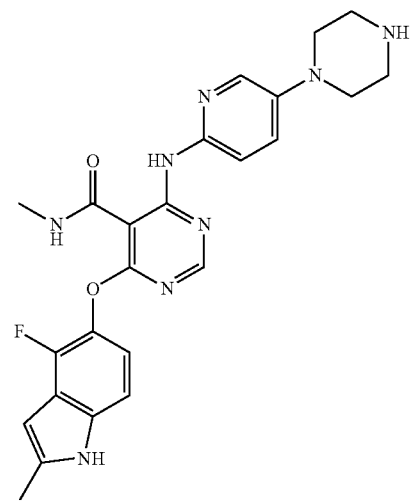
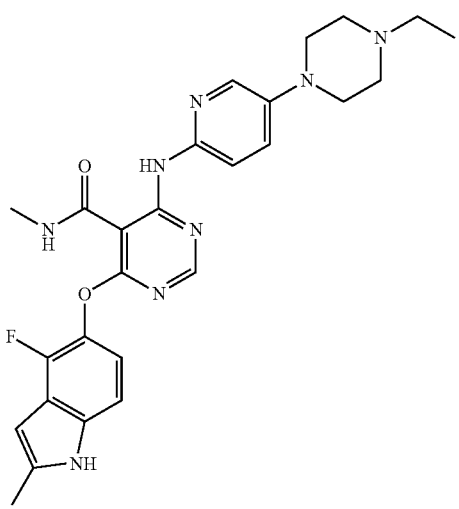
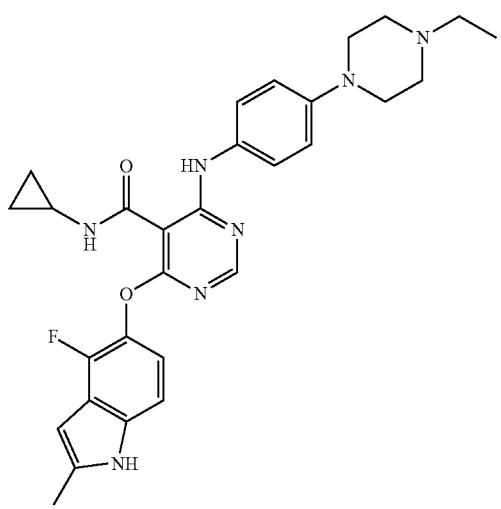

-continued
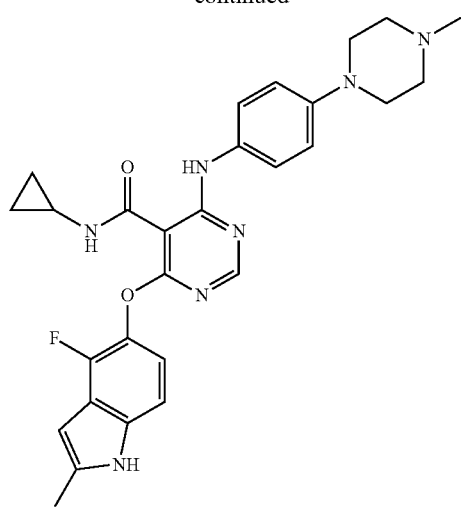
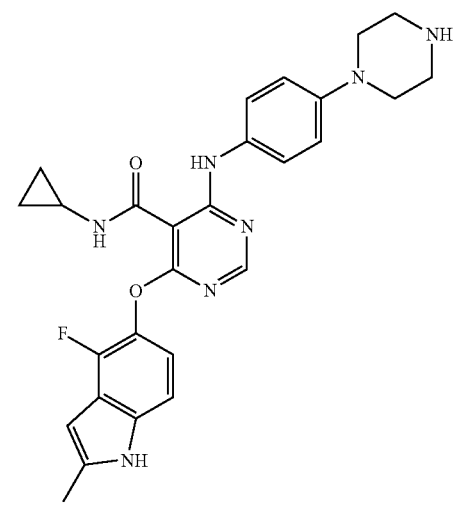
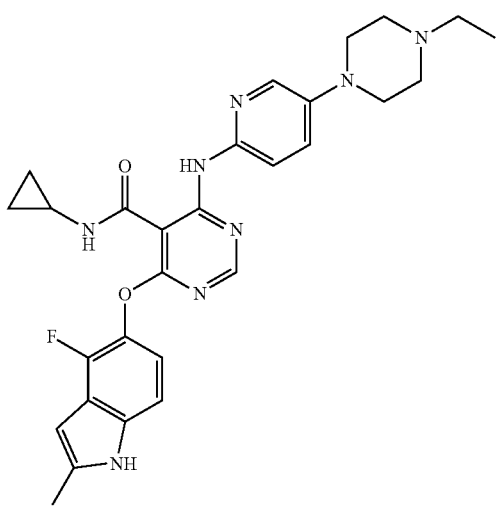
-continued
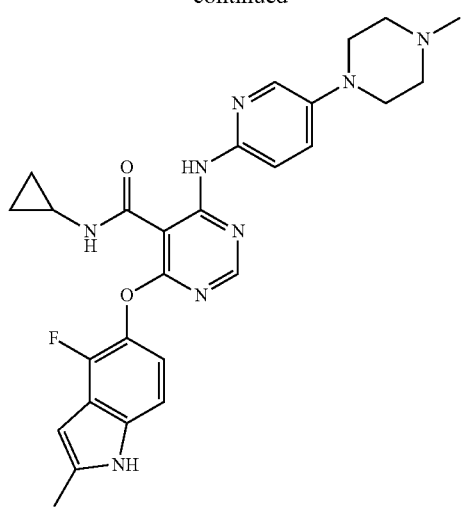
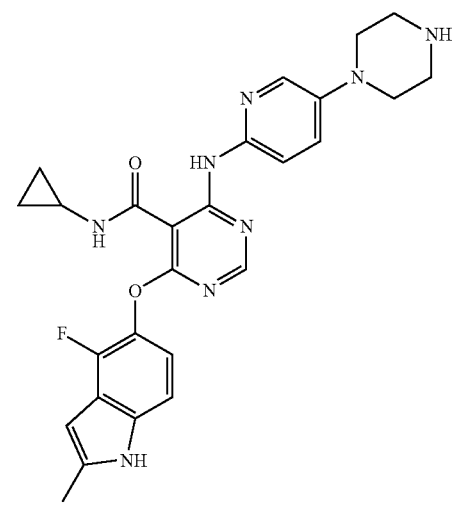
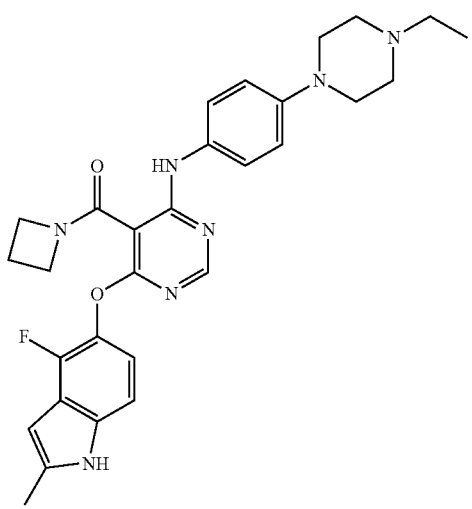

75
-continued
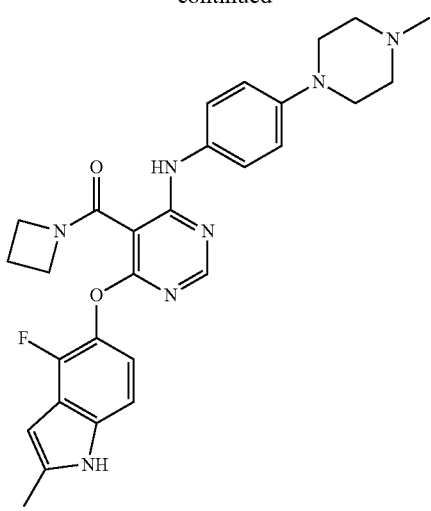
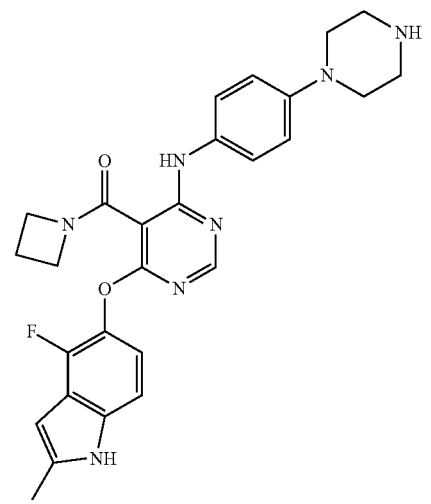
76
-continued
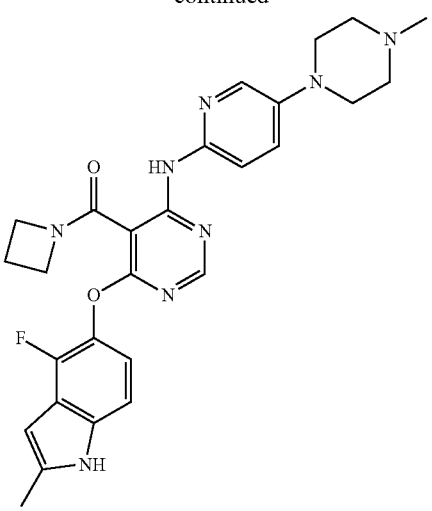
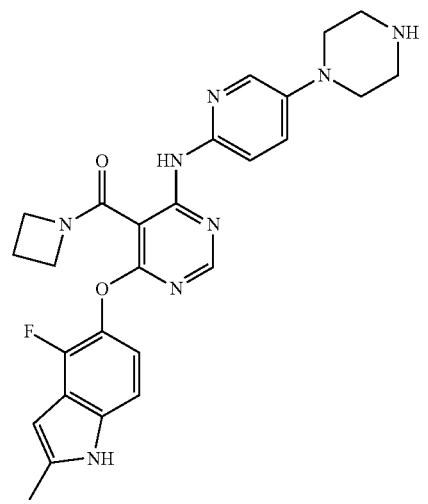

77
-continued
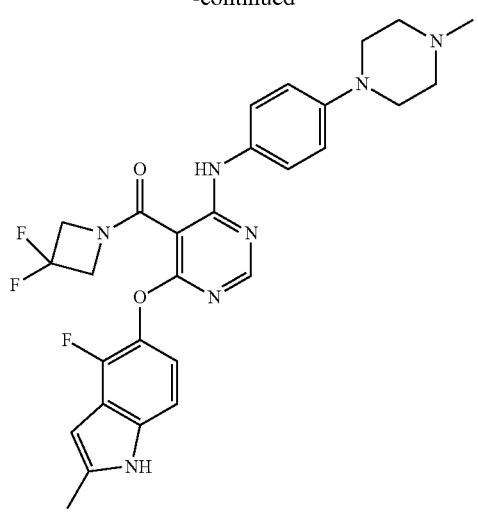
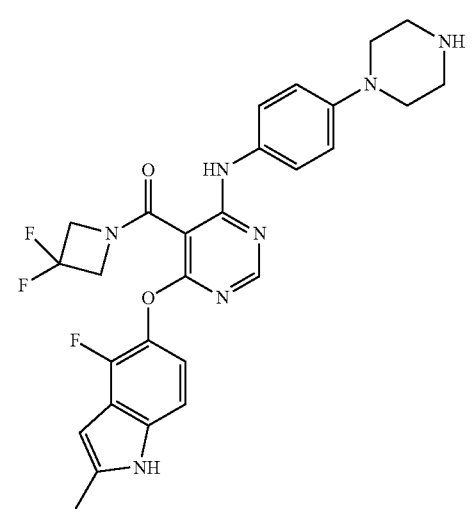
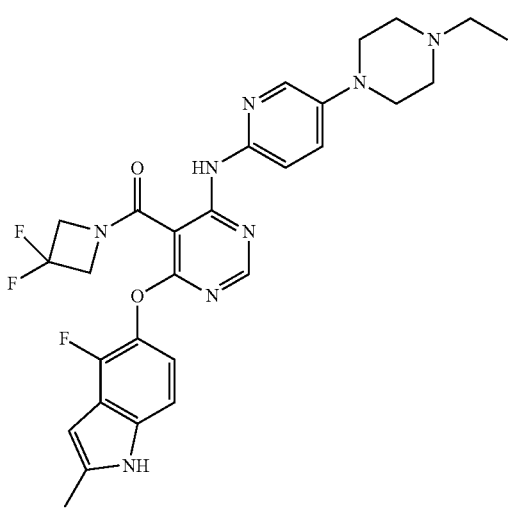
78
-continued
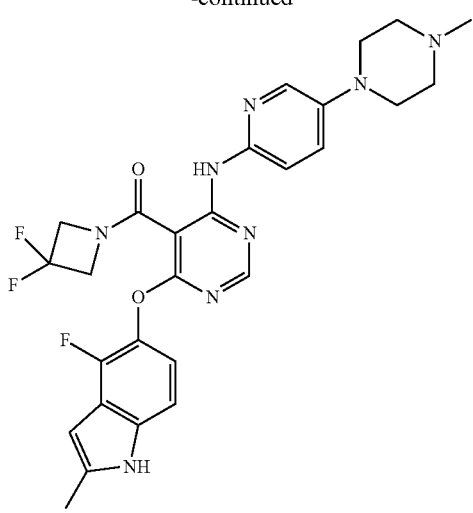
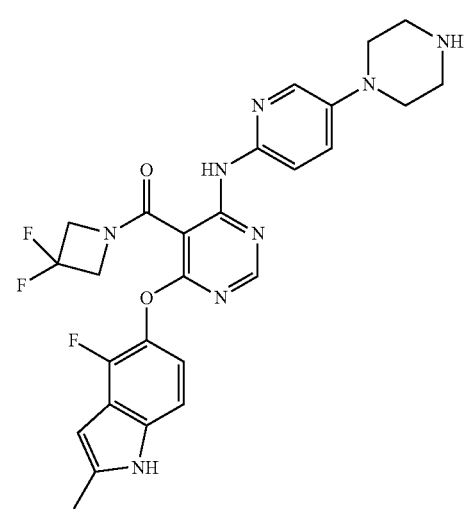

79
-continued
80
-continued
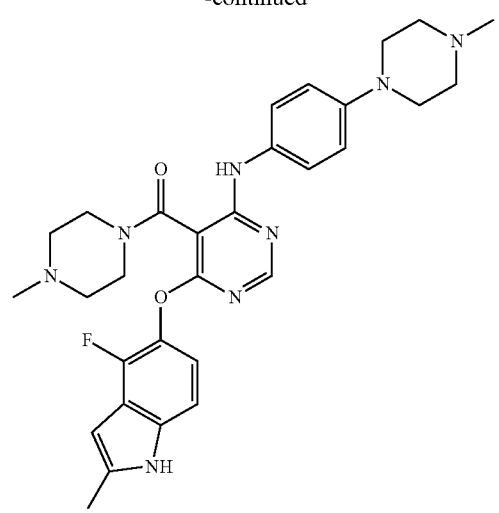
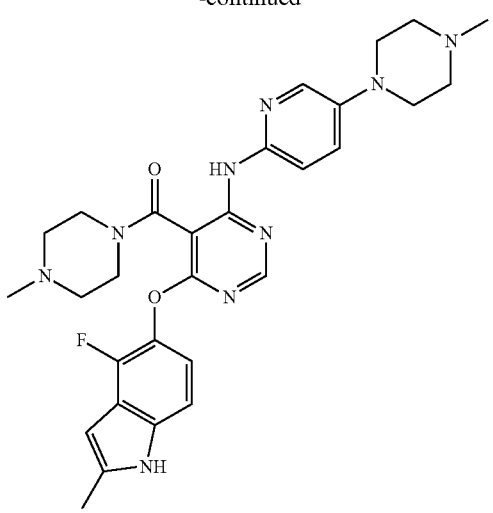
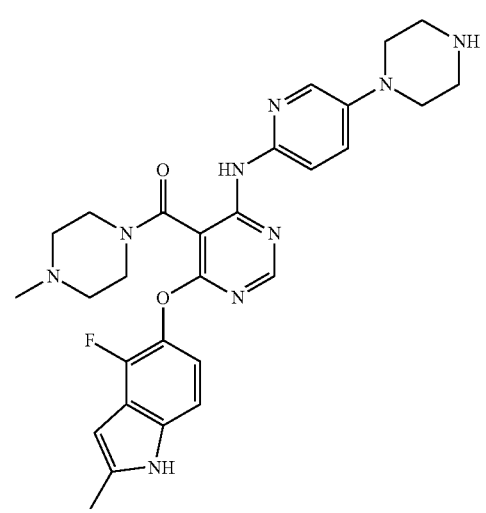
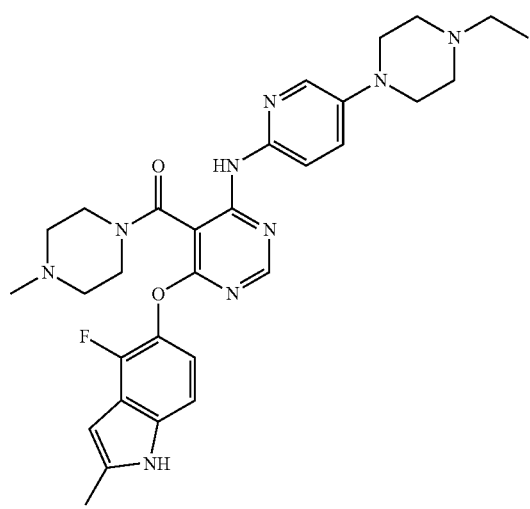

-continued
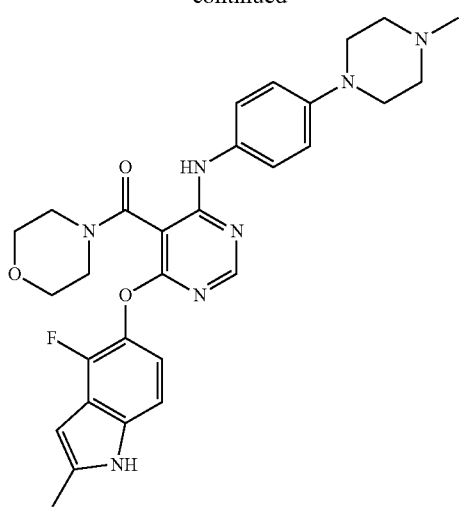
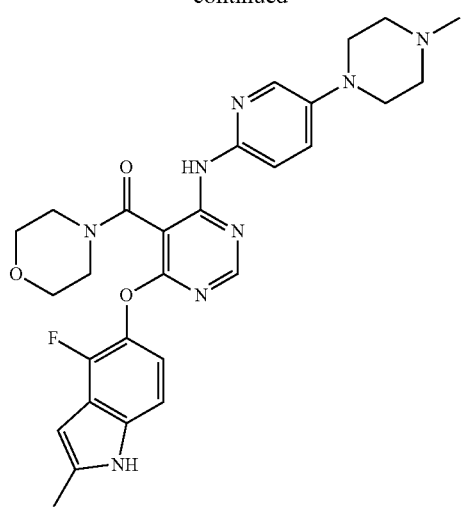
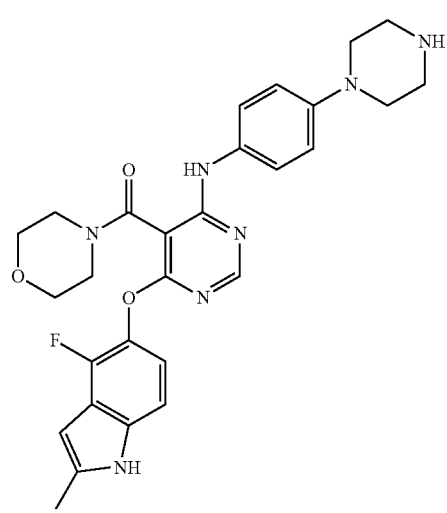
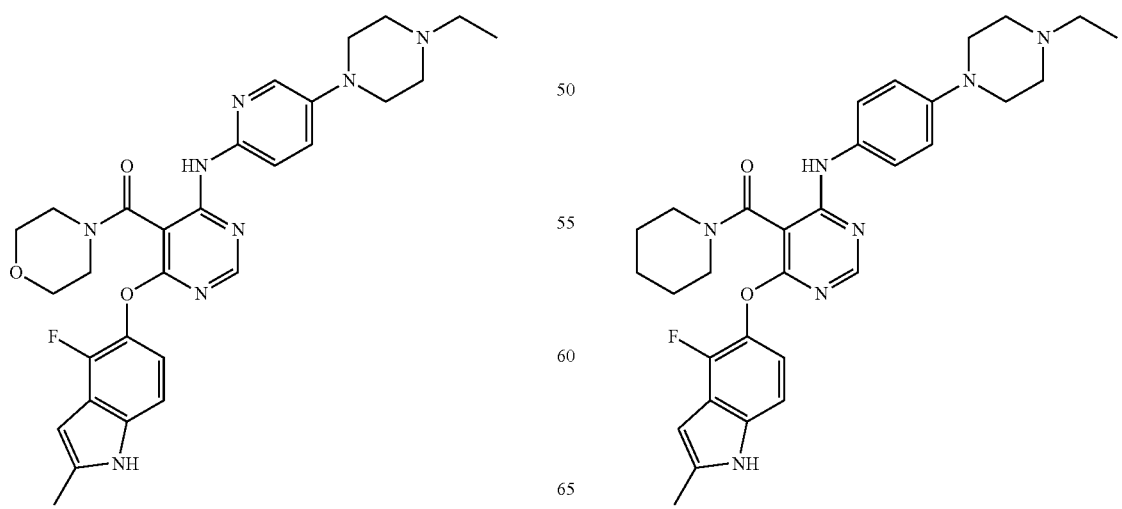

83
-continued
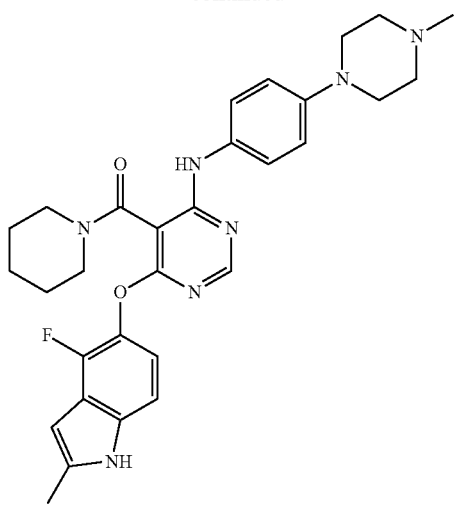
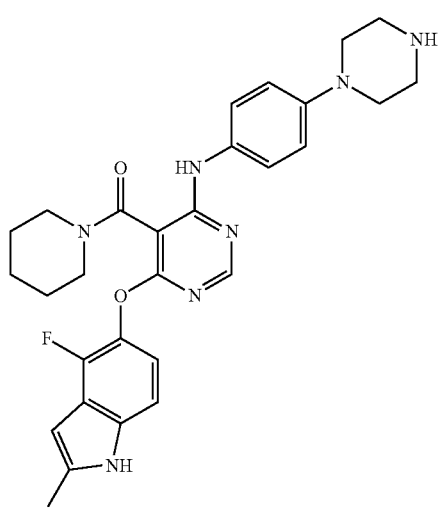
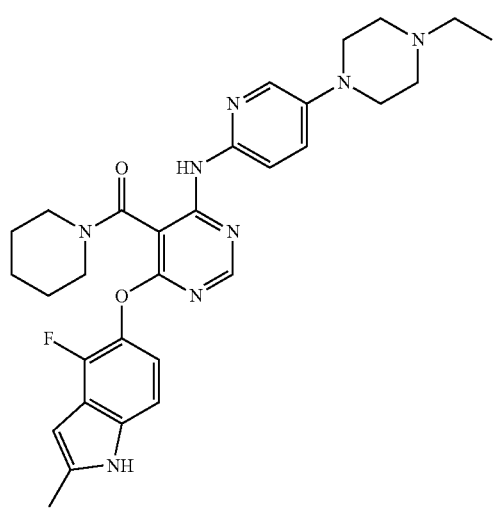
84
-continued
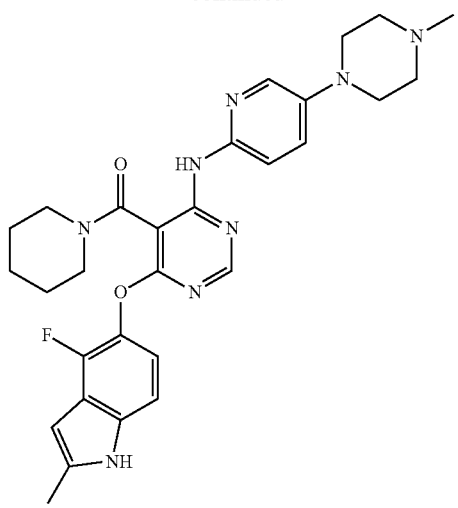
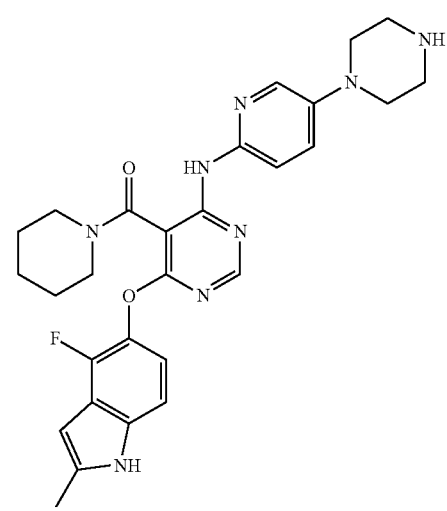
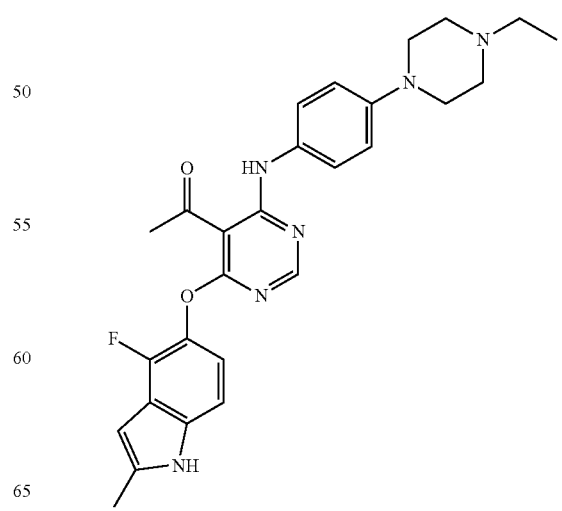

85
-continued
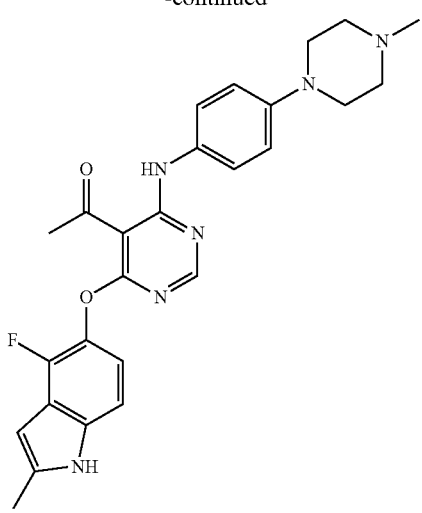
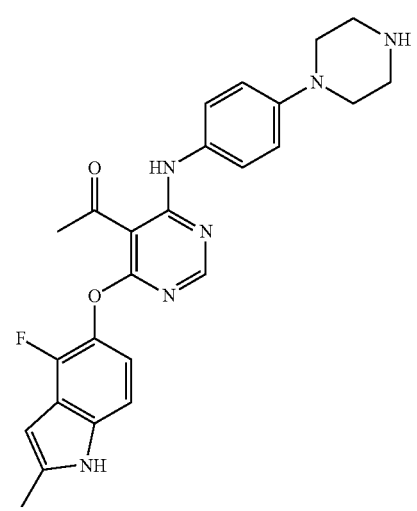
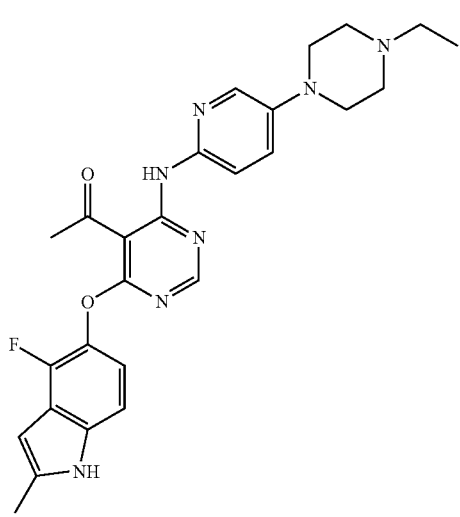
86
-continued
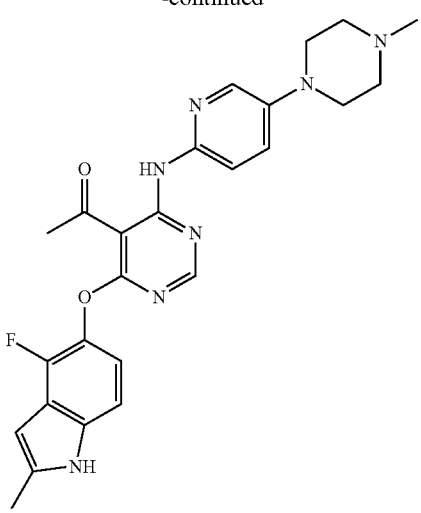
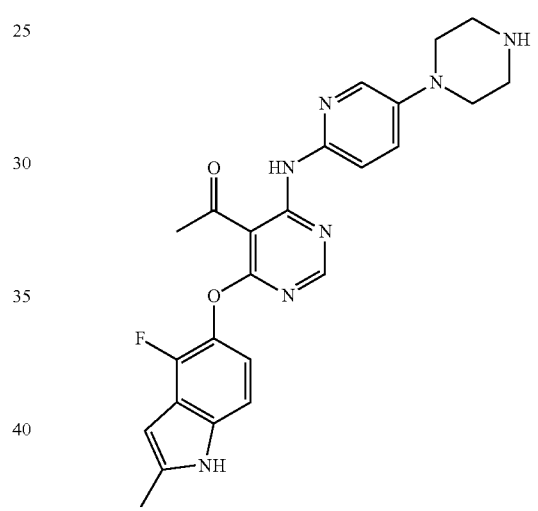
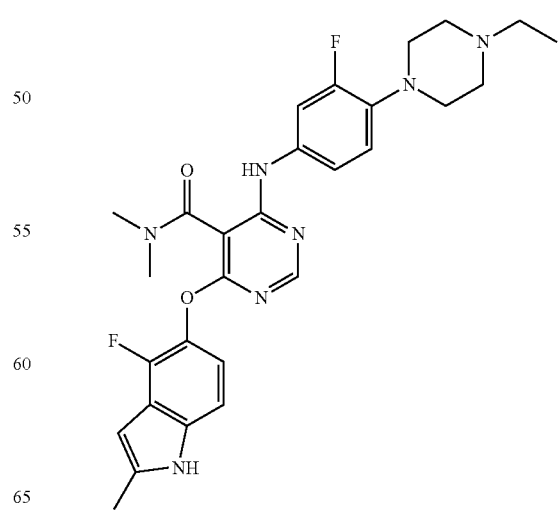

87
-continued
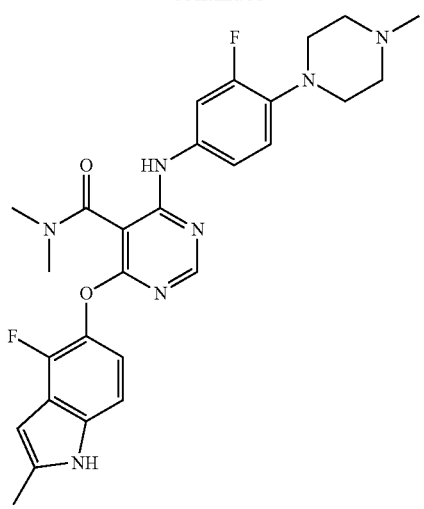
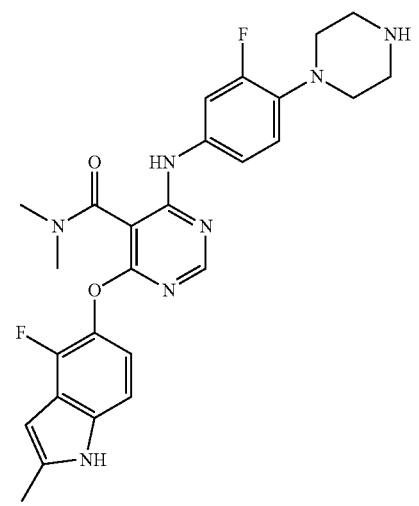
88
-continued
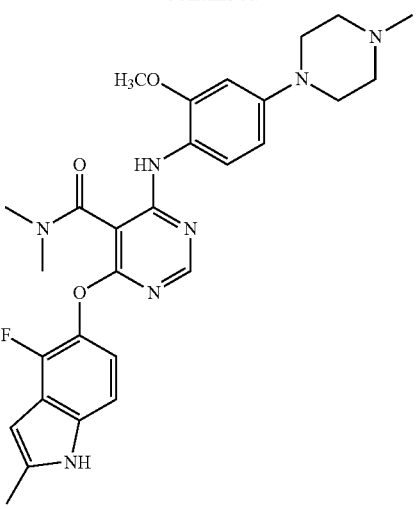
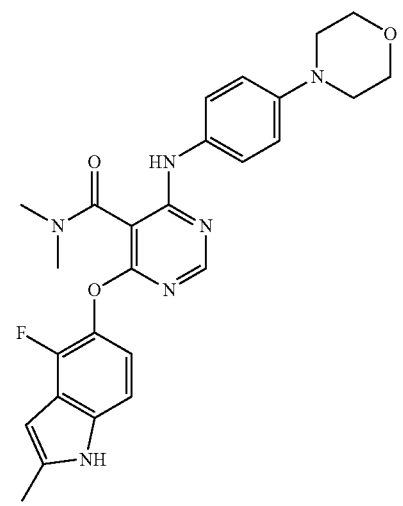

-continued
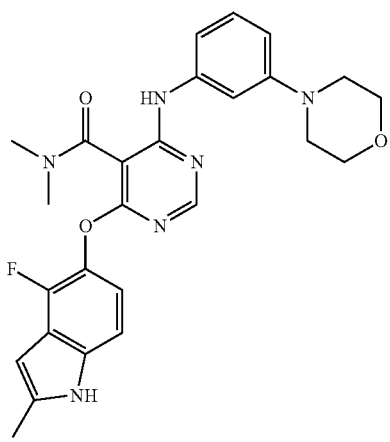
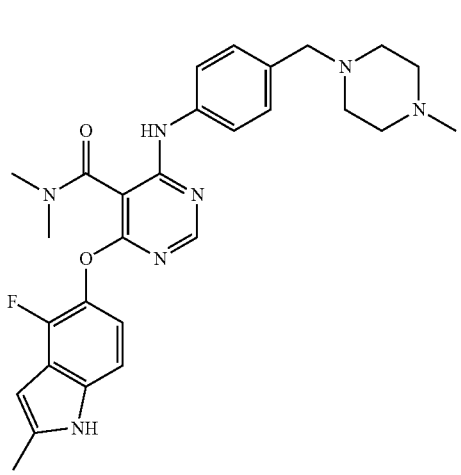
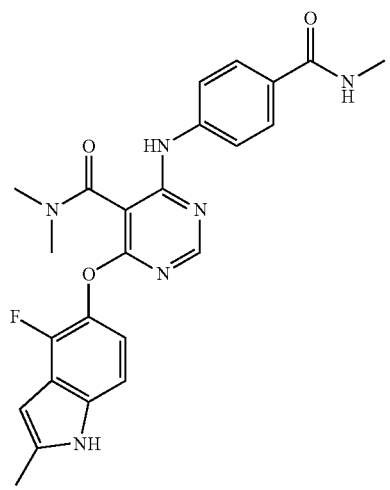
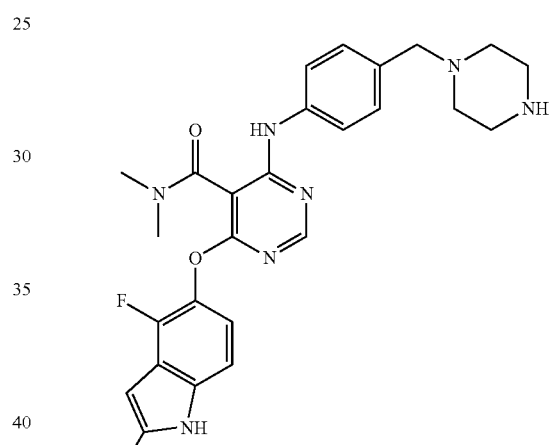
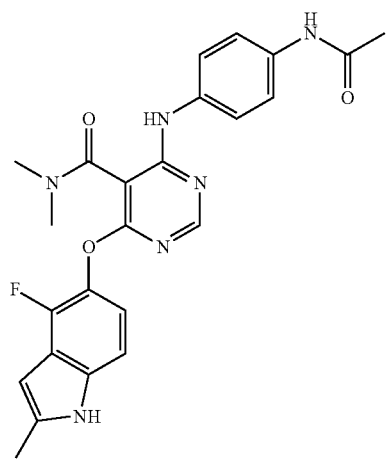
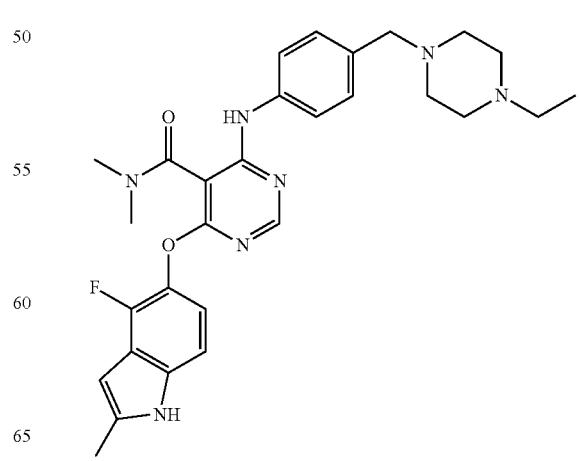

-continued
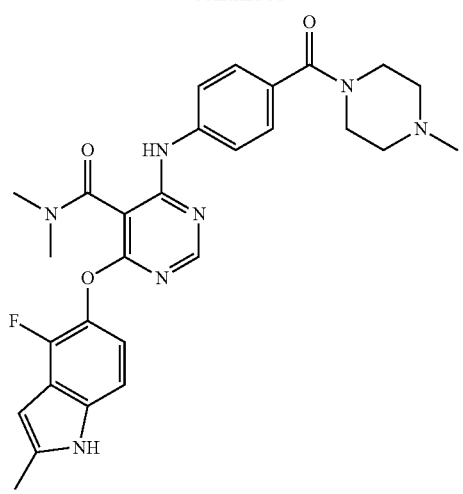
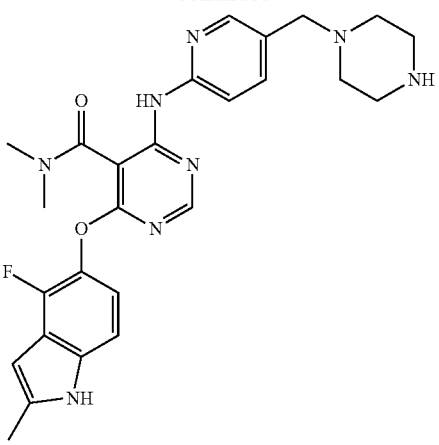
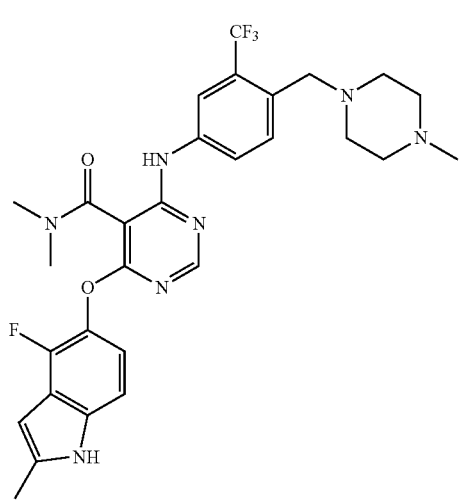
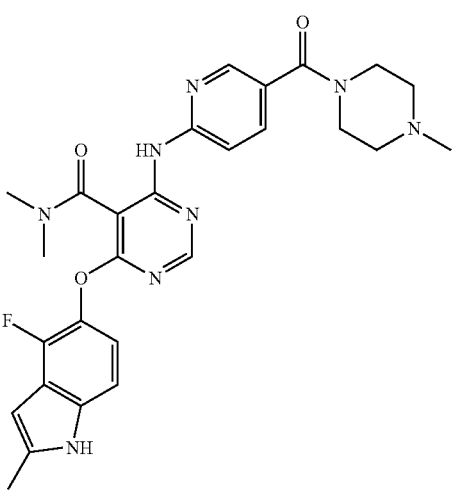

93
-continued
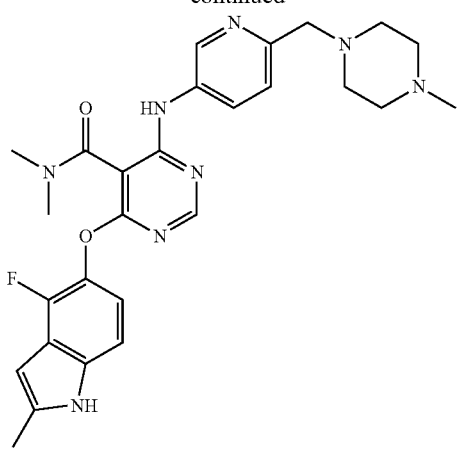
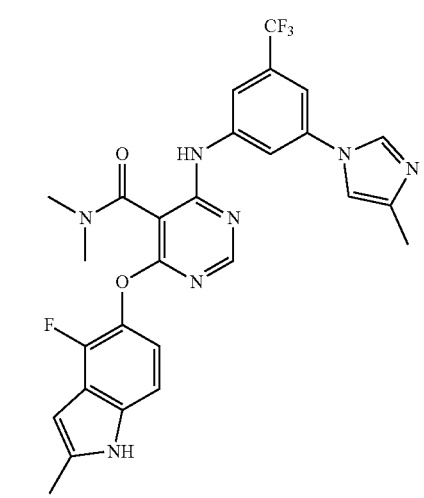
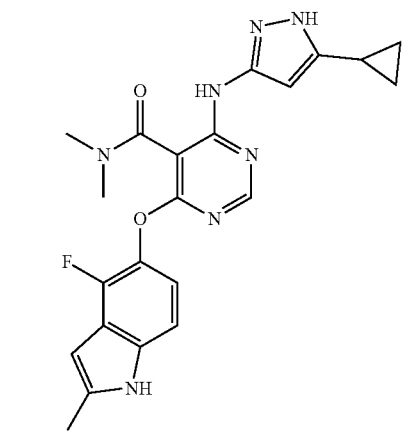
94
-continued
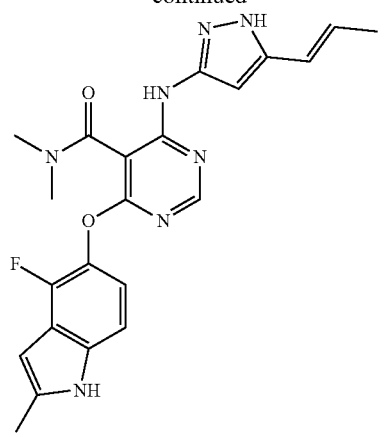
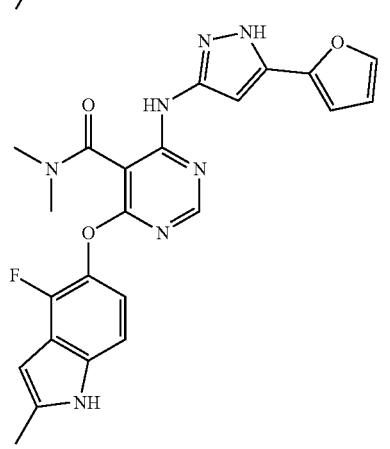
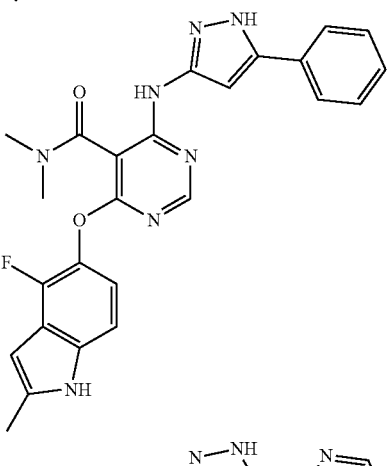
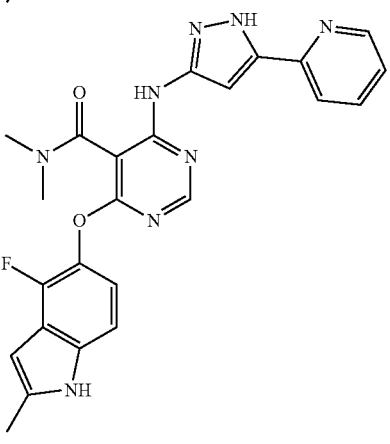

-continued
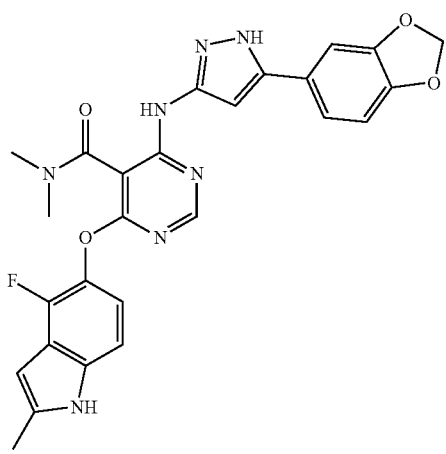
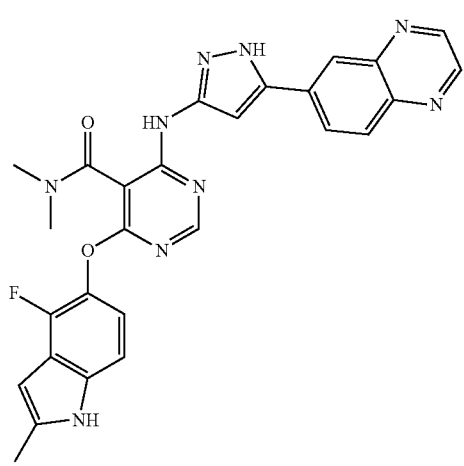
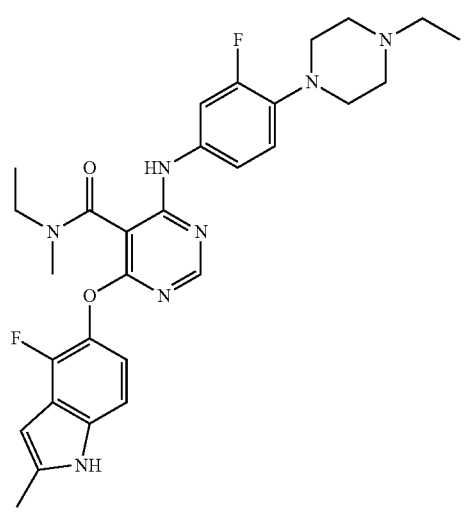
-continued
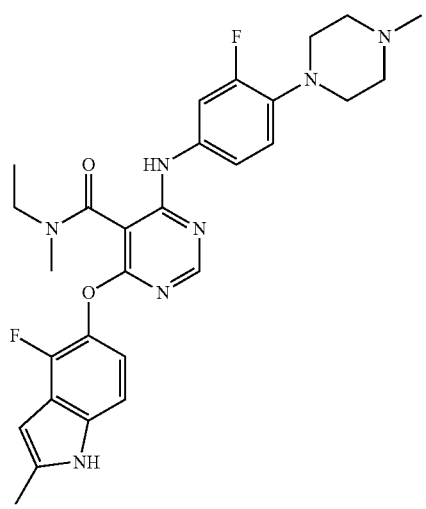
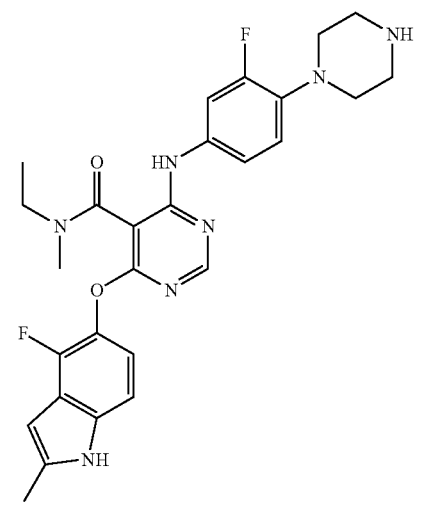

97
-continued
98
-continued
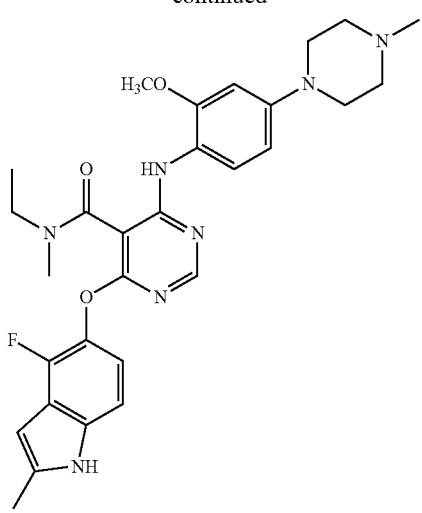
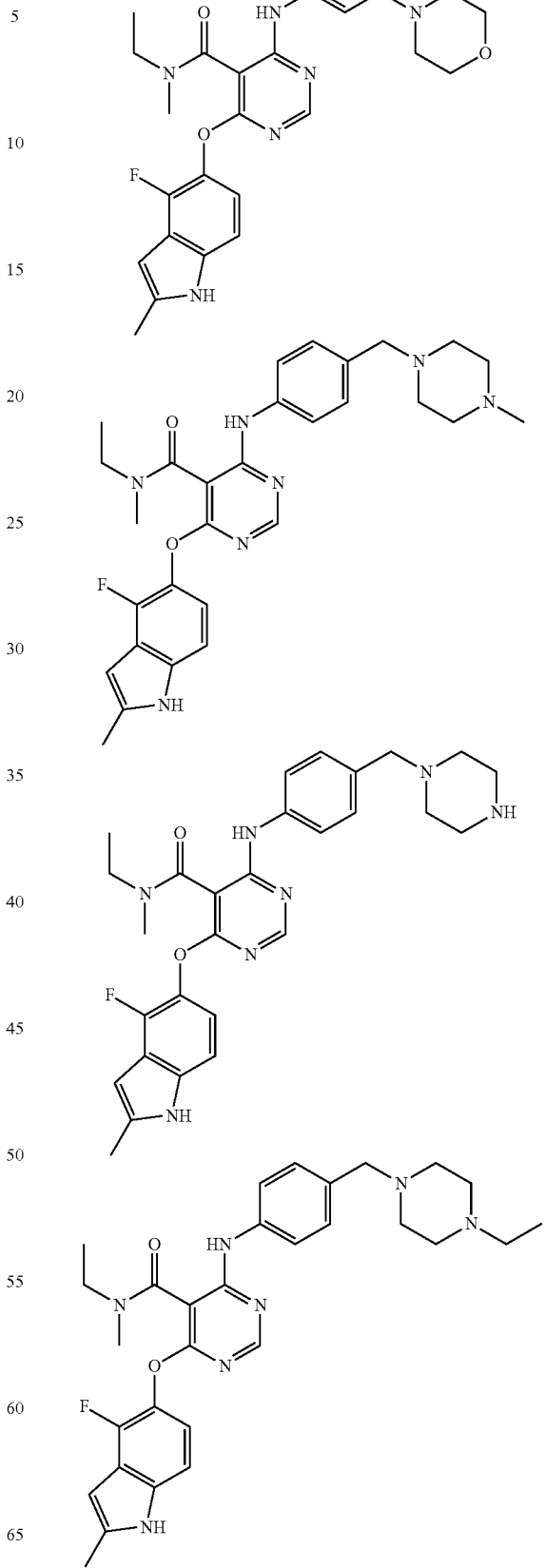

99
-continued
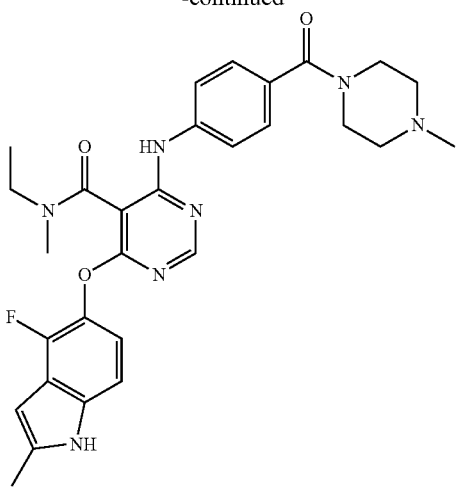
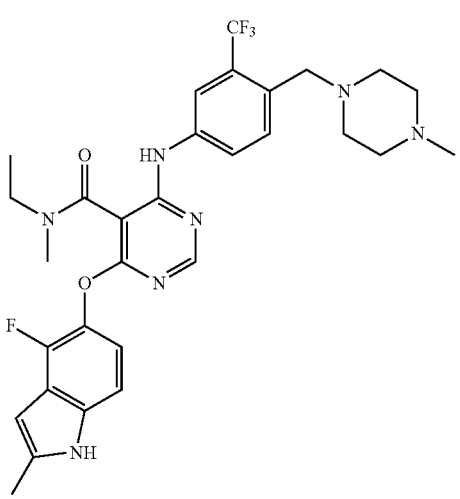
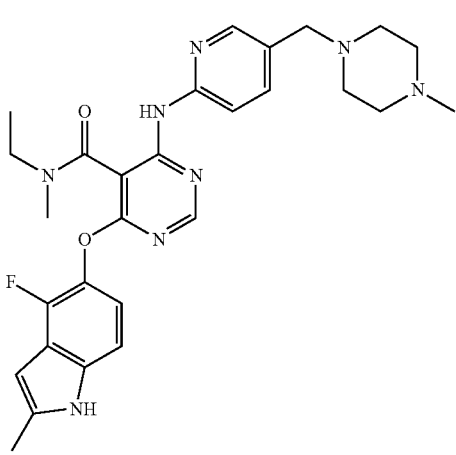
100
-continued
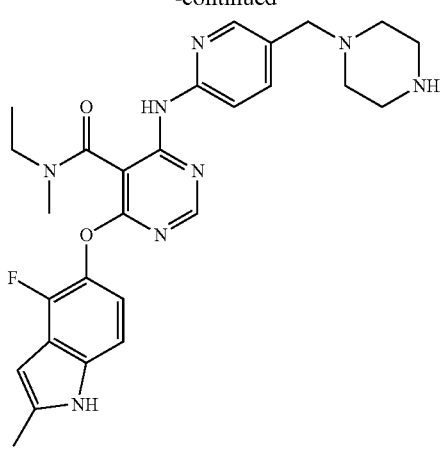
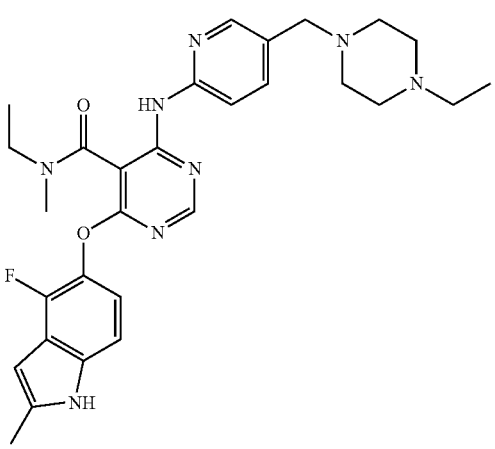
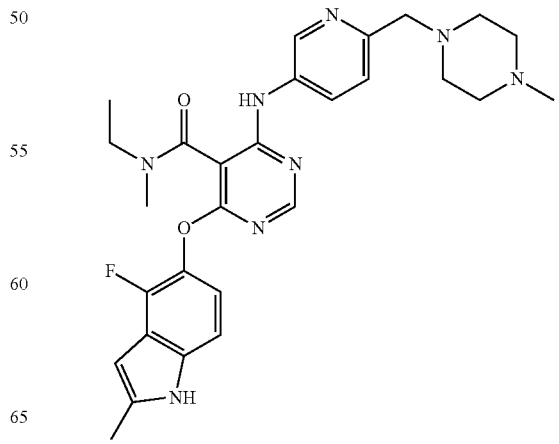

-continued
101
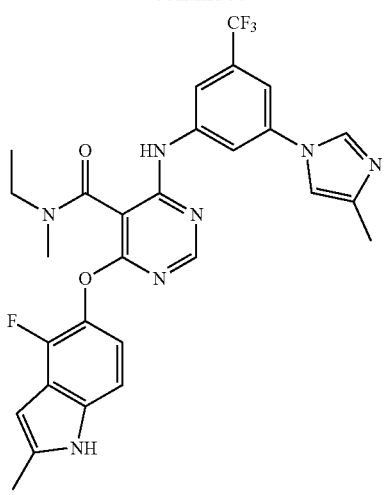
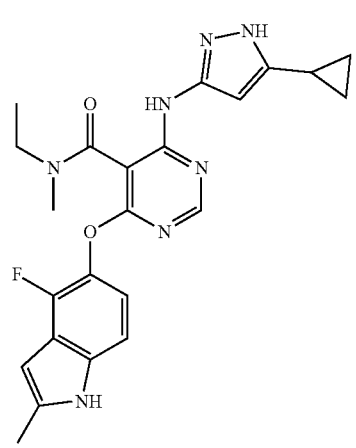
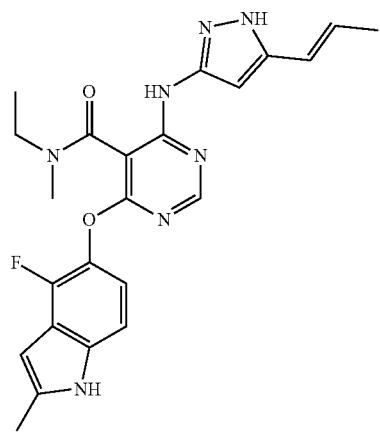
-continued
102
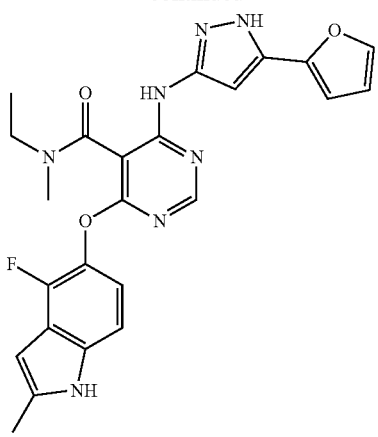
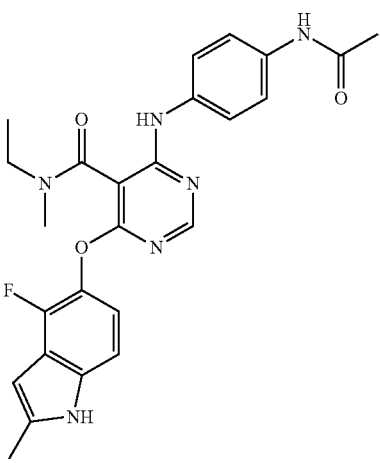
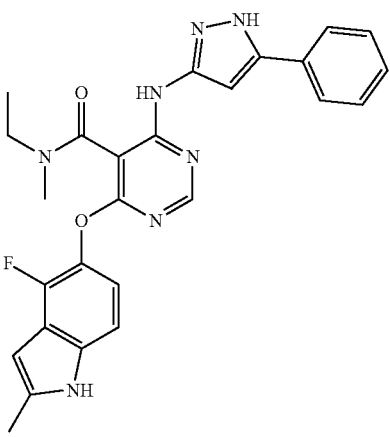

103
-continued
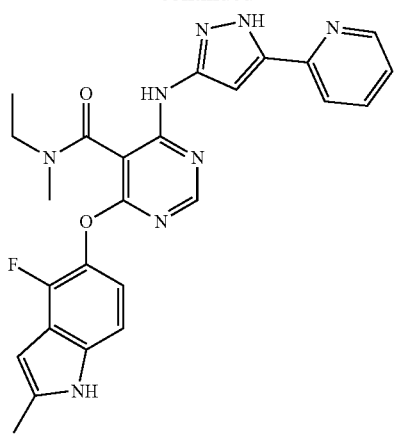
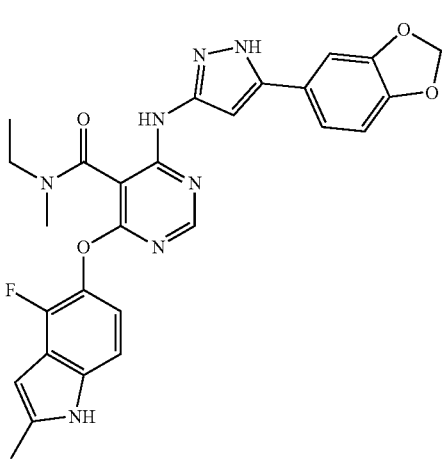
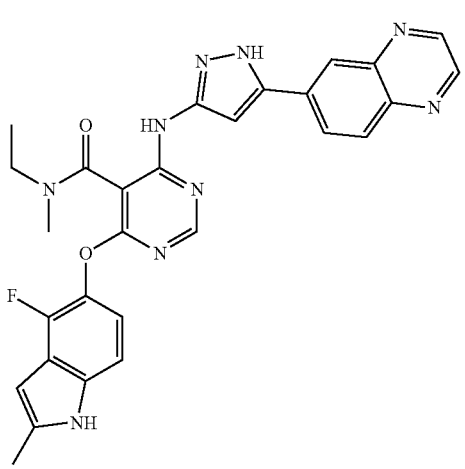
104
-continued
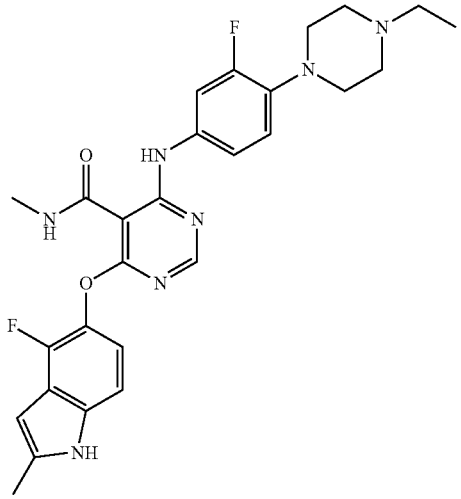
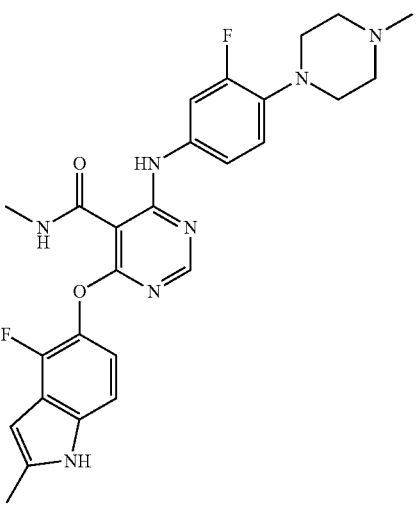
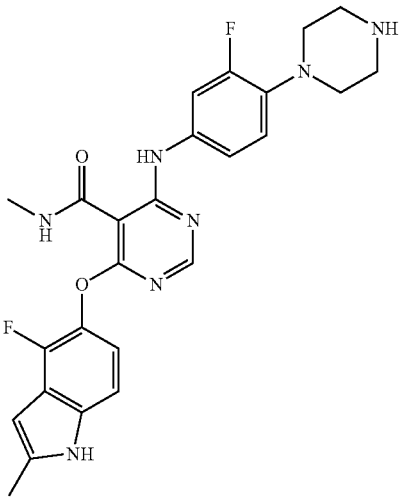

105
-continued
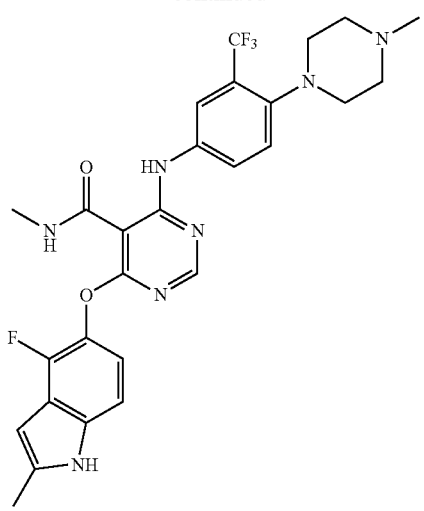
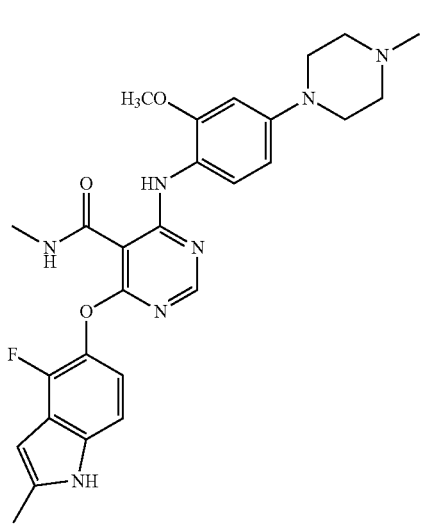
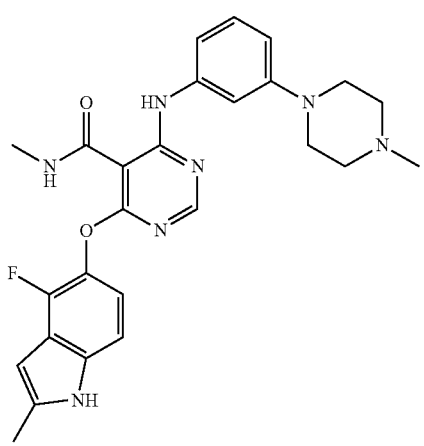
106
-continued
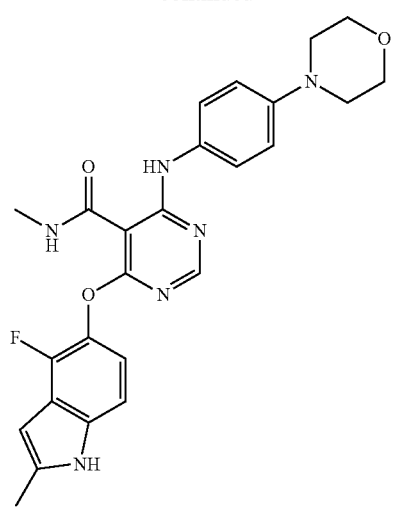
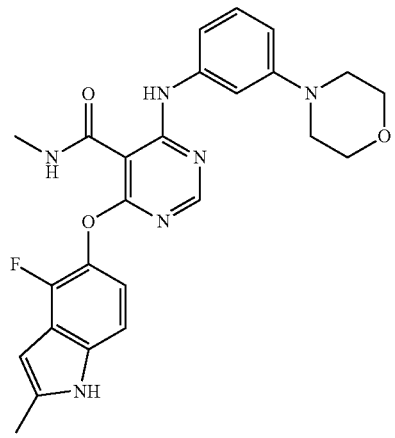
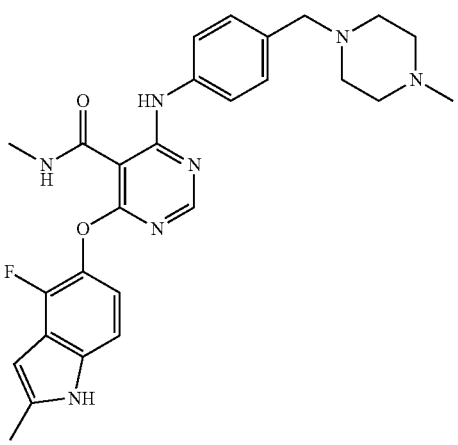

107
-continued
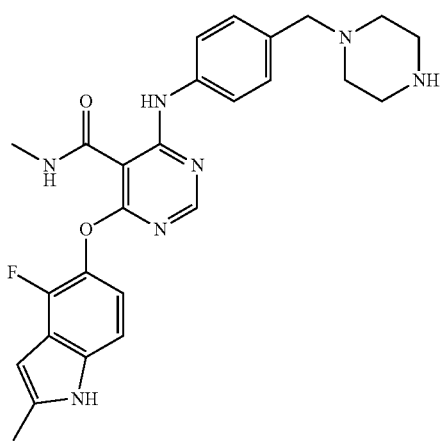
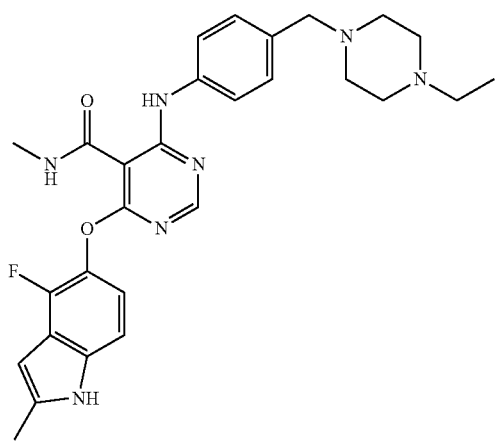
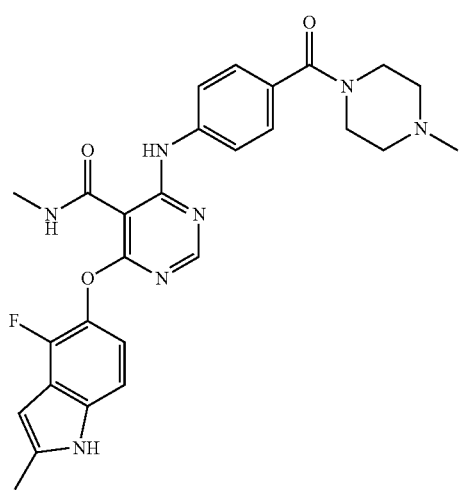
108
-continued
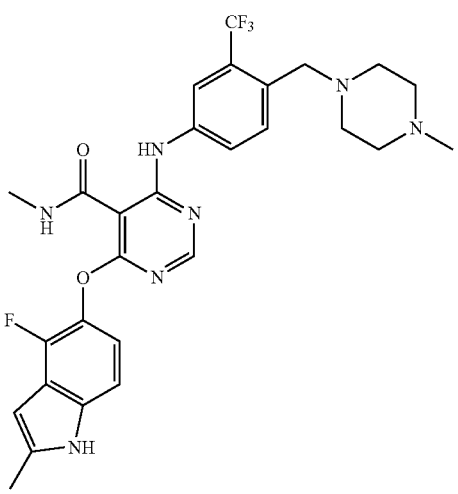
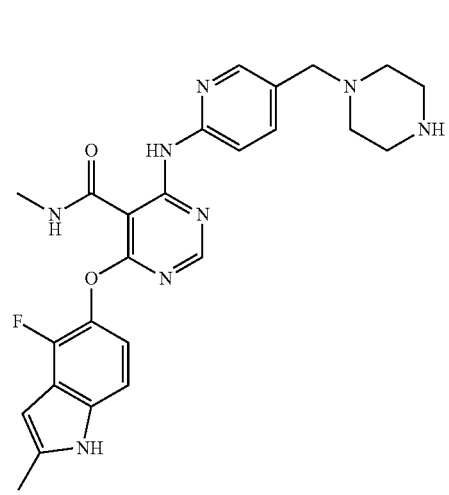

-continued
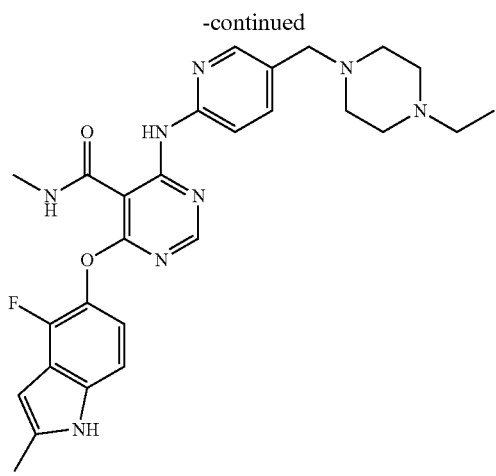
-continued
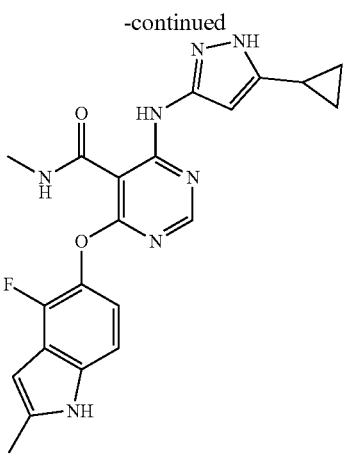
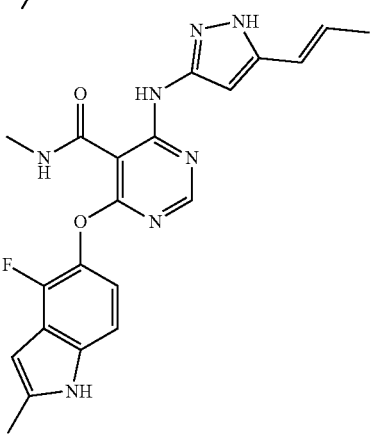
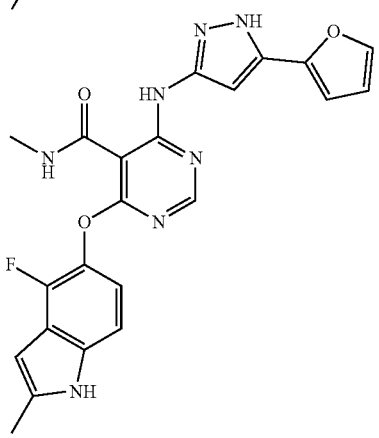
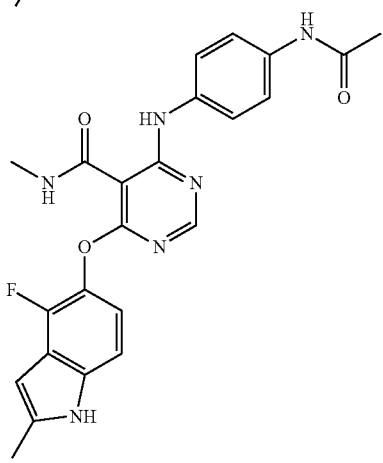

111
-continued
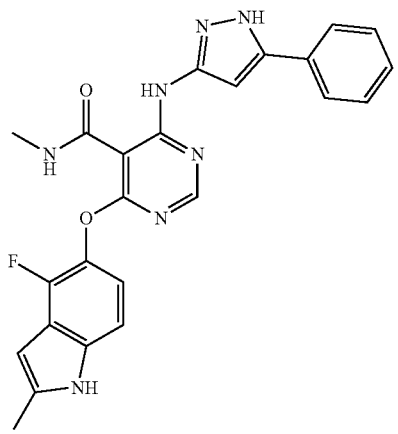
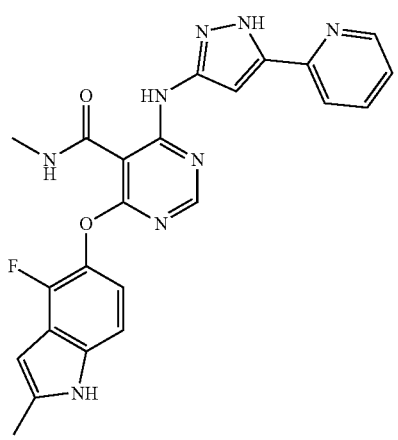
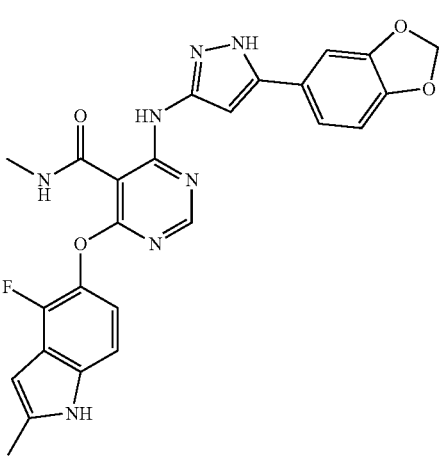
112
-continued
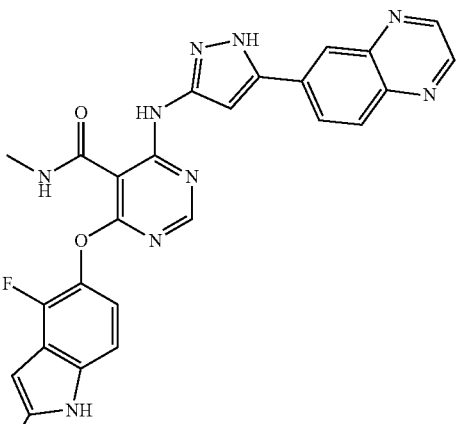
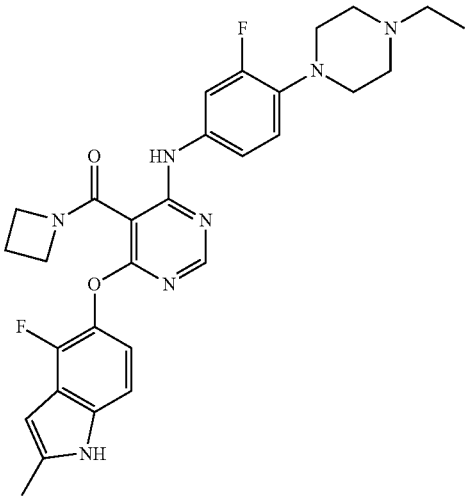
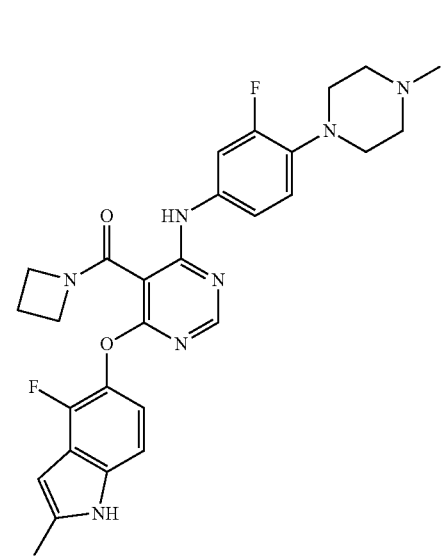

113
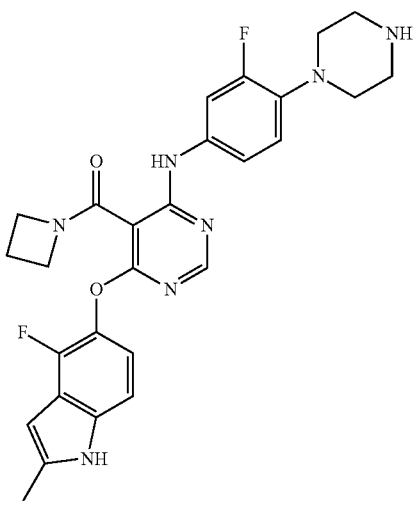
114
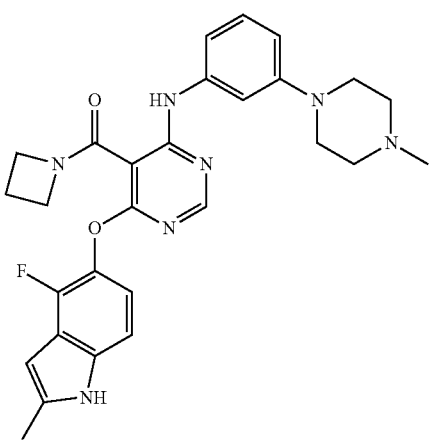
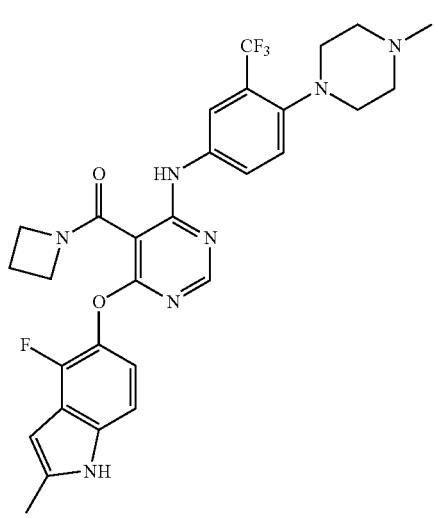
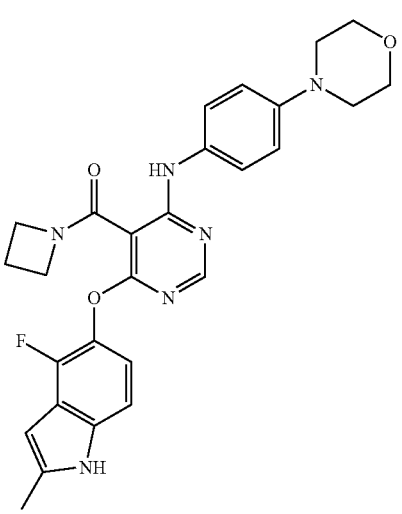
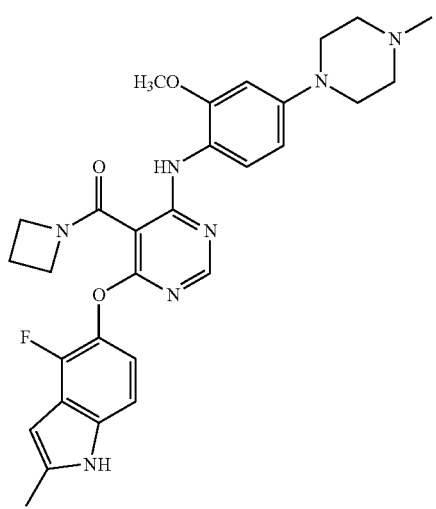
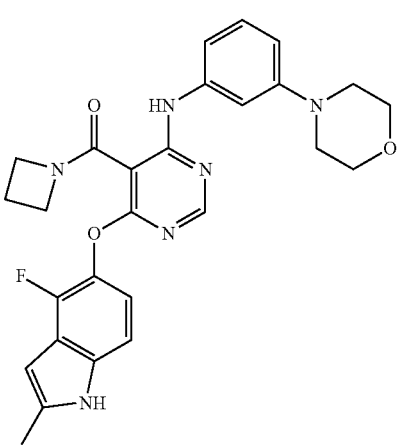

115
-continued
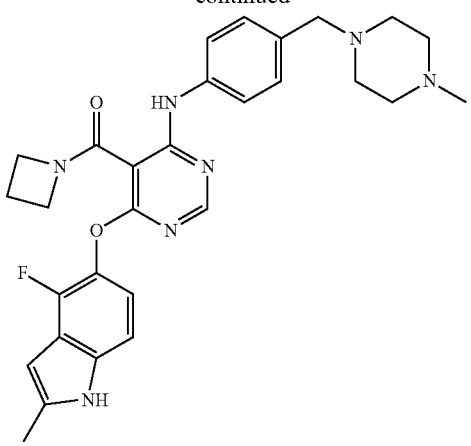
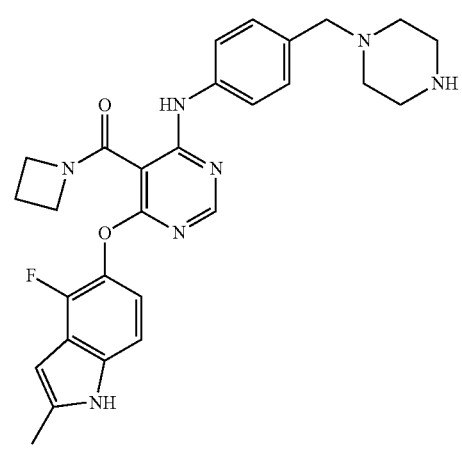
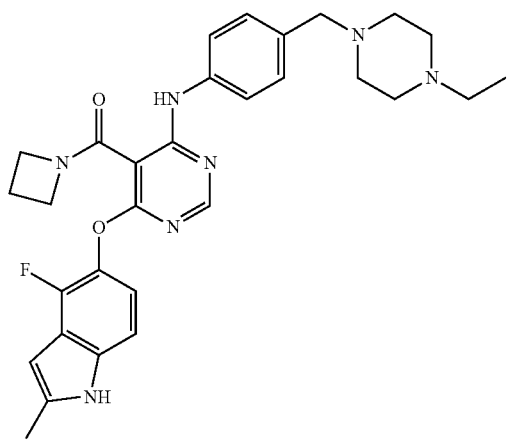
116
-continued
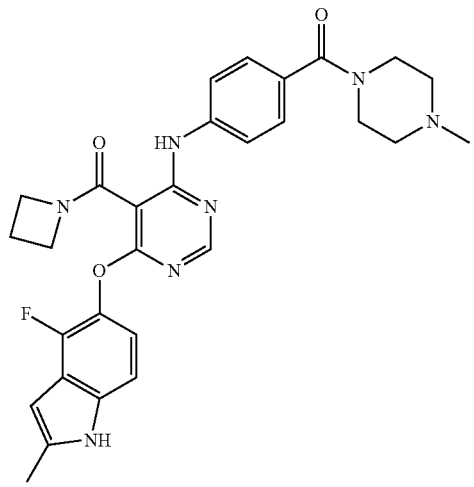
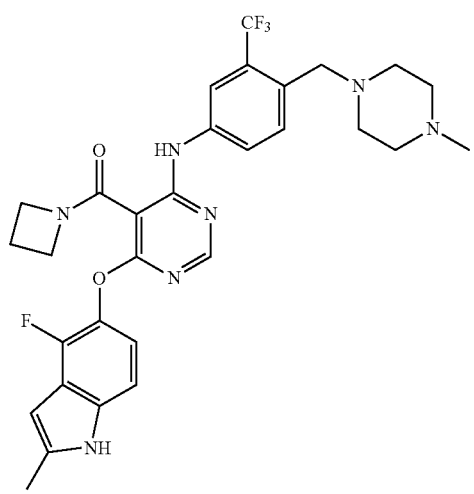
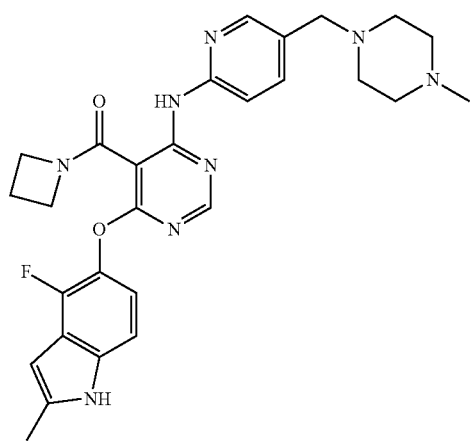

117
-continued
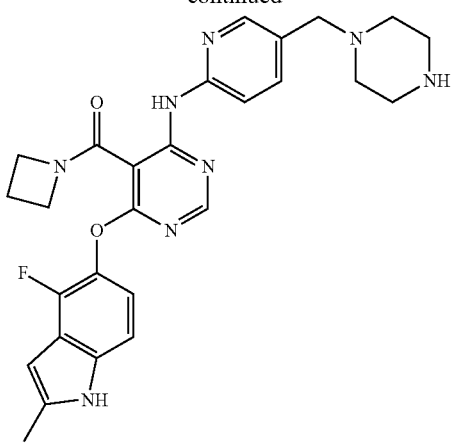
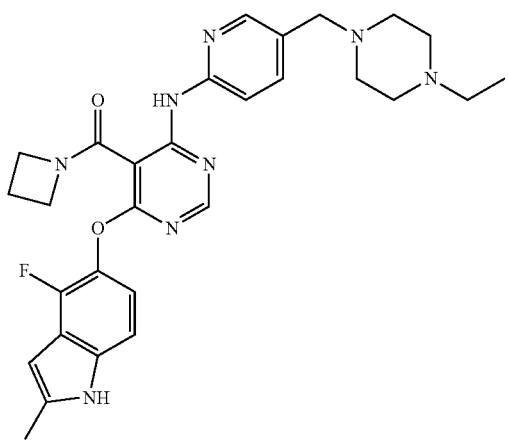
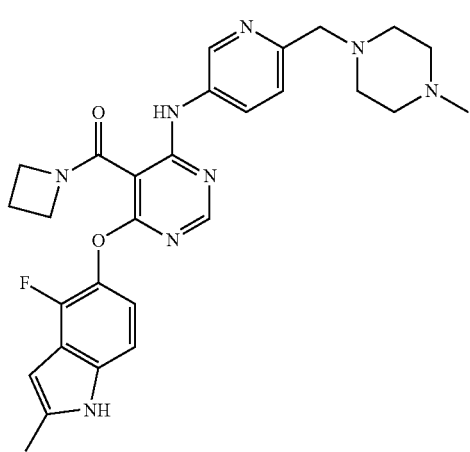
118
-continued
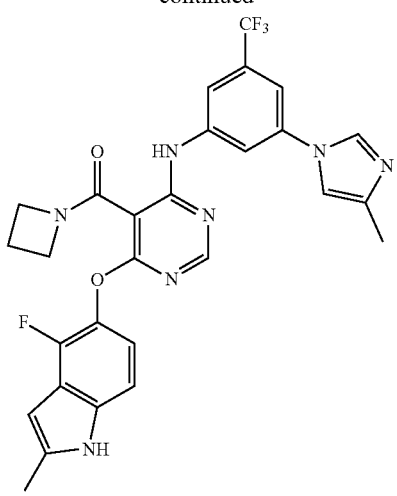
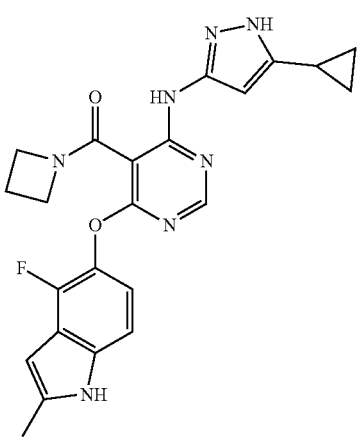
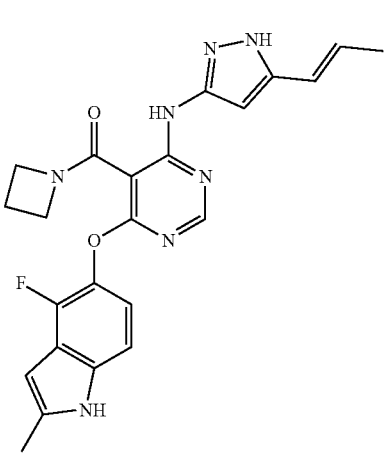

119
-continued
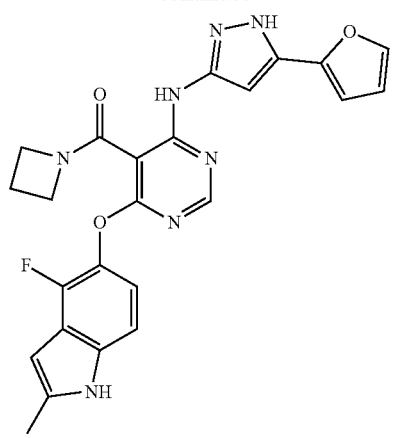
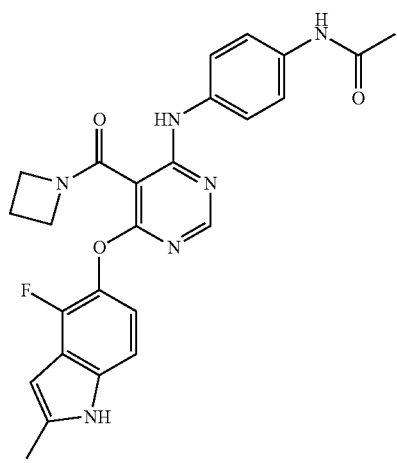
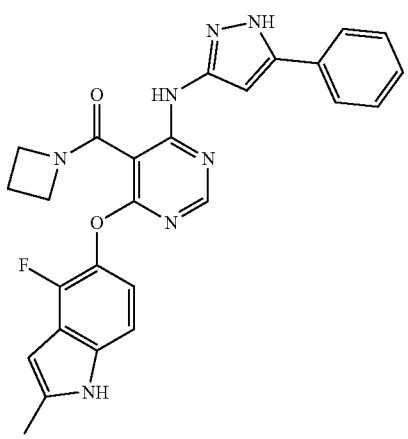
120
-continued
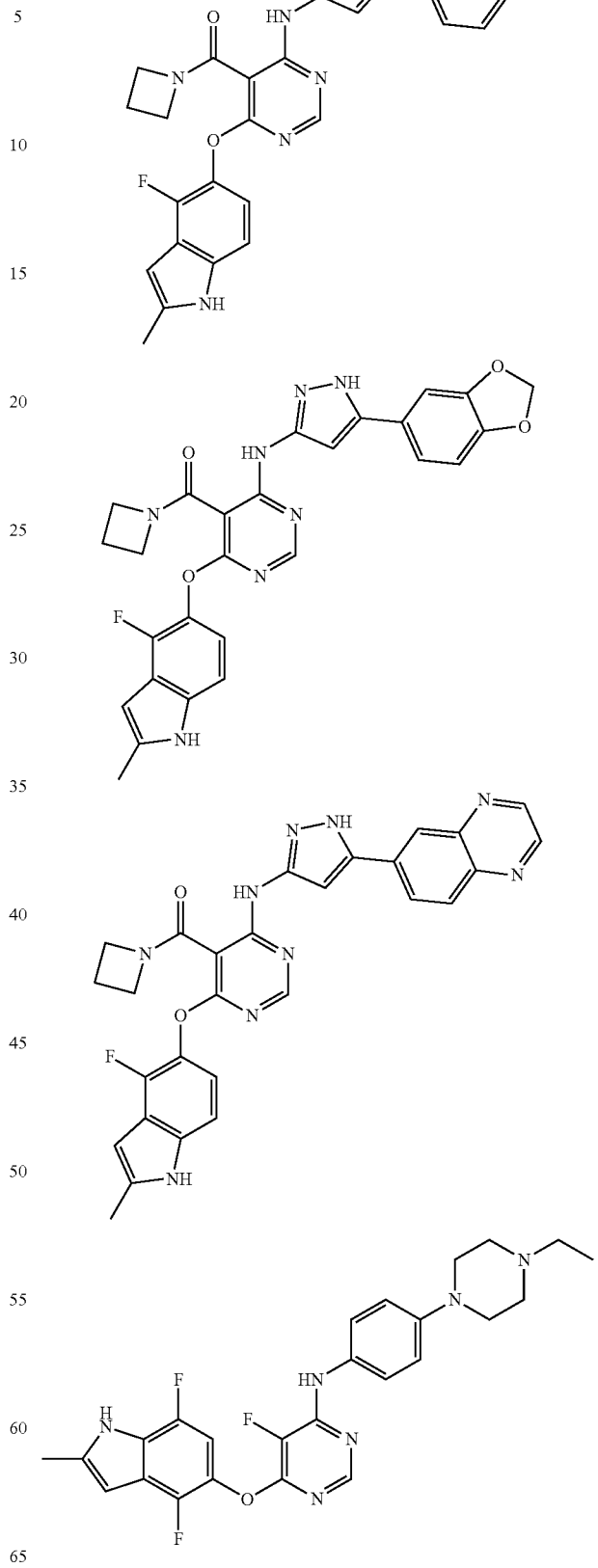

121
-continued
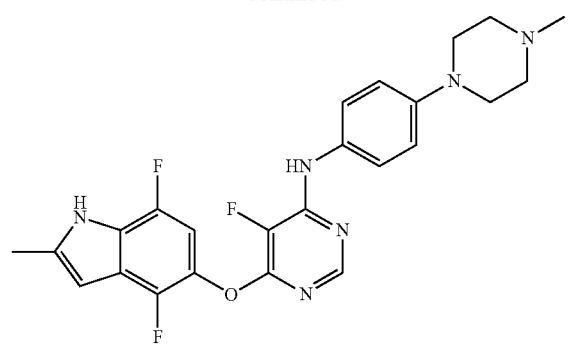
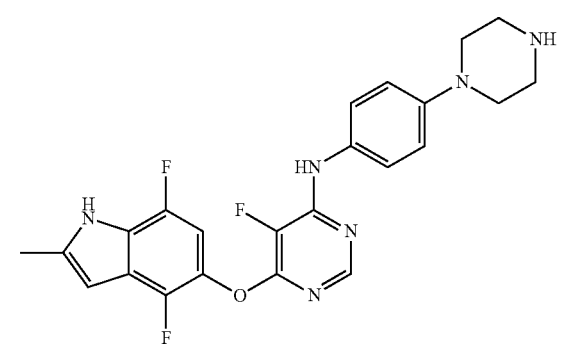
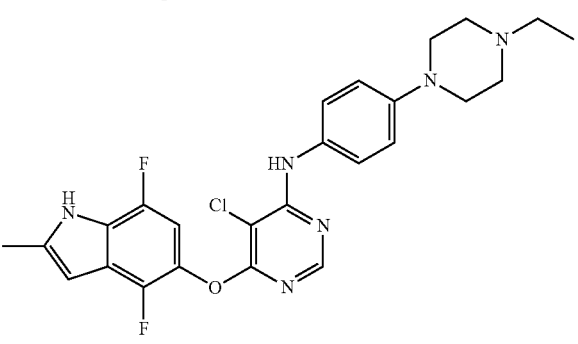
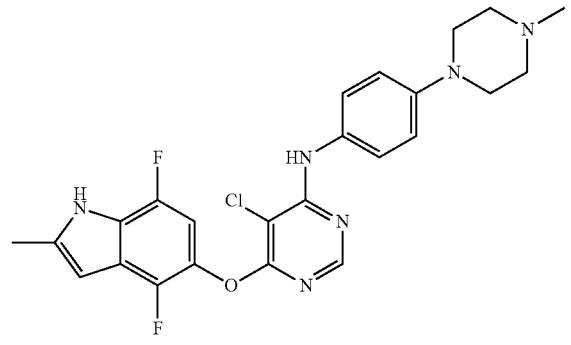
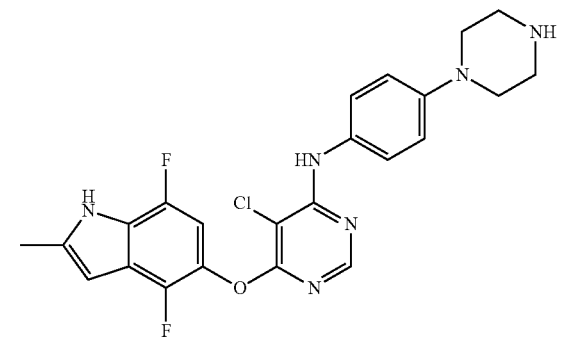
122
-continued
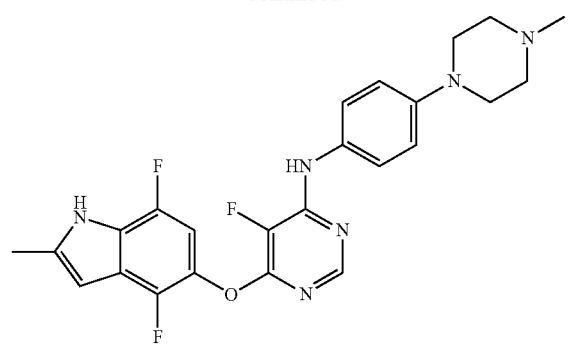
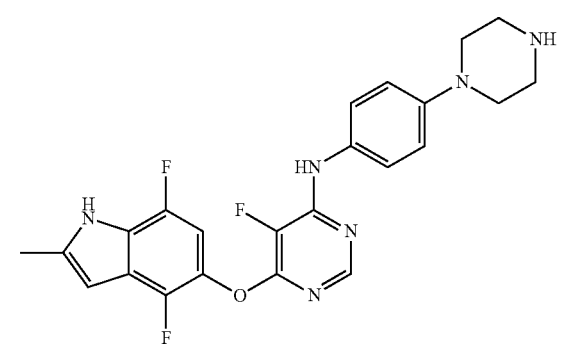
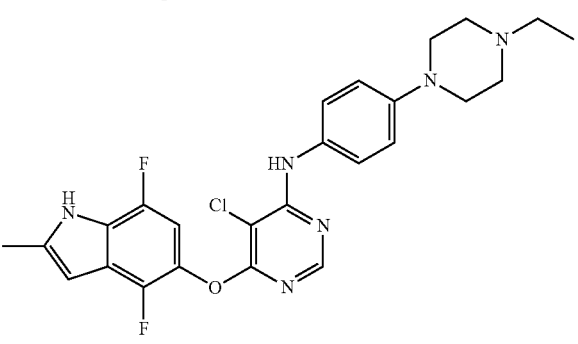
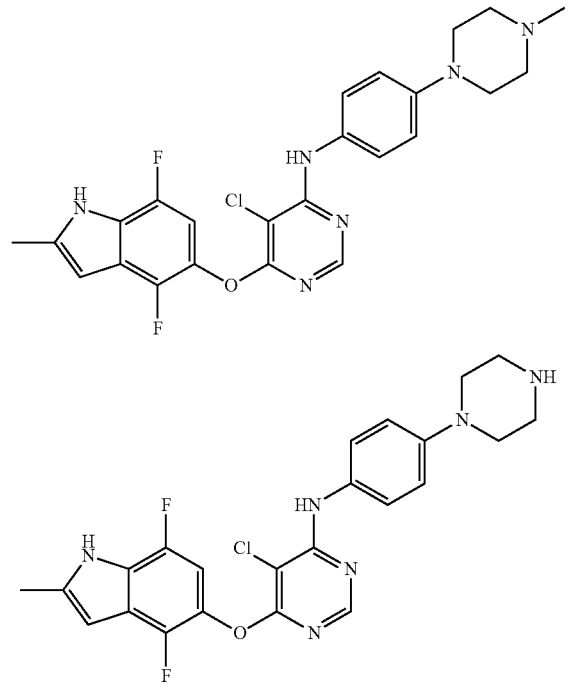
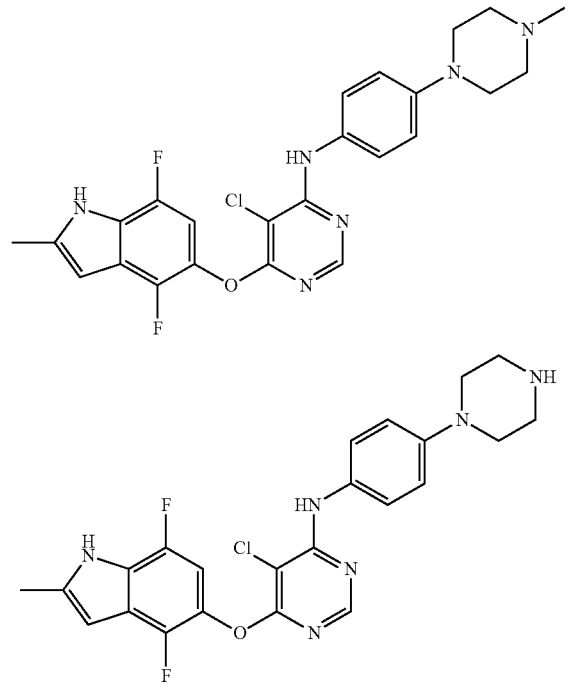

123
-continued
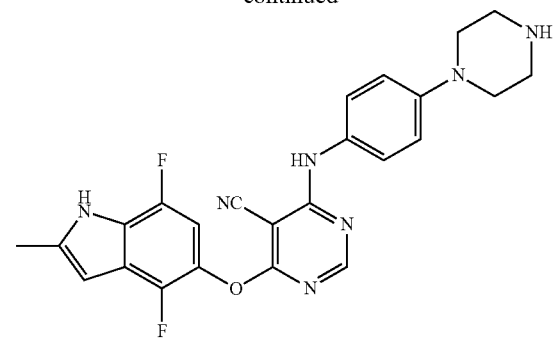
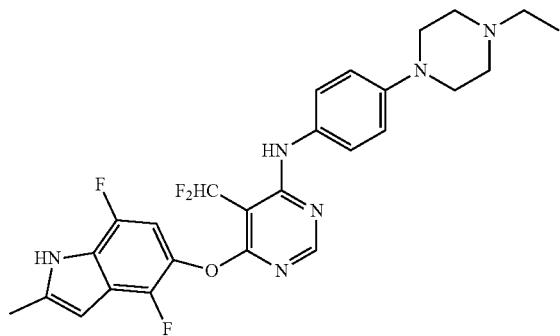
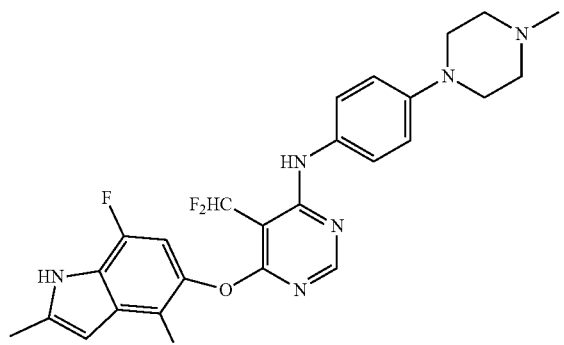
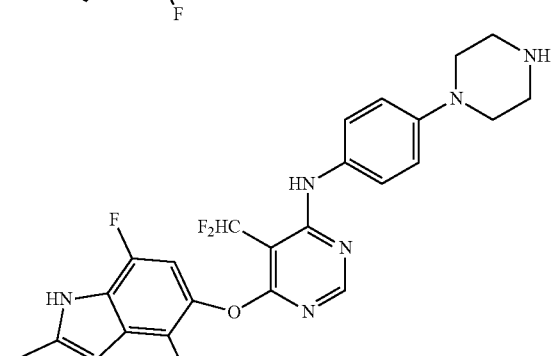
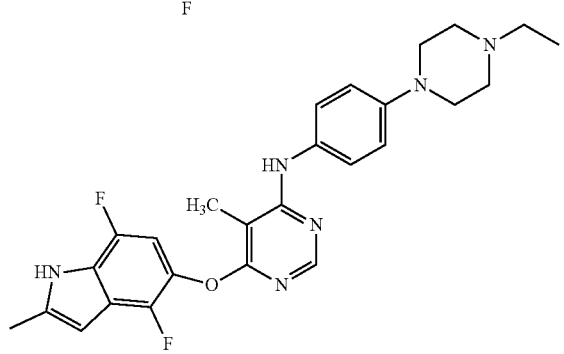
124
-continued
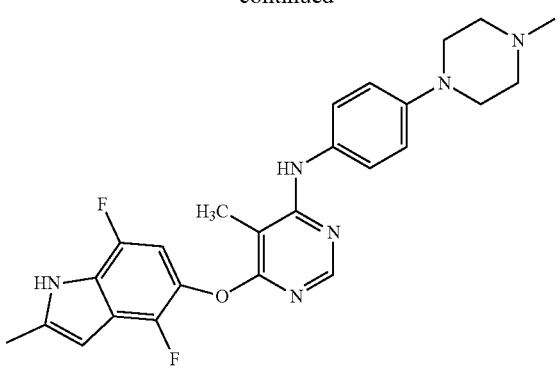
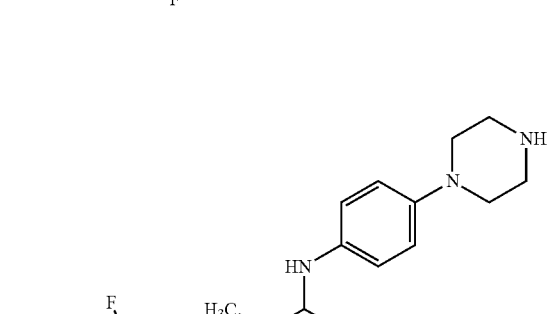
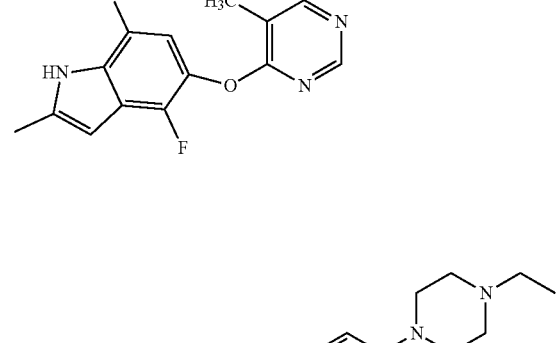
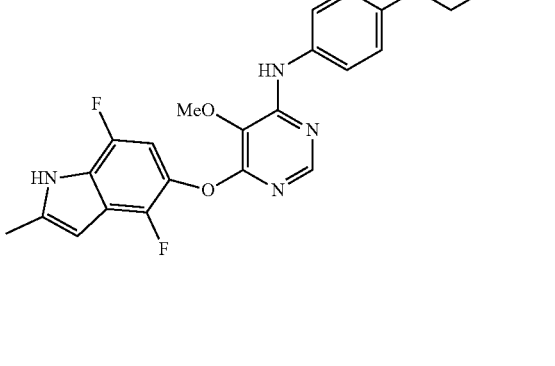
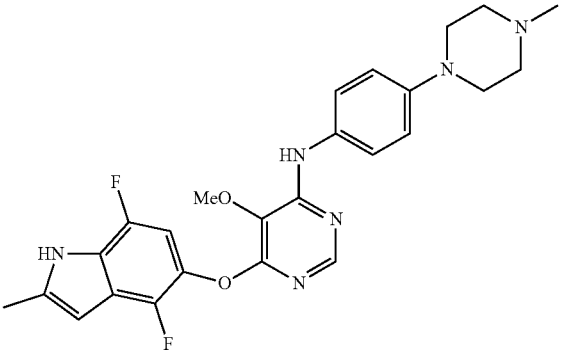

125
-continued
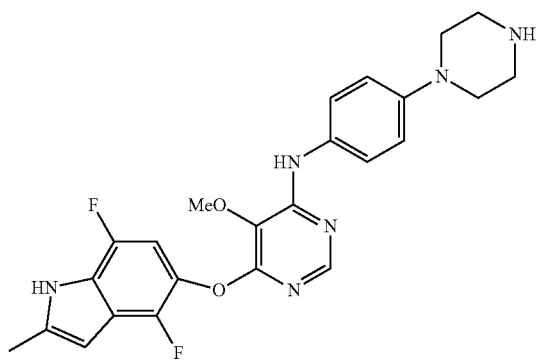
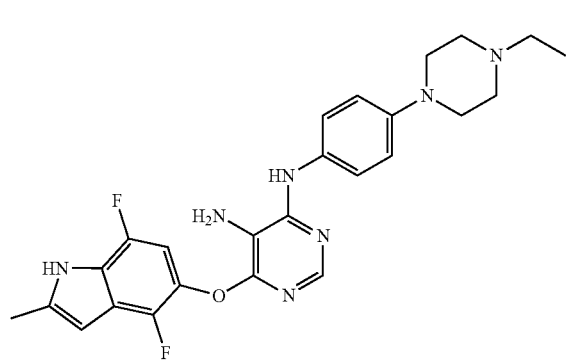
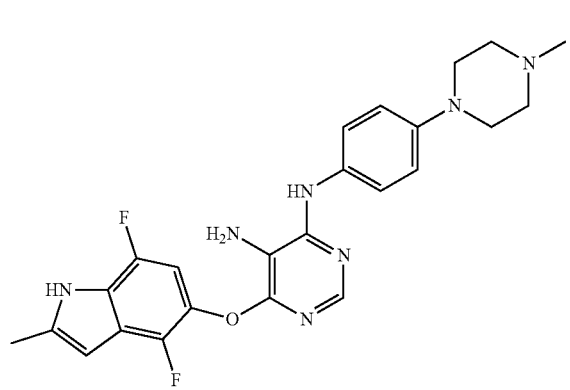
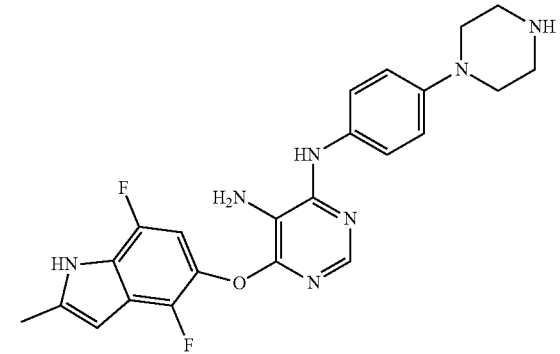
126
-continued
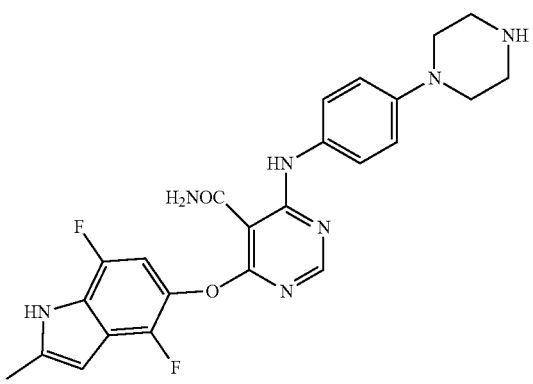
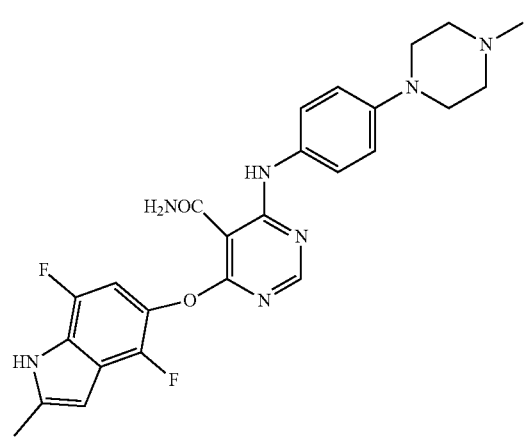
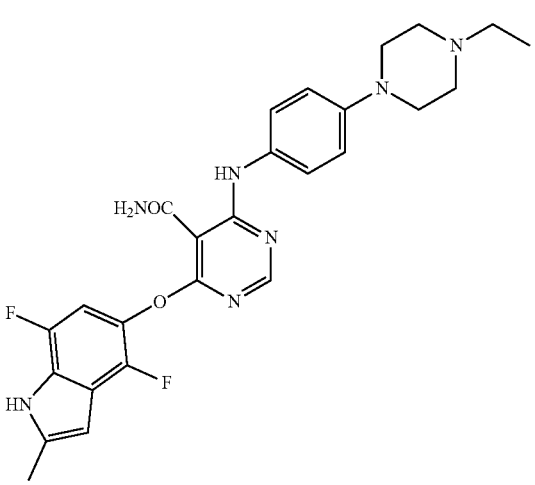
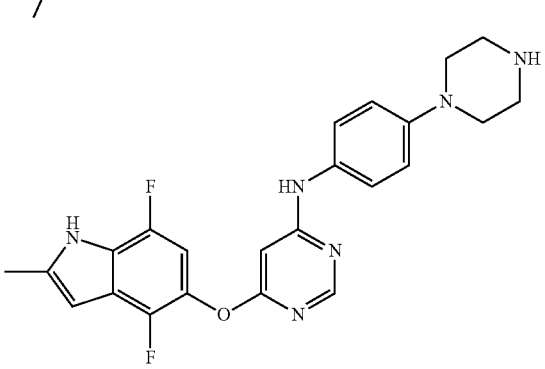

127
-continued
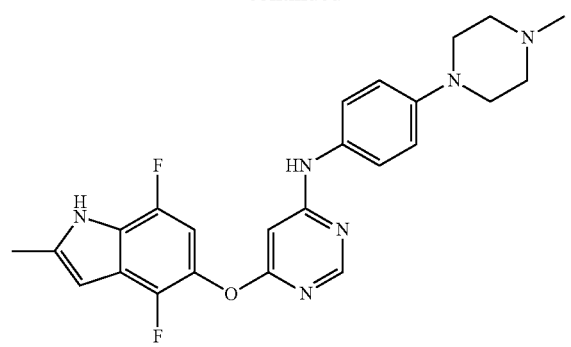
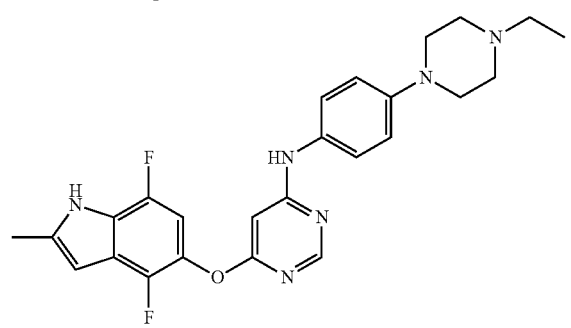
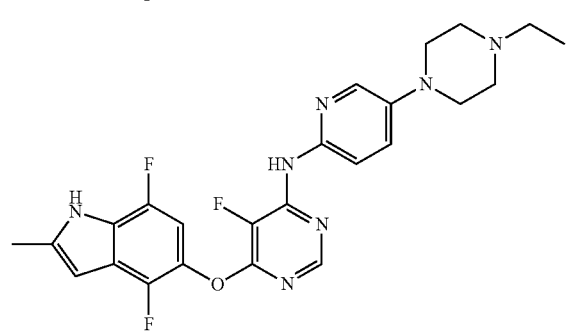
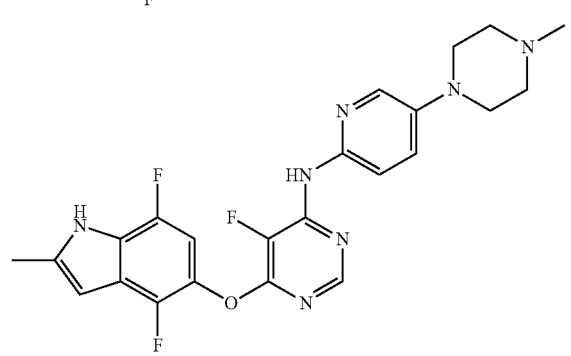
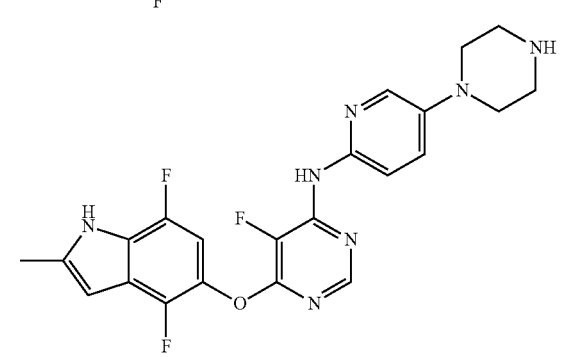
128
-continued
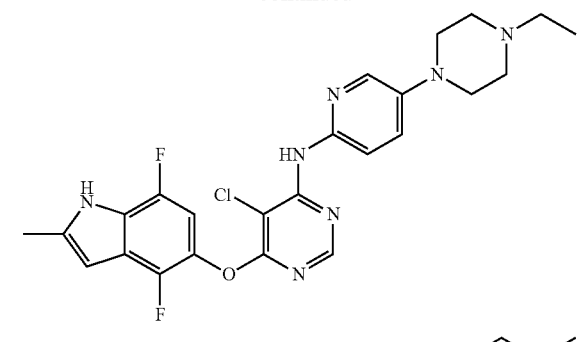
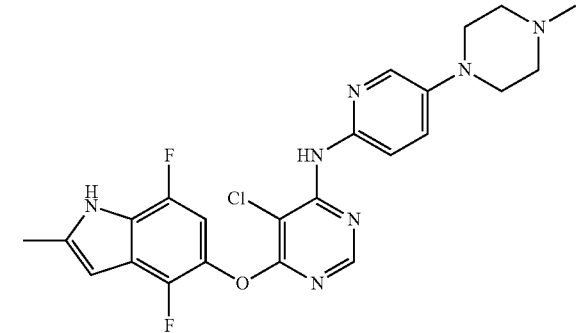
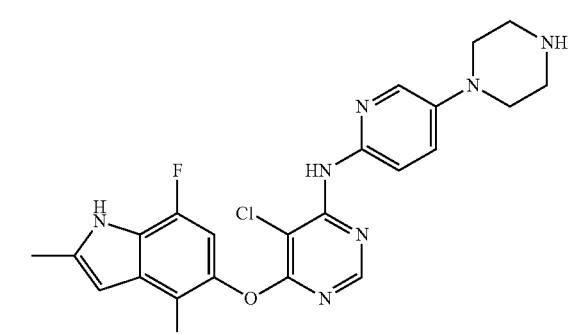
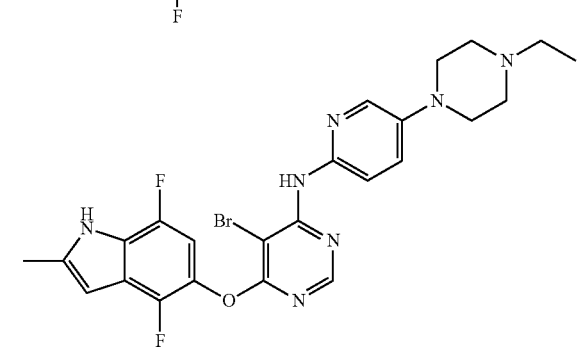
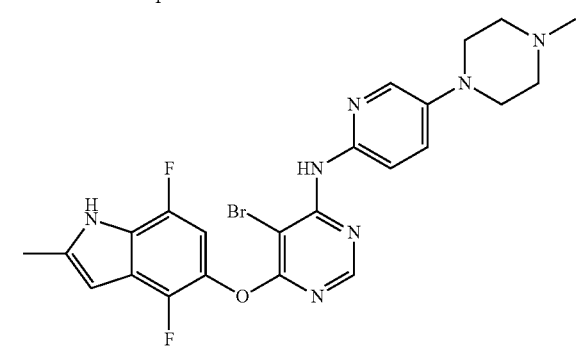

-continued
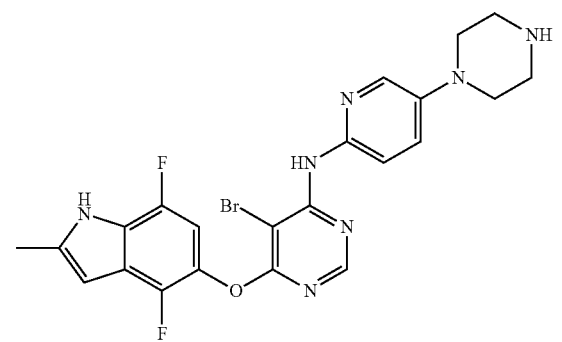
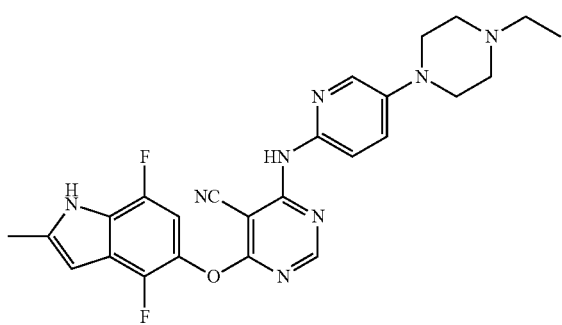
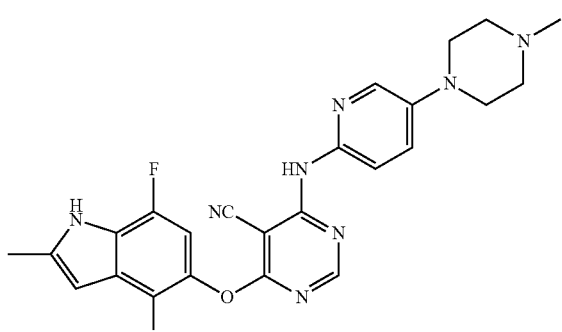
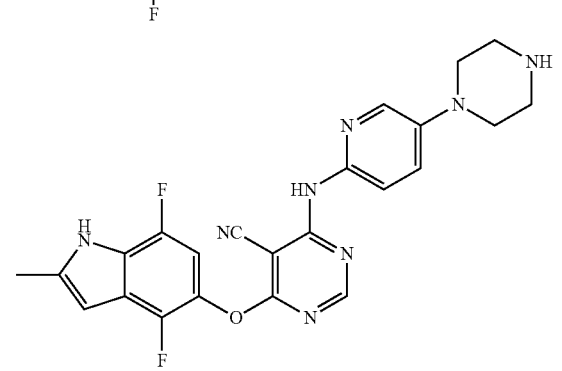
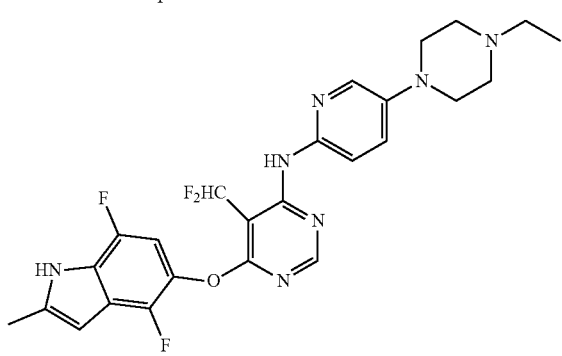
-continued
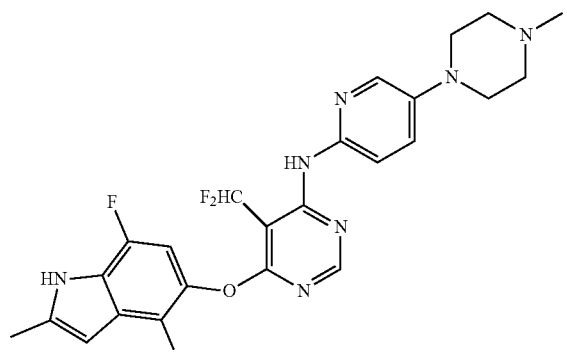
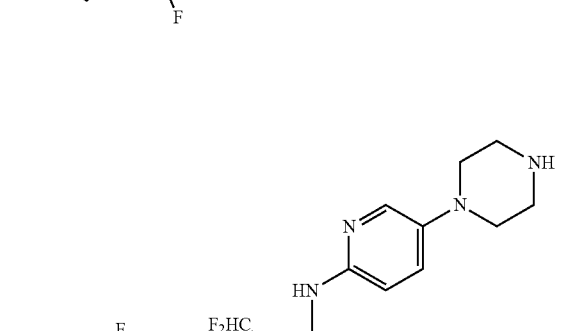
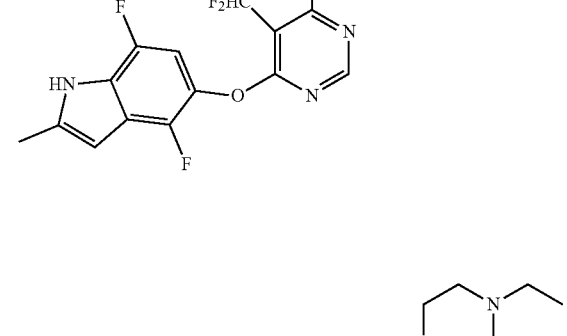
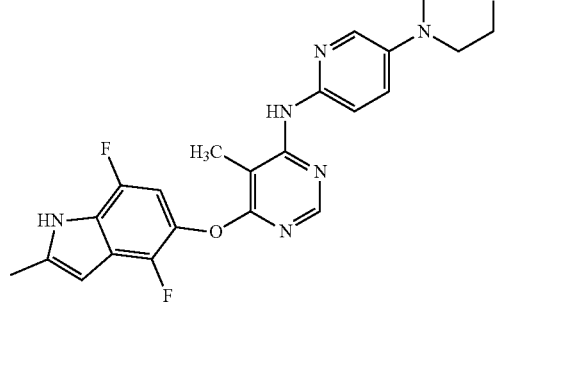
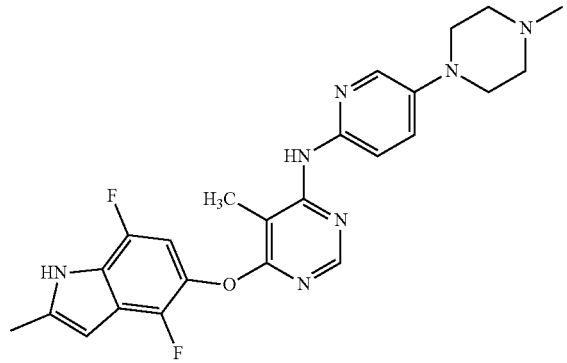

131
-continued
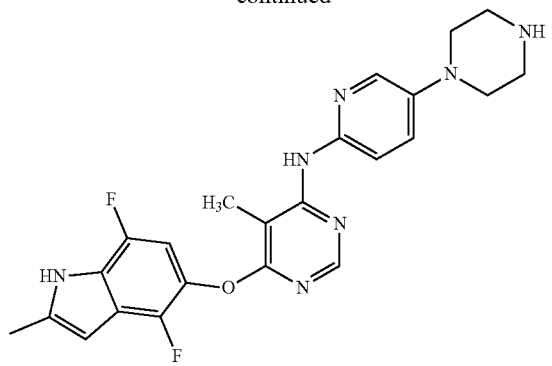
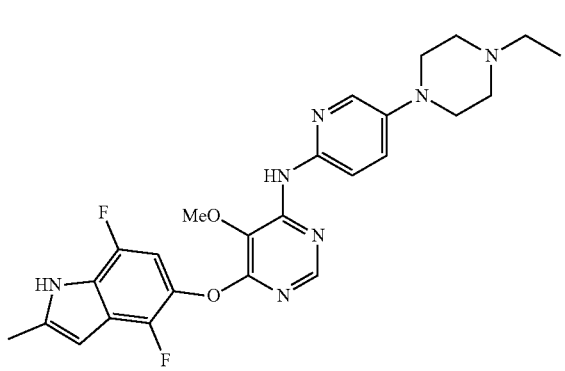
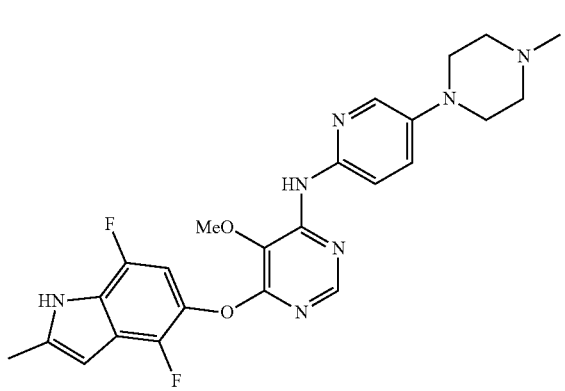
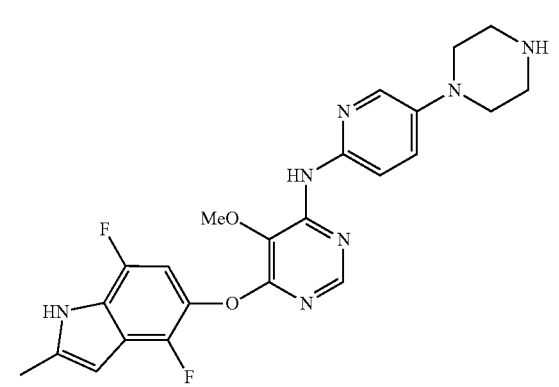
132
-continued
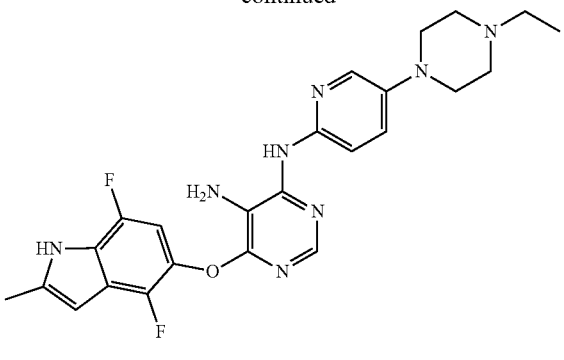
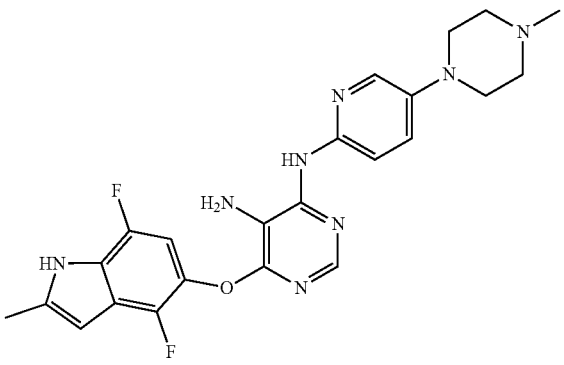
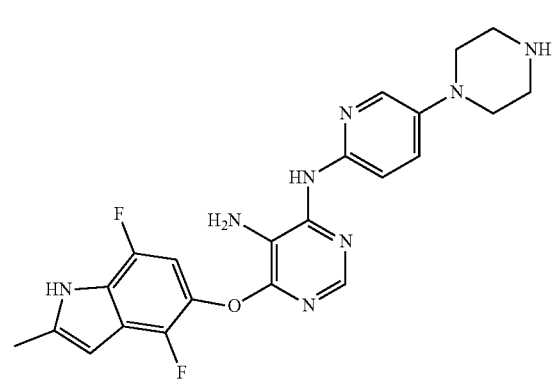
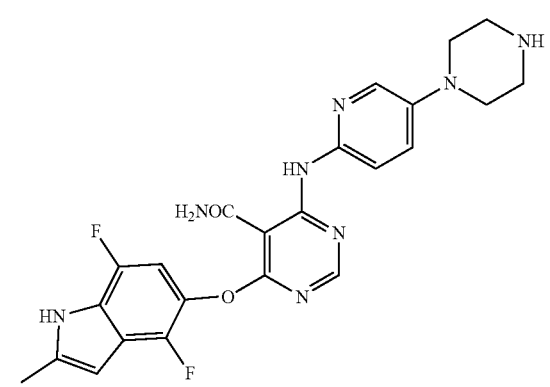

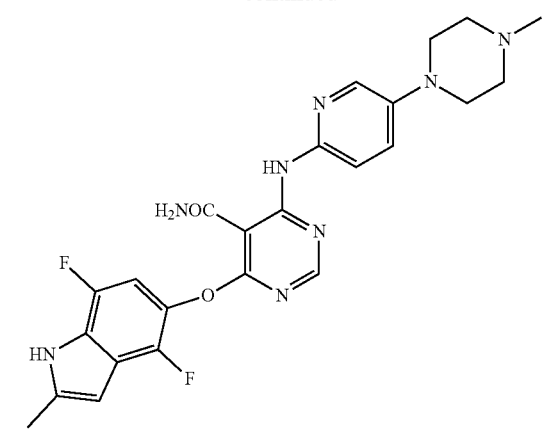
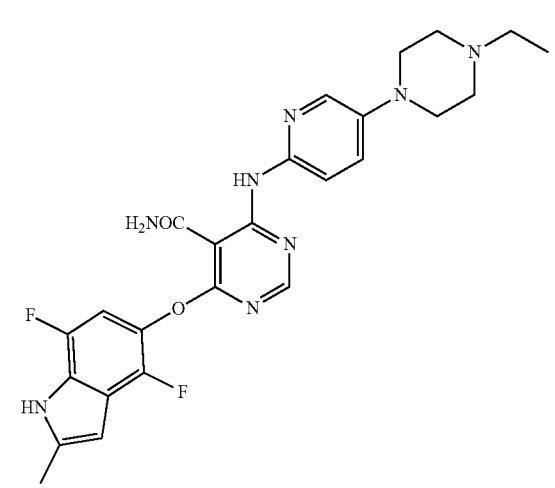
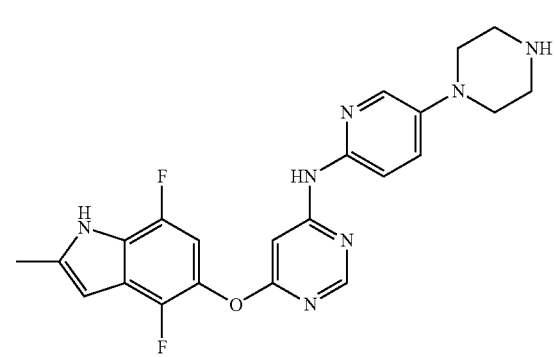
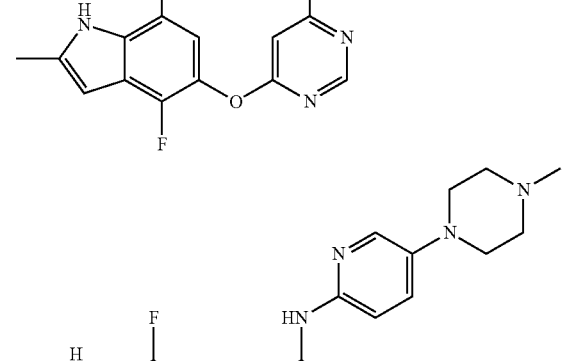
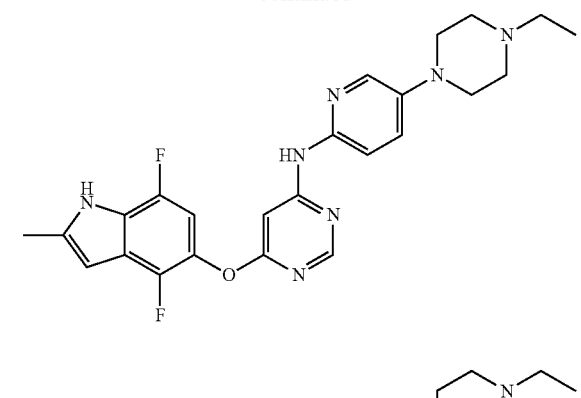
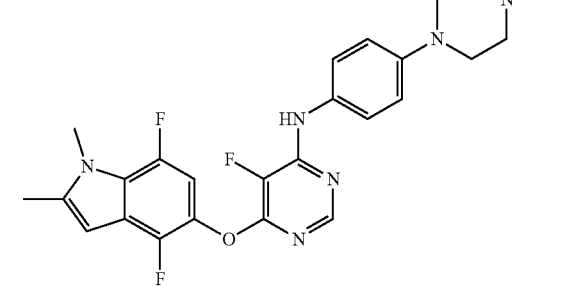
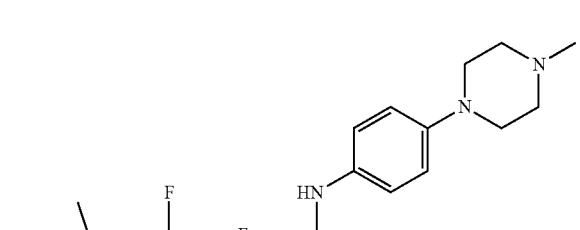
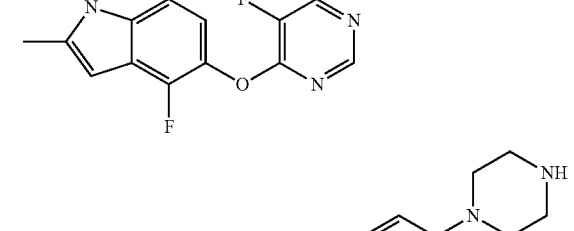
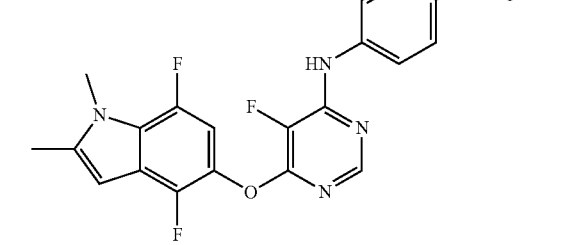
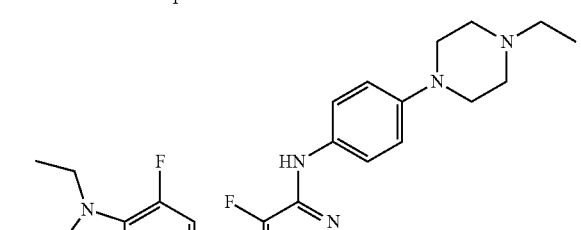

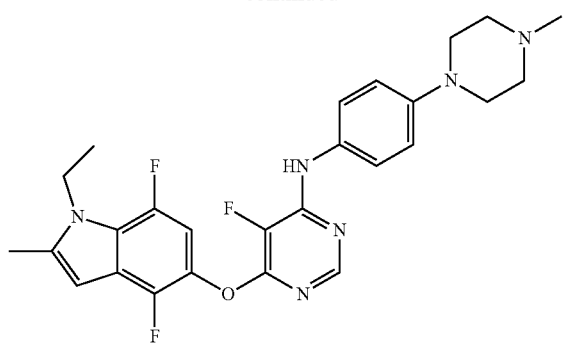
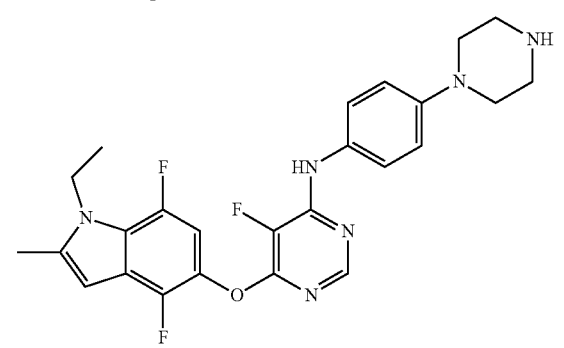
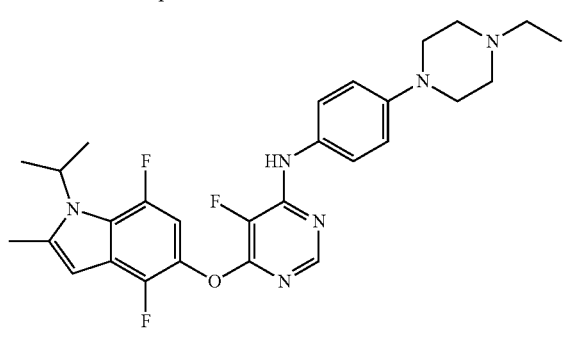
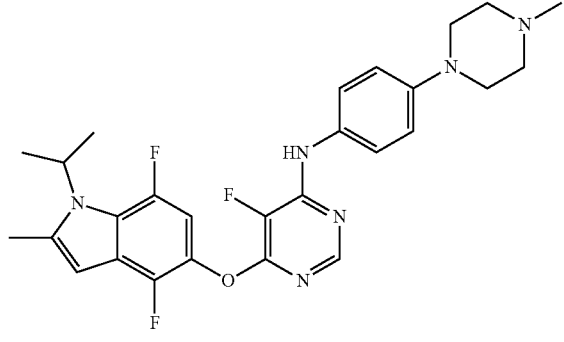
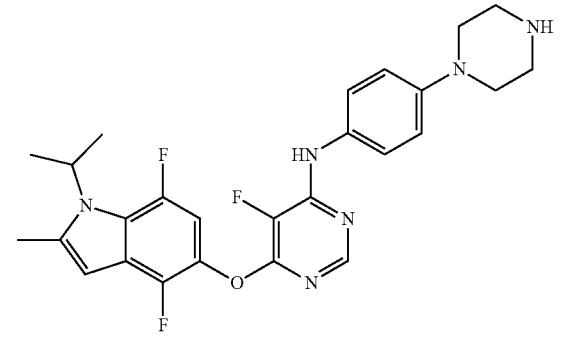
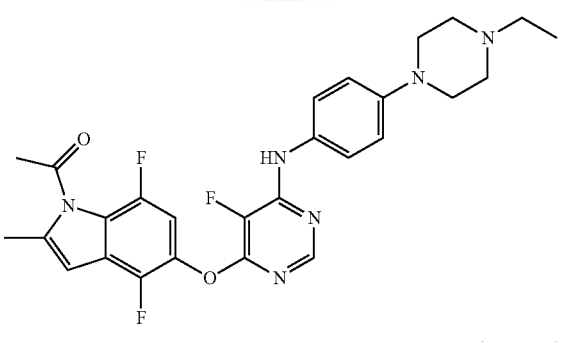
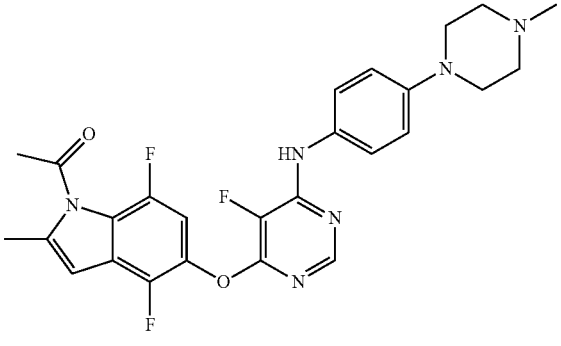
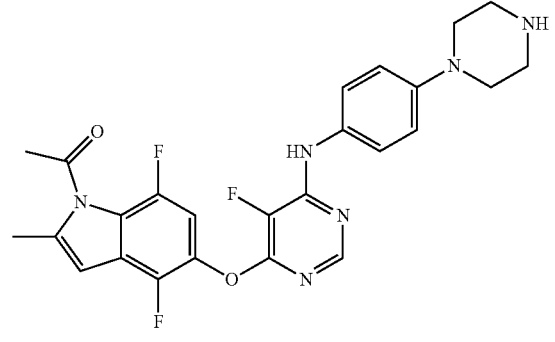
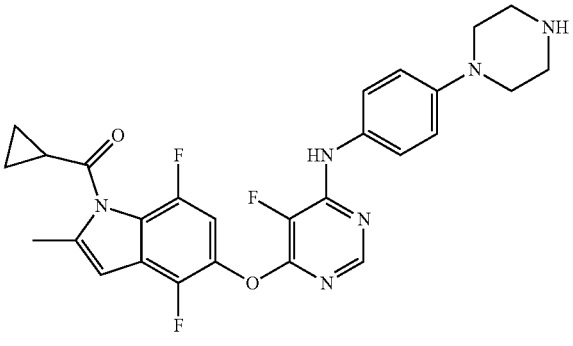
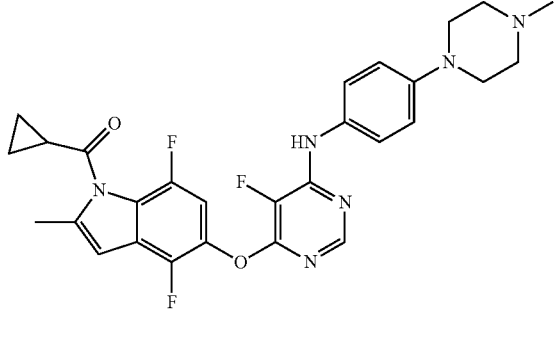

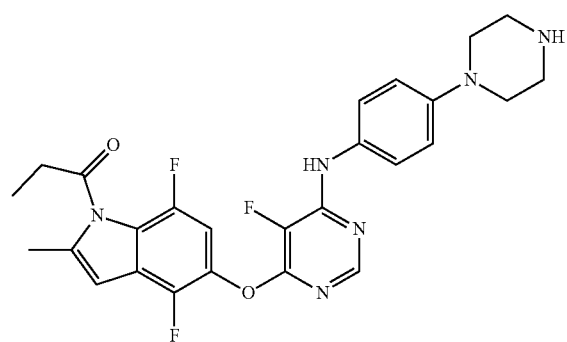
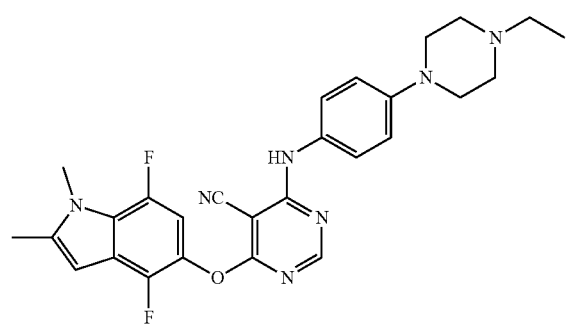
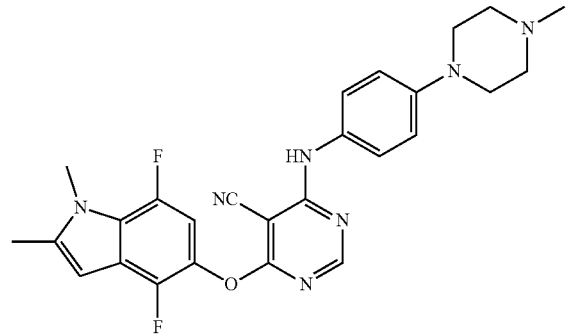
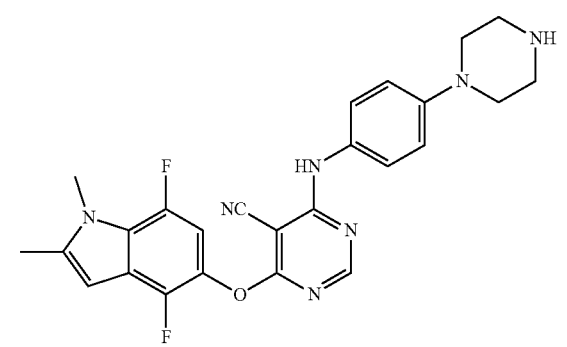
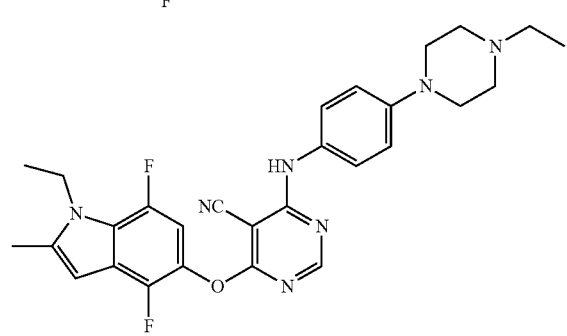
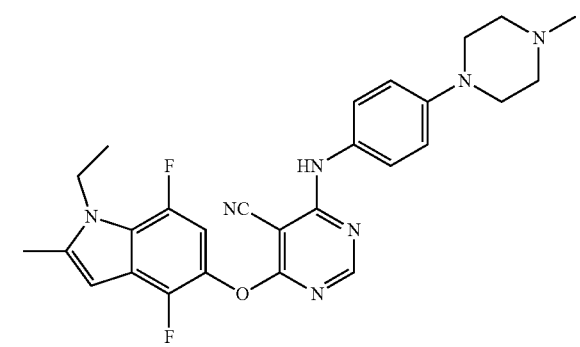
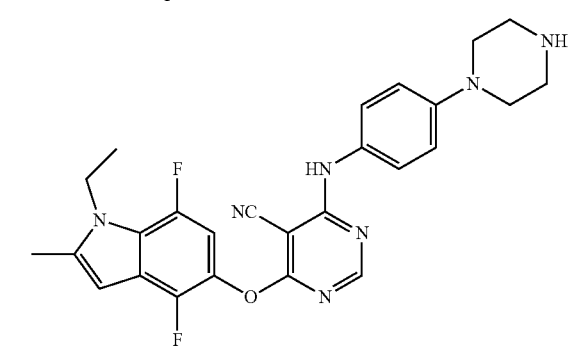
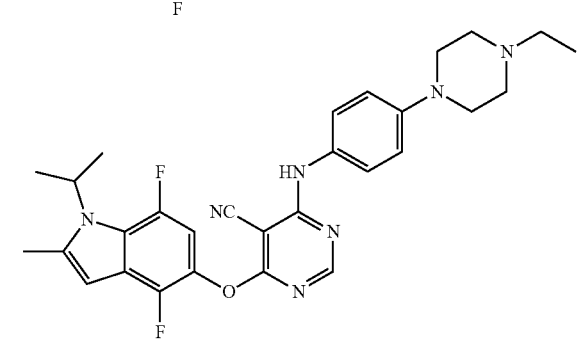
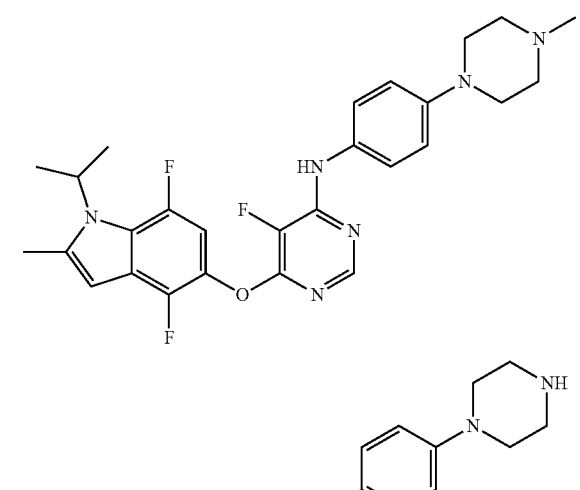
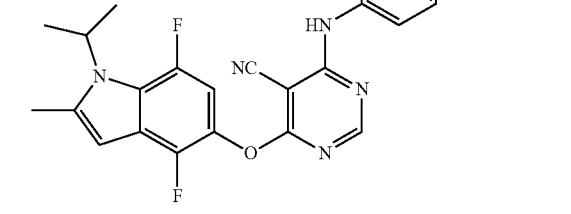

-continued
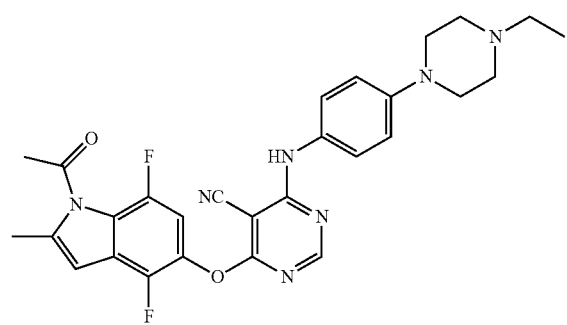
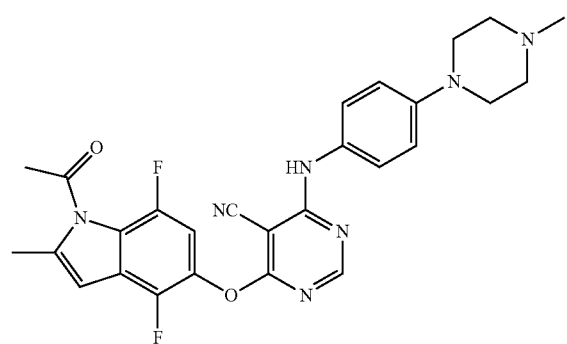
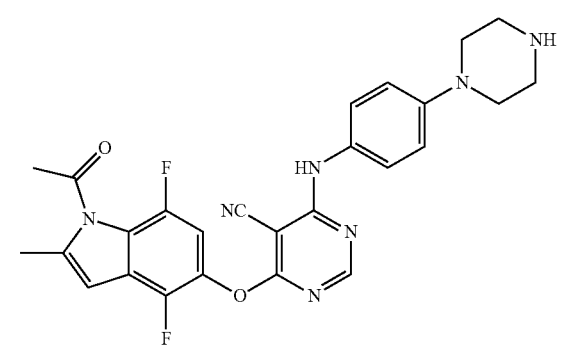
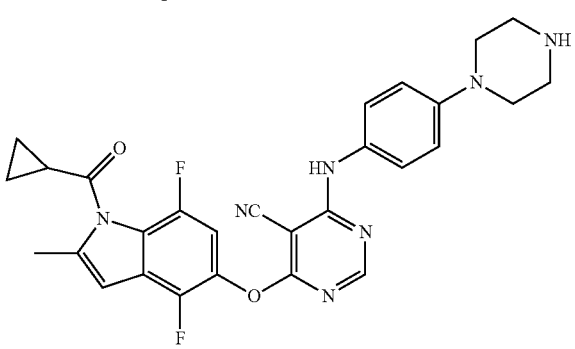
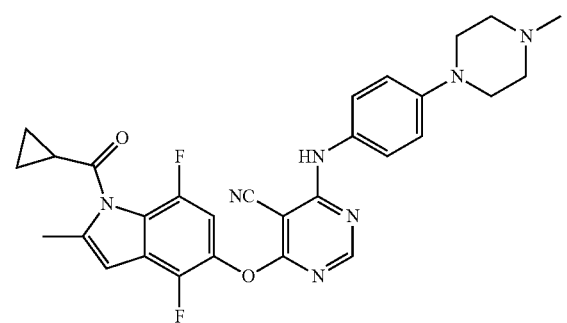
-continued
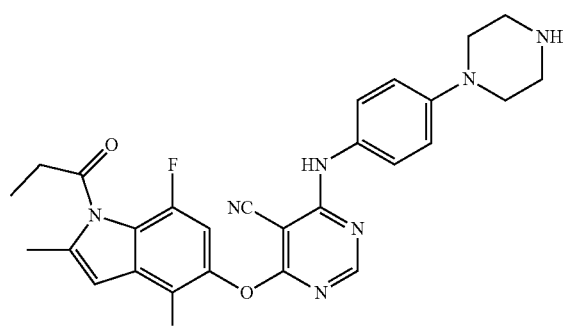
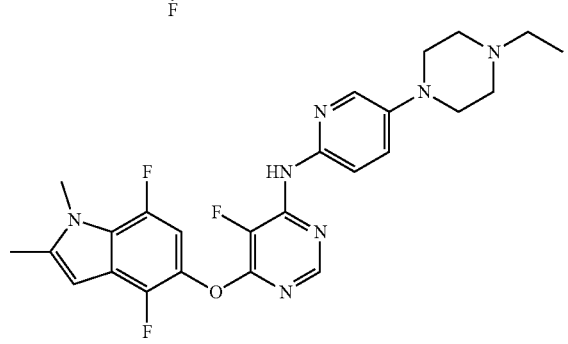
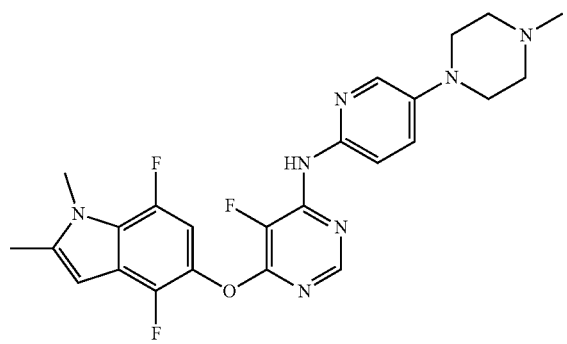
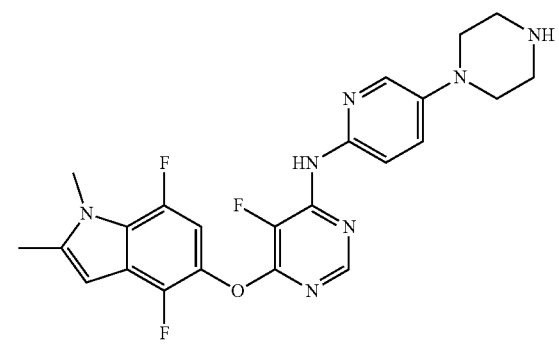
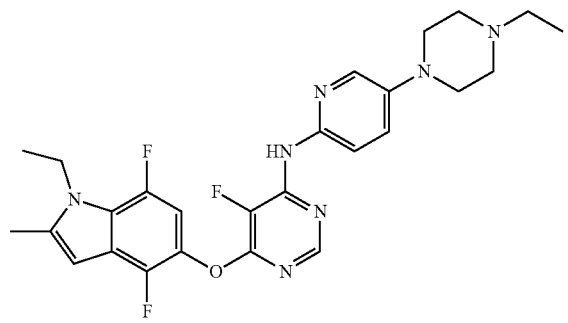

141
-continued
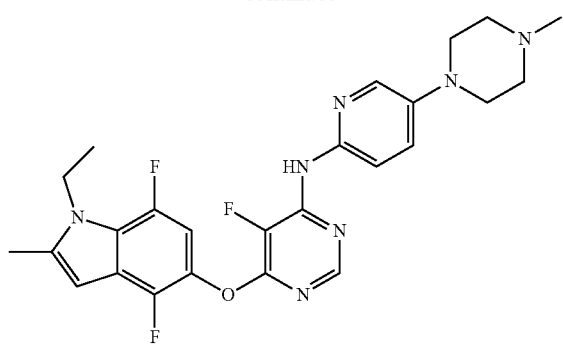
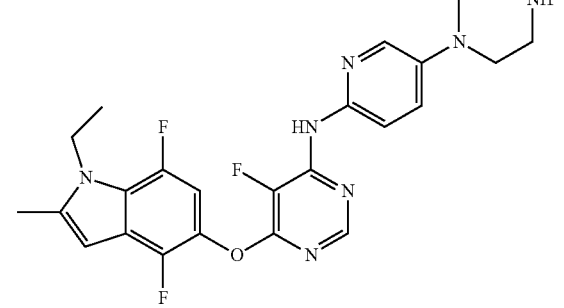
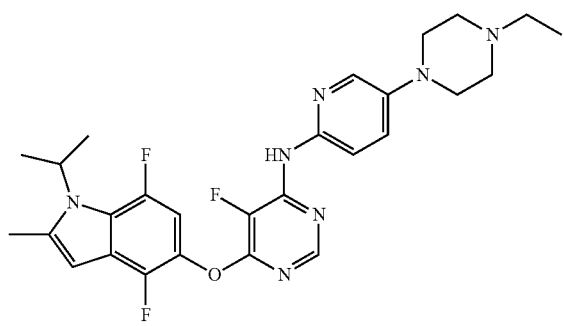
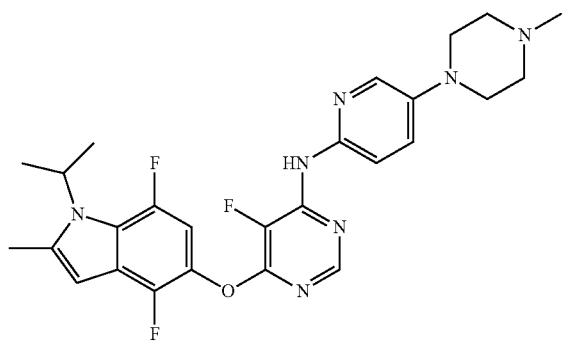
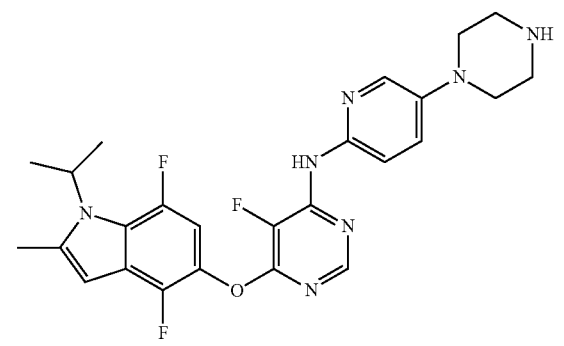
142
-continued
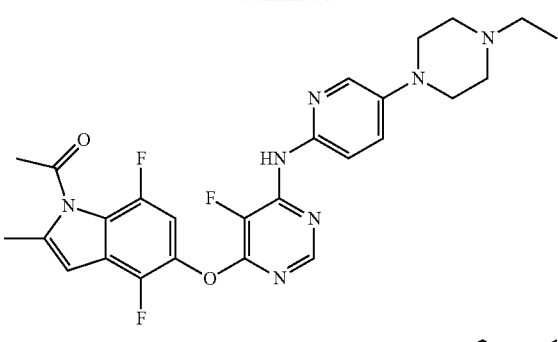
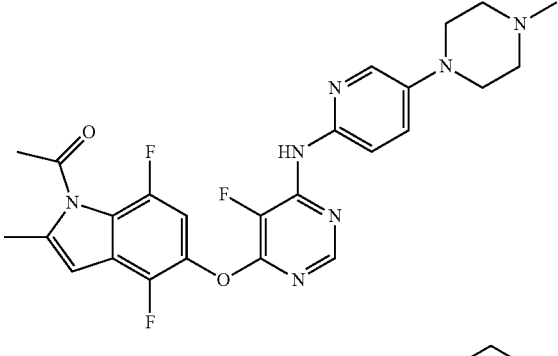
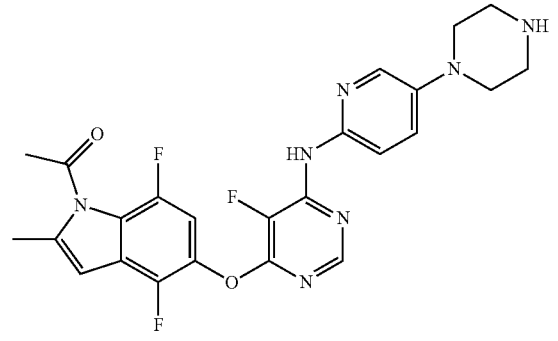
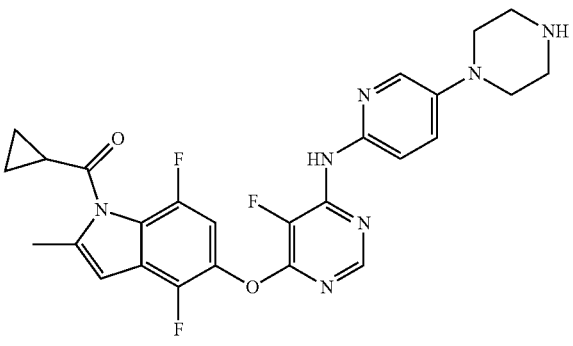
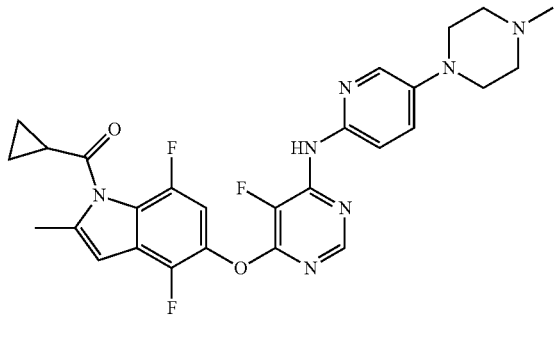

143
-continued
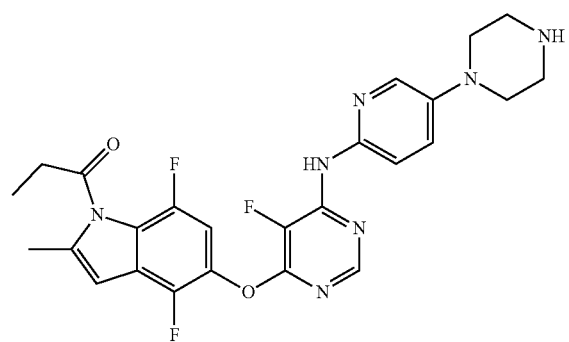
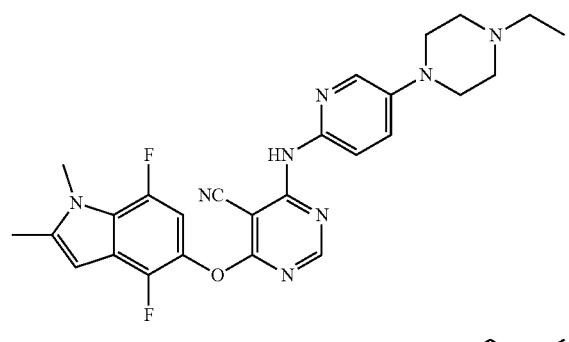
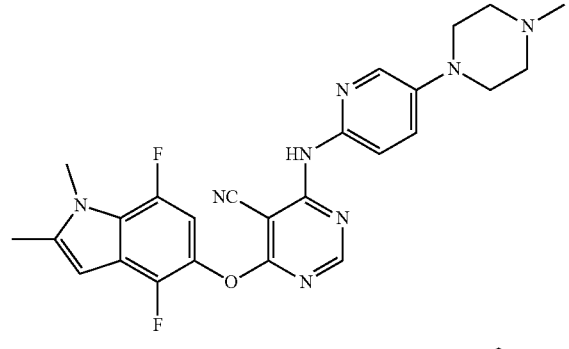
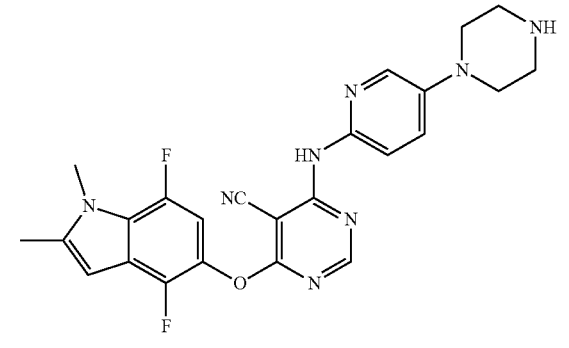
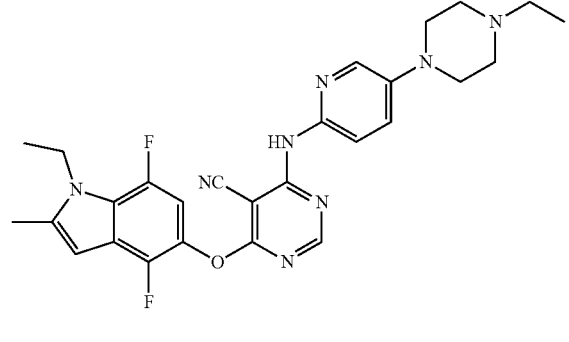
144
-continued
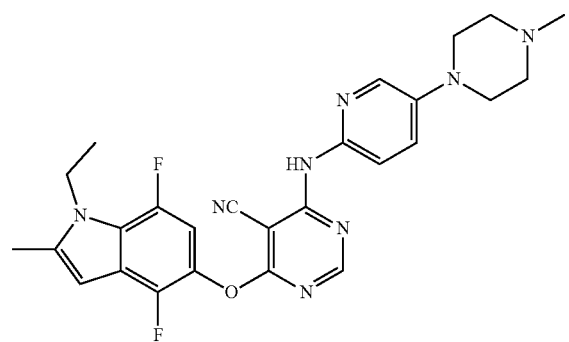
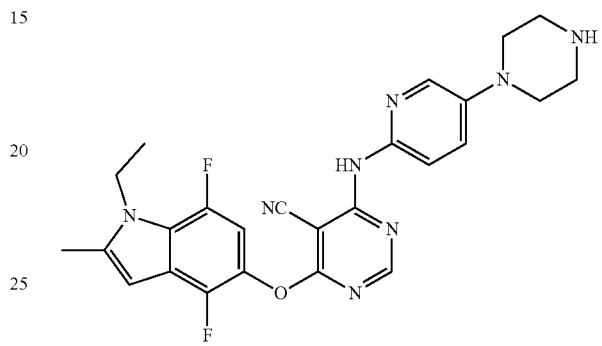
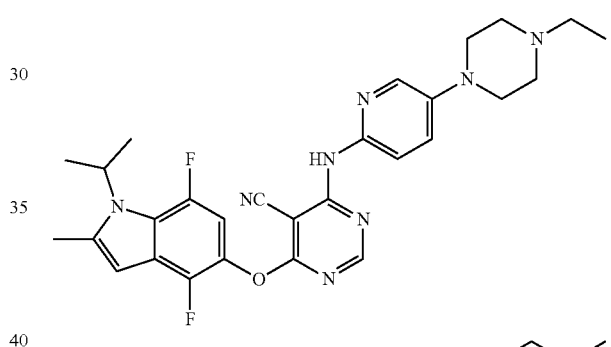
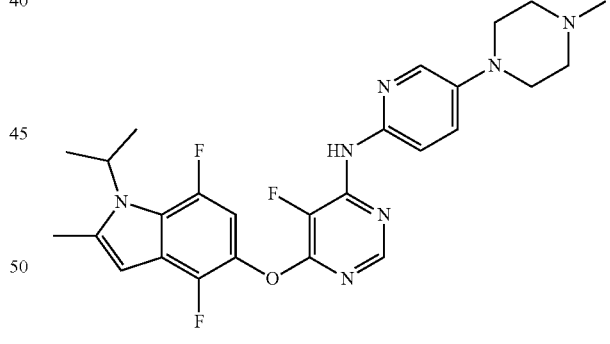
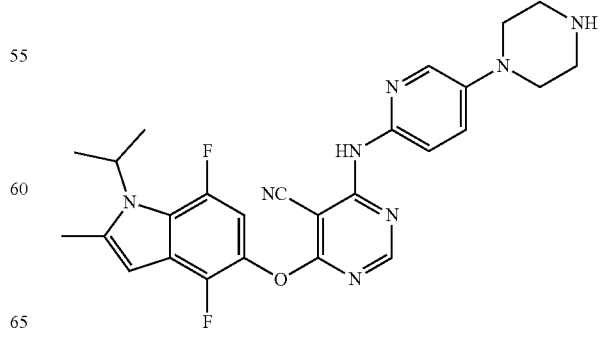

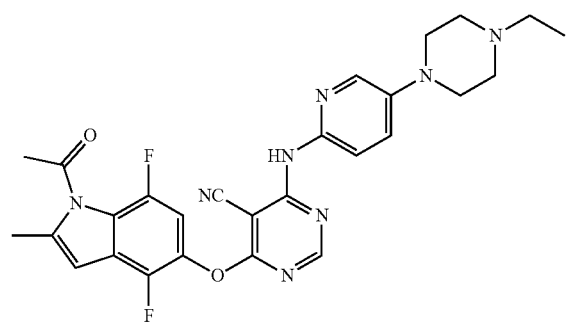
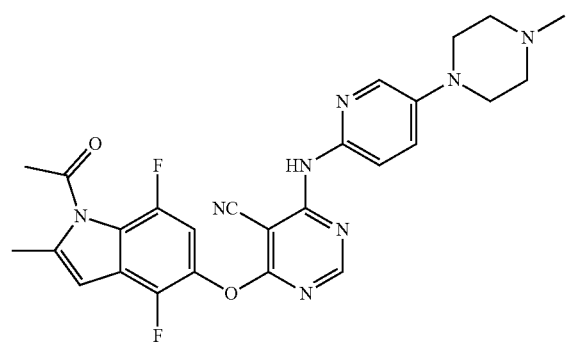
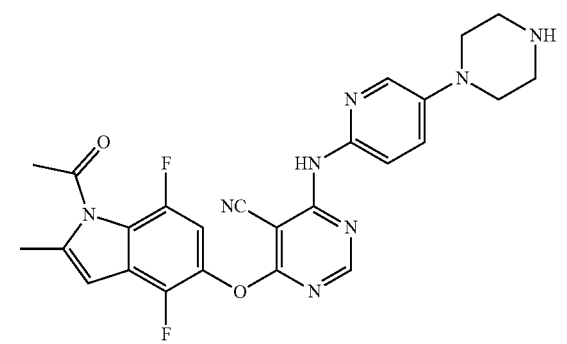
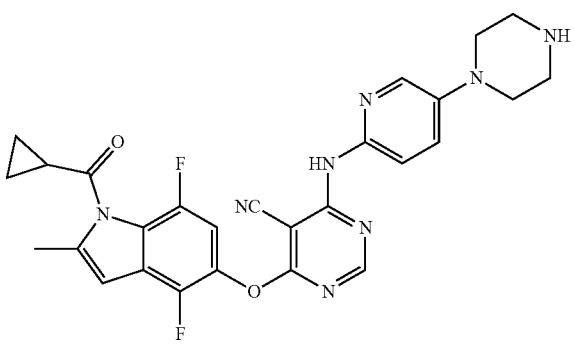
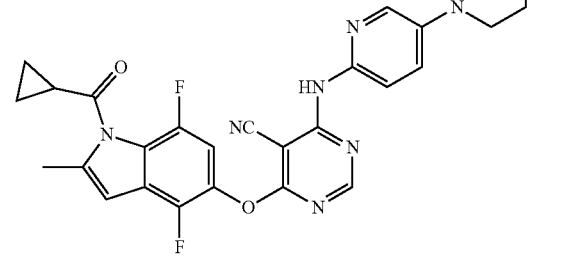
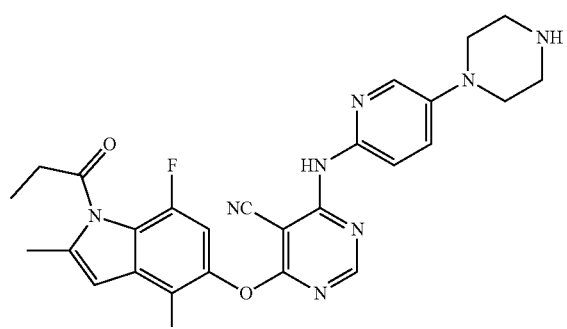
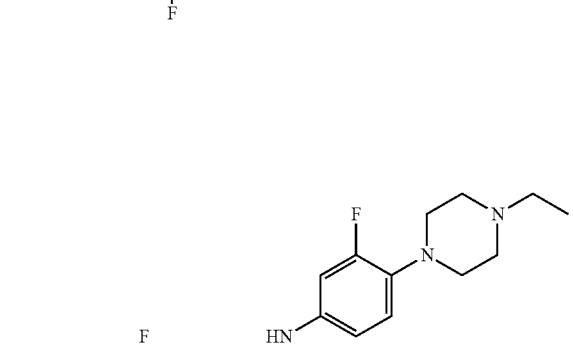
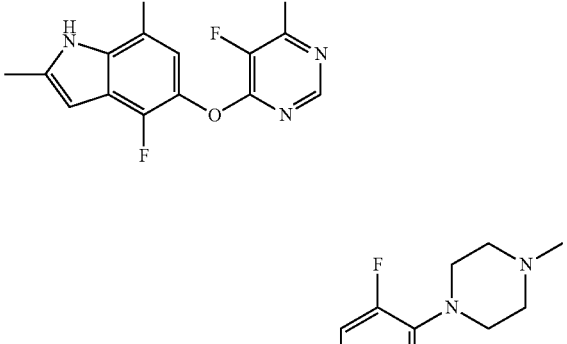
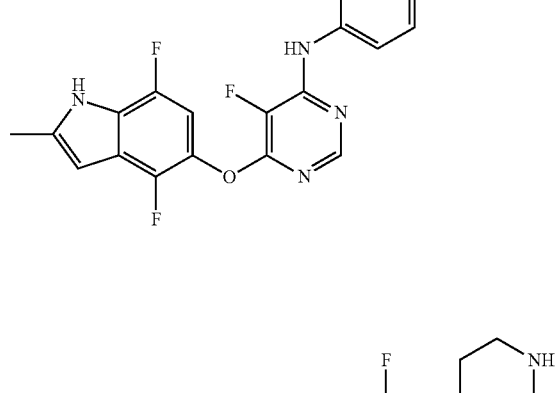
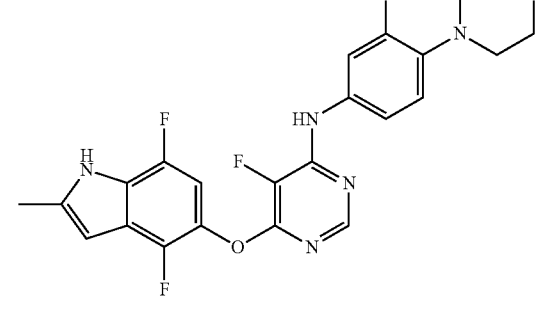

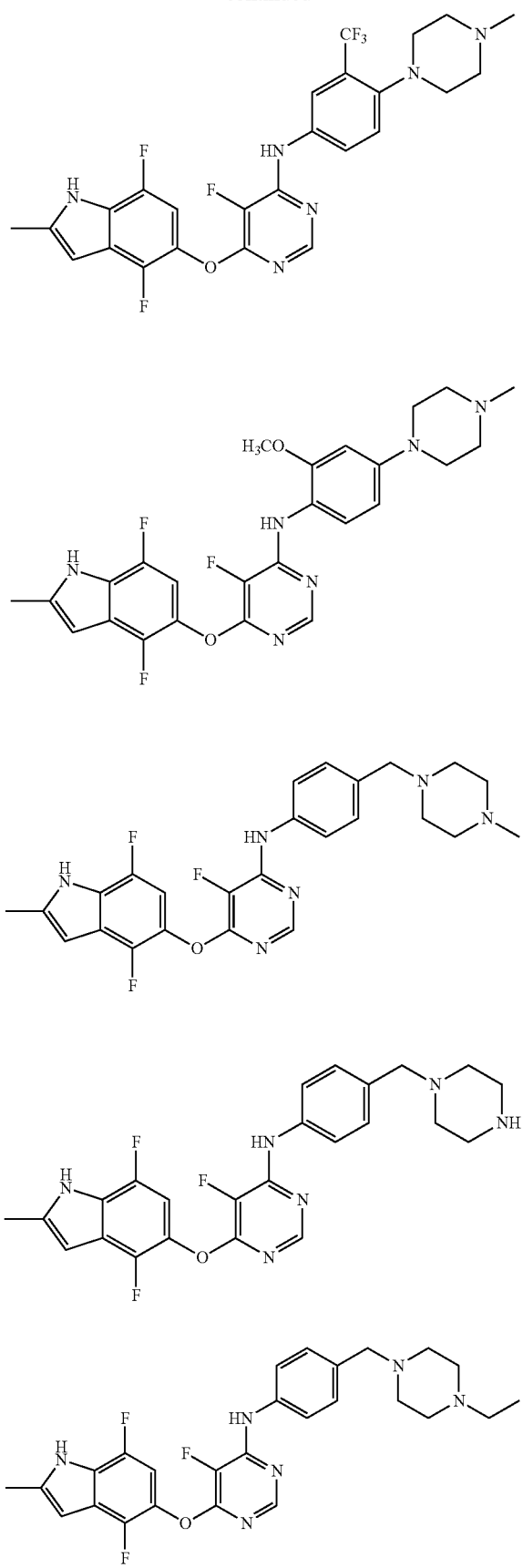
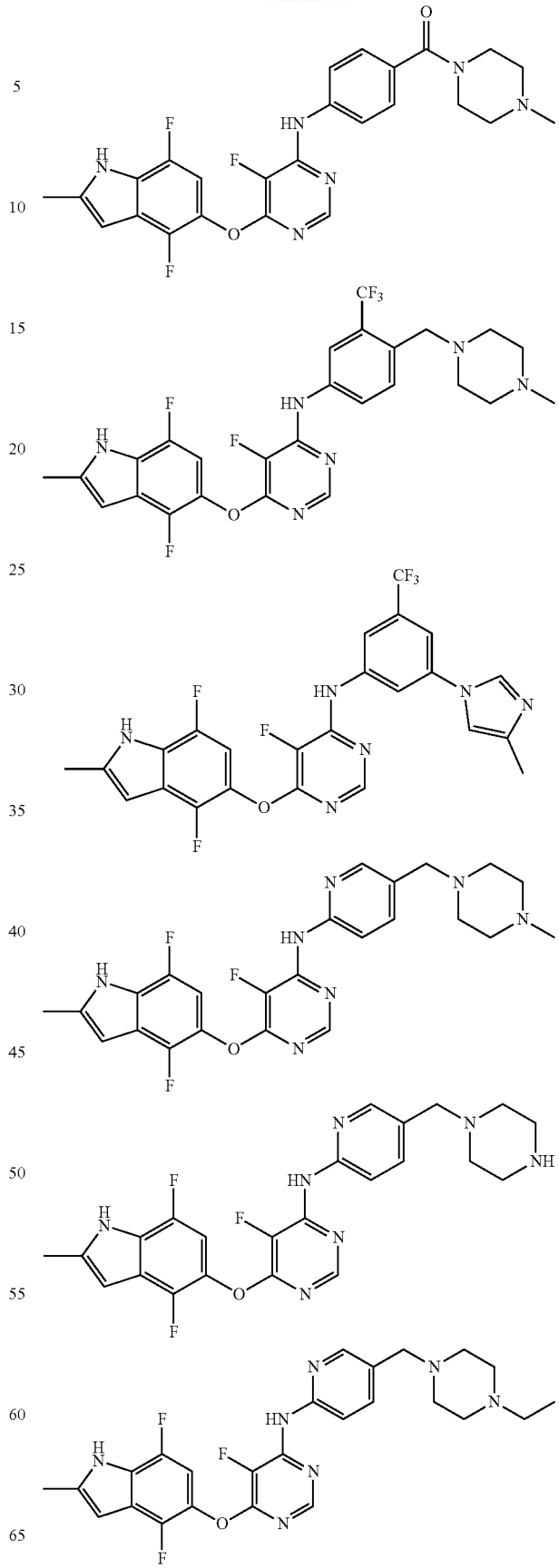

149
-continued
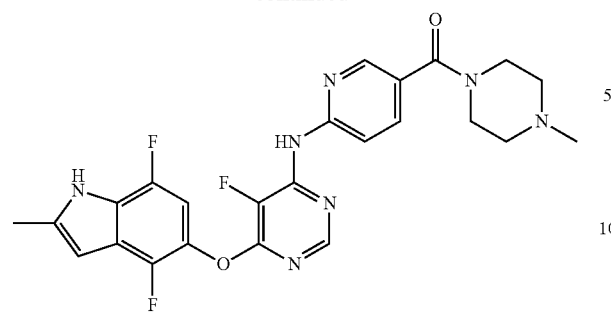
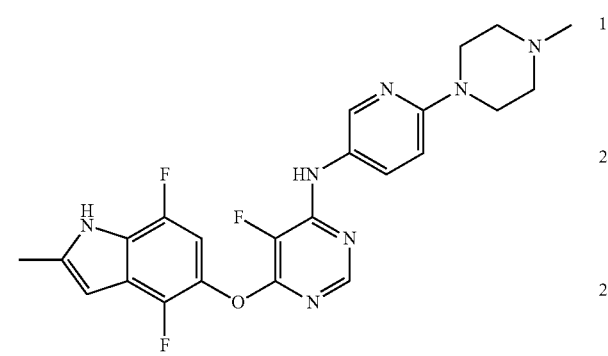
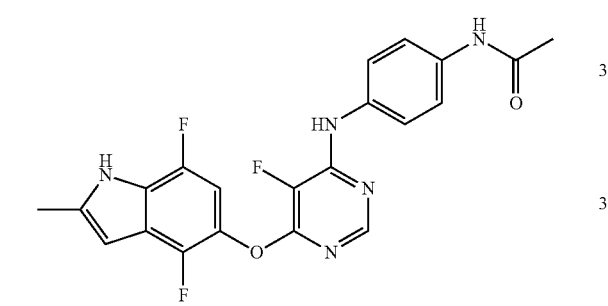
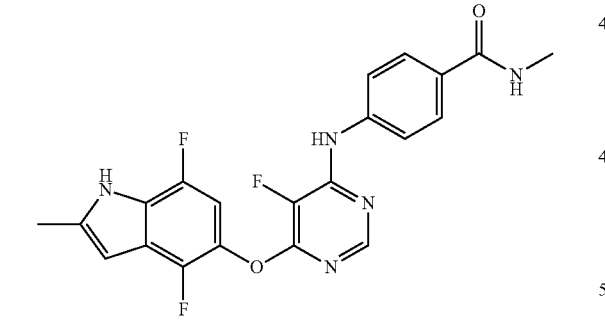
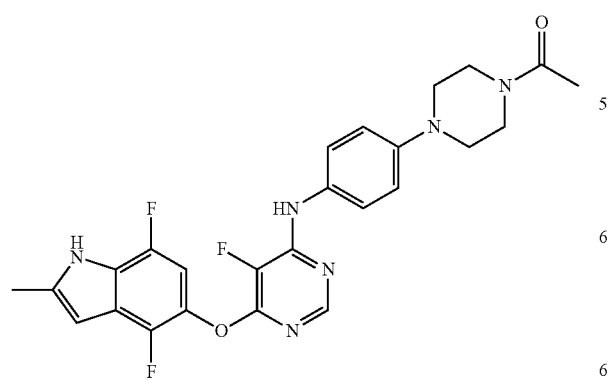
150
-continued
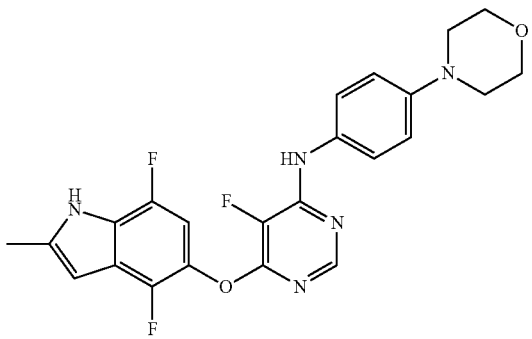
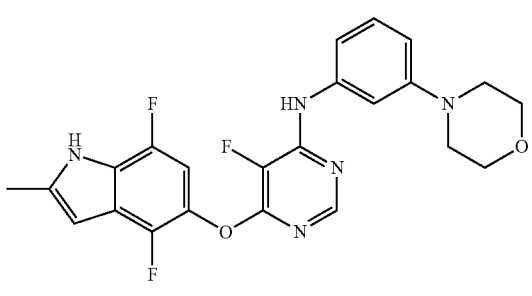
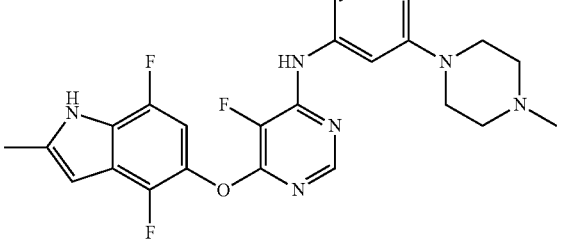
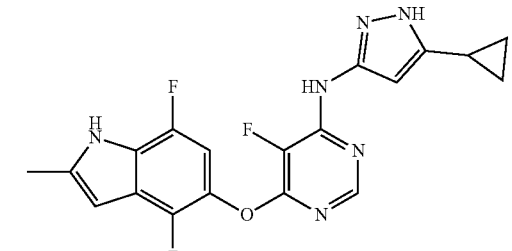
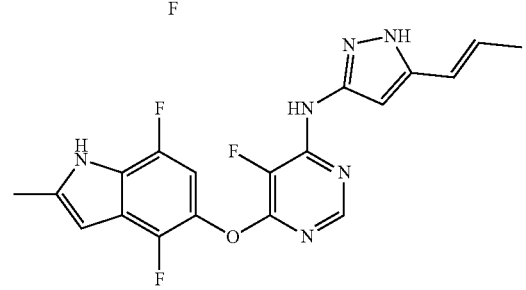
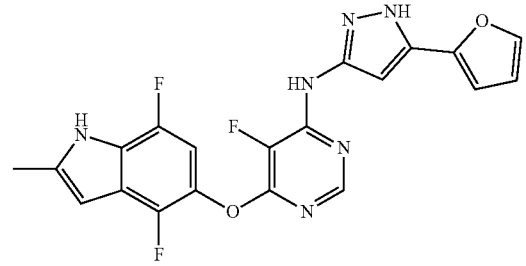

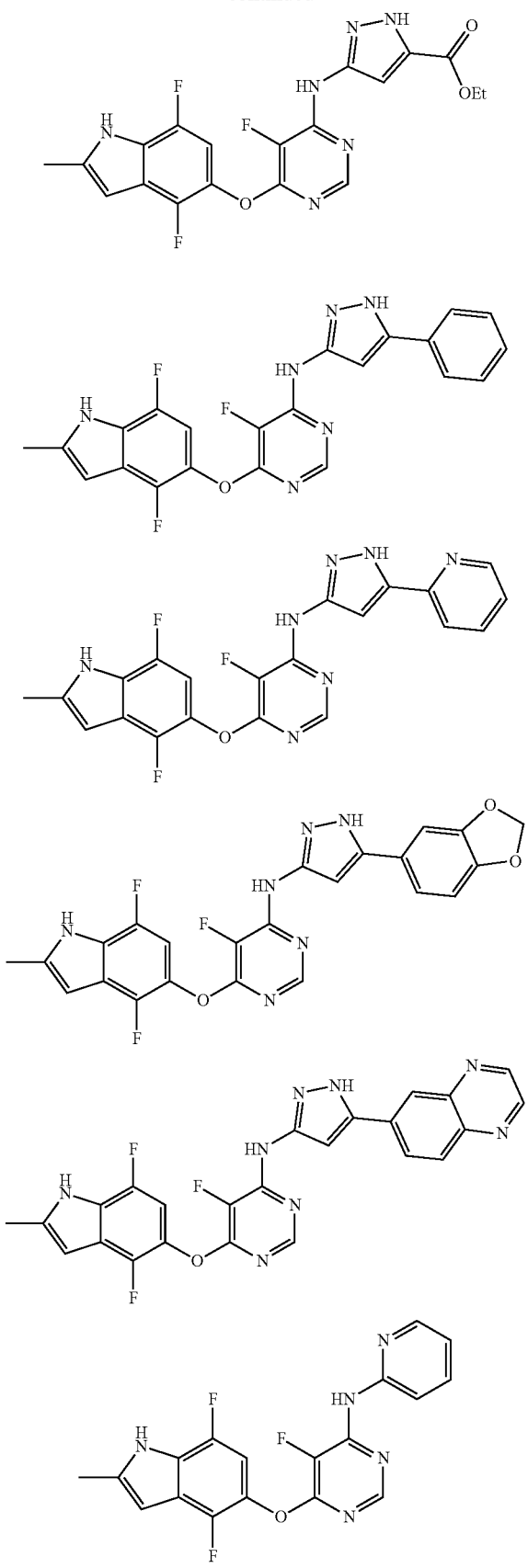
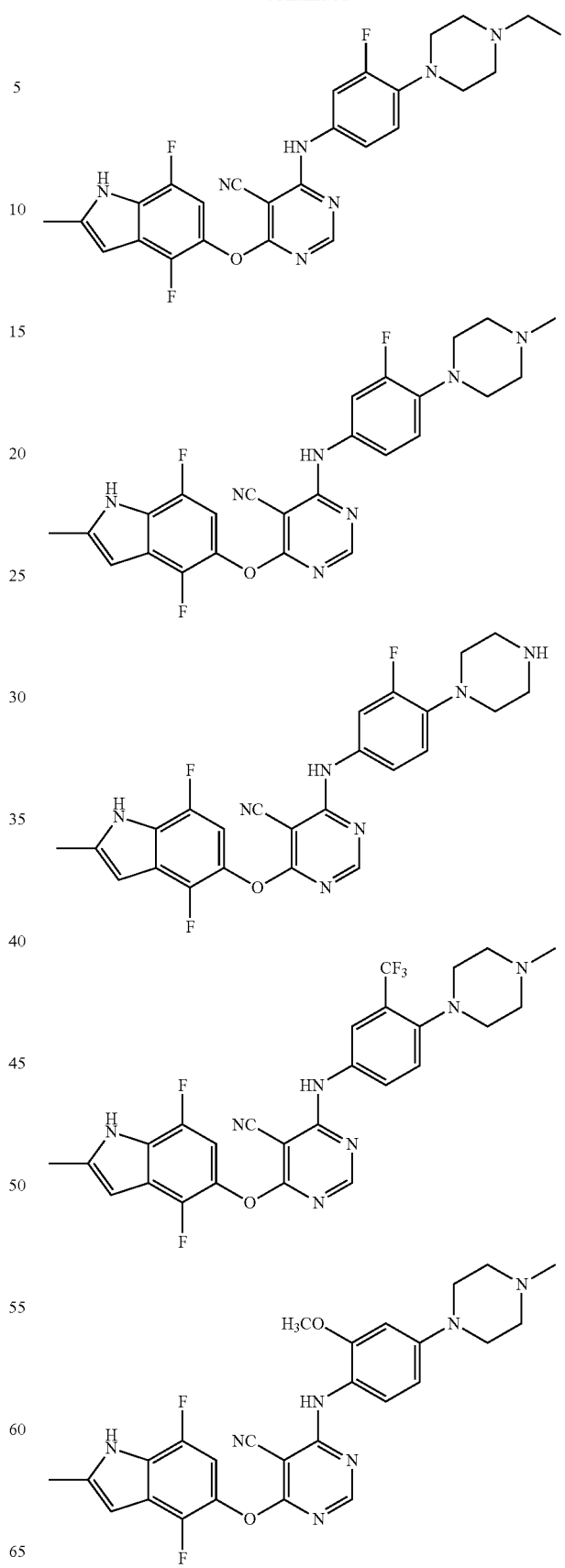

-continued

155
-continued
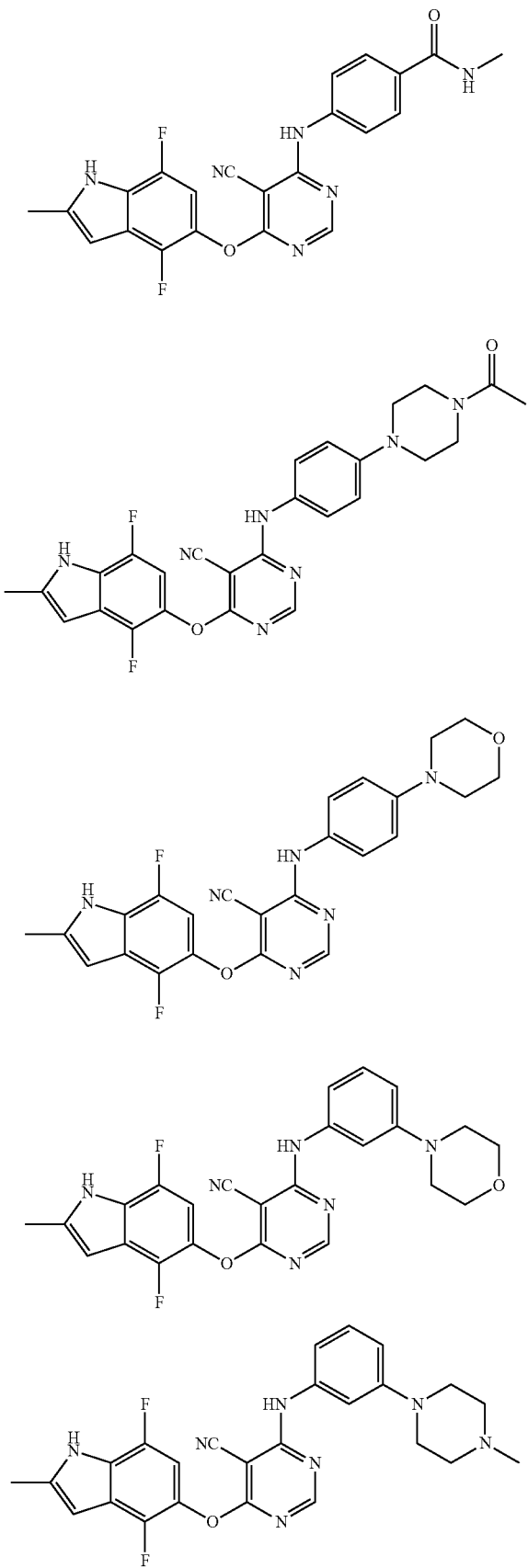
156
-continued
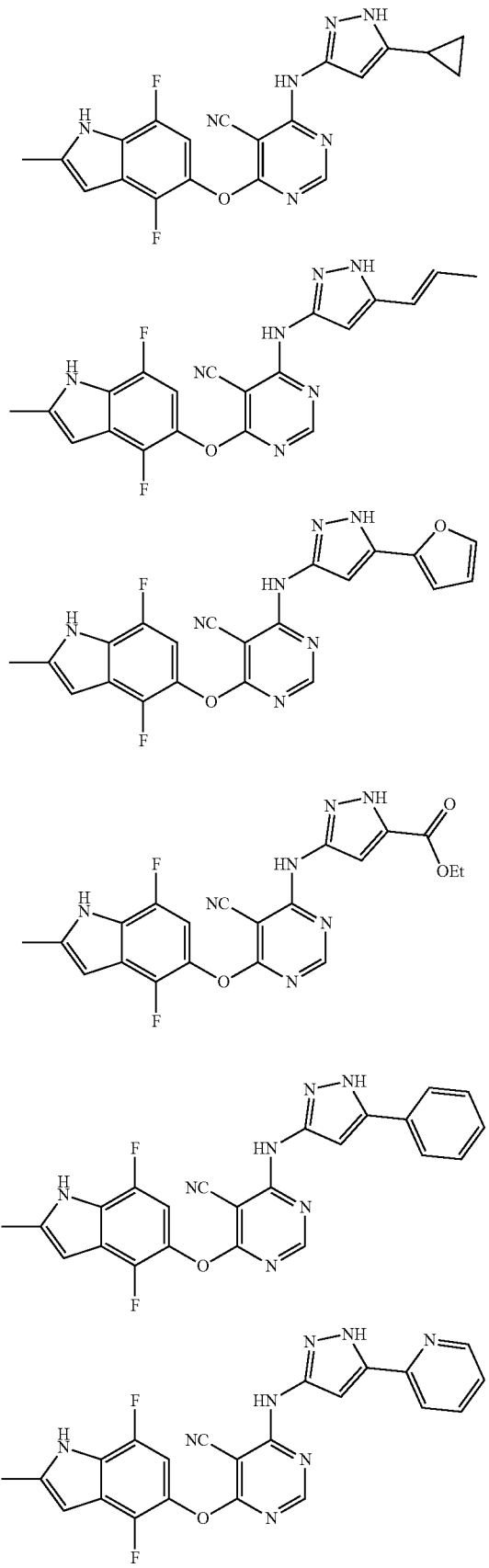

157
-continued
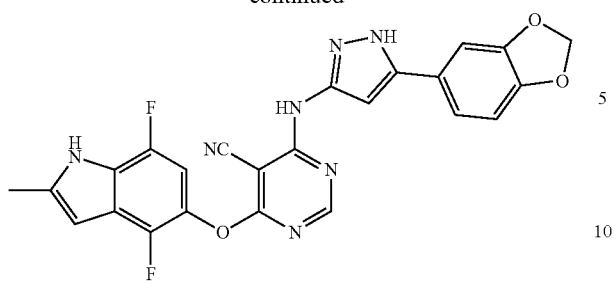
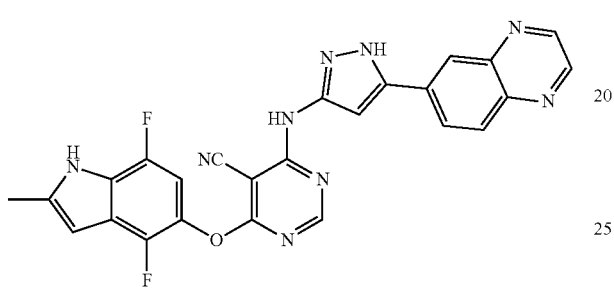
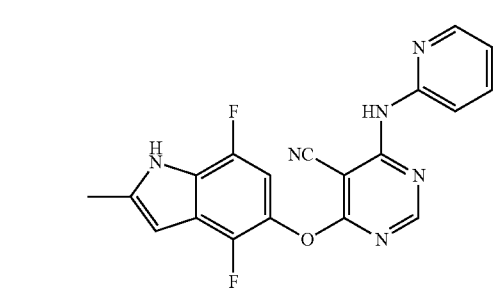
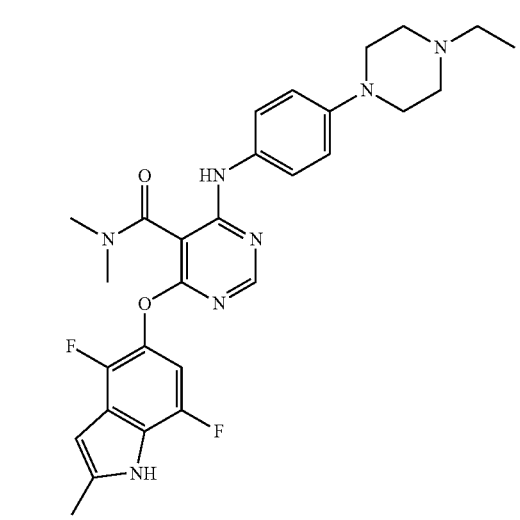
158
-continued
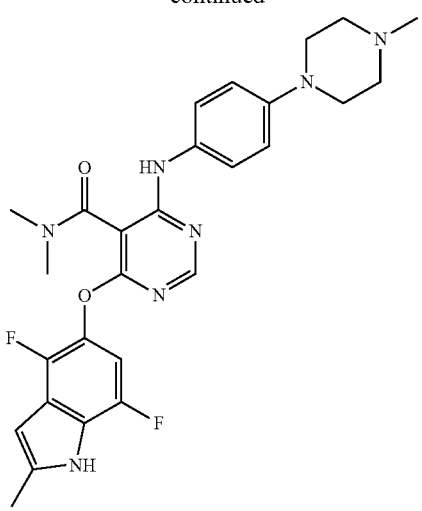
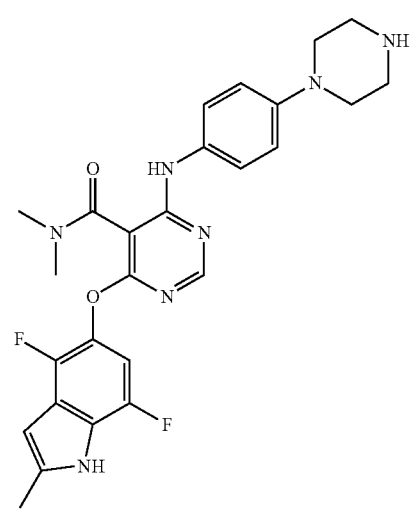
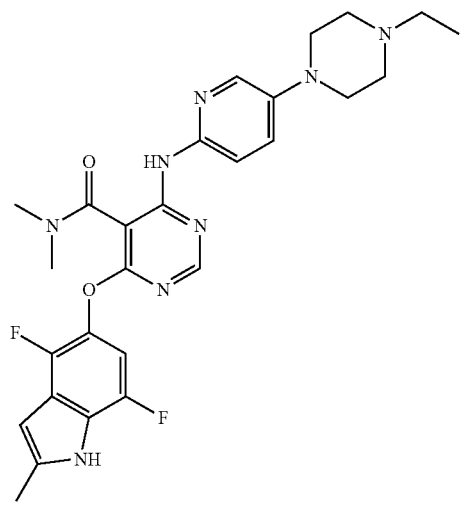

159
-continued
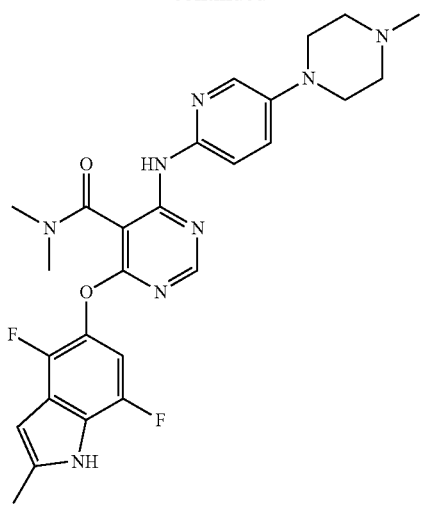
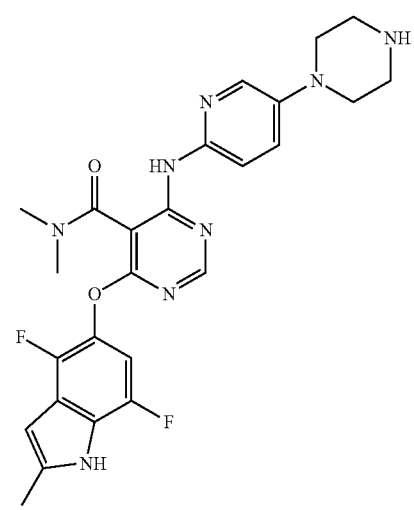
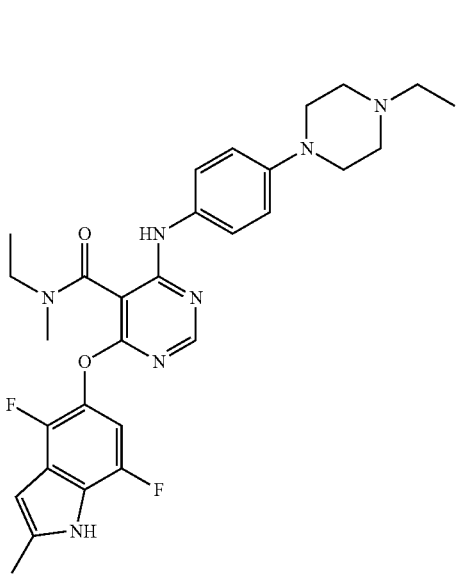
160
-continued
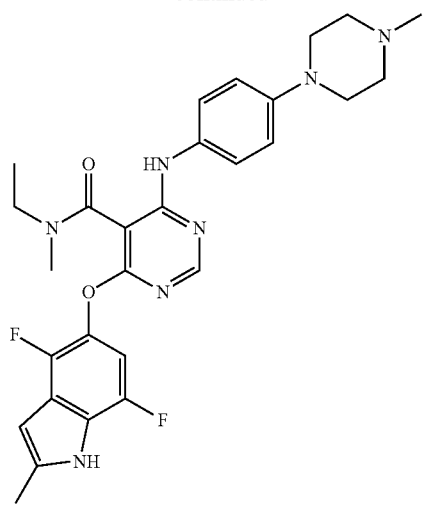
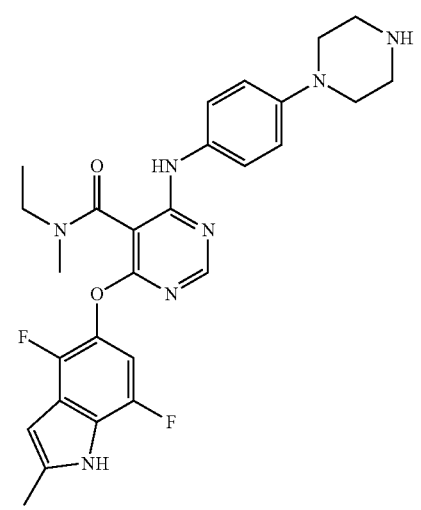
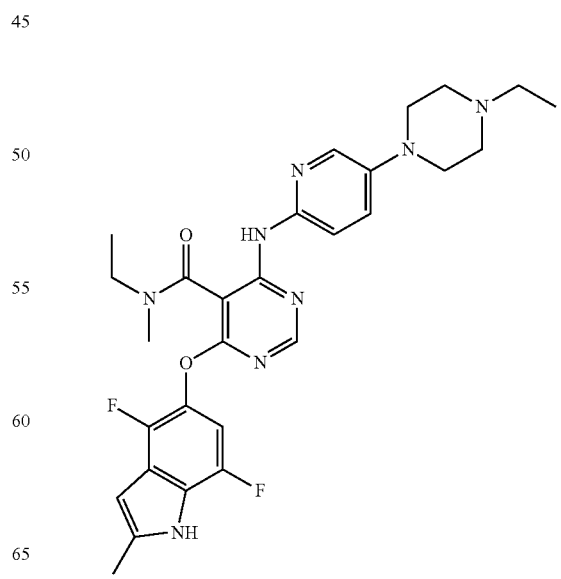

161
-continued
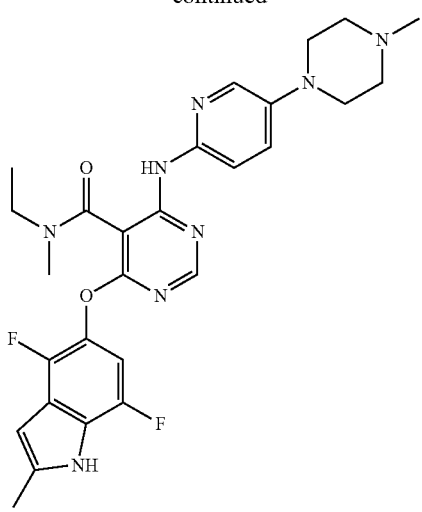
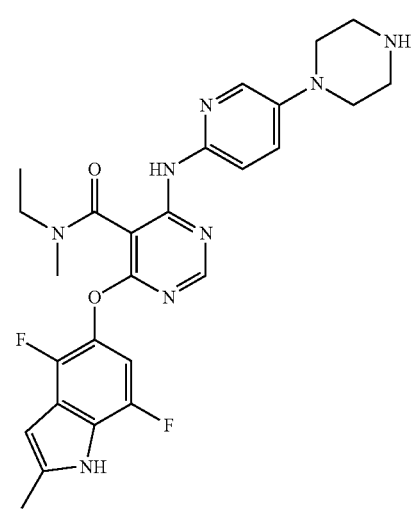
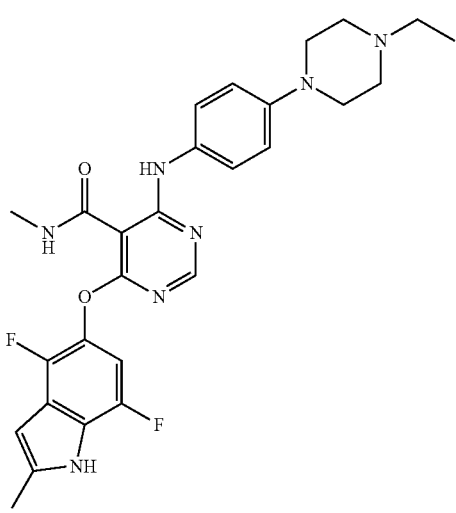
162
-continued
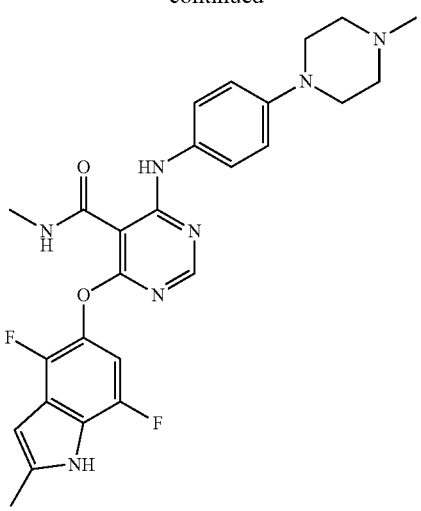
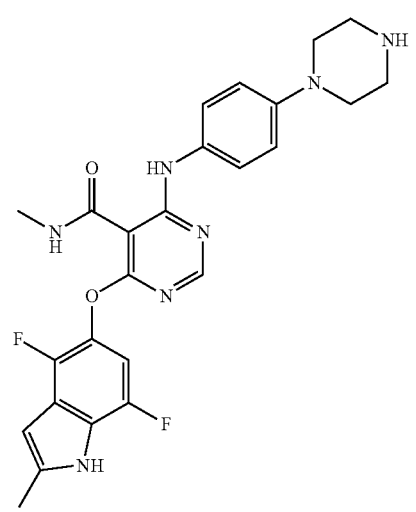
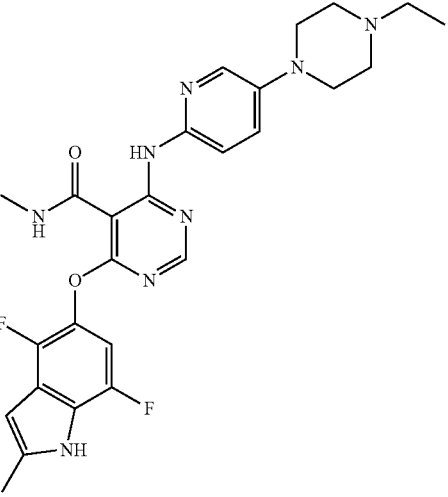

163
-continued
164
-continued
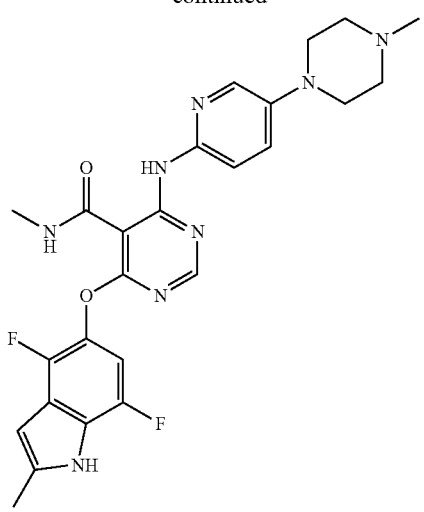
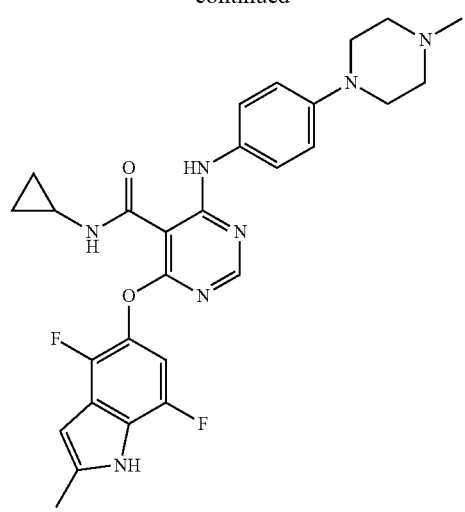
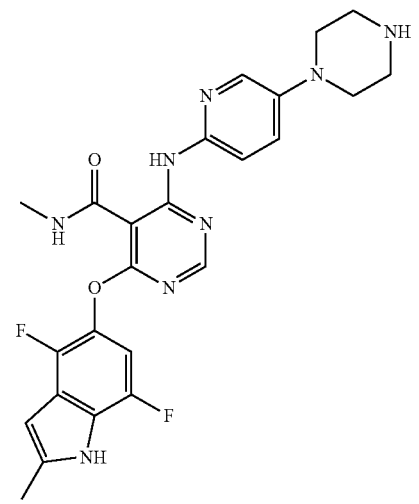
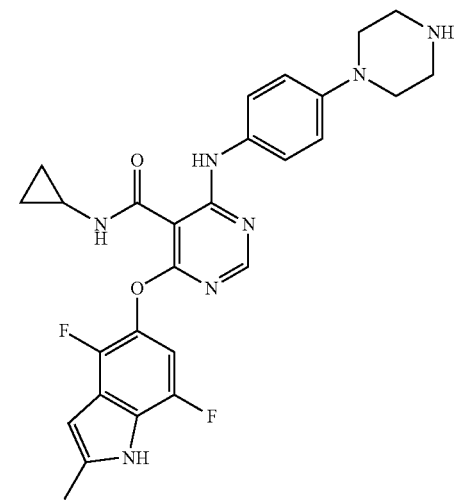

165
-continued
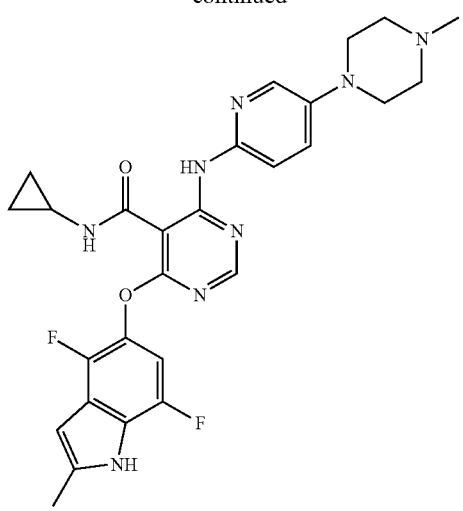
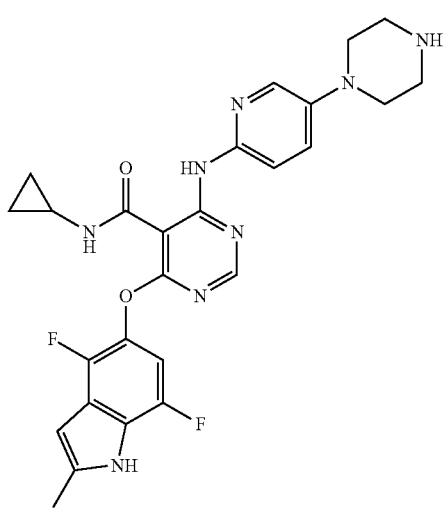
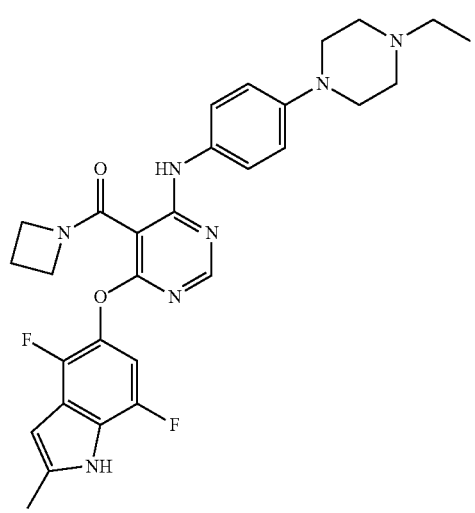
166
-continued
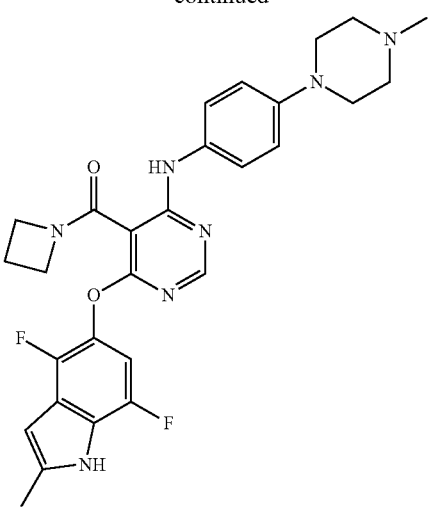
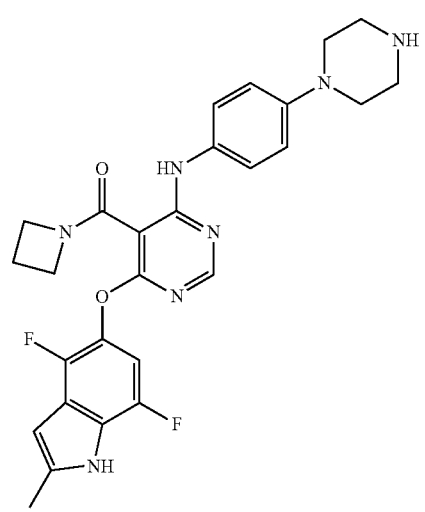
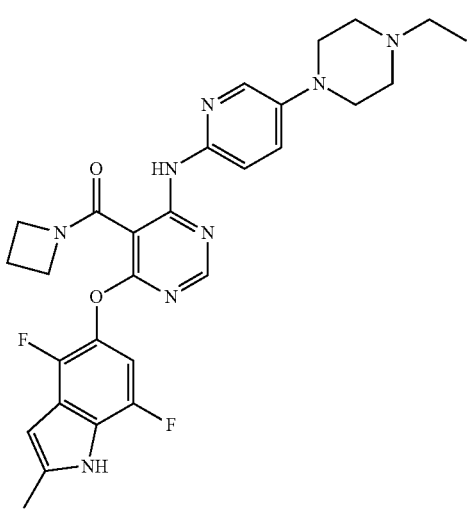

167
-continued
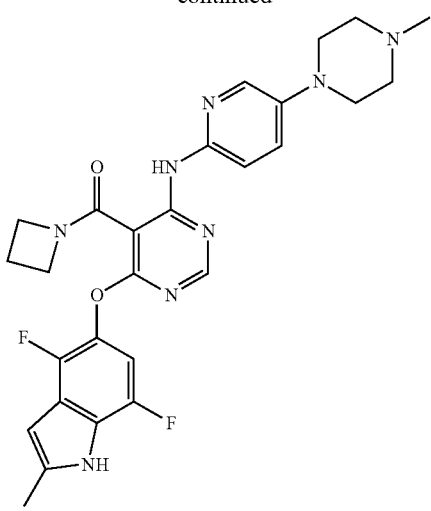
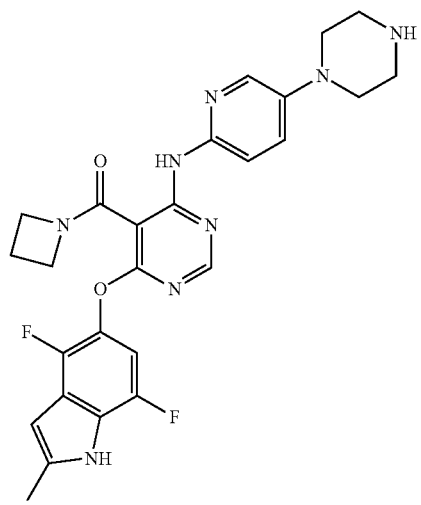
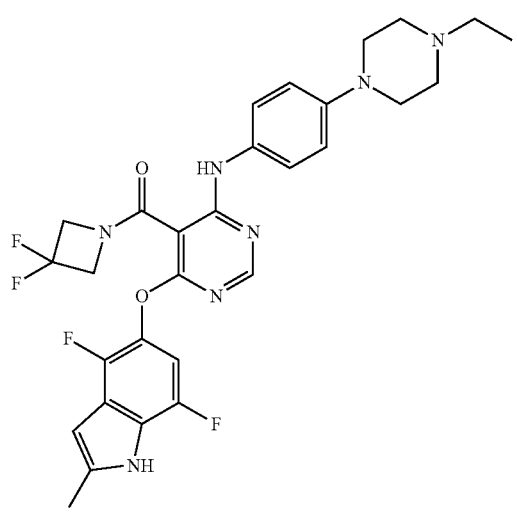
168
-continued
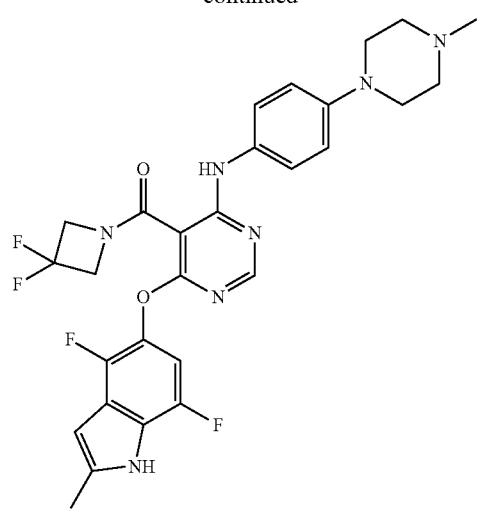
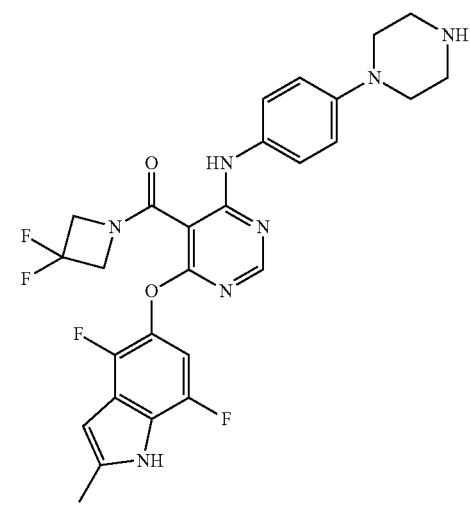
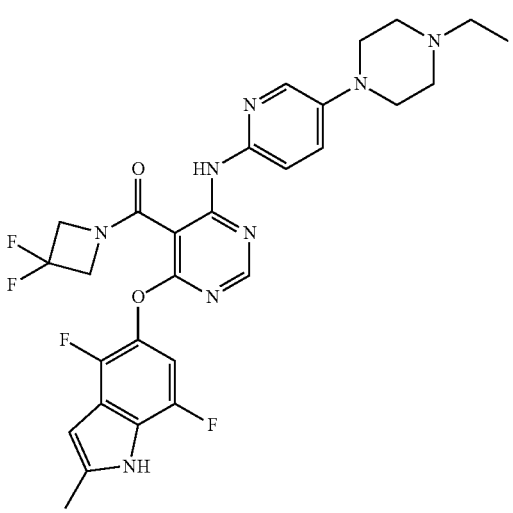

169
-continued
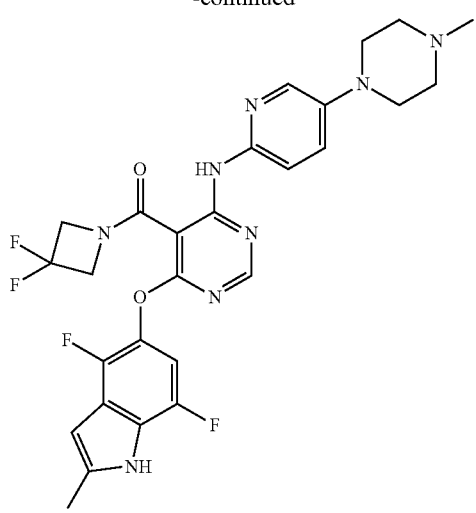
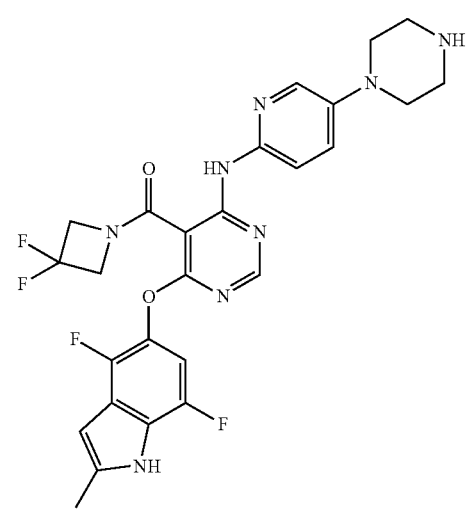
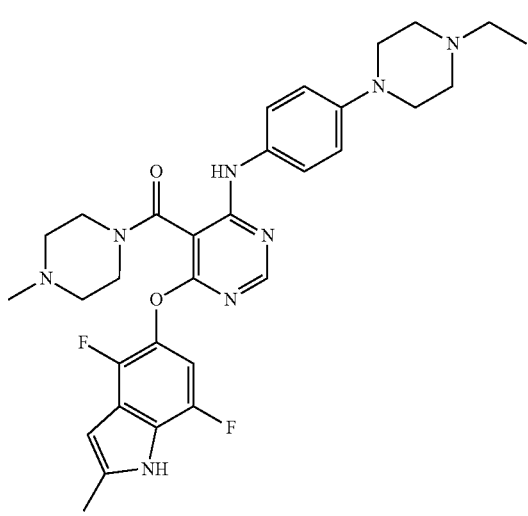
170
-continued
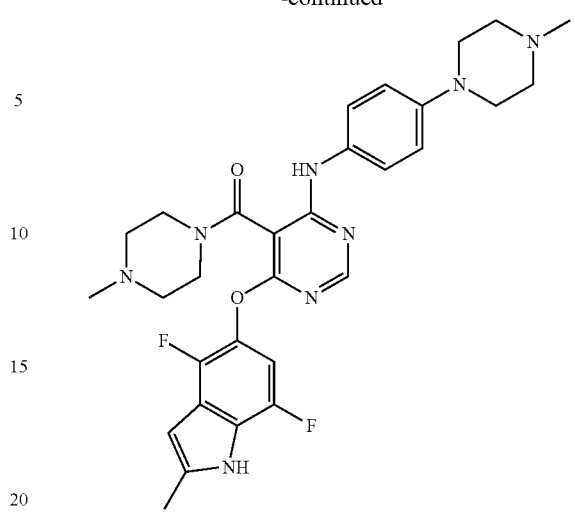
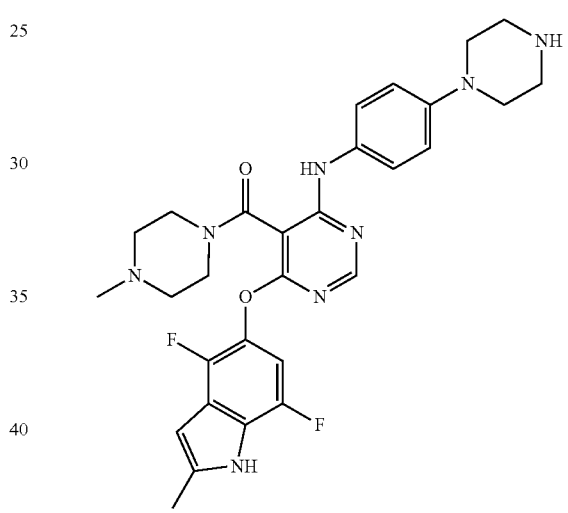
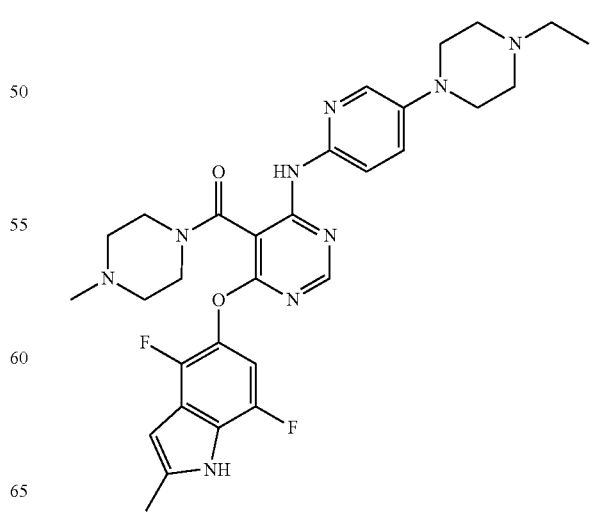

171
-continued
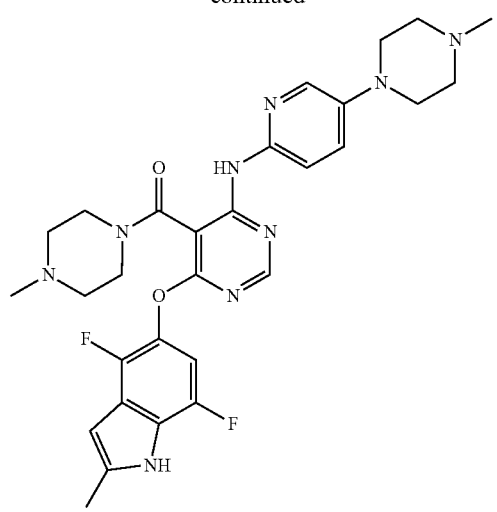
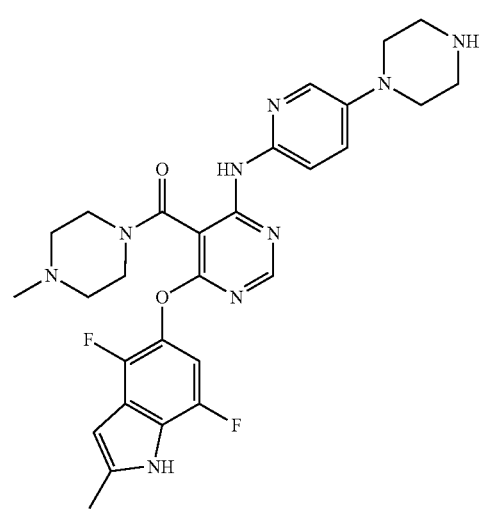
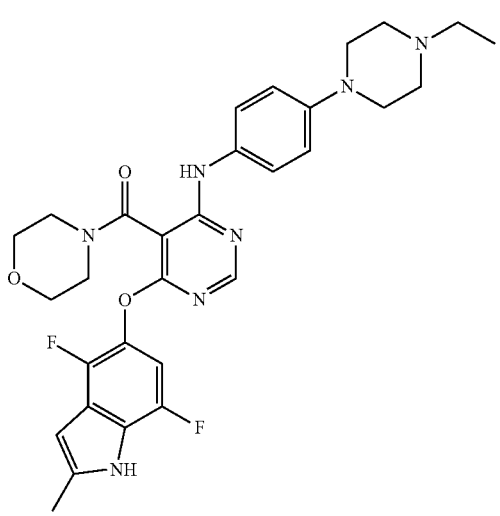
172
-continued
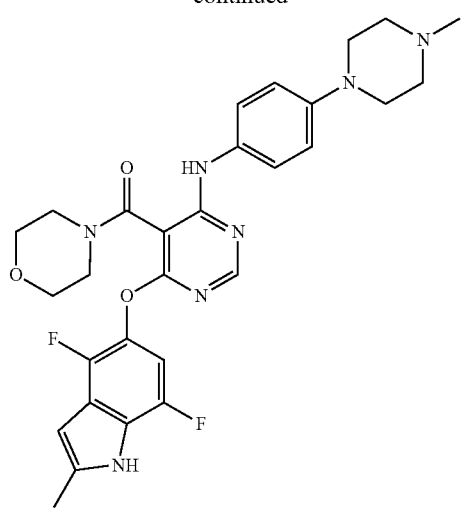

173
-continued
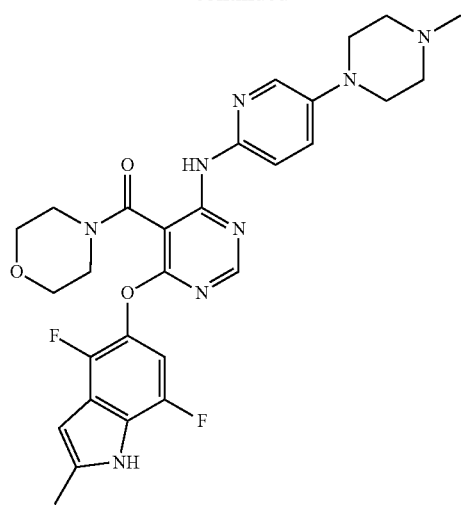
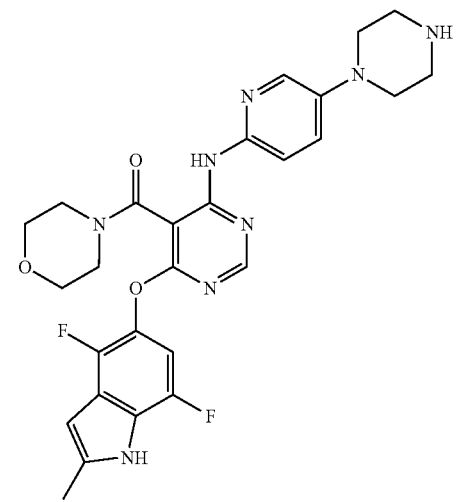
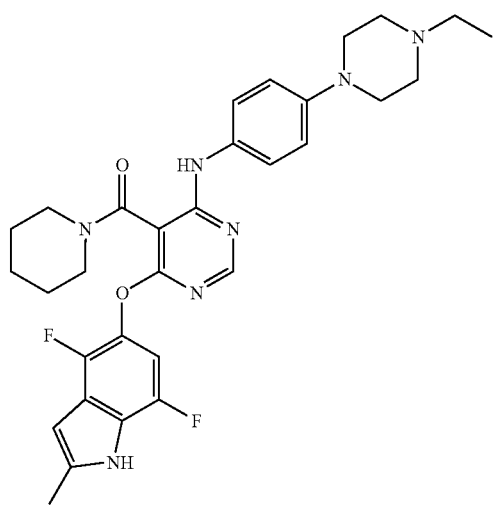
174
-continued
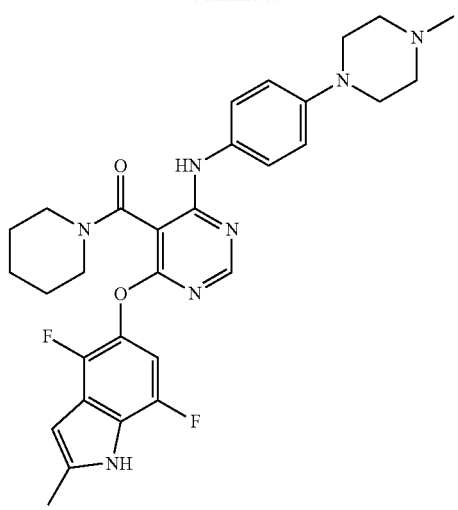
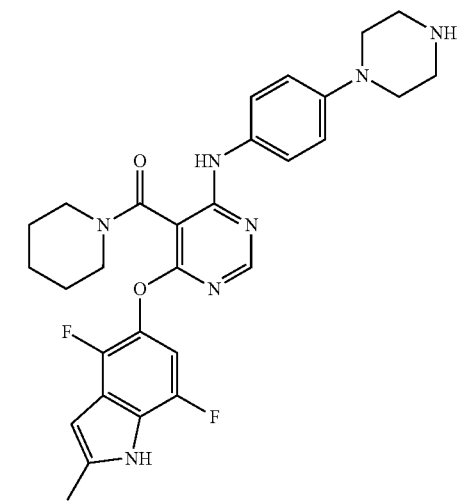

175
-continued
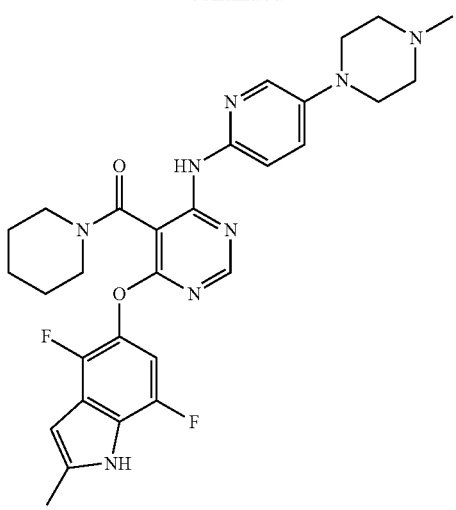
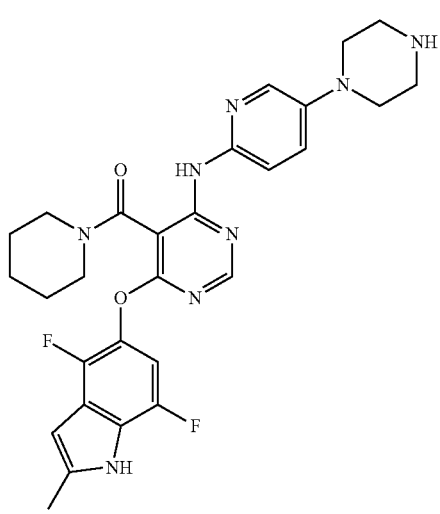
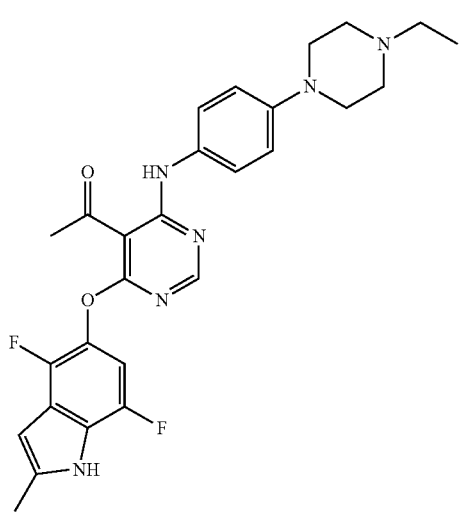
176
-continued
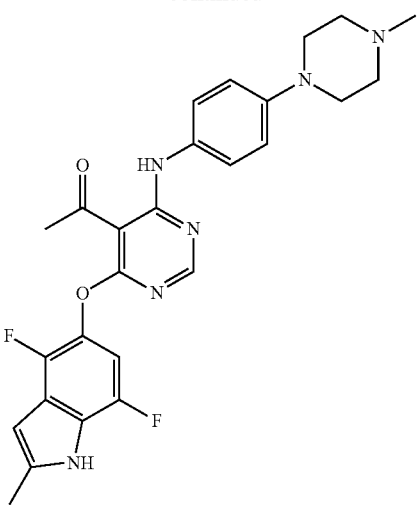
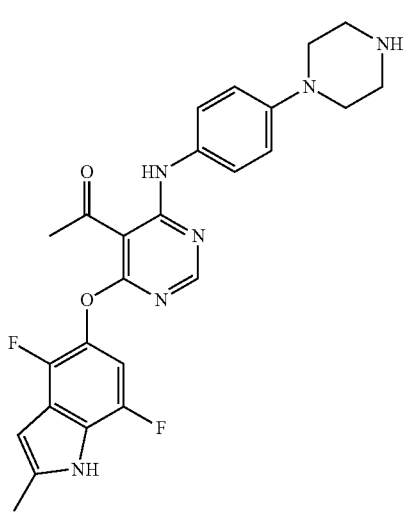
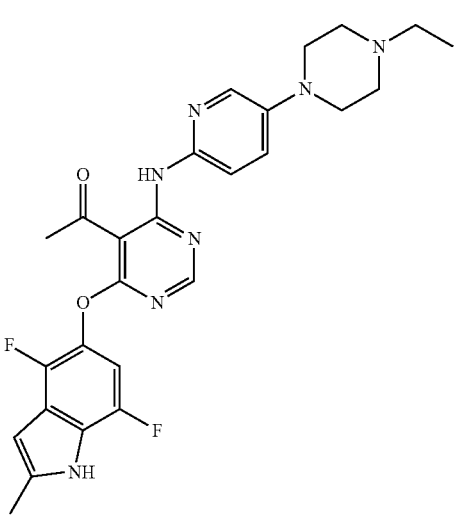

177
-continued
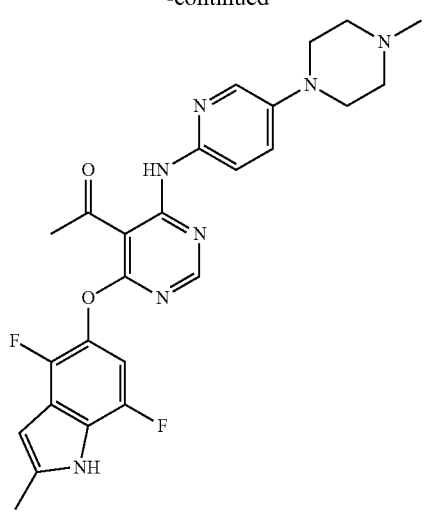
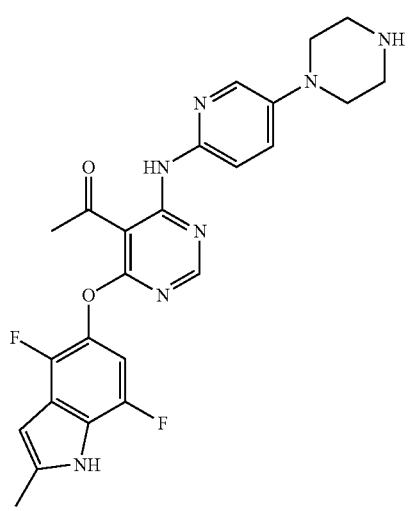
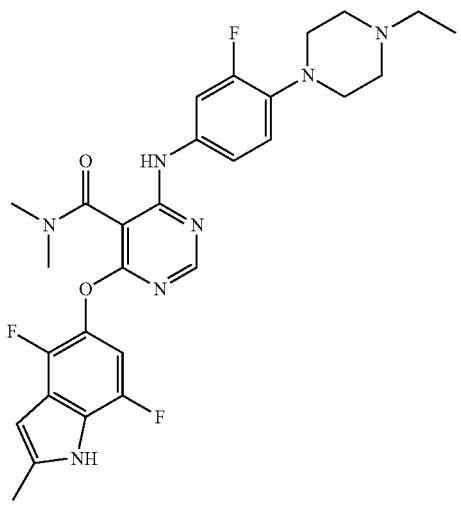
178
-continued
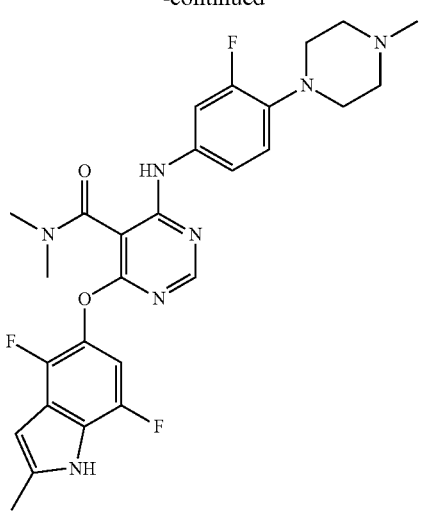
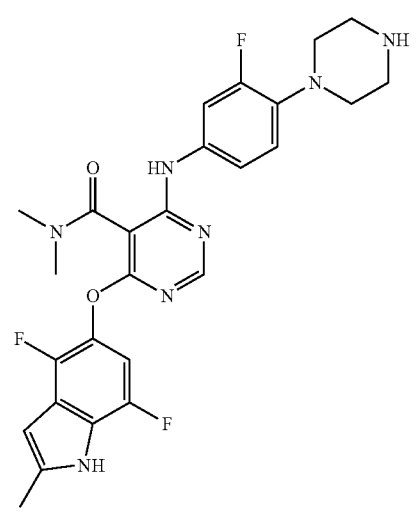
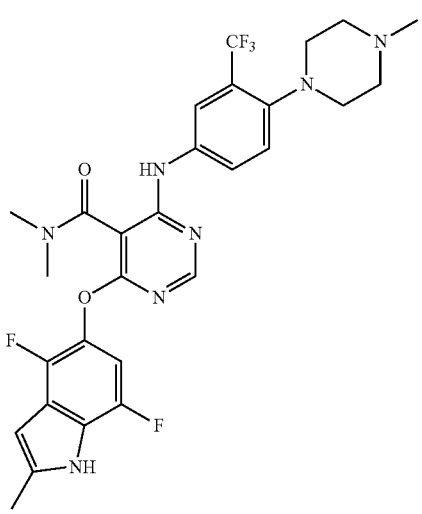

179
-continued
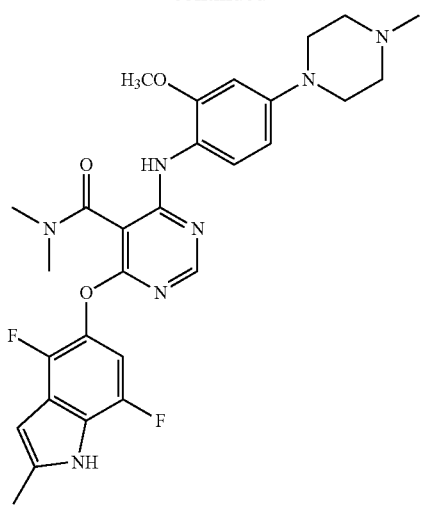
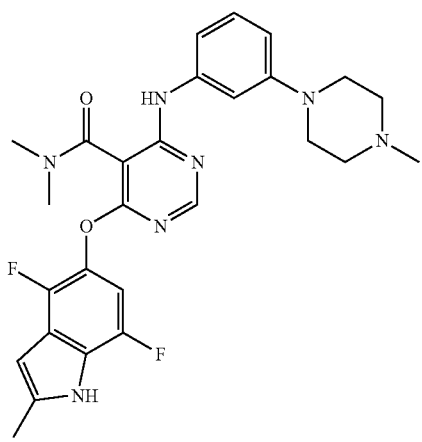
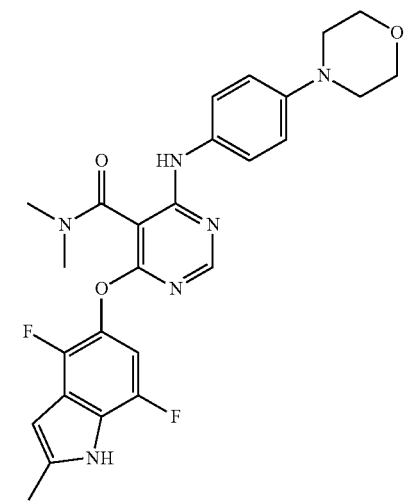
180
-continued
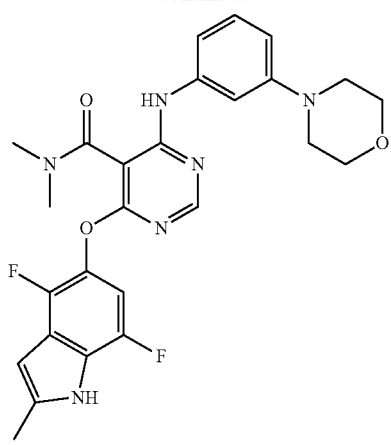
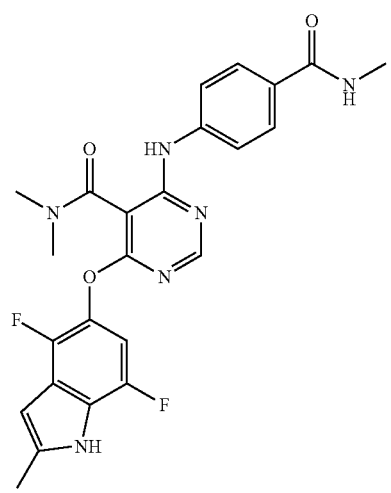
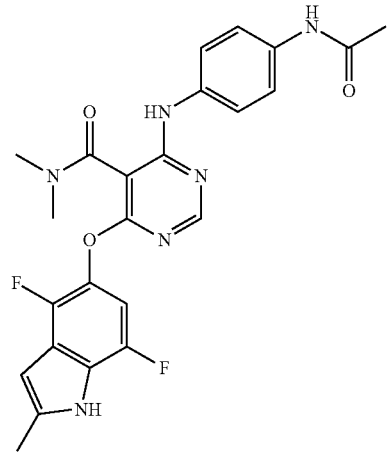

181
-continued
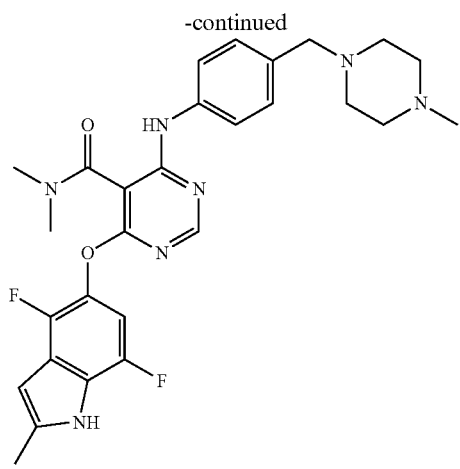
182
-continued
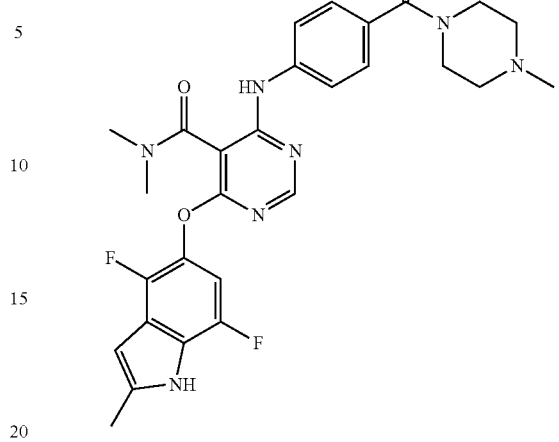
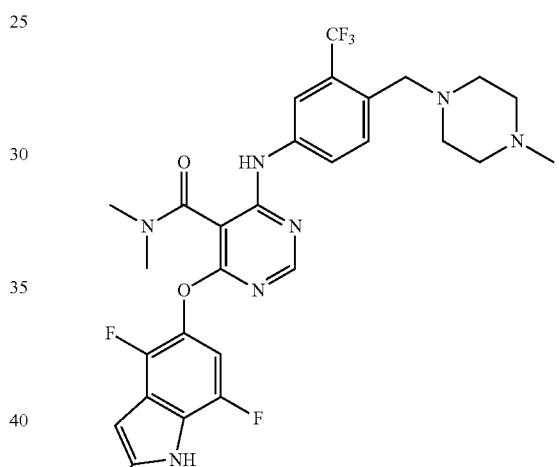
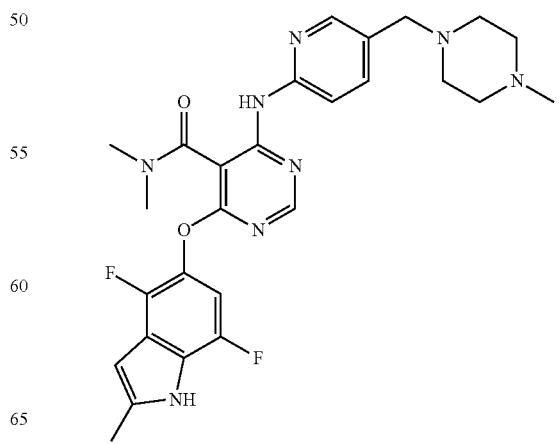

183
-continued
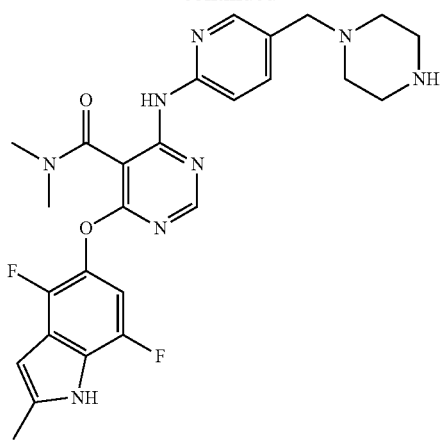
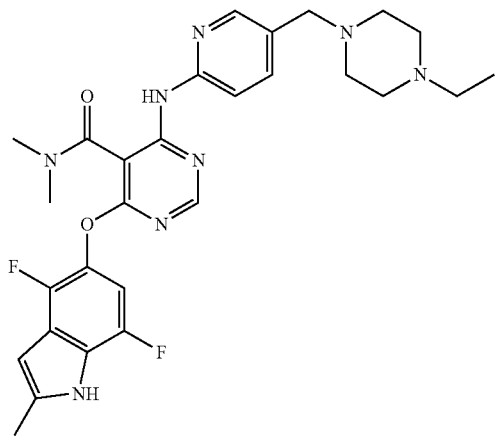
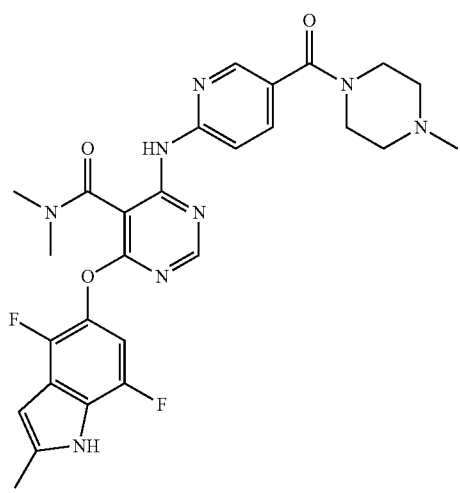
184
-continued
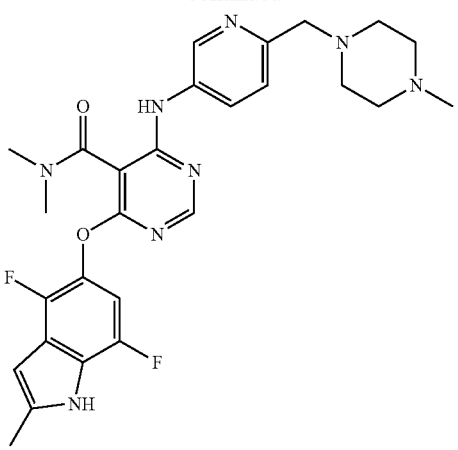
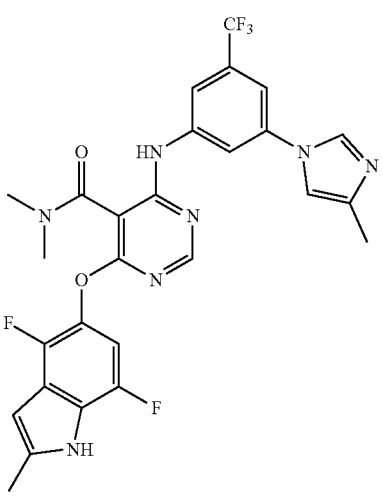
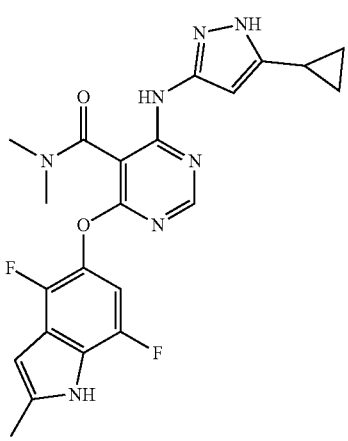

185
-continued
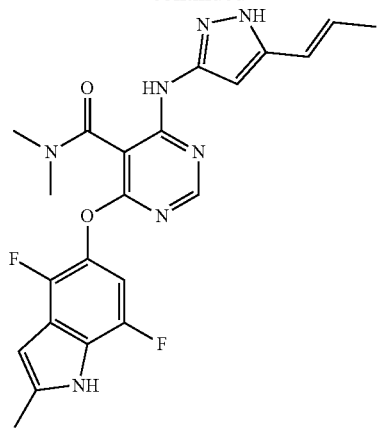
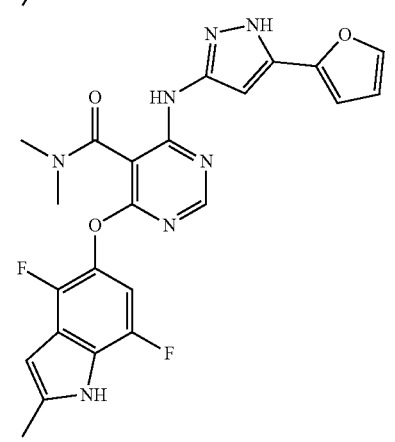
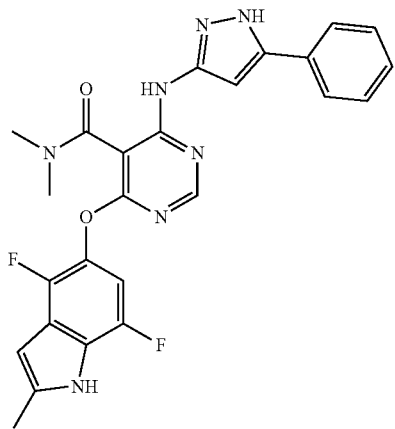
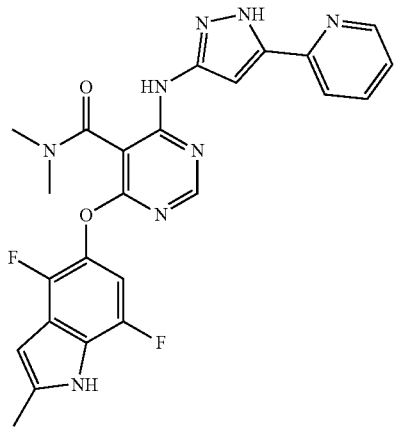
186
-continued
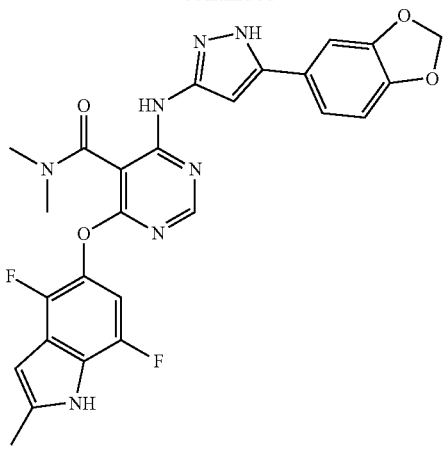

187
-continued
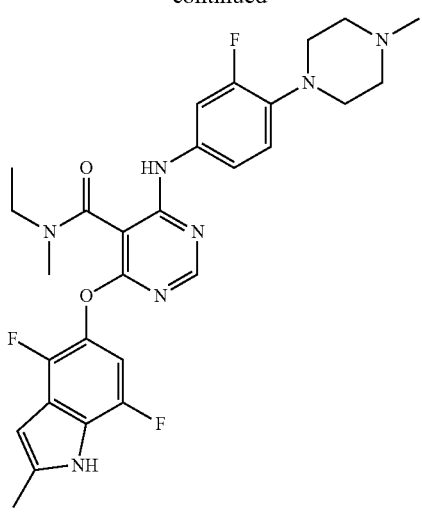
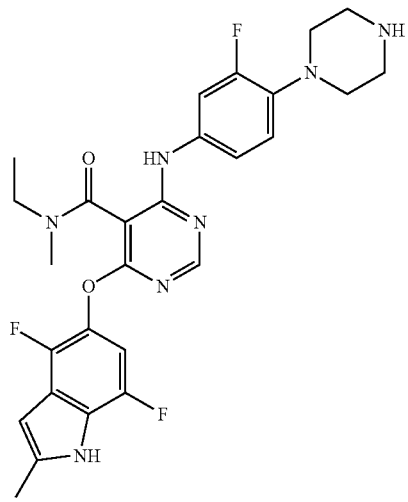
188
-continued
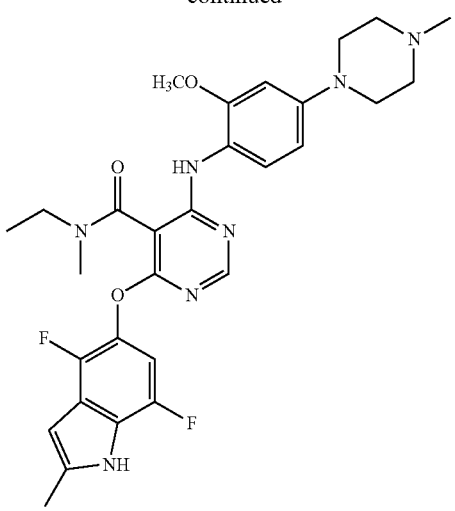
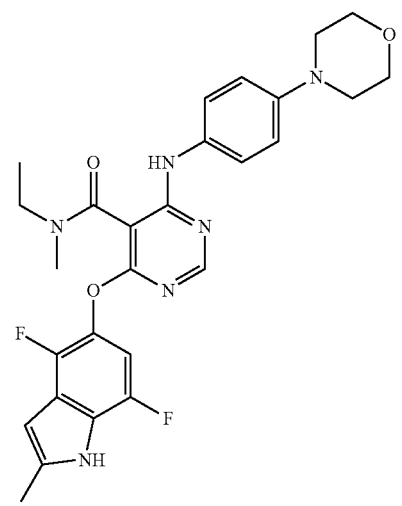

189
-continued
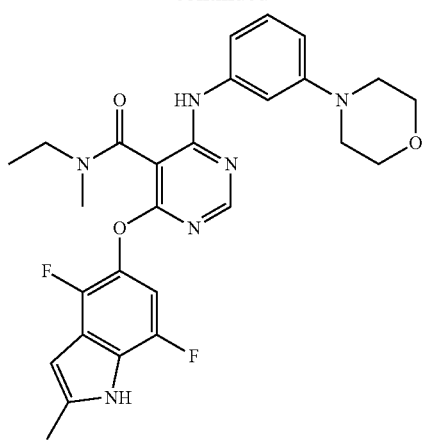
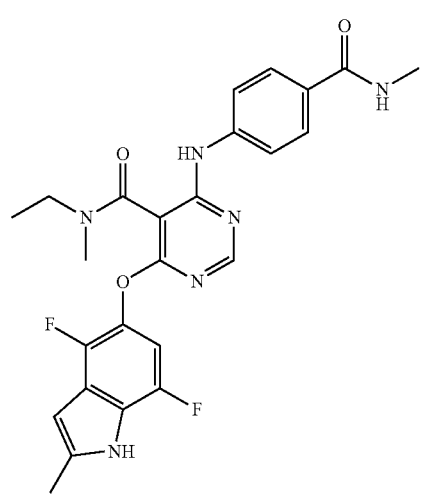
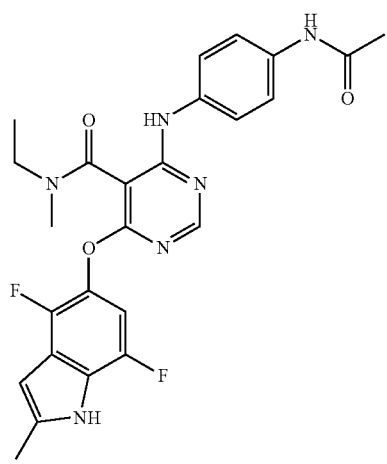
190
-continued
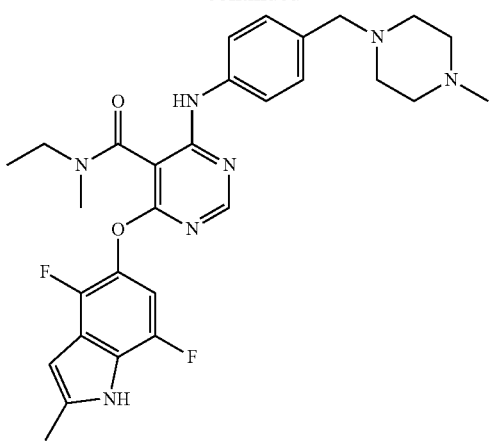
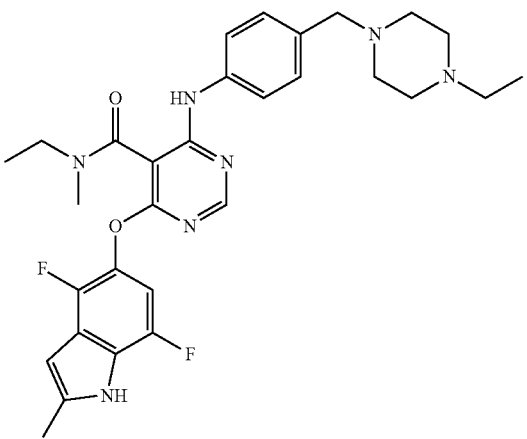

191
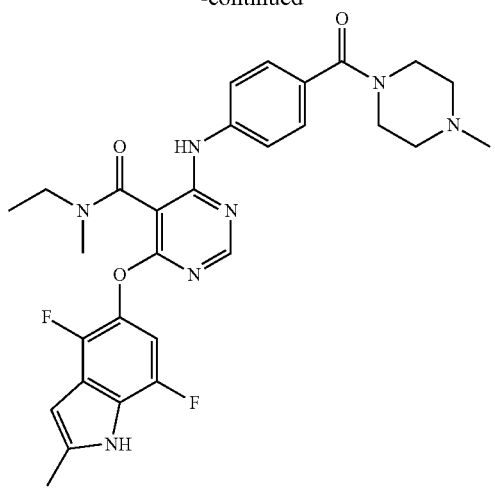
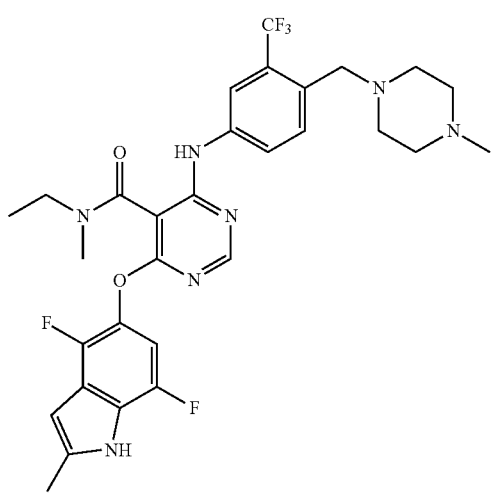
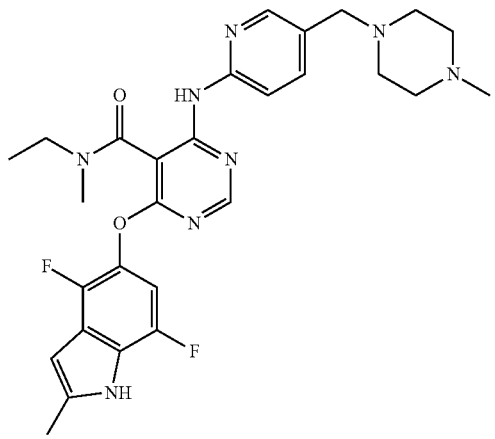
192
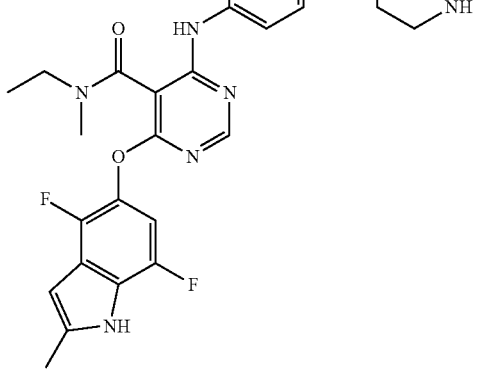
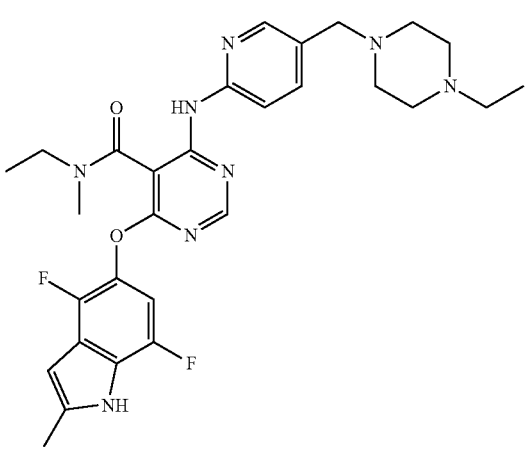
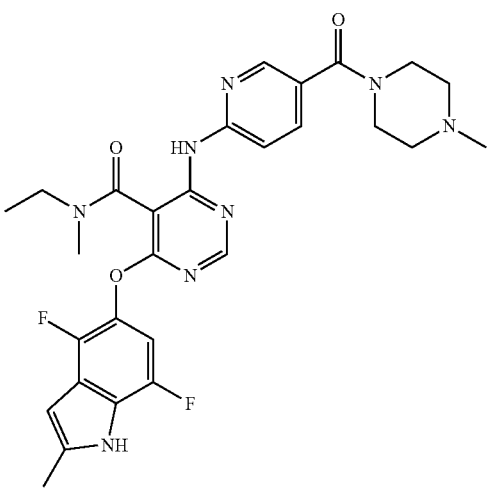

193
-continued
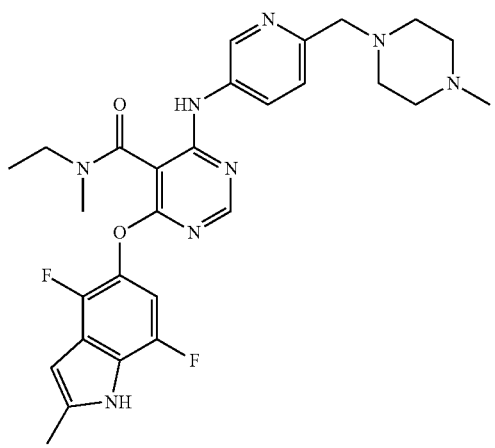
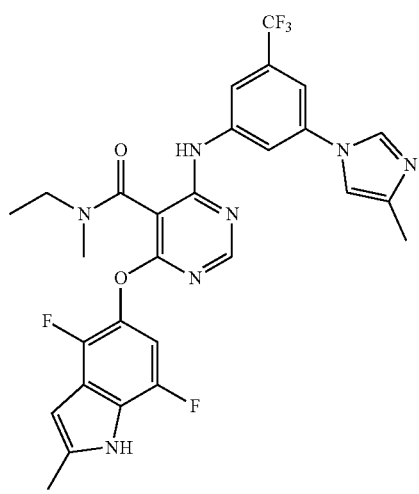
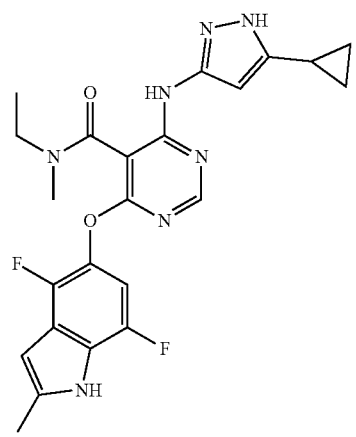
194
-continued
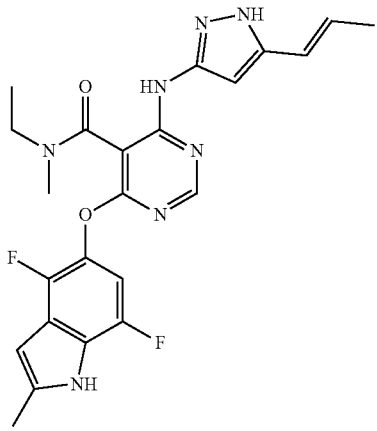
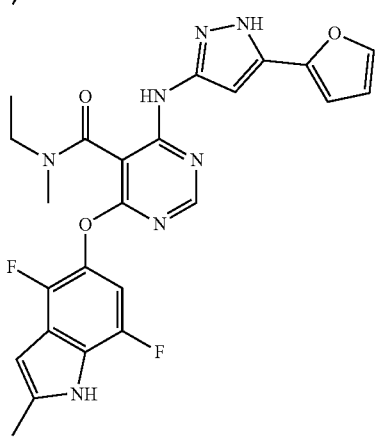
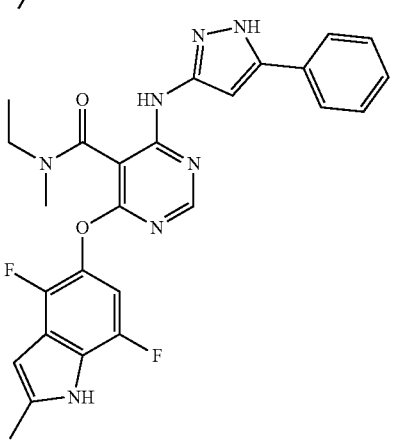
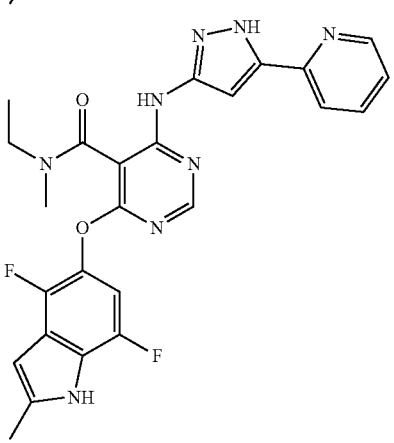

195
-continued
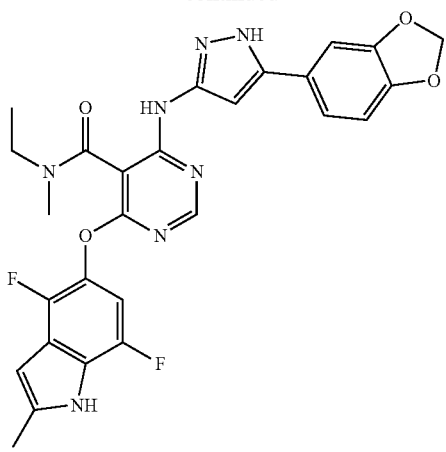
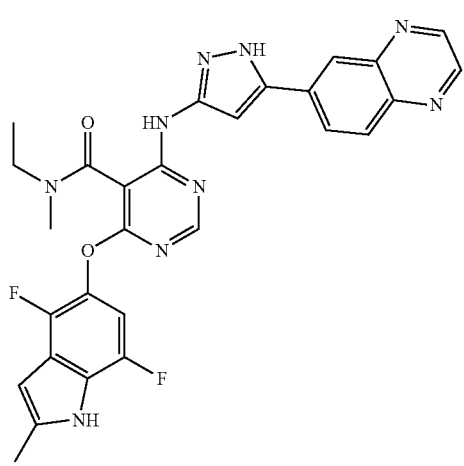
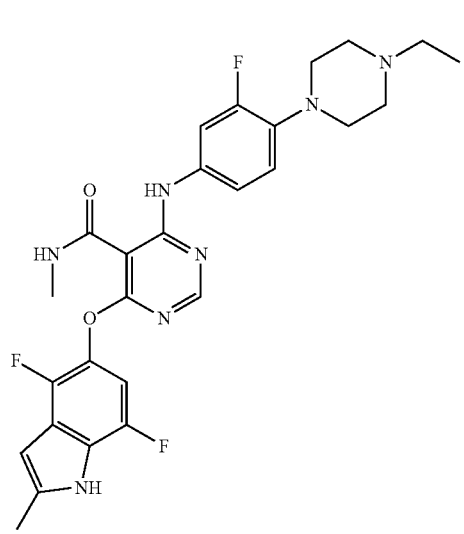
196
-continued
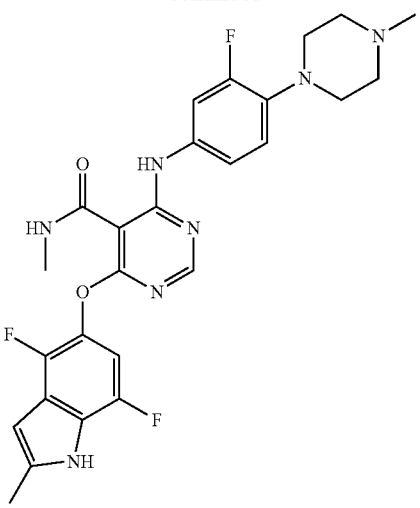
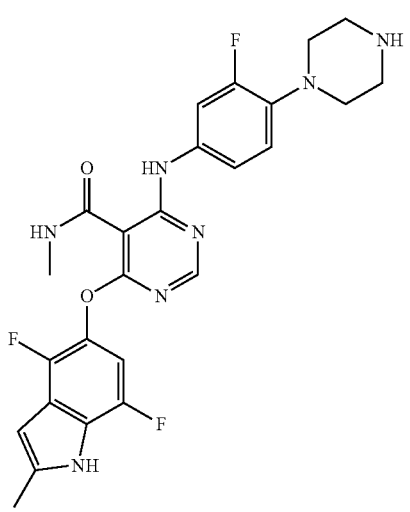
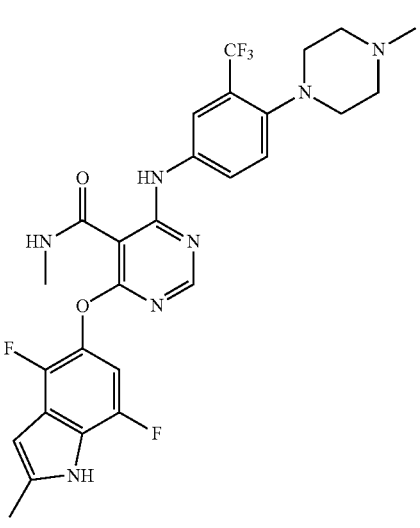

197
-continued
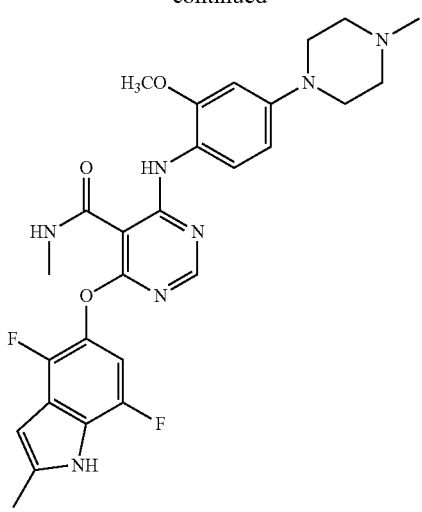
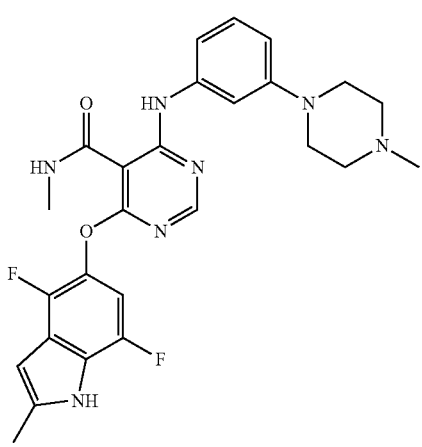
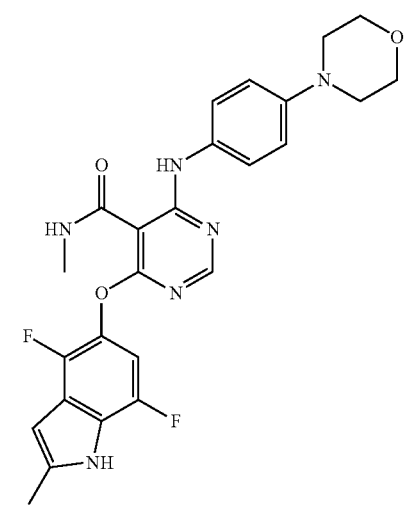
198
-continued
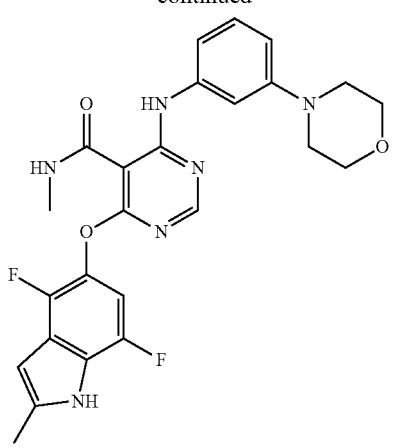
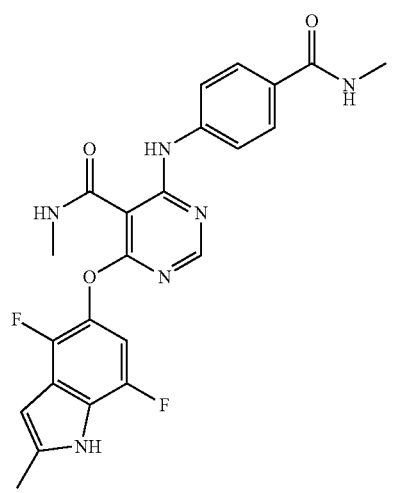
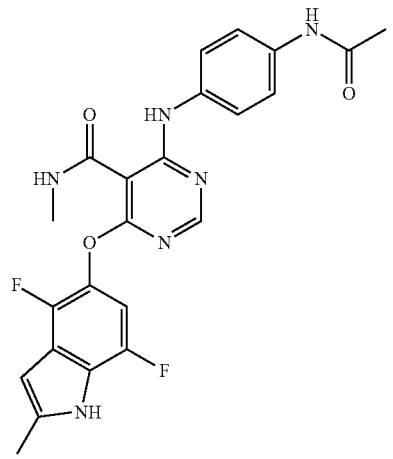

199
-continued
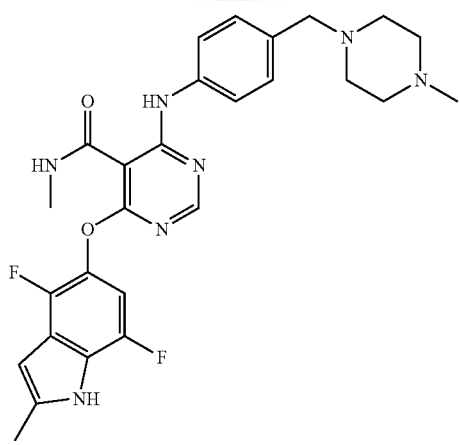
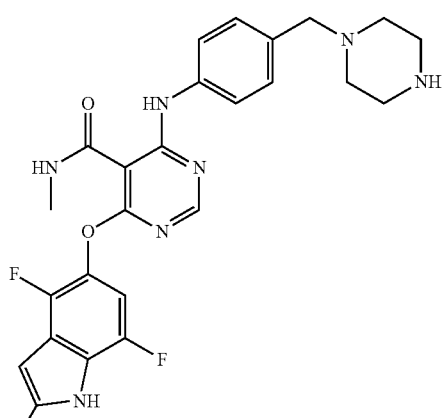
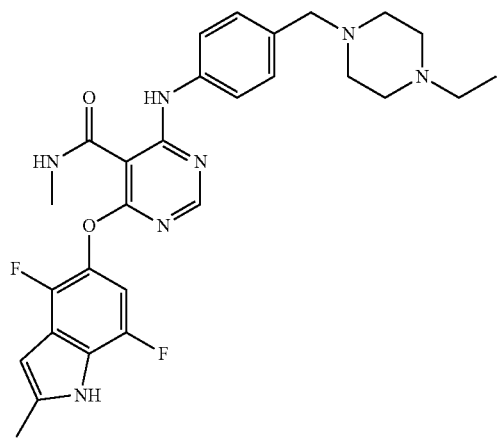
200
-continued
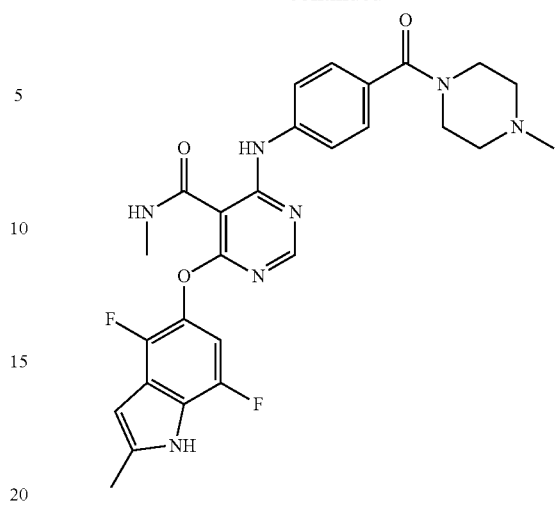
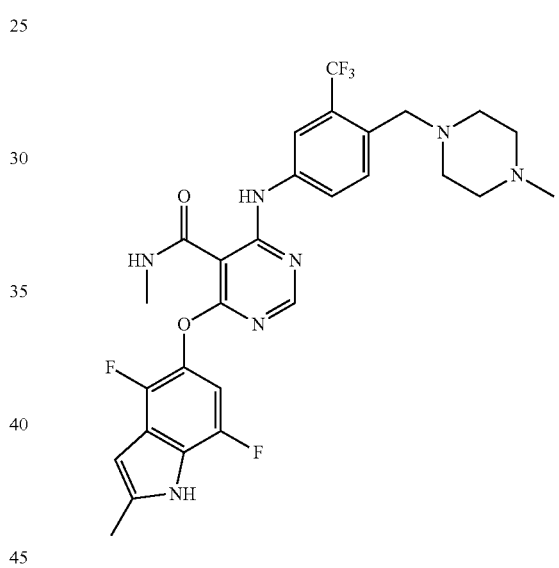
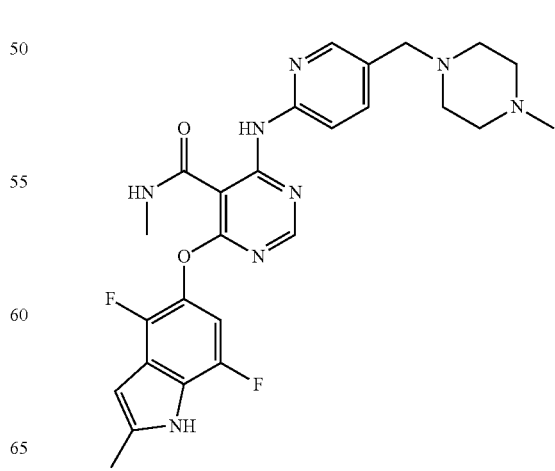

201
-continued
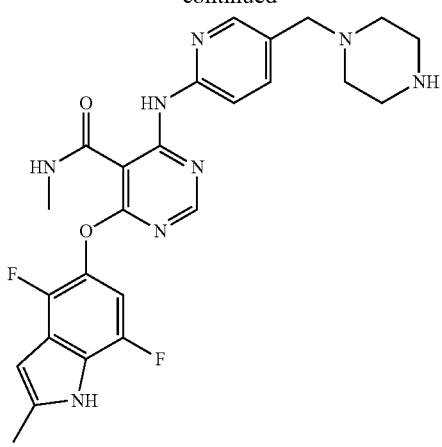
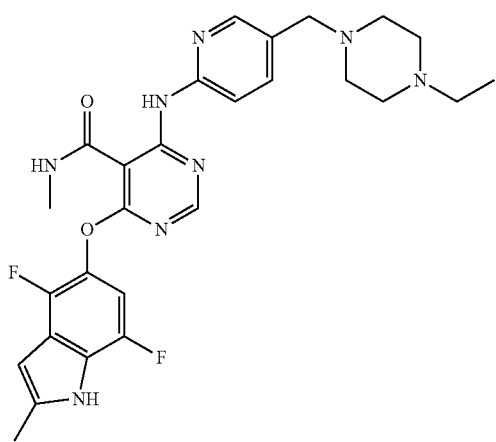
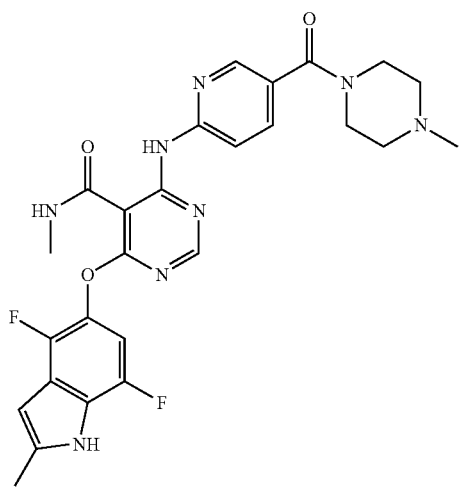
202
-continued
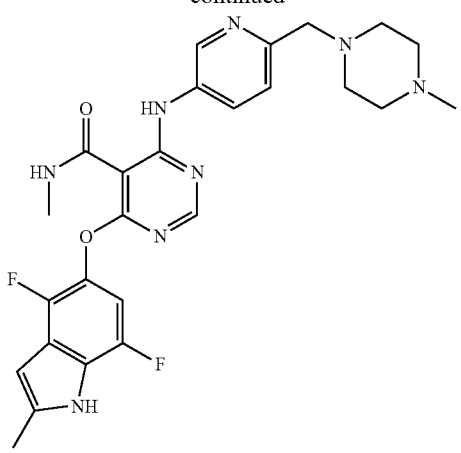
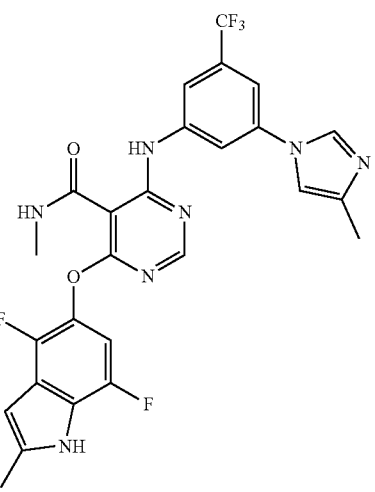
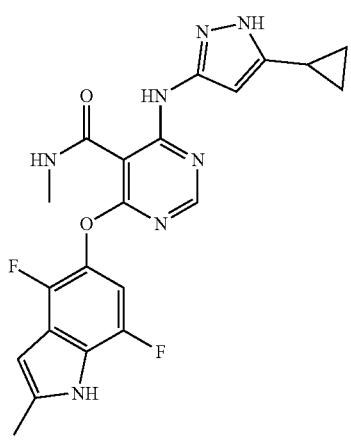

203
-continued
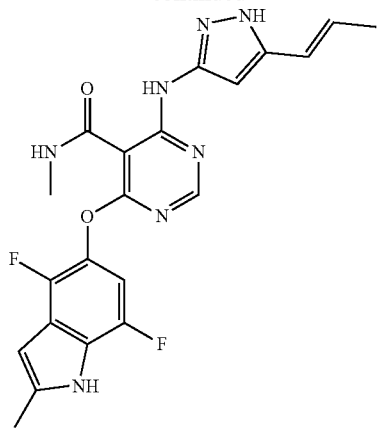
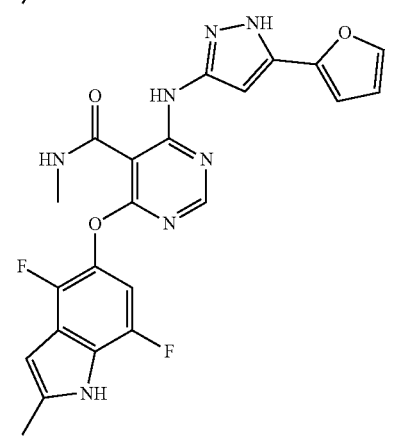
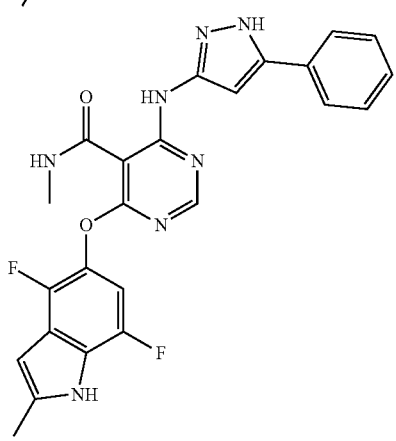
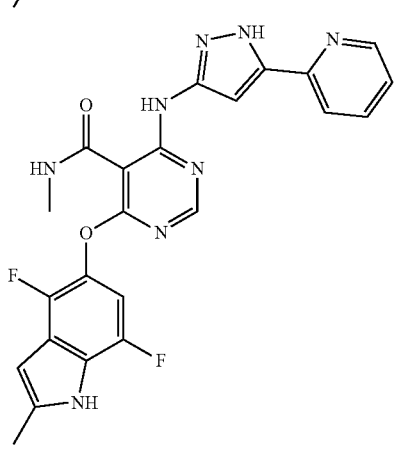
204
-continued
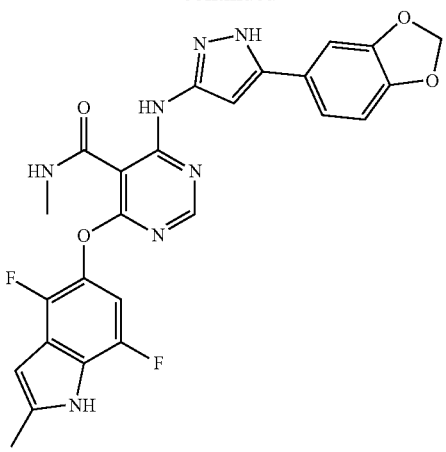
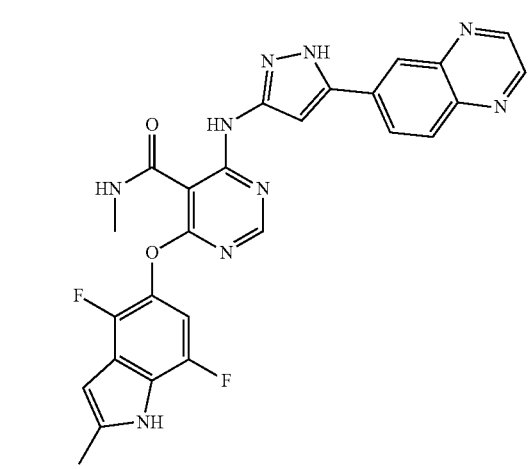
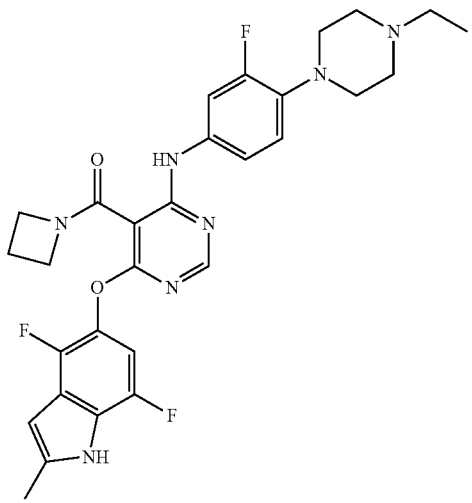

| 205 | 206 |
|---|---|
| -continued | -continued |
| 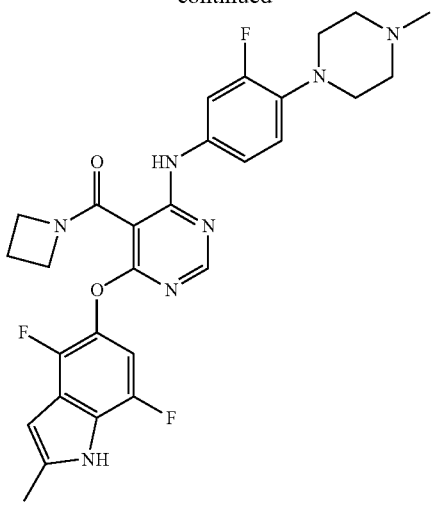 | 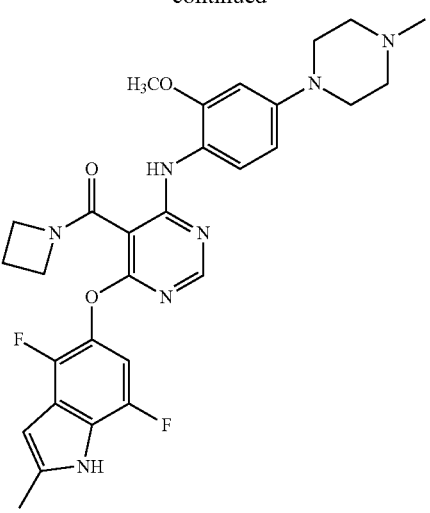 |
| 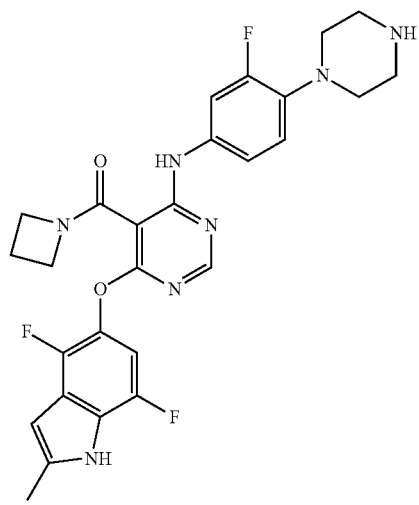 | 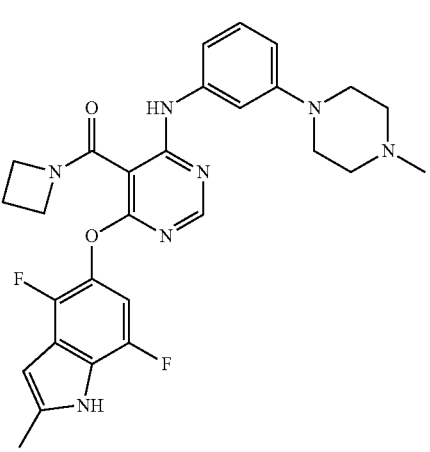 |
| 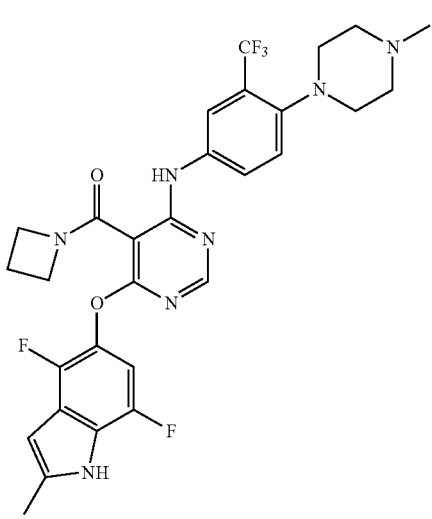 | 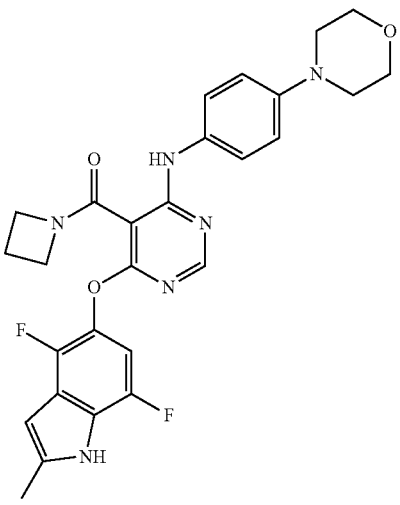 |

207
-continued
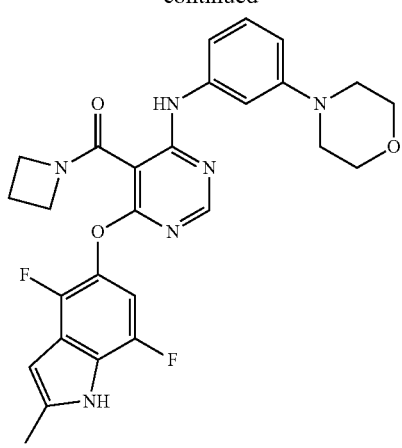
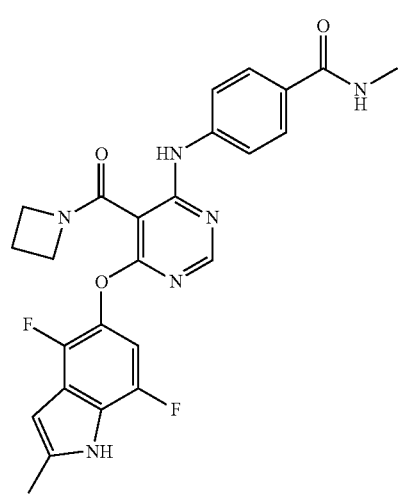
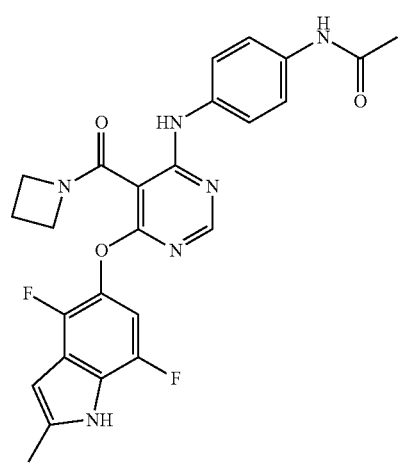
208
-continued
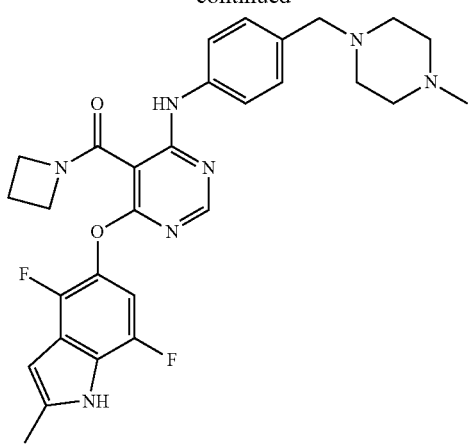
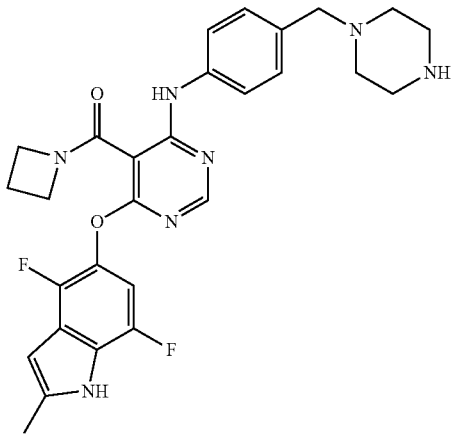
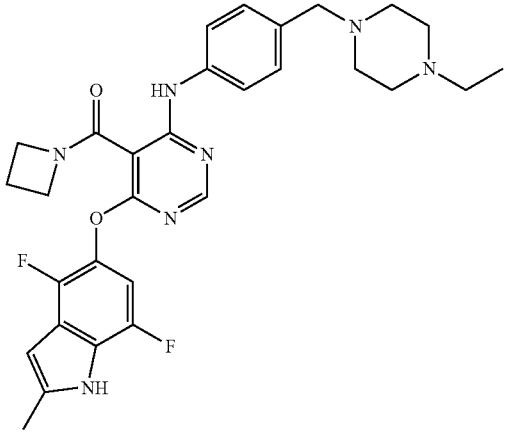

209
-continued
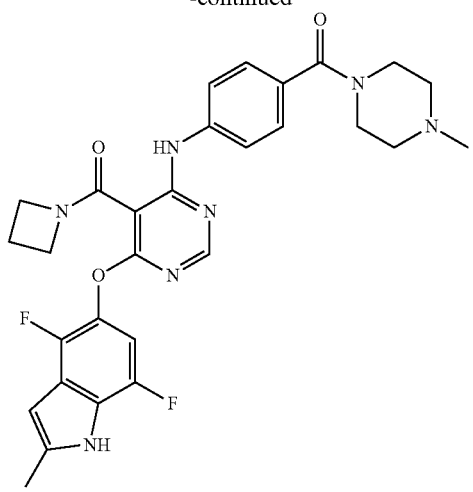
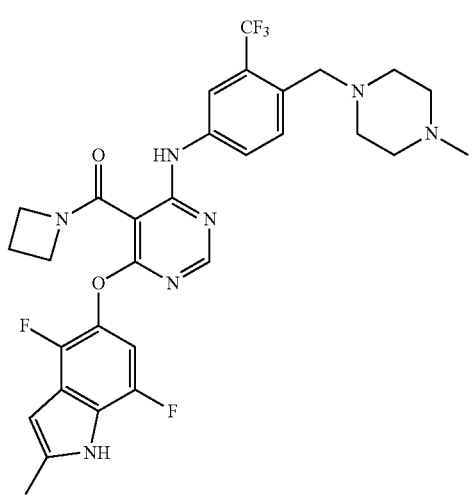
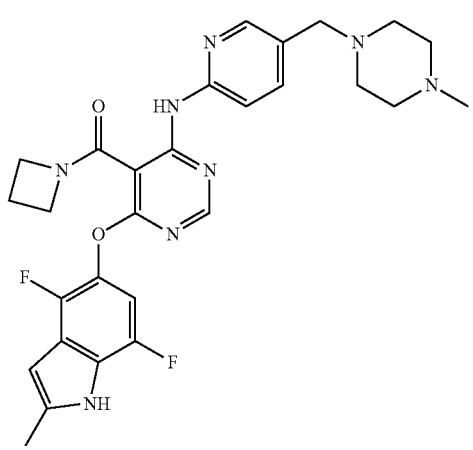
210
-continued
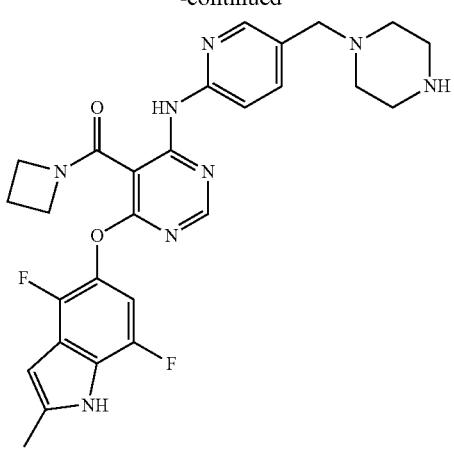
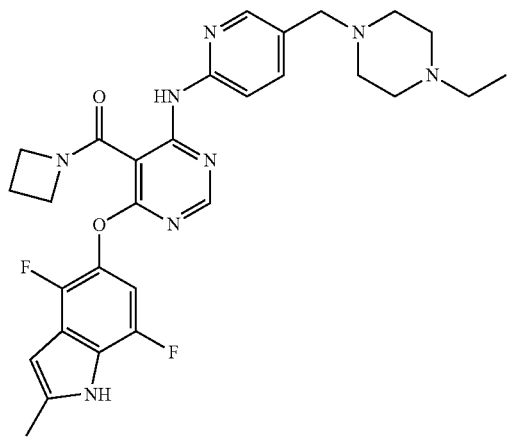
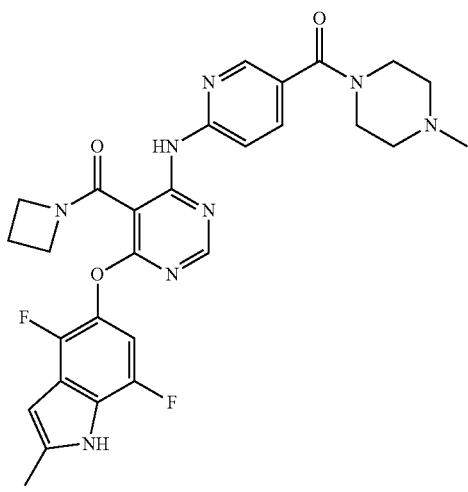

-continued
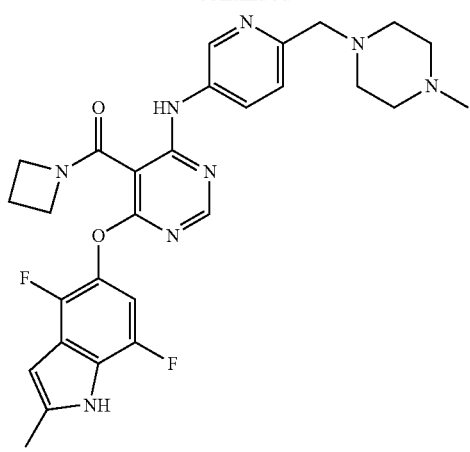
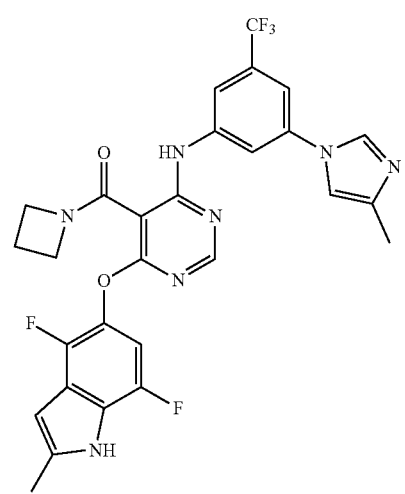
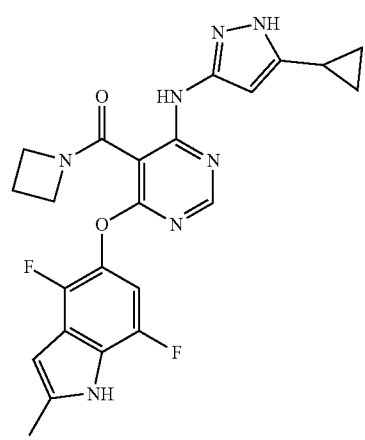
-continued
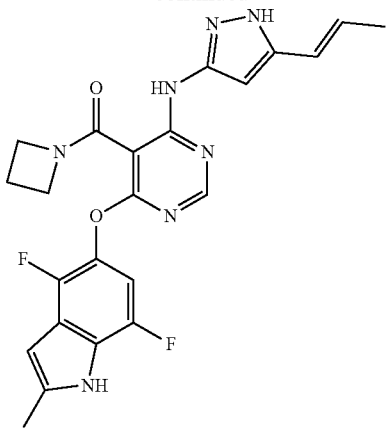
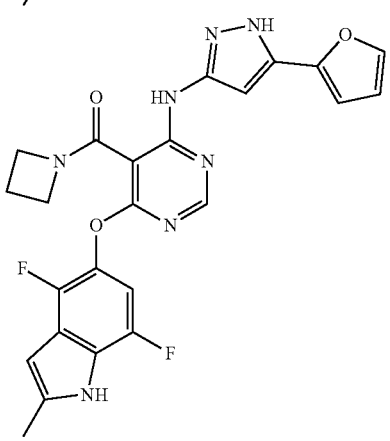
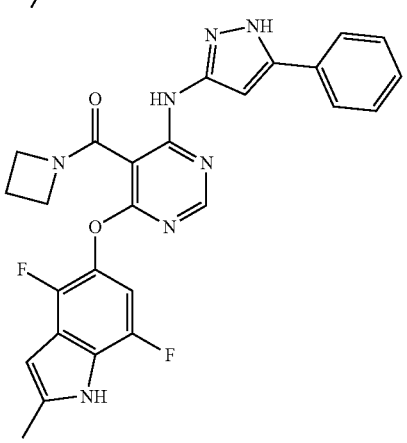
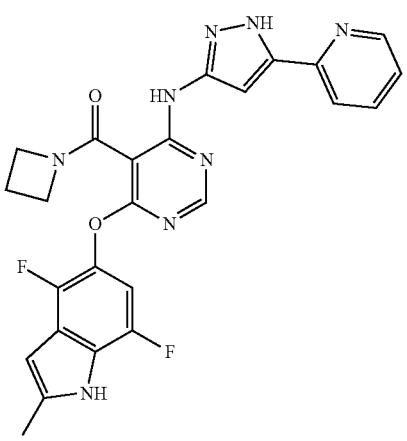

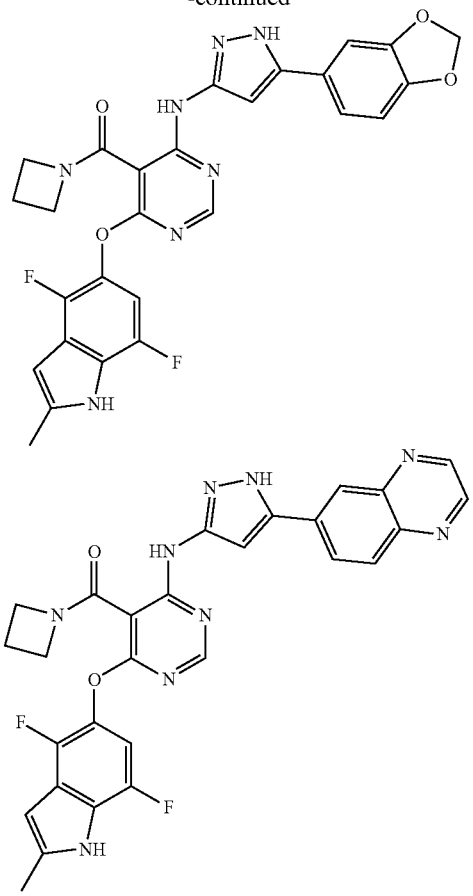

In another embodiment, a method of preparing the inventive compounds is provided. The compounds of the present invention can be generally prepared using 4, 6-dichloro-pyrimidine, with various substituents on position "5". Compound (I) may contain various stereoisomers, geometric isomers, tautomeric isomers, and the like. All of possible isomers and their mixtures are included in the present invention, and the mixing ratio is not particularly limited.

The pyrimidine derivative compounds of Formula (I) in this invention can be synthesized from commercially available precursors using established protocols. By way of example, a synthetic route similar to that shown in any of the following Schemes may be used, together with synthetic methods known in the art of synthetic organic chemistry, or variations thereon as appreciated by those skilled in the art. Each variable in the following schemes refers to any group consistent with the description of the compounds provided herein.

In the Schemes that follow the term "reduction" refers to the process of reducing a nitro functionality to an amino functionality, or the process of transforming an ester functionality to an alcohol. The reduction of a nitro group can be carried out in a number of ways well known to those skilled in the art of organic synthesis including, but not limited to, catalytic hydrogenation, reduction with SnCl2 and reduction with titanium bichloride. In the Schemes that follow, the term "hydrolyze" refers to the reaction of a substrate or reactant with water. More specifically, "hydrolyze" refers to the conversion of an ester or nitrite functionality into a carboxylic acid. This process can be catalyzed by a variety of acids or bases well known to those skilled in the art of organic synthesis.

The compounds of Formula (I) may be prepared by use of known chemical reactions and procedures. The following general preparative methods are presented to aid one of skill in the art in synthesizing the inhibitors, with more detailed examples being presented in the experimental section describing the working examples.

Propenyl-pyrazol amine as defined in formula (III) is not commercially available. It can be prepared by several methods as described earlier (see, e.g., U.S. provisional application No. 61/555,738).

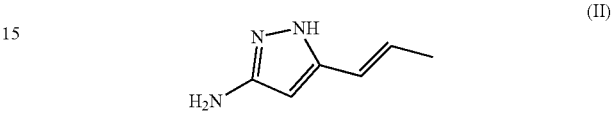

(II)

Precursors of substituted indol-5-ol as defined in formula (III) can be purchased from suppliers, or synthesized from commercially available precursors using established protocols. (WO 2004/009542, P 33-38; Journal of Medicinal Chemistry, 2006, Vol 49, No. 7, P 2143-2146; Org. Lett. Vol 10, No 12, 2008, P 2369-2372; WO 00/47212, P 245-250; WO 2009036055 A1, P 57).

Especially, precursor 47-difluoroindol-5-ol as defined in formula (IIIa) was not reported before and can be prepared by several methods as described earlier (WO2014145403 A1).

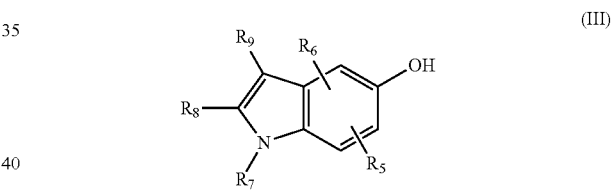

(III)

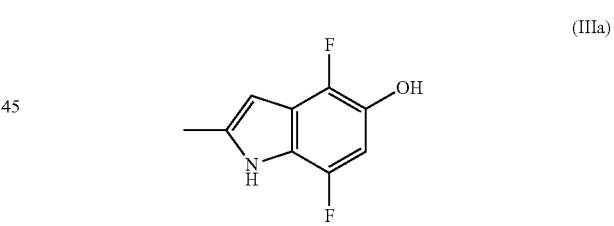

(IIIa)

Precursors of 5-substituted 4, 6-dichloro-pyrimidines as defined in formula (IV) can be purchased from suppliers. Especially, precursor as defined in formula (IVa) can be synthesized from commercially available precursors using established protocols (PCT Int. Appl., 2010141406, 9 Dec. 2010, Compound 310F).

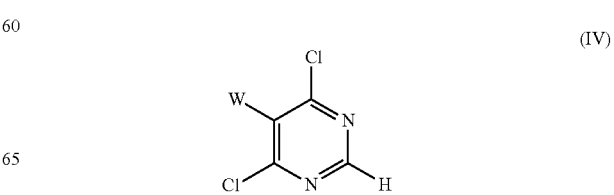

(IV)

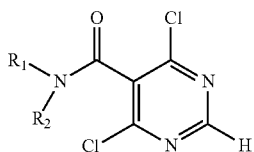

(IVa)

Generally, precursors of ArNH$_2$ can be purchased from suppliers. Precursors of ArNH$_2$ as defined in formula (V) can be purchased from suppliers, or synthesized from commercially available precursors using established protocols. (J. Med. Chem. 2010, 53, 7938-7957, specifically, P7949).

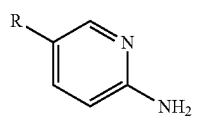

(V)

The preparation of the compounds of formula (I) in this invention can be carried out by methods listed in scheme 1.

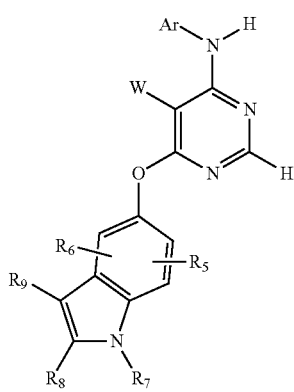

(I)

As shown in scheme 1, the pyrimidine derivative (I) can be synthesized by the reaction of 5-substituted 4,6-dichloropyrimidine with a sequence of substituted indole-5-ol to give monochlororopyrimidine intermediate of compound b, which can react with ArNH$_2$ to produce the final compound (I). The reaction can be stepwise or in one pot. Alternative sequence can also be used to make pyrimidine derivatives.

Scheme 1

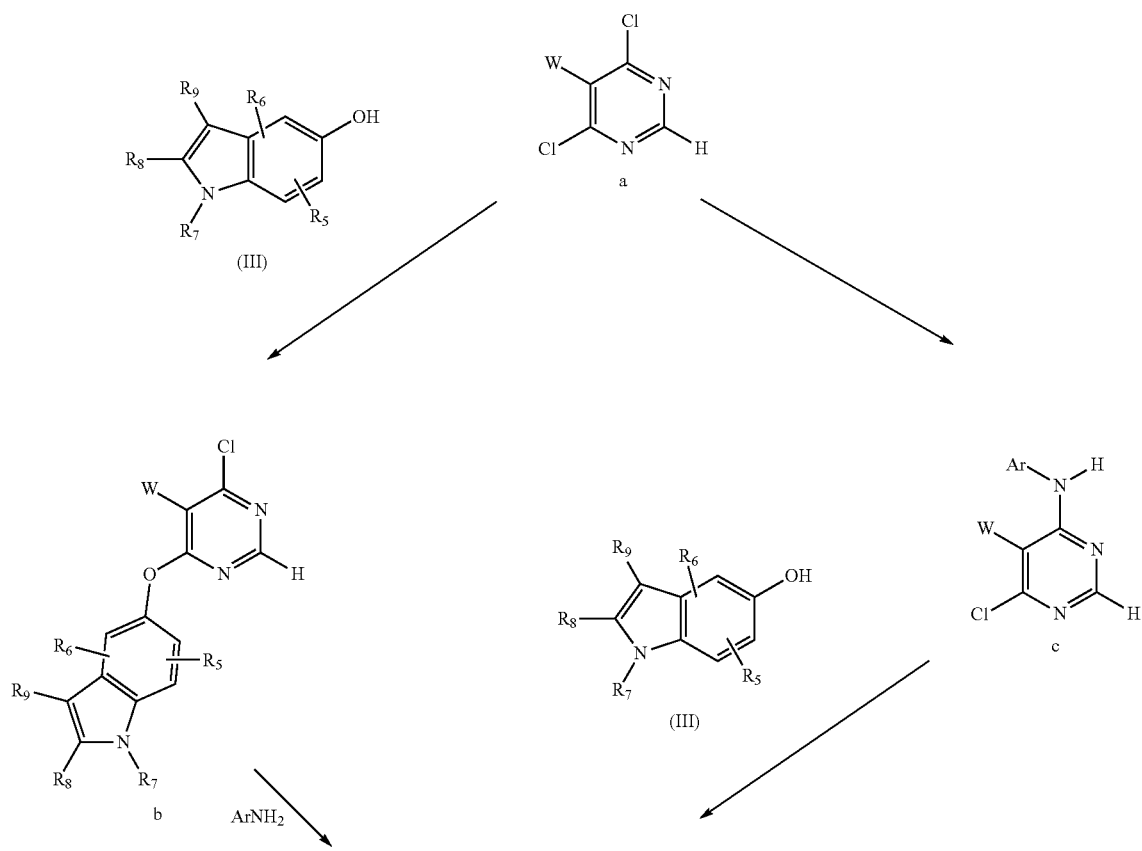

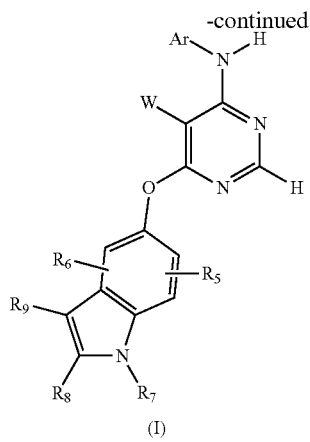

(I)

As shown in scheme 2, the final compounds as defined in (I-b), can be synthesized from the corresponding precursors, where W is "CN".

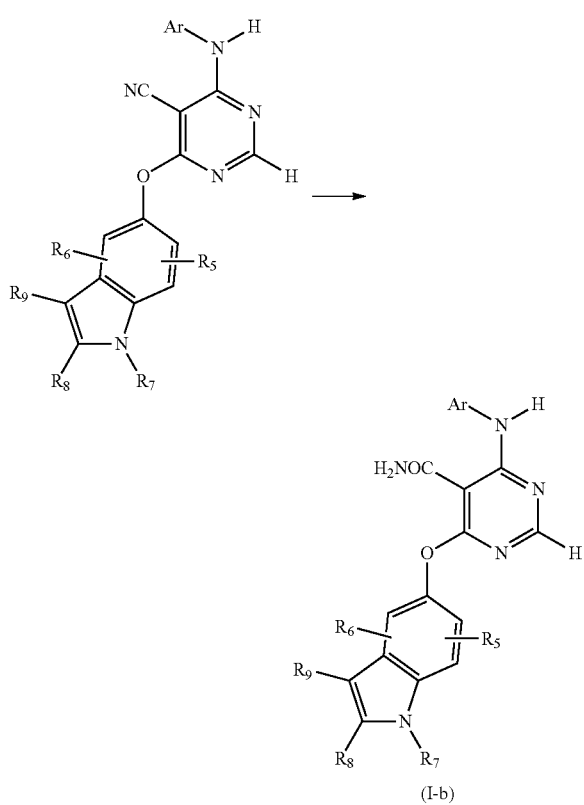

Scheme 2

(I-b)

The reaction is preferably conducted in the presence of an inert solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, especially aromatic and aliphatic hydrocarbons, such as methylene chloride, chloroform, carbon tetrachloride, dichloroethane, chlorobenzene and the dichlorobenzenes; esters, such as ethyl formate, ethyl acetate, propyl acetate, butyl acetate and diethyl carbonate; ethers, such as diethyl ether, diisopropyl ether, tetrahydrofuran, dioxane. dimethoxyethane and diethylene glycol dimethyl ether; ketones, such as acetone, methyl ethyl ketone, methyl isobutyl ketone, isophorone and cyclohexanone; nitro compounds, which may be nitroalkanes or nitroaranes, such as nitroethane and nitrobenzene; nitriles, such as acetonitrile and isobutyronitrile; amides, which may be fatty acid amides, such as formamide, dimethylformamide, dimethylacetamide and hexamethylphosphoric triamide; and sulphoxides, such as dimethyl sulphoxide and sulpholane.

The reaction can take place over a wide range of temperatures, and the precise reaction temperature is not critical to the invention. In general, we find it convenient to carry out the reaction at a temperature of from −50° C. to 100° C.

The present invention provides compositions of matter that are formulations of one or more active drugs and a pharmaceutically-acceptable carrier. In this regard, the invention provides a composition for administration to a mammalian subject, which may include a compound of formula I, or its pharmaceutically acceptable salts.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutically acceptable compositions of this invention may be orally administered in any orally acceptable dosage form including, but not limited to, capsules, tablets, troches, elixirs, suspensions, syrups, wafers, chewing gums, aqueous suspensions or solutions.

The oral compositions may contain additional ingredients such as: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or flavoring agent such as peppermint, methyl salicylate, or orange flavoring. When the dosage unit form is a capsule, it may additionally contain a liquid carrier such as a fatty oil. Other dosage unit forms may contain other various materials which modify the physical form of the dosage unit, such as, for example, a coating. Thus, tablets or pills may be coated with sugar, shellac, or other enteric coating agents. A syrup may contain, in addition to the active ingredients, sucrose as a sweetening agent and certain preservatives, dyes and colorings and flavors. Materials used in preparing these various compositions should be pharmaceutically or veterinarally pure and non-toxic in the amounts used.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. A single intravenous or intraperitoneal dose can be administered. Alternatively, a slow long-term infusion or multiple short-term daily infusions may be utilized, typically lasting from 1 to 8 days. Alternate day dosing or dosing once every several days may also be utilized.

Sterile, injectable solutions may be prepared by incorporating a compound in the required amount into one or more appropriate solvents to which other ingredients, listed above or known to those skilled in the art, may be added as required. Sterile injectable solutions may be prepared by incorporating the compound in the required amount in the appropriate solvent with various other ingredients as required. Sterilizing procedures, such as filtration, may then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. In all cases, the final form, as noted, must be sterile and should also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

In accordance with the invention, there are provided compositions containing pyrimidine derivatives and methods useful for the in vivo delivery of pyrimidine derivatives in the form of nanoparticles, which are suitable for any of the aforesaid routes of administration.

U.S. Pat. Nos. 5,916,596, 6,506,405 and 6,537,579 teach the preparation of nanoparticles from the biocompatible polymers, such as albumin. Thus, in accordance with the present invention, there are provided methods for the formation of nanoparticles of the present invention by a solvent evaporation technique from an oil-in-water emulsion prepared under conditions of high shear forces (e.g., sonication, high pressure homogenization, or the like).

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

In accordance with the invention, the compounds of the invention may be used to treat diseases associated with cellular proliferation or hyperproliferation, such as cancers which include but are not limited to tumors of the nasal cavity, paranasal sinuses, nasopharynx, oral cavity, oropharynx, larynx, hypopharynx, salivary glands, and paragangliomas. The compounds of the invention may also be used to treat cancers of the liver and biliary tree (particularly hepatocellular carcinoma), intestinal cancers, particularly colorectal cancer, ovarian cancer, small cell and non-small cell lung cancer, breast cancer, sarcomas (including fibrosarcoma, malignant fibrous histiocytoma, embryonal rhabdomysocarcoma, leiomysosarcoma, neuro-fibrosarcoma, osteosarcoma, synovial sarcoma, liposarcoma, and alveolar soft part sarcoma), neoplasms of the central nervous systems (particularly brain cancer), and lymphomas (including Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma).

The compounds and methods of the present invention, either when administered alone or in combination with other agents (e.g., chemotherapeutic agents or protein therapeutic agents described below) are also useful in treating a variety of disorders, including but not limited to, for example: stroke, cardiovascular disease, myocardial infarction, congestive heart failure, cardiomyopathy, myocarditis, ischemic heart disease, coronary artery disease, cardiogenic shock, vascular shock, pulmonary hypertension, pulmonary edema (including cardiogenic pulmonary edema), pleural effusions, rheumatoid arthritis, diabetic retinopathy, retinitis pigmentosa, and retinopathies, including diabetic retinopathy and retinopathy of prematurity, inflammatory diseases, restenosis, asthma, acute or adult respiratory distress syndrome (ARDS), lupus, vascular leakage, protection from ischemic or reperfusion injury such as ischemic or reperfusion injury incurred during organ transplantation, transplantation tolerance induction; ischemic or reperfusion injury following angioplasty; arthritis (such as rheumatoid arthritis, psoriatic arthritis or osteoarthritis); multiple sclerosis; inflammatory bowel disease, including ulcerative colitis and Crohn's disease; lupus (systemic lupus erythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including those where kineses such as Src-family kineses are activated or overexpressed, such as colon carcinoma and thymoma, or cancers where kinase activity facilitates tumor growth or survival; glomerulonephritis, serum sickness; uticaria; allergic diseases such as respiratory allergies (asthma, hayfever, allergic rhinitis) or skin allergies; mycosis fungoides; acute inflammatory responses (such as acute or adult respiratory distress syndrome and ischemial reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; morphea; peripheral limb ischemia and ischemic limb disease; bone disease such as osteoporosis, osteomalacia, hyperparathyroidism, Paget's disease, and renal osteodystrophy; vascular leak syndromes, including vascular leak syndromes induced by chemotherapies or immunomodulators such as IL-2; spinal cord and brain injury or trauma; glaucoma; retinal diseases, including macular degeneration; vitreoretinal disease; pancreatitis; vasculatides, including vasculitis, Kawasaki disease, thromboangiitis obliterans, Wegener s granulomatosis, and Behcet's disease; seleroderma; preeclampsia; thalassemia; Kaposi's sarcoma; von Hippel Lindau disease; and the like.

In accordance with the invention, the compounds of the invention may be used to treat diseases associated with undesired cellular proliferation or hyperproliferation comprising identifying the mammal afflicted with said disease or condition and administering to said afflicted mammal a composition comprising the compound of formula I, wherein the disease or condition is associated with a kinase.

The invention also provides methods of treating a mammal afflicted with the above diseases and conditions. The amount of the compounds of the present invention that may be combined with the carrier materials to produce a composition in a single dosage faun will vary depending upon the host treated, the particular mode of administration. Preferably, the compositions should be formulated so that a dosage of between 0.01-100 mg/kg body weight/day of the inhibitor can be administered to a patient receiving these compositions.

In one aspect, the invention compounds are administered in combination with chemotherapeutic agent, an anti-inflammatory agent, antihistamines, chemotherapeutic agent, immunomodulator, therapeutic antibody or a protein kinase inhibitor, e.g., a tyrosine kinase inhibitor, to a subject in need of such treatment.

The method includes administering one or more of the inventive compounds to the afflicted mammal. The method may further include the administration of a second active agent, such as a cytotoxic agent, including alkylating agents, tumor necrosis factors, intercalators, microtubulin inhibitors, and topoisomerase inhibitors. The second active agent may be co-administered in the same composition or in a second composition. Examples of suitable second active agents include, but are not limited to, a cytotoxic drug such as Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-□a; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

In accordance with the invention, the compounds and compositions may be used at sub-cytotoxic levels in combination with other agents in order to achieve highly selective activity in the treatment of non-neoplastic disorders, such as heart disease, stroke and neurodegenerative diseases (Whitesell et al., Curr Cancer Drug Targets (2003), 3(5), 349-58).

The exemplary therapeutical agents that may be administered in combination with invention compounds include EGFR inhibitors, such as gefitinib, erlotinib, and cetuximab. Her2 inhibitors include canertinib, EKB-569, and GW-572016. Also included are Src inhibitors, dasatinib, as well as Casodex (bicalutamide), Tamoxifen, MEK-1 kinase inhibitors, MARK kinase inhibitors, PI3 inhibitors, and PDGF inhibitors, such as imatinib, Hsp90 inhibitors, such as 17-AAG and 17-DMAG. Also included are anti-angiogenic and antivascular agents which, by interrupting blood flow to solid tumors, render cancer cells quiescent by depriving them of nutrition. Castration, which also renders androgen dependent carcinomas non-proliferative, may also be utilized. Also included are IGF1R inhibitors, inhibitors of non-receptor and receptor tyrosine kineses, and inhibitors of integrin.

The pharmaceutical composition and method of the present invention may further combine other protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay. The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

Other therapeutic agents for the combinatory therapy include cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and for gpn39 (i.e., CD154), fusion proteins constructed from CD40 and gp39 (CD40Ig and CD8 gp39), inhibitors, such as nuclear translocation inhibitors, of NF-kappa B function, such as deoxyspergualin (DSG), cholesterol biosynthesis inhibitors such as HM:G CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one having ordinary skill in the art.

EXAMPLES

The following examples are provided to further illustrate the present invention but, of course, should not be construed as in any way limiting its scope.

All experiments were performed under anhydrous conditions (i.e. dry solvents) in an atmosphere of argon, except where stated, using oven-dried apparatus and employing standard techniques in handling air-sensitive materials. Aqueous solutions of sodium bicarbonate (NaHCO3) and sodium chloride (brine) were saturated.

Analytical thin layer chromatography (TLC) was carried out on Merck Kiesel gel 60 F254 plates with visualization by ultraviolet and/or anisaldehyde, potassium permanganate or phosphomolybdic acid dips.

NMR spectra: 1H Nuclear magnetic resonance spectra were recorded at 400 MHz. Data are presented as follows: chemical shift, multiplicity (s=singlet, d=doublet, t=triplet, q=quartet, qn=quintet, dd=doublet of doublets, m=multiplet, bs=broad singlet), coupling constant (J/Hz) and integration. Coupling constants were taken and calculated directly from the spectra and are uncorrected.

Low resolution mass spectra: Electrospray (ES+) ionization was used. The protonated parent ion (M+H) or parent sodium ion (M+Na) or fragment of highest mass is quoted. Analytical gradient consisted of 10% ACN in water ramping up to 100% ACN over 5 minutes unless otherwise stated.

High performance liquid chromatography (HPLC) was use to analyze the purity of derivatives. HPLC was performed on a Phenomenex Synergi Polar-RP, 4 u, 80 A, 150×4.6 mm column using a Shimadzu system equipted with SPD-M10A Phosphodiode Array Detector. Mobile phase A was water and mobile phase B was acetonitrile with a gradient from 20% to 80% B over 60 minutes and re-equilibrate at A/B (80:20) for 10 minutes. UV detection was at 220 and 54 nm.

Example 1

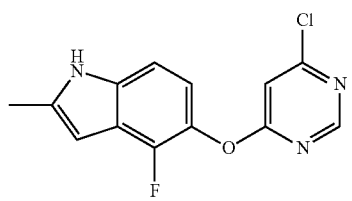
(1)

To a solution of 4-fluoro-2-methyl-1H-indol-5-ol (2.00 g, 12.11 mmol) and 4,6-dichloropyridine (2.00 g, 13.44 mmol) in DMSO (18 ml) was added potassium carbonate (3.77 g, 27.25 mmol) and the mixture was heated at 80° C. for 60 min. with Biotage microwave initiator. TLC was checked and the starting material was consumed. The reaction mixture was added to a container with water (350 mL) and the mixture was stirred at room temperature for 1 hour then aged at 4° C. overnight. The pH was adjusted to 6-7 with 2N HCl and the mixture was cooled with ice bath. The solids were collected by filtration and washed by water. After drying on vac line, compound 1 was obtained as yellow solids (3.1 g, 92% yield). No further purification was performed and the product was directly used for the next step reaction. $^1$H NMR (400 MHz, DMSO-d$_6$) δ 11.37 (br, 1H), 8.63 (s, 1H), 7.43 (s, 1H), 7.13 (d, J=8.8 Hz, 1H), 6.95 (t, J=7.6 Hz, 1H), 6.25 (s, 1H), 2.40 (s, 3H); ESI-MS: calcd for (C13H9ClFN3O) 277, found 278 (MH$^+$).

Example 2

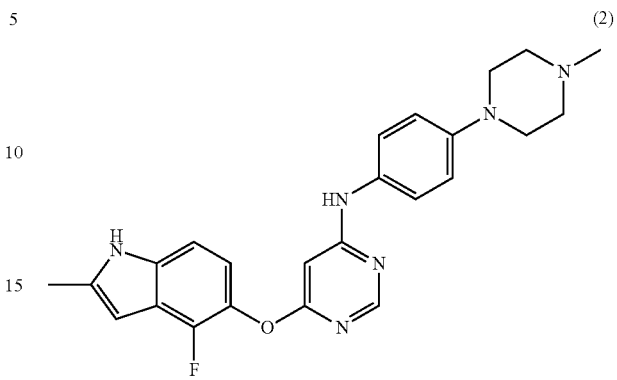
(2)

A mixture of compound 1 (161 mg, 0.58 mmol), 4-(4-Methylpiperazineno)aniline (138 mg, 0.72 mmol), palladium(II) acetate (20 mg, 0.09 mmol), xantphos (4,5-diphenylphosphanyl-9,9'-dimethyl-9-H-xanthene, 83 mg, 0.15 mmol) and K$_2$CO$_3$ (500 mg, 3.62 mmol) in 1,4-dioxane (8 ml) was purged with argon for 30 min. The mixture was heated with Biotage microwave initiator at 120° C. for 15 min. TLC was checked and the reaction was completed. The reaction mixture was diluted with DCM and washed by sat. NH$_4$Cl, brine, dried over sodium sulfate and concentrated. The crude product was purified by column chromatography (silica gel, 0-15% MeOH in DCM) to give compound 2 as yellow solids (93 mg, 37% yield). $^1$H NMR (400 MHz, DMSO-d$_6$) δ 11.27 (br, 1H), 9.25 (s, 1H), 8.18 (s, 1H), 7.31 (d, J=8.8 Hz, 2H), 7.08 (d, J=8.8 Hz, 1H), 6.84 (m, 3H), 6.20 (s, 1H), 5.90 (br, 1H), 3.02 (m, 4H), 2.41 (m, 4H), 2.36 (br, 3H), 2.18 (s, 3H); ESI-MS: calcd for (C24H25FN6O) 432, found 433 (MH$^+$).

Example 3

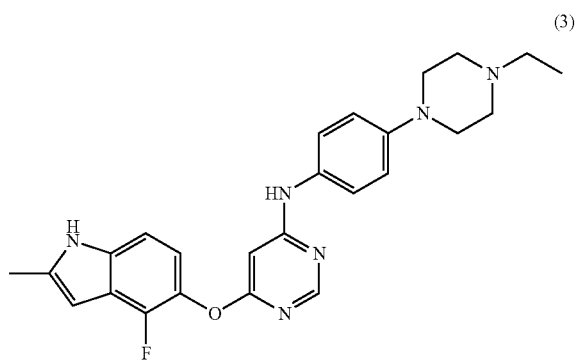 [SMILES: CCN1CCN(c2ccc(Nc3cc(Oc4ccc5[nH]c(C)cc5c4F)ncn3)cc2)CC1]
(3)

A mixture of compound 1 (180 mg, 0.65 mmol), 4-(4-Ethylpiperazine-1-yl)aniline (121 mg, 0.59 mmol), palladium(II) acetate (20 mg, 0.09 mmol), xantphos (4,5-diphenylphosphanyl-9,9'-dimethyl-9-H-xanthene, 83 mg, 0.15 mmol) and K$_2$CO$_3$ (500 mg, 3.62 mmol) in 1,4-dioxane (8 ml) was purged with argon for 30 min. The mixture was heated with oil bath at 100° C. for 2 h. TLC was checked and the reaction was completed. The reaction mixture was diluted with DCM/IPA (10/1) and washed by sat. NH$_4$Cl, brine, dried over sodium sulfate and concentrated. The crude product was purified by column chromatography (silica gel, 0-15% MeOH in DCM) to give compound 3 as yellow solids (131 mg, 50% yield). $^1$H NMR (400 MHz, DMSO-d$_6$) δ 11.31 (br, 1H), 9.24 (s, 1H), 8.21 (s, 1H), 7.35 (d, J=8.8 Hz, 2H), 7.13 (d, J=8.8 Hz, 1H), 6.87 (m, 3H), 6.28 (s, 1H), 5.94 (br, 1H), 3.06 (m, 4H), 2.49 (m, 4H), 2.39 (m, 5H), 1.02 (t, J=6.8 Hz, 3H); ESI-MS: calcd for (C25H27FN6O) 446, found 447 (MH$^+$).

Example 4

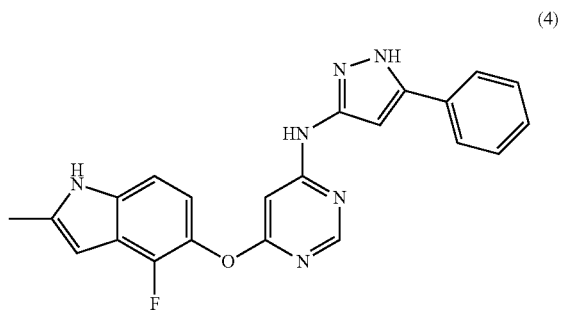 [SMILES: Cc1cc2c(F)c(Oc3cc(Nc4cc(-c5ccccc5)[nH]n4)ncn3)ccc2[nH]1]

(4)

The solution of compound 1 (180 mg, 0.65 mmol), 3-amino-5-phenylpyrazole (124 mg, 0.78 mmol) and DIPEA (0.23 ml, 1.30 mmol) in DMSO (3.5 ml) was stirred at 120° C. for 120 hours. After cooled to room temperature, water (10 ml) was added and the reaction mixture was extracted by IPA/DCM (1/9). The combined organic was washed by brine, dried over sodium sulfate and concentrated. The crude product was purified by column chromatography (0-10% MeOH in DCM) to give compound 4 as brown solids (60 mg, 23% yield). $^1$H NMR (400 MHz, DMSO-d$_6$) δ 12.75 (br, 1H), 11.25 (br, 1H), 9.90 (br, 1H), 8.24 (s, 1H), 7.67 (d, J=7.6 Hz, 2H), 7.42 (t, J=7.6 Hz, 2H), 7.32 (t, J=7.6 Hz, 1H), 7.10 (d, J=8.8 Hz, 1H), 6.86 (t, J=8.4 Hz, 1H), 6.80-6.50 (br, 2H), 6.20 (s, 1H), 2.37 (br, 3H); ESI-MS: calcd for (C22H17FN6O) 400, found 401 (MH$^+$).

Example 5

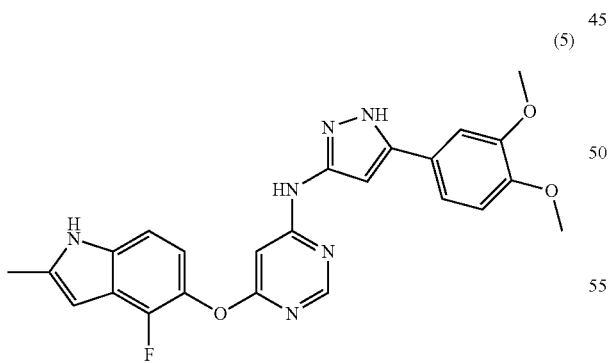

(5)

The solution of compound 1 (150 mg, 0.54 mmol), 5-(3,4-dimethoxyphenyl)-1H-pyrazol-3-amine (142 mg, 0.65 mmol) and DIPEA (0.19 ml, 1.08 mmol) in DMSO (5 ml) was stirred at 120° C. for 96 hours. After cooled to room temperature, the mixture was added to water (75 ml) and stirred at room temperature for 30 min. The pH of the mixture was adjusted to 1~2 using 2N HCl. Cooled with ice bath and the solids were collected by filtration, washed by water to give the crude product. The crude product was purified by column chromatography (0-10% MeOH in DCM) to provide compound 5 as yellow solids (61 mg, 25% yield). $^1$H NMR (400 MHz, DMSO-d$_6$) δ 12.61 (br, 1H), 11.30 (br, 1H), 9.89 (br, 1H), 8.27 (s, 1H), 7.30 (s, 1H), 7.23 (d, J=8.4 Hz, 1H), 7.13 (d, J=8.8 Hz, 1H), 7.02 (d, J=8.4 Hz, 1H), 6.89 (t, J=8.4 Hz, 1H), 6.80-6.50 (br, 2H), 6.23 (s, 1H), 3.82 (s, 3H), 3.78 (s, 3H), 2.40 (br, 3H); ESI-MS: calcd for (C24H21FN6O3) 460, found 461 (MH$^+$).

Example 6

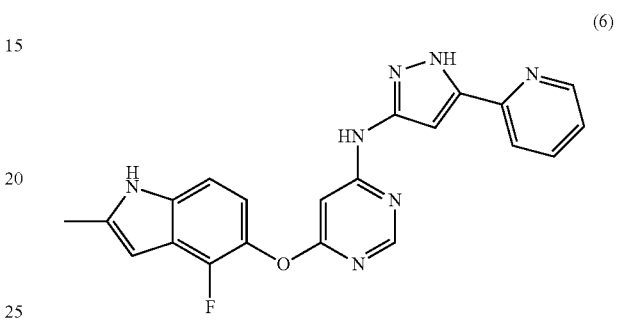

(6)

The solution of compound 1 (100 mg, 0.36 mmol), 5-Pyridin-2-yl-2h-pyrazol-3-ylamine (58 mg, 0.36 mmol) and DIPEA (0.13 ml, 0.72 mmol) in DMSO (5 ml) was stirred at 120° C. for 96 hours. After cooled to room temperature, water (10 ml) was added and the reaction mixture was extracted by IPA/DCM (1/9). The combined organic was washed by brine, dried over sodium sulfate and concentrated. The crude product was purified by column chromatography (0-10% MeOH in DCM) to give compound 6 as brown solids (33 mg, 23% yield). $^1$H NMR (400 MHz, DMSO-d$_6$) δ 13.01 (br, 1H), 11.30 (br, 1H), 9.96 (br, 1H), 8.61 (br, 1H), 8.28 (s, 1H), 7.90-7.70 (m, 2H), 7.32 (m, 1H), 7.13 (d, J=8.4 Hz, 1H), 6.89 (t, J=8.4 Hz, 1H), 7.00-6.50 (br, 2H), 6.23 (s, 1H), 2.40 (br, 3H); ESI-MS: calcd for (C21H16FN7O) 401, found 402 (MH$^+$).

Example 7

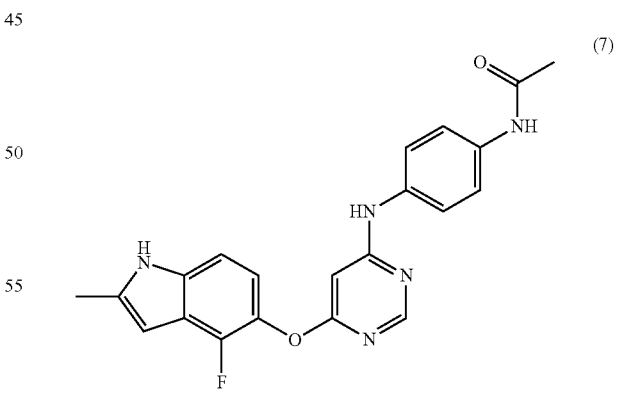

(7)

The solution of compound 1 (300 mg, 1.08 mmol), N-(4-aminophenyl)acetamide (154 mg, 1.03 mmol) and DIPEA (0.47 ml, 2.70 mmol) in DMSO (10 ml) was stirred at 100° C. for 24 hours. After cooled to room temperature, the mixture was added to water/brine (75 ml) and stirred at room temperature for 30 min and cooled with ice bath and the solids were collected by filtration, washed by water to give the crude product about 200 mg. The crude product was purified by column on silica gel (0-10% MeOH in DCM) to give compound 7 as solid (68 mg, 16% yield). $^1$H NMR (400 MHz, DMSO-d$_6$) δ 11.32 (br, 1H), 9.85 (br, 1H), 8.27 (s, 1H), 7.50 (m, 4H), 7.12 (d, J=8.8 Hz, 1H), 6.89 (t, J=8.4 Hz, 1H), 6.24 (br, 1H), 6.23 (s, 1H), 2.40 (s, 3H), 2.01 (s, 3H); ESI-MS: calcd for (C21H18FN5O2) 460, found 461 (MH$^+$).

Example 8

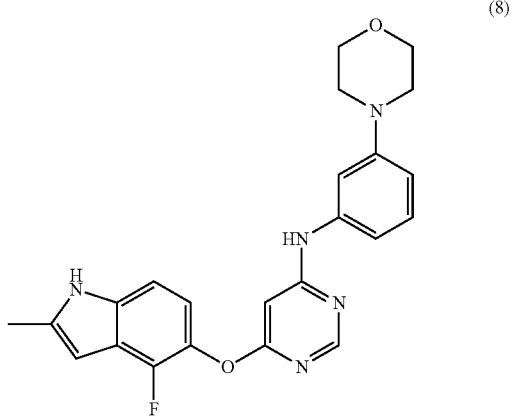 [SMILES: Cc1cc2c(F)c(Oc3cc(Nc4cccc(N5CCOCC5)c4)ncn3)ccc2[nH]1]

(8)

The solution of compound 1 (200 mg, 0.72 mmol), 3-morpholinoaniline (122 mg, 0.95 mmol) and DIPEA (0.31 ml, 1.80 mmol) in DMSO (10 ml) was stirred at 100° C. for 40 hours. After cooled to room temperature, the mixture was extracted with ethyl acetate (3×35 ml) and washed with cold water and brine. The organic layers were evaporated and the resulting crude product was purified by column on silica gel (0-5% MeOH in DCM) to give compound 8 as solid (50 mg, 17% yield). $^1$H NMR (400 MHz, DMSO-d$_6$) δ 11.33 (br, 1H), 9.39 (br, 1H), 8.30 (s, 1H), 7.15 (m, 3H), 7.01 (m, 1H), 6.89 (m, 1H), 6.62 (br, 1H), 6.23 (brs, 1H), 6.06 (m, 1H), 3.71 (m, 4H) 3.03 (m, 4H), 2.40 (s, 3H); ESI-MS: calcd for (C23H22FN5O2) 419, found 420 (MH$^+$).

Example 9

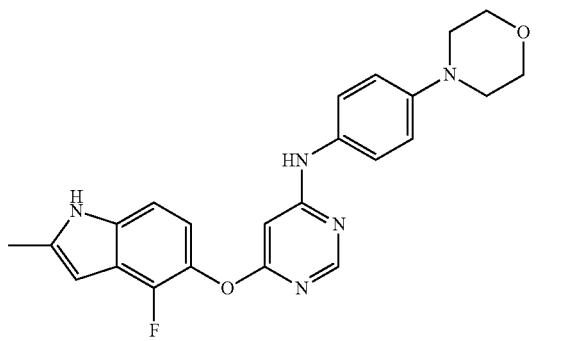

(9)

The solution of compound 1 (200 mg, 0.72 mmol), 4-morpholinoaniline (122 mg, 0.95 mmol) and DIPEA (0.31 ml, 1.80 mmol) in DMSO (10 ml) was stirred at 100° C. for 30 hours. After cooled to room temperature, the mixture was extracted with ethyl acetate (3×35 ml) and washed with cold water and brine. The organic layers were evaporated and the resulting crude product was purified by column on silica gel (0-5% MeOH in DCM) to give compound 9 as solid (130 mg, 43% yield). $^1$H NMR (400 MHz, DMSO-d$_6$) δ 11.31 (br, 1H), 9.26 (br, 1H), 8.26 (s, 1H), 7.37 (m, 2H), 7.11 (m, 1H), 6.88 (m, 3H), 6.23 (brs, 1H), 5.95 (s, 1H), 5.75 (s, 1H), 3.72 (m, 4H), 3.05 (m, 4H), 2.40 (s, 3H); ESI-MS: calcd for (C23H22FN5O2) 419, found 420 (MH$^+$).

Example 10

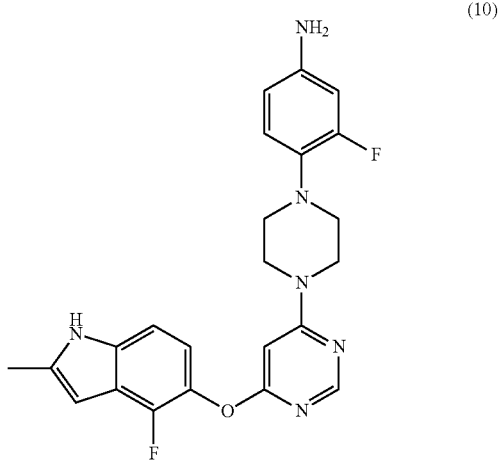 [SMILES: Cc1cc2c(F)c(Oc3cc(N4CCN(c5ccc(N)cc5F)CC4)ncn3)ccc2[nH]1]

(10)

The solution of compound 1 (200 mg, 0.72 mmol), 3-fluoro-4-(4-methylpiperazin-1-yl)aniline (143 mg, 0.68 mmol) and DIPEA (0.31 ml, 1.80 mmol) in DMSO (10 ml) was stirred at 100° C. for 16 hours After cooled to room temperature, the mixture was added to water/brine (75 ml) and stirred at room temperature for 30 min and cooled with ice bath and the solids were collected by filtration, washed by water to give the crude product. The organic layers were evaporated and the resulting crude product was purified by column on silica gel (0-5% MeOH in DCM) to give compound 10 as solid (130 mg, 43% yield). $^1$H NMR (400 MHz, DMSO-d$_6$) δ 11.26 (br, 1H), 8.14 (br s, 1H), 8.14 (s, 1H), 7.09 (m, 1H), 6.83 (m, 2H), 6.47 (m, 2H), 6.40 (s, 1H), 6.32 (s, 1H), 6.20 (s, 1H), 3.71 (m, 4H), 2.91 (m, 4H), 2.40 (s, 3H); ESI-MS: calcd for (C23H22F2N6O) 436, found 437 (MH$^+$).

Example 11

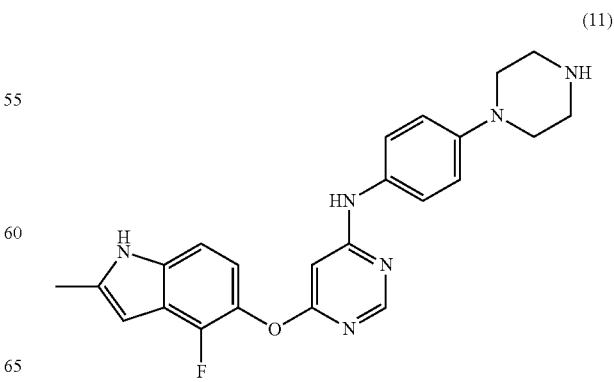

(11)

A mixture of compound 1 (300 mg, 0.68 mmol), tert-Butyl 4(4-aminophenyl)piperazine-1-carboxylate (285 mg, 1.03 mmol) and DIPEA (0.47 ml, 2.70 mmol) in DMSO (10 ml) was stirred at 100° C. for overnight. After cooled to room temperature, the mixture was added to water (100 ml) and stirred at room temperature for 30 min. After cooled with ice-bath, the solids were collected by filtration, washed by water. After air-drying at room temperature overnight, the solids were suspended into DCM/TFA (10/1, 10 mL). The mixture was stirred at room temperature for overnight. After overnight stirring, solvents were evaporated and the residue was dissolved in the DCM/MeOH (8/2, 15 ml) and washed with saturated sodium bicarbonate solution. The organic was dried over sodium sulfate and concentrated. The crude product was purified by column chromatography (silica gel, 0-15% MeOH in DCM) to give the compound 11 as off white solids (130 mg, 42% yield). $^1$H NMR (400 MHz, DMSO-d$_6$) δ 11.70 (br, 1H), 11.33 (br s, 1H), 9.28 (s, 1H), 8.22 (s, 1H), 7.37 (m, 2H), 7.14 (m, 1H), 6.89 (m, 1H), 6.23 (br, 1H), 5.94 (s, 1H), 2.99 (m, 4H), 2.85 (m, 4H), 2.40 (bs, 3H); ESI-MS: calcd for (C23H23FN6O) 418, found 419 (MH$^+$).

Example 12

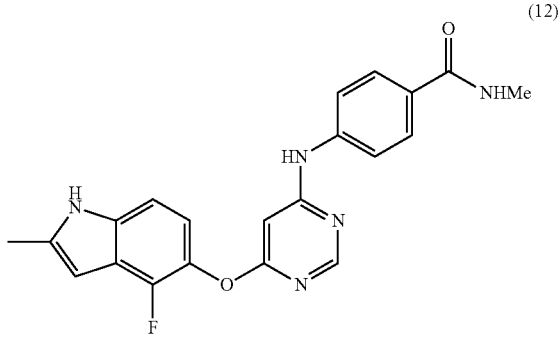 [SMILES: CNC(=O)c1ccc(Nc2cc(Oc3ccc4[nH]c(C)cc4c3F)ncn2)cc1]
(12)

A mixture of compound 1 (200 mg, 0.72 mmol), 4-amino-N-methylbenzamide (108 mg, 0.72 mmol), xantphos (4,5-diphenylphosphanyl-9,9'-dimethyl-9-H-xanthene, 104 mg, 0.18 mmol), K$_2$CO$_3$ (1.59 g, 11.52 mmol) and palladium(II) acetate (24 mg, 0.11 mmol) in 1,4-dioxane (12 ml) was purged with argon for 1 hour. The mixture was heated in microwave for 30 min at 120° C. TLC was checked and the starting material was almost consumed. After cooling to room temperature, the reaction mixture was diluted with DCM/MeOH 8/2) and passed a pad of Celite and concentrated. The crude product was purified by column chromatography (silica gel, 5% MeOH in DCM). After removing the solvents, compound 12 was obtained as brow solids (134 mg, 48% yield). $^1$H NMR (400 MHz, DMSO-d$_6$) δ 11.35 (s, 1H), 9.75 (br s, 1H), 8.40 (s, 1H), 8.27 (m, 1H), 7.77 (m, 2H), 7.70 (m, 2H), 7.16 (m, 1H), 6.94 (m, 1H), 6.25 (s, 1H), 6.14 (s, 1H), 2.77 (s, 3H), 2.40 (s, 3H); ESI-MS: calcd for (C21H18FN5O2) 391, found 392 (MH$^+$).

Example 13

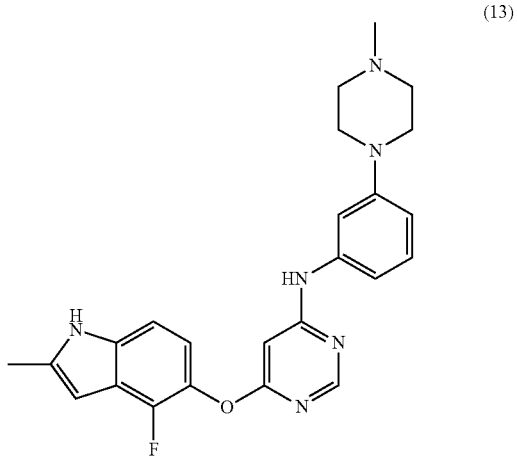 [SMILES: Cc1cc2c(F)c(Oc3cc(Nc4cccc(N5CCN(C)CC5)c4)ncn3)ccc2[nH]1]
(13)

A mixture of compound 1 (200 mg, 0.72 mmol), 4-amino-N-methylbenzamide (108 mg, 0.72 mmol), xantphos (4,5-diphenylphosphanyl-9,9'-dimethyl-9-H-xanthene, 104 mg, 0.18 mmol), K$_2$CO$_3$ (1.59 g, 11.52 mmol) and palladium(II) acetate (24 mg, 0.11 mmol) in 1,4-dioxane (12 ml) was purged with argon for 1 hour. The mixture was heated in microwave for 30 min at 120° C. TLC was checked and the starting material was almost consumed. After cooling to room temperature, the reaction mixture was diluted with DCM/MeOH 8/2) and passed a pad of Celite and concentrated. The crude product was purified by column chromatography (silica gel, 0-10% MeOH in DCM). After removing the solvents, compound 13 was obtained as brow solids (75 mg, 24% yield). $^1$H NMR (400 MHz, DMSO-d$_6$) δ 11.33 (s, 1H), 9.37 (br s, 1H), 8.29 (s, 1H), 7.11 (m, 3H), 7.01 (m, 1H), 6.89 (m, 1H), 6.61 (m, 1H), 6.24 (br s, 1H), 6.01 (m, 1H), 3.07 (s, 3H), 2.40 (m, 7H), 2.21 (s, 3H); ESI-MS: calcd for (C24H25FN6O) 432, found 433 (MH$^+$).

Example 14

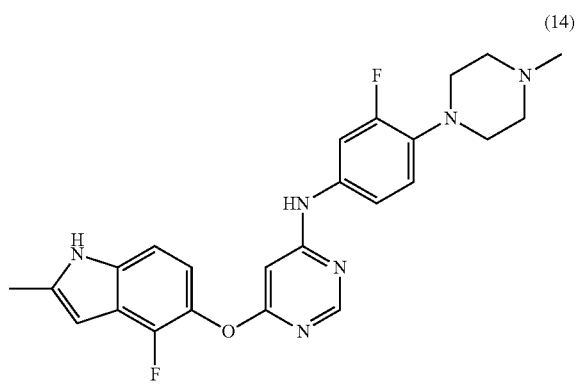
(14)

A mixture of compound 1 (200 mg, 0.72 mmol), 3-fluoro-4-(4-methylpiperazin-1-yl)aniline (150.72 mg, 0.72 mmol), xantphos (4,5-diphenylphosphanyl-9,9'-dimethyl-9-H-xanthene, 104 mg, 0.18 mmol), K$_2$CO$_3$ (1.59 g, 11.52 mmol) and palladium(II) acetate (24 mg, 0.11 mmol) in 1,4-dioxane (12 ml) was purged with argon for 1 hour. The mixture was heated in microwave for 45 min at 120° C. TLC was checked and the starting material was almost consumed. After cooling to room temperature, the reaction mixture was diluted with DCM/MeOH 8/2) and passed a pad of Celite and concentrated. The crude product was purified by column chromatography (silica gel, 0-12% MeOH in DCM). After removing the solvents, compound 14 was obtained as brow solids (68 mg, 21% yield). $^1$H NMR (400 MHz, DMSO-d$_6$) δ 11.33 (br s, 1H), 9.50 (s, 1H), 8.32 (s, 1H), 7.61 (m, 1H), 7.15 (m, 2H), 6.90 (m, 2H), 6.24 (s, 1H), 6.01 (s, 1H), 2.95 (m, 4H), 2.46 (m, 4H), 2.40 (s, 3H), 2.23 (s, 3H); ESI-MS: calcd for (C24H24F2N6O) 450, found 451 (MH$^+$).

Example 15

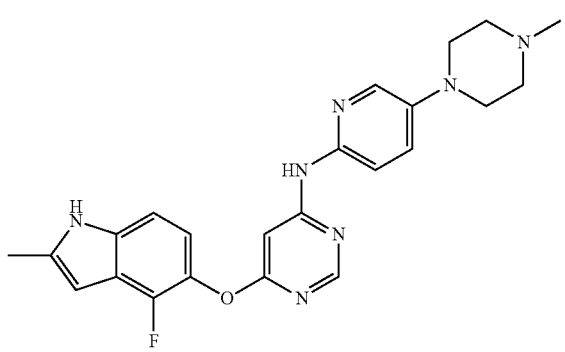

(15)

A mixture of compound 1 (200 mg, 0.72 mmol), 5-(4-methylpiperazin-1-yl)pyridin-2-amine (138.48 mg, 0.72 mmol), xantphos (4,5-diphenylphosphanyl-9,9'-dimethyl-9-H-xanthene, 104 mg, 0.18 mmol), K$_2$CO$_3$ (1.59 g, 11.52 mmol) and palladium(II) acetate (24 mg, 0.11 mmol) in 1,4-dioxane (12 ml) was purged with argon for 1 hour. The mixture was heated in microwave for 45 min at 120° C. TLC was checked and the starting material was almost consumed. After cooling to room temperature, the reaction mixture was diluted with DCM/MeOH 8/2) and passed a pad of Celite and concentrated. The crude product was purified by column chromatography (silica gel, 0-12% MeOH in DCM). After removing the solvents, compound 15 was obtained (84 mg, 27% yield). $^1$H NMR (400 MHz, DMSO-d$_6$) δ 11.29 (br s, 1H), 9.94 (s, 1H), 8.26 (s, 1H), 7.93 (m, 1H), 7.43 (m, 2H), 7.23 (br s, 1H), 7.11 (m, 1H), 6.89 (m, 1H), 6.22 (s, 1H), 3.09 (m, 4H), 2.46 (m, 4H), 2.40 (s, 3H), 2.22 (s, 3H); ESI-MS: calcd for (C23H24FN7O) 433, found 434 (MH$^+$). HPLC: retention time: 7.71 min. purity: 97%.

Example 16

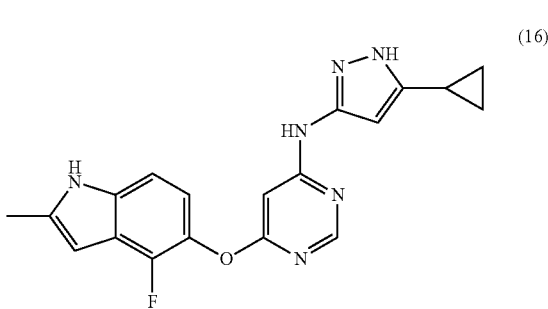 [SMILES: Cc1cc2c(F)c(Oc3cc(Nc4cc(C5CC5)[nH]n4)ncn3)ccc2[nH]1]

(16)

To a solution of compound 1 (0.150 g, 0.540 mmol), 3-cyclopropyl-1H-pyrazole-5-amine (0.080 g, 0.648 mmol), diisopropylethylamine (0.140 g, 1.080 mmol), and sodium iodide (0.089 g, 0.540 mmol) in dimethylsulfoxide (1.5 mL) under argon atmosphere were heated to 150° C. for 24 h in a sealed tube. After cooling, the mixtures were extracted with ethyl acetate (100 mL) and washed with sat. NaHCO$_3$. The combined organic layers were dried over anhydrous Na$_2$SO$_4$ and concentrated in vacuo. The residue was purified by flash chromatography over silica gel with CH$_2$Cl$_2$:MeOH (9:1) to give compound 16 (0.029 g, 15%) as a beige solid. $^1$H NMR (400 MHz, DMSO-d): δ 11.99 (bs, 1H), 11.29 (s, 1H), 9.71 9 s, 1H), 8.21 (s, 1H), 7.010 (d, 1H, J=8.4 Hz), 6.87 (m, 1H), 6.22 (s, 1H), 5.85 (bs, 1H), 2.40 (s, 3H), 1.84 (m, 1H), 0.89 (m, 2H), 0.65 (m, 2H). MS (ESI): Calcd. for C$_{19}$H$_{17}$FN$_6$O: 364, found 365 (M+H).

Example 17

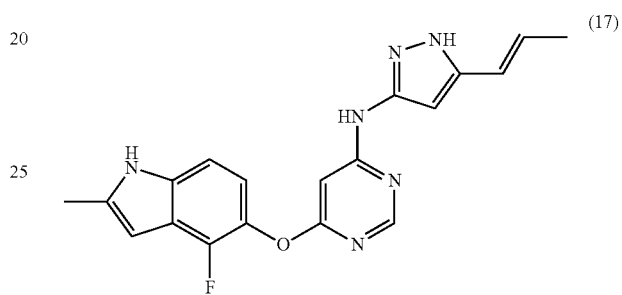

(17)

To a solution of compound 1 (0.100 g, 0.360 mmol), (E)-5-(prop-1-en-1-yl)-1H-pyrazol-3-amine (0.044 g, 0.360 mmol), diisopropylethylamine (0.093 g, 0.720 mmol), and sodium iodide (0.059 g, 0.396 mmol) in dimethylsulfoxide (1.0 mL) under argon atmosphere were heated to 100° C. for 2 days in a sealed tube. After cooling, the mixtures were extracted with ethyl acetate (100 mL) and washed with sat. NaHCO$_3$. The combined organic layers were dried over anhydrous Na$_2$SO$_4$ and concentrated in vacuo. The residue was purified by flash chromatography over silica gel with CH$_2$Cl$_2$:MeOH (9:1) to give compound 17 (0.037 g, 29%) as a brown solid. $^1$H NMR (400 MHz, DMSO-d): δ 12.24 (s, 1H), 11.29 (s, 1H), 9.80 (s, 1H), 8.23 (s, 1H), 7.11 (d, 1H, J=8.8 Hz), 6.70-6.90 (m, 2H), 6.22 (m, 4H), 2.40 (s, 3H), 1.81 (d, 3H, J=4.4 Hz). MS (ESI): Calcd. for C$_{19}$H$_{17}$FN$_6$O: 364, found 365 (M+H).

Example 18

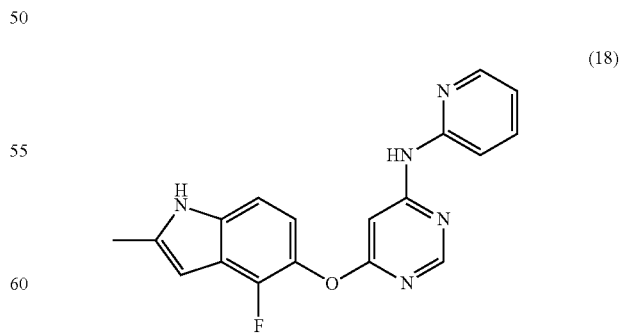

(18)

To an argon purged solution of compound 1 (0.100 g, 0.360 mmol), 2-aminopyridine (0.042 g, 0.450 mmol), 4,5-bis(diphenylphosphino)-9,9-dimethyl-xanthene (0.038 g, 0.064 mmol), and cesium carbonate (0.352 g, 1.080 mmol)

in anhydrous dioxane (4 mL) was added palladium(II) acetate (0.015 g, 0.065 mmol). The solution mixtures were under continuous argon bubbling for addition 30 min prior to seal. The sealed tube was heated to 80° C. oil bath for 16 h. After cooling, the mixtures were diluted with 8:2 dichloromethane/isopropanol (6 mL) and filtered through Celite. The solution was concentrated and the residue was purified by flash chromatography over silica gel with $CH_2Cl_2$:MeOH (95:5) to give compound 18 (0.097 g, 80%) as a white solid. $^1H$ NMR (400 MHz, DMSO-d): δ DMSO-d): δ 11.30 (s, 1H), 10.21 (s, 1H), 8.34 (s, 1H), 8.25 (m, 1H), 7.71 (m, 1H), 7.55 (d, 1H, J=8.0 Hz), 7.48 (s, 1H), 7.12 (d, 1H, J 8.8 Hz), 6.97 (m, 1H), 6.90 (m, 1H), 6.23 (bs, 1H). MS (ESI): Calcd. for $C_{18}H_{15}FN_5O$: 335, found 336 (M+H).

Example 19

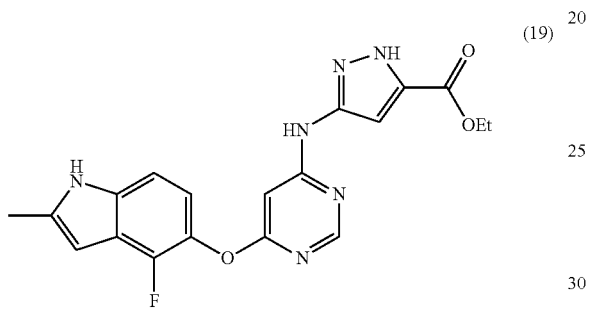

(19)

To a solution of compound 1 (0.100 g, 0.360 mmol), 5-ethyl 1-methyl 3-amino-1H-pyrazole-1,5-dicarboxylate (0.077 g, 0.360 mmol), diisopropylethylamine (0.093 g, 0.720 mmol), and sodium iodide (0.059 g, 0.396 mmol) in dimethylsulfoxide (1.0 mL) under argon atmosphere were heated to 100° C. for 2 days in a sealed tube. After cooling, the mixtures were extracted with ethyl acetate (100 mL) and washed with sat. $NaHCO_3$. The combined organic layers were dried over anhydrous $Na_2SO_4$ and concentrated in vacuo. The residue was purified by flash chromatography over silica gel with $CH_2Cl_2$:MeOH (9:1) to give compound 19 (0.018 g, 13%) as a dark brown solid. $^1H$ NMR (400 MHz, DMSO-d): δ 13.44 (s, 1H), 11.30 (s, 1H), 10.05 (s, 1H), 8.30 (s, 1H), 7.11 (m, 1H), 6.50-6.90 (m, 3H), 6.22 (s, 1H), 4.29 (q, 2H, J=6.8 Hz), 2.40 (s, 1H), 1.30 (t, 3H, J=6.8 Hz). MS (ESI): Calcd. for $C_{19}H_{17}FN_6O_3$: 396, found 397 (M+H).

Example 20

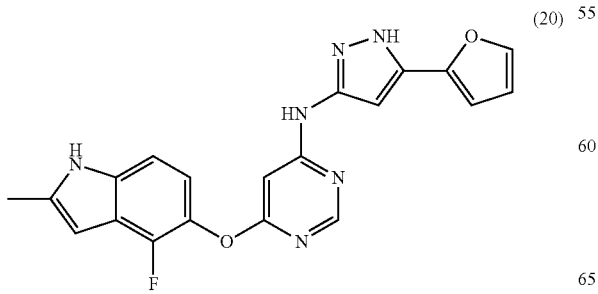

(20)

To a solution of compound 1 (0.100 g, 0.360 mmol), 3-amino-5-(2-furyl)pyrazole (0.107 g, 0.720 mmol), diisopropylethylamine (0.093 g, 0.720 mmol), and sodium iodide (0.093 g, 0.432 mmol) in dimethylsulfoxide (1.0 mL) under argon atmosphere were heated to 100° C. for 2 days in a sealed tube. After cooling, the mixtures were extracted with ethyl acetate (100 mL) and washed with sat. $NaHCO_3$. The combined organic layers were dried over anhydrous $Na_2SO_4$ and concentrated in vacuo. The residue was purified by flash chromatography over silica gel with $CH_2Cl_2$:MeOH (9:1) to give compound 20 (0.032 g, 23%) as a beige solid. $^1H$ NMR (400 MHz, DMSO-d): δ 12.80 (bs, 1H), 11.30 (s, 1H), 9.96 (bs, 1H), 8.28 (s, 1H), 7.75 (s, 1H), 7.12 (d, 1H, J=8.4 Hz), 6.89 (m, 1H), 6.81 (bs, 1H), 6.60 (bs, 1H), 6.54 (m, 1H), 6.23 (bs, 1H). MS (ESI): Calcd. for $C_{20}H_{15}FN_6O_2$: 390, found 391 (M+H).

Example 21-A

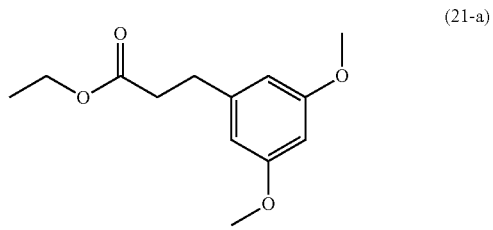 [SMILES: CCOC(=O)CCc1cc(OC)cc(OC)c1]

(21-a)

Reference procedure: ACS Catalysis, 3(6), 1356-1359; 2013

To a solution of 3-(3,5-dimethoxyphenylpropanoic acid (5.00 g, 23.78 mmol) in EtOH (50 mL), SOCl2 (5 mL) was added slowly. The reaction mixture was heated at reflux for 4.5 h and then evaporated to remove EtOH. Ethyl acetate (40 mL), water (20 mL) and saturated aqueous solution of NaOH were added to adjust the pH to 8-9. After separation, the aqueous was extracted with ethyl acetate (15 ml×2). The combined organic phase was washed with water (20 mL) and brine (20 mL), dried ($Na_2SO_4$) and concentrated. To give title compound 21-a as yellow oil (5.57 g 8%. The product was used directly in next step without further purification. $^1H$ NMR (400 MHz, DMSO-d6) δ 6.39 (d, J=2.4 Hz, 2H), 6.32 (br, 1H), 4.04 (q, J=6.8 Hz, 2H), 3.71 (s, 6H), 2.78 (t, J=7.2 Hz, 2H), 2.57 (t, J=7.2 Hz, 2H), 1.16 (t, J=7.2 Hz, 3H); ESI-MS: calcd for (C13H18O4) 238, found 239 (MH$^+$).

Example 21-B

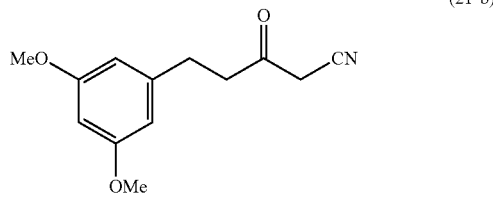

(21-b)

To a solution of diisopropylamine (2.80 g, 27.70 mmol) in dry tetrahydrofuran (100 mL) under argon atmosphere cooled to −78° C. was slowly added n-butyllithium (10.07 mL, 2.5 M in hexanes, 25.18 mmol) and stirred for 15 min., then warm to 0° C. for 15 min., followed by retooled to −78° C. for addition 30 min. To this freshly prepared LDA solution was added dropwise anhydrous acetonitrile (1.29 g, 1.64 mL, 31.48 mmol) and stirred for 1 hr. Then a solution of 21-a (3.00 g, 12.59 mmol) in anhydrous tetrahydrofuran (10 mL) was added dropwise and continued to stir for another hour. The mixtures were then warm to room temperature and stirred overnight (15 hr). The mixtures were diluted with dichloromethane (500 mL) and quenched with water (300 mL). Extraction with dichloromethane (2×200 mL) and the combined organic layers were dried over anhydrous sodium sulfate, filtered, and concentrated. The concentrated crude was then purified by flash chromatography over silica with 100% $CH_2Cl_2$ to give compound 21-b (2.57 g, 87%) as a white solid. $^1H$ NMR (400 MHz, DMSO-d): δ 6.36 (s, 2H), 6.31 (s, 1H), 4.06 (bs, 2H), 3.71 (s, 6H), 2.79 (bs, 2H), 2.72 (m, 2H). MS (ESI): Calcd. for $C_{13}H_{15}NO_3$: 233, found 234 (M+H).

Example 21-C

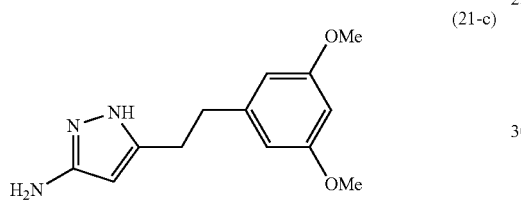

(21-c)

To a suspension of compound 21-b (2.50 g, 10.72 mmol) in absolute ethanol (100 mL) was added hydrazine hydrate (2.61 mL, 53.59 mmol). The mixtures were refluxed under argon overnight (16 hr). After cooled, the solvent was removed by vacuum and diethyl ether (100 mL) was added followed by sonication to induce precipitation. The precipitated solid was cooled in refrigerator for 1 hour prior to filtration to give compound 21-c (2.65 g, 100%) as a light yellow solid. $^1H$ NMR (400 MHz, DMSO-d): δ 6.37 (s, 2H), 6.30 (s, 1H), 5.19 (s, 1H), 4.43 (bs, 2H), 3.70 (s, 6H), 2.77 (m, 2H), 2.67 (m, 2H). MS (ESI): Calcd. for $C_{13}H_{17}N_3O_2$: 247, found 248 (M+H).

Example 21

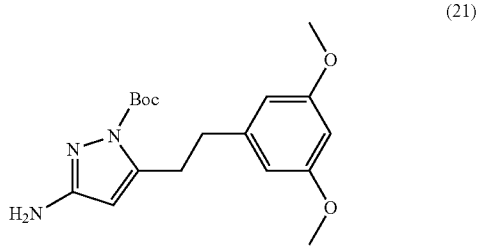 [SMILES: COc1cc(CCc2cc(N)nn2C(=O)OC(C)(C)C)cc(OC)c1]

(21)

A solution of 5-(3,5-dimethoxyphenethyl)-1H-pyrazol-3-amine (compound 21-c) (800 mg, 3.24 mmol) in THF (20 ml) was added to a cold suspension of sodium hydride (60% in mineral oil, 162 mg, 4.04 mmol) in THF (6 ml) at 0° C. slowly. After stirring at 0° C. for 60 minute, di-tert-butyl-dicarboxate (791 mg, 3.62 mmol) was added. (THF was used to help the addition of di-tert-butyldicarboxate, total 30 mL was in the bottle). The mixture was stirred at 0° C. for 60 minute. TLC was checked and the starting material was consumed. The reaction mixture was quenched with ice-water, extracted with ethyl acetate (3×15 ml). The combined organic was washed by brine, dried over sodium sulfate and concentrated to minimum amount solvents. Hexanes were added (~20 ml), and the mixture was sonicated to make a homogenous suspension. The hexanes were decanted and the yellow residue was further concentrated to give the desired product compound 21 as yellow sticky syrup with a mixture of 2 isomers (about 4:5) of protection group on the ring (1.06 g, 95% yield). $^1H$ NMR (400 MHz, DMSO-$d_6$) δ: 6.42 and 6.40 (d, d, J=2.0 Hz, 2H), 6.32 and 6.30 (t, t, J=2.4 Hz, 1H), 6.25 and 5.30 (br, 2H), 5.62 and 5.21 (s, s, 1H), 3.71 (s, 6H), 3.08-2.64 (m, 4H), 1.54 and 1.51 (s, s, 9H).

Example 22

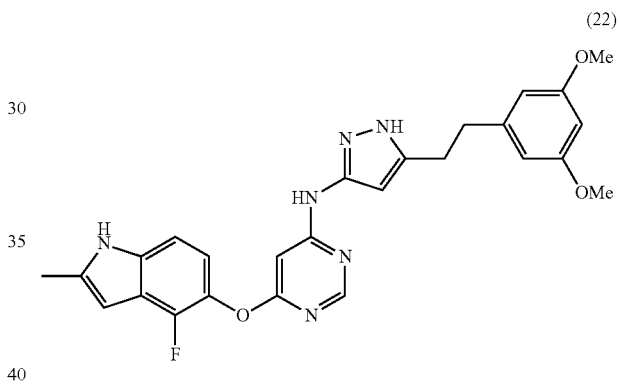

(22)

To an argon purged solution of compound 1 (0.100 g, 0.360 mmol), tert-butyl 3-amino-5-(3,5-dimethoxyphenethyl)-1H-pyrazole-1-carboxylate (0.156 g, 0.450 mmol), 4,5-bis(diphenylphosphino)-9,9-dimethyl-xanthene (0.038 g, 0.065 mmol), and cesium carbonate (0.352 g, 1.08 mmol) in anhydrous dioxane (4 mL) bubbling with argon was added palladium(II) acetate (0.015 g, 0.065 mmol). The solution mixtures were under continuous argon bubbling for addition 10 min. The sealed tube was microwave at 120° C. for 35 min. After cooling, the mixtures were diluted with 8:2 dichloromethane/isopropanol (6 mL) and filtered through Celite. The solution was concentrated and dried under vacuum overnight. The crude residue was redissolved in 20% trifluoromethyl acetic acid/dichloromethane (2 mL/16 mL) and stirred for 4 hours. The mixtures were quenched with sat. sodium bicarbonate for 1 hour of stirring until bubbling subsided, then extracted with ethyl acetate (2×100 mL), washed water (2×100 mL), and dried over anhydrous $Na_2SO_4$. The residue was purified by flash chromatography over silica gel with $CH_2Cl_2$:MeOH (95:5) to give compound 22 (0.072 g, 41%) as a light yellow solid. $^1H$ NMR (400 MHz, DMSO-d): δ DMSO-d): δ 12.01 (s, 1H), 11.28 (s, 1H), 9.74 (s, 1H), 8.21 (s, 1H), 7.10 (d, 1H, J=8.4 Hz), 6.87 (t, 2H, J=8.0 Hz), 6.38 (m, 3H), 6.30 (m, 2H), 6.22 (s, 1H), 3.70 (s, 6H), 2.82 (bs, 4H), 2.39 9 s, 3H). MS (ESI): Calcd. for $C_{26}H_{25}FN_6O_3$: 488, found 489 (M+H).

Example 23

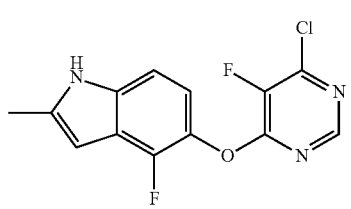
(23)

To a solution of 4-fluoro-2-methyl-1H-indol-5-ol (2.00 g, 12.11 mmol) and 4,6-dichloro-5-fluoropyridine (2.02 g, 12.11 mmol) in DMSO (18 ml) was added potassium carbonate (6.02 g, 43.59 mmol) and the mixture was heated at 85° C. for 2.5 hours (oil bath). After cooled to room temperature, the reaction mixture was added to a container with water (250 mL) and the mixture was stirred at room temperature for 1 hour then aged at 4° C. overnight. The pH was adjusted to 6-7 with 2N HCl and cooled with ice bath. The solids were collected by filtration and washed by water. Compound 23 was obtained as yellow solids (3.29 g, 92% yield). No further purification was performed and the product was used for the next step reaction. $^1$H NMR (400 MHz, DMSO-$d_6$) δ 11.40 (br, 1H), 8.42 (s, 1H), 7.15 (d, J=8.8 Hz, 1H), 6.99 (t, J=7.6 Hz, 1H), 6.25 (s, 1H), 2.40 (s, 3H); ESI-MS: calcd for (C13H8ClF2N3O) 295, found 296 (MH$^+$).

Example 24

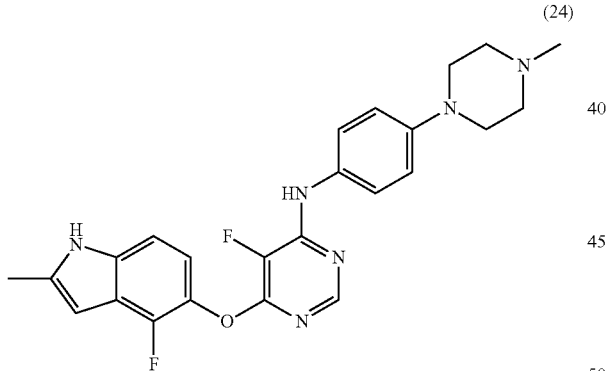
(24)

A mixture of compound 23 (200 mg, 0.68 mmol), 4-(4-Methylpiperazineno)aniline (194 mg, 1.01 mmol), and DIPEA (0.30 ml, 1.69 mmol) in DMSO (3.5 ml) was stirred at 100° C. for overnight. After cooled to room temperature, the mixture was added to water/sat. NH$_4$Cl (50 ml/50 ml) and stirred at room temperature for 30 min. The pH of the mixture was adjusted to 6~7 using 2N HCl. After stored at 4° C. for overnight, the solids were collected by filtration and washed by water to give the crude product. The crude product was purified by column chromatography (0-15% MeOH in DCM) to give compound 24 as brown solids (92 mg, 30% yield). $^1$H NMR (400 MHz, DMSO-$d_6$) δ 11.31 (br, 1H), 9.37 (s, 1H), 7.92 (s, 1H), 7.48 (d, J=9.2 Hz, 2H), 7.10 (d, J=8.8 Hz, 1H), 6.92 (m, 3H), 6.22 (s, 1H), 3.08 (m, 4H), 2.45 (m, 4H), 2.38 (br, 3H), 2.22 (s, 3H); ESI-MS: calcd for (C24H24F2N6O) 450, found 451 (MH$^+$).

Example 25

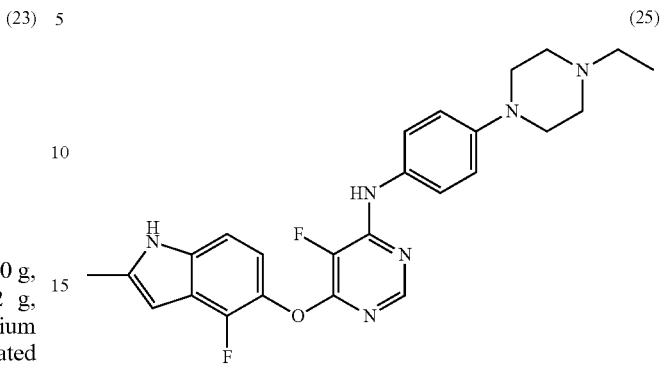
(25)

A mixture of compound 23 (200 mg, 0.68 mmol), 4-(4-Ethylpiperazine-1-yl))aniline (208 mg, 1.01 mmol), and DIPEA (0.30 ml, 1.69 mmol) in DMSO (3.5 ml) was stirred at 100° C. for overnight. After cooled to room temperature, the mixture was added to water/sat. NH$_4$Cl (50 ml/50 ml) and stirred at room temperature for 30 min. The pH of the mixture was adjusted to 6~7 using 2N HCl. After stored at 4° C. for overnight, the solids were collected by filtration and washed by water to give the crude product. The crude product was purified by column chromatography (0-15% MeOH in DCM) to give compound 25 as brown solids (160 mg, 51% yield). $^1$H NMR (400 MHz, DMSO-$d_6$) δ 11.35 (br, 1H), 9.42 (s, 1H), 7.94 (s, 1H), 7.53 (d, J=8.8 Hz, 2H), 7.10 (d, J=8.8 Hz, 1H), 6.95 (m, 3H), 6.22 (s, 1H), 3.02-2.20 (m, 10H), 2.39 (s, 3H), 1.20 (br, 3H); ESI-MS: calcd for (C25H26F2N6O) 464, found 465 (MH$^+$).

Example 26

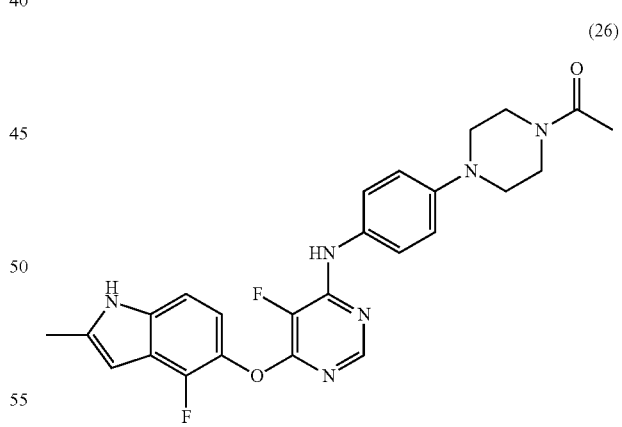
(26)

A mixture of compound 23 (200 mg, 0.68 mmol), 1-Actyl-4-(4-aminophenyl)piperazine (159 mg, 0.73 mmol), and DIPEA (0.30 ml, 1.69 mmol) in DMSO (3.5 ml) was stirred at 100° C. for overnight. After cooled to room temperature, the mixture was added to water/sat. NH$_4$Cl (50 ml/50 ml) and stirred at room temperature for 30 min. The pH of the mixture was adjusted to 6~7 using 2N HCl. After stored at 4° C. for overnight, the solids were collected by filtration, washed by water to give the crude product. The crude product was purified by column chromatography (0-15%

MeOH in DCM) to give compound 26 as brown solids (201 mg, 65% yield). $^1$H NMR (400 MHz, DMSO-$d_6$) δ 11.29 (br, 1H), 9.38 (s, 1H), 7.91 (s, 1H), 7.49 (d, J=9.2 Hz, 2H), 7.09 (d, J=8.8 Hz, 1H), 6.92 (m, 3H), 6.20 (s, 1H), 3.56 (m, 4H), 3.09 (m 2H), 3.02 (m, 2H), 2.38 (s, 3H), 2.02 (s, 3H); ESI-MS: calcd for (C25H24F2N6O2) 478, found 479 (MH$^+$).

Example 27

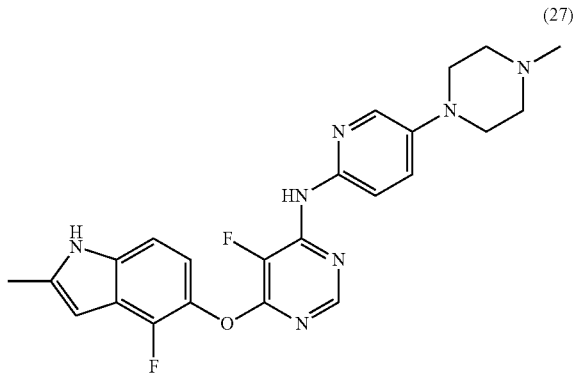

(27)

A mixture of compound 23 (200 mg, 0.67 mmol), 5-(4-methylpiperazin-1-yl)pyridin-2-amine (135 mg, 0.70 mmol), palladium(II) acetate (23 mg, 0.10 mmol), xantphos (4,5-diphenylphosphanyl-9,9'-dimethyl-9-H-xanthene, 97 mg, 0.17 mmol) and K$_2$CO$_3$ (325 mg, 2.35 mmol) in 1,4-dioxane (15 ml) was purged with argon for 30 min. The mixture was heated with Biotage microwave initiator at 120° C. for 15 min. The reaction mixture was passed a pad of Celite, eluted with DCM/MeOH (8/2, 20 ml). The crude product was purified by column chromatography (silica gel, 0-15% MeOH in DCM) to give compound 27 as yellow solids (139 mg, 46% yield). $^1$H NMR (400 MHz, DMSO-$d_6$) δ 11.32 (br, 1H), 9.69 (s, 1H), 8.04 (d, J=2.8 Hz, 1H), 8.01 (s, 1H), 7.77 (d, J=9.2 Hz, 1H), 7.42 (dd, J=9.2 Hz, J=1.2 Hz, 1H), 7.12 (d, J=9.2 Hz, 2H), 6.93 (t, J=7.2 Hz, 1H), 6.23 (s, 1H), 3.15 (m, 4H), 2.45 (m, 4H), 2.40 (br, 3H), 2.22 (s, 3H); ESI-MS: calcd for (C23H23F2N7O) 451, found 452 (MH$^+$).

Example 28

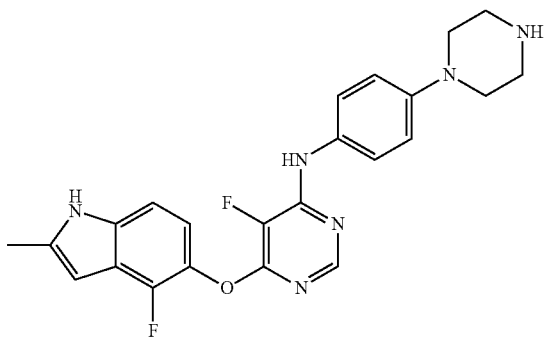

(28)

A mixture of compound 23 (200 mg, 0.67 mmol), tert-Butyl 4-(4-aminophenyl)piperazine-1-carboxylate (195 mg, 0.70 mmol), palladium(II) acetate (23 mg, 0.10 mmol), xantphos (4,5-diphenylphosphanyl-9,9'-dimethyl-9-H-xanthene, 97 mg, 0.17 mmol) and K$_2$CO$_3$ (325 mg, 2.35 mmol) in 1,4-dioxane (15 ml) was purged with argon for 30 min. The mixture was heated with Biotage microwave initiator at 120° C. for 75 min. The reaction mixture was passed a pad of Celite, eluted with DCM/MeOH (8/2, 20 ml). The solution was concentrated to a residue and dissolved into DCM (5 mL). 1 mL of TFA was added and the mixture was stirred at room temperature for overnight. After concentrated, the residue was dissolved into DCM/MeOH (8/2, 15 ml) and water was added. The pH of the mixture was adjusted to about 7 with aqueous solution of sat. sodium bicarbonate. The organic was dried over sodium sulfate and concentrated. The crude product was purified by column chromatography (silica gel, 0-15% MeOH in DCM) to give the compound 28 as yellow solids (123 mg, 42% yield). $^1$H NMR (400 MHz, DMSO-$d_6$) δ 11.31 (br, 1H), 9.40 (s, 1H), 7.93 (s, 1H), 7.52 (d, J=8.8 Hz, 2H), 7.12 (d, J=8.8 Hz, 1H), 6.92 (m, 3H), 6.22 (s, 1H), 3.11 (m, 4H), 3.01 (m, 4H), 2.40 (s, 3H), 1.41 (s, 1H); ESI-MS: calcd for (C23H22F2N6O) 436, found 437 (MH$^+$).

Example 29

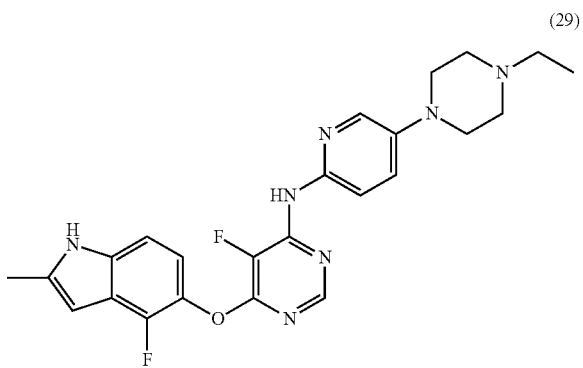 [SMILES: CCN1CCN(c2ccc(Nc3ncnc(Oc4ccc5[nH]c(C)cc5c4F)c3F)nc2)CC1]

(29)

A mixture of compound 23 (200 mg, 0.676 mmol), 5-(4-ethylpiperazin-1-yl)pyridin-2-amine (147 mg, 0.710 mmol), Pd(OAc)$_2$ (23 mg, 0.10 mmol), xantphos (98 mg, 0.17 mmol), K$_2$CO$_3$ (327 mg, 2.37 mmol) and anhydrous dioxane (12.0 mL) was sealed in a microwavable tube and degassed with argon for 20 min. The mixture was then heated to 120° C. for 15 min under microwave irradiation. The resulting mixture was filtered over a cotton pad and concentrated. The resulting residue was purified by flash column chromatography on silica gel using 0-10% MeOH in DCM (v/v) as eluent. The resulting residue was further purified by crystallization out of EtOAc to afford the desired product N-(5-(4-ethylpiperazin-1-yl)pyridin-2-yl)-5-fluoro-6-((4-fluoro-2-methyl-1H-indol-5-yl)oxy)pyrimidin-4-amine (compound 29) as a white solid (54 mg, 17% yield).

$^1$H NMR (DMSO-d6, 400 MHz) δ 11.32 (br s, 1H), 9.69 (br s, 1H), 8.04-8.01 (m, 2H), 7.77 (d, J=9.2 Hz, 1H), 7.44-7.41 (m, 1H), 7.11 (d, J=8.8 Hz, 1H), 6.95-6.91 (m, 1H), 6.23 (s, 1H), 3.16 (t, J=4.4 Hz, 4H), 2.52 (4H, obscured by DMSO peak), 2.40 (s, 3H), 2.37 (q, J=7.2 Hz, 2H), 1.03 (t, J=7.2 Hz, 3H); MS (ESI): calcd for C24H25F2N7O: 465, found: 467 (MH$^+$).

Example 30

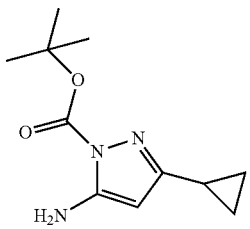

(30)

A solution of 3-cyclopropyl-1-H-pyrazole-5-amine (3.05 g, 24.77 mmol) in THF (20 ml) was added to a cold suspension of sodium hydride (60% in mineral oil, 1.09 g, 27.24 mmol) in THF (20 ml) at 0° C. slowly. After stirring at 0° C. for 30 minute, di-tert-butyldicarboxate (5.95 g, 27.24 mmol) was added. (THF was used to help the addition of di-tert-butyldicarboxate, total 125 mL was in the bottle). The mixture was stirred at 0° C. for 30 minute. TLC was checked and the starting material was consumed. The reaction mixture was quenched with ice-water, extracted with ethyl acetate (3×50 ml). The combined organic was washed by brine, dried over sodium sulfate and concentrated to minimum amount solvents. Hexanes were added (~100 ml), and the mixture was sonicated to make a homogenous suspension. The yellow solids were collected by filtration, washed by hexanes to give the desired product compound 30 as a mixture of 2 isomers (about 1:3) of protection group on the ring (3.73 g, 69% yield). 1H NMR (400 MHz, DMSO-d6) δ: for the major isomer: 6.16 (br, 2H), 4.92 (s, 1H), 1.68 (m, 1H), 1.49 (s, 9H), 0.86 (m, 2H), 0.78 (m, 2H); for the minor isomer: 5.35 (s, 1H), 5.20 (br, 2H), 2.05 (m, 1H), 1.49 (s, 9H), 0.88 (m, 2H), 0.78 (m, 2H).

Example 31

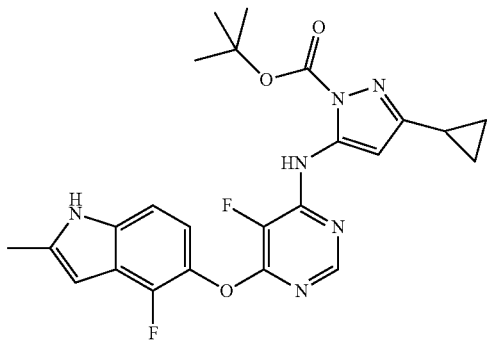

(31)

A mixture of compound 23 (265 mg, 0.896 mmol), compound 30 (200 mg, 0.896 mmol), Pd(OAc)2 (40 mg, 0.18 mmol), xantphos (181 mg, 0.31 mmol), K2CO3 (500 mg, 3.62 mmol) and anhydrous dioxane (12.0 mL) was sealed in a tube and degassed with argon for 10 min. The mixture was then warmed to 120° C. in an oil bath and stirred for 15 min. The resulting mixture was partitioned between EtOAc and aq. NaHCO3 (50% saturation), and the organic layer was separated, dried over anhydrous Na2SO4 and concentrated. The resulting residue was purified by flash column chromatography on silica gel using 0-100% EtOAc in hexanes (v/v) as eluent to afford the desired product tert-butyl 3-cyclopropyl-5-((5-fluoro-6-((4-fluoro-2-methyl-1H-indol-5-yl)oxy)pyrimidin-4-yl)amino)-1H-pyrazole-1-carboxylate (compound 31) as a yellow solid (255 mg, 56% yield). 1H NMR (DMSO-d6, 400 MHz) δ 11.34 (br s, 1H), 9.98 (br s, 1H), 8.14 (s, 1H), 7.13 (d, J=8.8 Hz, 1H), 6.96-6.92 (m, 1H), 6.49 (s, 1H), 6.19 (s, 1H), 2.40 (s, 3H), 1.97-1.90 (m, 1H), 1.55-1.54 (m, 9H), 0.96-0.91 (m, 2H), 0.75-0.71 (m, 2H); MS (ESI): calcd for C24H24F2N6O3: 482, found: 384 (MH+-tBOC).

Example 32

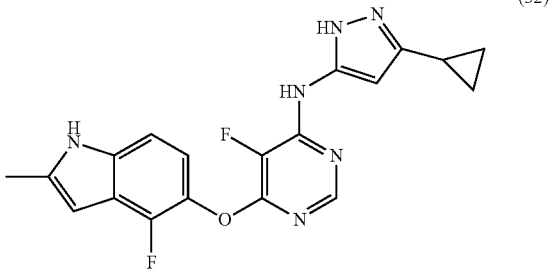

(32)

To a mixture of tert-butyl 3-cyclopropyl-5-((5-fluoro-6-((4-fluoro-2-methyl-1H-indol-5-yl)oxy)pyrimidin-4-yl)amino)-1H-pyrazole-1-carboxylate (91 mg, 0.19 mmol) in DCM (9 mL) was added TFA (1 mL) and the mixture was stirred at room temperature for ca 17 h. The mixture was then partitioned between EtOAc and aq. NaHCO3 (50% saturation), and the organic layer was separated, dried over anhydrous Na2SO4 and concentrated. The resulting residue was purified by flash column chromatography on silica gel using 0-100% EtOAc in hexanes (v/v) as eluent to afford the desired product N-(3-cyclopropyl-1H-pyrazol-5-yl)-5-fluoro-6-((4-fluoro-2-methyl-1H-indol-5-yl)oxy) pyrimidin-4-amine (compound 32) as a white solid (44 mg, 61% yield). ¹H NMR (DMSO-d6, 400 MHz) δ 12.11 (br s, 1H), 11.30 (br s, 1H), 9.76-9.76 (m, 1H), 7.96 (s, 1H), 7.11 (d, J=8.8 Hz, 1H), 6.94-6.90 (m, 1H), 6.25-6.22 (m, 2H), 2.40 (s, 3H), 1.92-1.85 (m, 1H), 0.92-0.90 (m, 2H), 0.69-0.68 (m, 2H); MS (ESI): calcd for C19H16F2N6O: 382, found: 384 (MH+).

Example 33

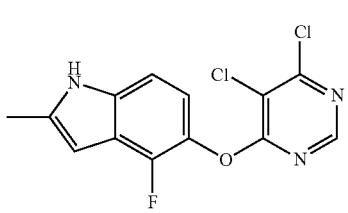

(33)

A mixture of 4,5,6-trichloropyrimidine (2.22 g, 12.1 mmol), 4-fluoro-2-methyl-1H-indol-5-ol (2.00 g, 12.1 mmol), K2CO3 (5.85 g) and DMSO (20 mL) was warmed to 80° C. and stirred for 2 hrs. The mixture was cooled to room temperature and poured into water (200 mL) forming a colloidal mixture. Then aq. 2 M HCl (ca. 30 mL) was added dropwise to the stirring colloidal mixture whereupon a precipitate formed. The precipitate was filtered and washed with water affording the desired product 5-((5,6-dichloropyrimidin-4-yl)oxy)-4-fluoro-2-methyl-1H-indole (compound 33) as a brown solid (3.66 g, 97% yield). ¹H NMR (DMSO-d6, 400 MHz) δ 11.39 (s, 1H), 8.53 (s, 1H), 7.15 (d, J=8.4 Hz, 1H), 6.99-6.95 (m, 2H), 6.25 (s, 1H), 2.40 (s, 3H); MS (ESI): calcd for C13H8Cl2FN3O: 311, found: weak signal.

Example 34

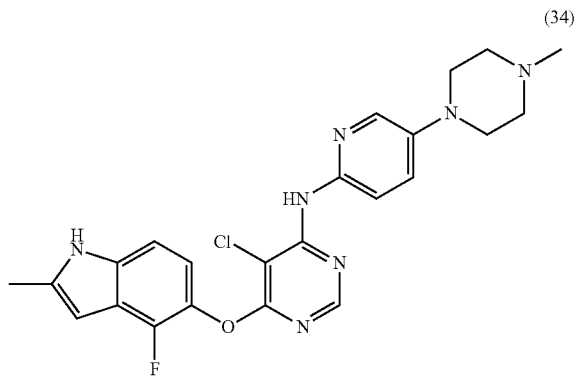

(34)

A mixture of compound 33 (200 mg, 0.641 mmol), 5-(4-methylpiperazin-1-yl)pyridin-2-amine (129 mg, 0.673 mmol), Pd(OAc)$_2$ (42 mg, 0.19 mmol), xantphos (186 mg, 0.322 mmol), K$_2$CO$_3$ (310 mg, 2.24 mmol) and anhydrous dioxane (10 mL) was sealed in a microwavable tube and degassed with argon for 10 min. The mixture was then heated to 120° C. for 20 min under microwave irradiation. The resulting mixture was partitioned between EtOAc and aq. NaHCO$_3$ (50% saturation), the organic layer was dried over anhydrous Na$_2$SO$_4$ and concentrated. The resulting residue was purified by flash column chromatography on silica gel using 0-10% MeOH in DCM (v/v) as eluent. The resulting residue was further purified by crystallization out of EtOAc to afford the desired product 5-chloro-6-((4-fluoro-2-methyl-1H-indol-5-yl)oxy)-N-(5-(4-methylpiperazin-1-yl)pyridin-2-yl)pyrimidin-4-amine (compound 34) as a yellow solid (36 mg, 12% yield). $^1$H NMR (DMSO-d6, 400 MHz) δ 11.31 (br s, 1H), 8.90 (br s, 1H), 8.13 (s, 1H), 8.07 (d, J=3.2 Hz, 1H), 7.78 (d, J=8.8 Hz, 1H), 7.46-7.43 (m, 1H), 7.11 (d, J=8.4 Hz, 1H), 6.93-6.89 (m, 1H), 6.22 (s, 1H), 3.18-3.15 (m, 4H), 2.48-2.45 (m, 4H), 2.40 (s, 3H), 2.23 (s, 3H); MS (ESI): calcd for C23H23ClFN7O: 467, found: 469 (MH$^+$).

Example 35

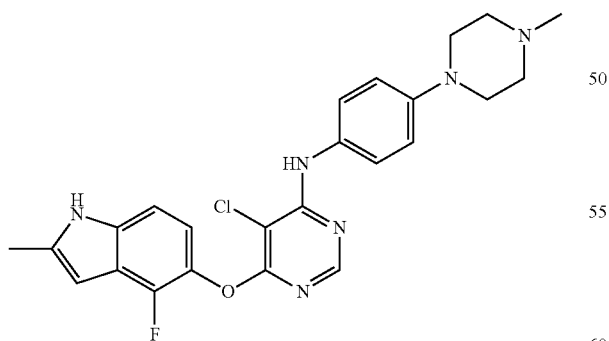

(35)

A mixture of compound 33 (200 mg, 0.641 mmol), 4-(4-methylpiperazin-1-yl)aniline (150 mg, 0.784 mmol), Pd(OAc)$_2$ (22 mg, 0.10 mmol), xantphos (93 mg, 0.16 mmol), K$_2$CO$_3$ (310 mg, 2.24 mmol) and anhydrous dioxane (10 mL) was sealed in a microwavable tube and degassed with argon for 10 min. The mixture was then heated to 120° C. for 20 min under microwave irradiation. The resulting mixture was partitioned between EtOAc and aq. NaHCO$_3$ (50% saturation), the organic layer was dried over anhydrous Na$_2$SO$_4$ and concentrated. The resulting residue was purified by flash column chromatography on silica gel using 0-10% MeOH in DCM (v/v) as eluent. The resulting residue was further purified by crystallization out of EtOAc to afford the desired product 5-chloro-6-((4-fluoro-2-methyl-1H-indol-5-yl)oxy)-N-(4-(4-methylpiperazin-1-yl)phenyl)pyrimidin-4-amine (compound 35) as an off-white solid (29 mg, 10% yield). $^1$H NMR (DMSO-d6, 400 MHz) δ 11.30 (br s, 1H), 8.96 (br s, 1H), 8.00 (s, 1H), 7.38-7.36 (m, 2H), 7.10 (d, J=8.8 Hz, 1H), 6.93-6.87 (m, 2H), 6.22 (s, 1H), 3.12-3.10 (m, 4H), 2.46-2.44 (m, 4H), 2.40 (s, 3H), 2.22 (s, 3H); MS (ESI): calcd for C24H24ClFN6O: 466, found: 468 (MH$^+$).

Example 36

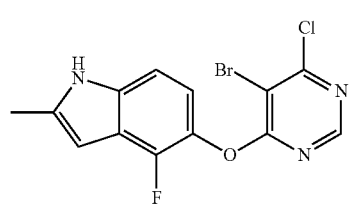

(36)

A mixture of 5-bromo-4,6-dichloropyrimidine (2.76 g, 12.1 mmol), 4-fluoro-2-methyl-1H-indol-5-ol (2.00 g, 12.1 mmol), K$_2$CO$_3$ (5.85 g) and DMSO (20 mL) was warmed to 80° C. and stirred for 2 hrs. The mixture was cooled to room temperature and poured into water (200 mL) forming a colloidal mixture. Then aq. 2 M HCl (ca. 30 mL) was added dropwise to the stirring colloidal mixture whereupon a precipitate formed. The precipitate was filtered and washed with water, and it was further purified by flash column chromatography on silica gel using 0-10% MeOH in DCM (v/v) as eluent to afford the desired product 5-((5-bromo-6-chloropyrimidin-4-yl)oxy)-4-fluoro-2-methyl-1H-indole (compound 36) as a brown solid (1.73 g, 40% yield). $^1$H NMR (DMSO-d6, 400 MHz) δ 11.38 (br s, 1H), 8.53 (br s, 1H), 7.15 (d, J=8.8 Hz, 1H), 6.98-6.94 (m, 1H), 6.25 (s, 1H), 2.40 (s, 3H); MS (ESI): calcd for C13H8BrClFN3O: 355, found: weak signal.

Example 37

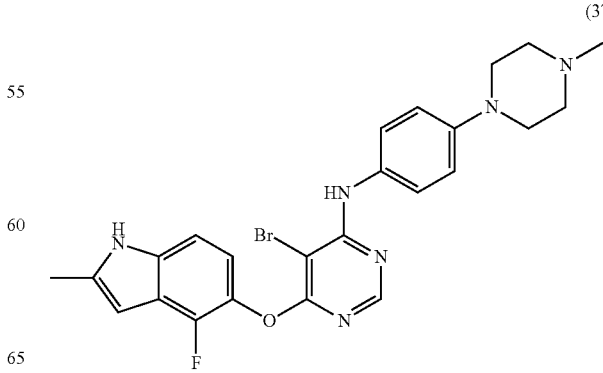

(37)

A mixture of compound 36 (228 mg, 0.641 mmol), 4-(4-methylpiperazin-1-yl)aniline (129 mg, 0.673 mmol), Pd(OAc)$_2$ (22 mg, 0.10 mmol), xantphos (93 mg, 0.16 mmol), K$_2$CO$_3$ (310 mg, 2.24 mmol) and anhydrous dioxane (10 mL) was sealed in a microwavable tube and degassed with argon for 10 min. The mixture was then heated to 120° C. for 20 min under microwave irradiation. The resulting mixture was filtered over a cotton pad and concentrated. The resulting residue was purified by flash column chromatography on silica gel using 0-10% MeOH in DCM (v/v) as eluent. The resulting residue was further purified by crystallization out of EtOAc to afford the desired product 5-bromo-6-((4-fluoro-2-methyl-1H-indol-5-yl)oxy)-N-(4-(4-methylpiperazin-1-yl)phenyl)pyrimidin-4-amine (compound 37) as an off-white solid (131 mg, 40% yield). $^1$H NMR (DMSO-d6, 400 MHz) δ 11.30 (br s, 1H), 8.73 (br s, 1H), 7.99 (s, 1H), 7.34 (d, J=8.8 Hz, 2H), 7.10 (d, J=8.4 Hz, 1H), 6.93-6.86 (m, 3H), 6.21 (s, 1H), 3.12-3.10 (m, 4H), 2.46-2.44 (m, 4H), 2.40 (s, 3H), 2.22 (s, 3H); MS (ESI): calcd for C24H24BrFN6O: 510, found: 513 (MH$^+$).

Example 38

(38)

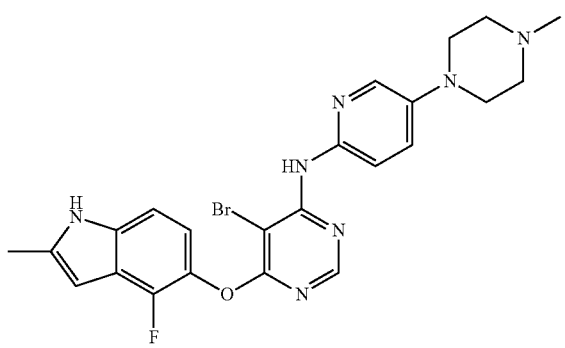

A mixture of compound 36 (200 mg, 0.563 mmol), 4-(4-methylpiperazin-1-yl)aniline (114 mg, 0.592 mmol), Pd(OAc)$_2$ (19 mg, 0.08 mmol), xantphos (81 mg, 0.14 mmol), K$_2$CO$_3$ (272 mg, 1.97 mmol) and anhydrous dioxane (10 mL) was sealed in a microwavable tube and degassed with argon for 10 min. The mixture was then heated to 120° C. for 20 min under microwave irradiation. The resulting mixture was filtered over a cotton pad and concentrated. The resulting residue was purified by flash column chromatography on silica gel using 0-10% MeOH in DCM (v/v) as eluent. The resulting residue was further purified by crystallization out of EtOAc to afford the desired product 5-bromo-6-((4-fluoro-2-methyl-1H-indol-5-yl)oxy)-N-(5-(4-methylpiperazin-1-yl)pyridin-2-yl)pyrimidin-4-amine (compound 38) as a yellow solid (139 mg, 48% yield). $^1$H NMR (DMSO-d6, 400 MHz) δ 11.31 (br s, 1H), 8.53 (br s, 1H), 8.15 (s, 1H), 8.06 (d, J=2.8 Hz, 1H), 7.85 (d, J=8.8 Hz, 1H), 7.47-7.44 (m, 1H), 7.11 (d, J=8.4 Hz, 1H), 6.91 (d, J=8.0 Hz, 1H), 3.18-3.15 (m, 4H), 2.48-2.45 (m, 4H), 2.40 (s, 3H), 2.23 (s, 3H); MS (ESI): calcd for C23H23BrFN7O: 511, found: weak signal.

Example 39

(39)

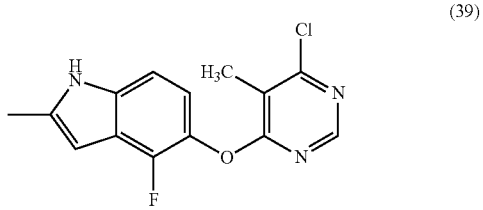 [SMILES: Cc1cc2c(F)c(Oc3ncnc(Cl)c3C)ccc2[nH]1]

To a solution of 4,6-dichloro-5-methylpyrimidine (1.5 g, 9.20 mmol) and 4-fluoro-2-methyl-1H-indol-5-ol (1.5 g, 9.20 mmol) in DMSO (15.0 mL) was added potassium carbonate (4.4 g, 32.21 mmol) and the mixture was stirred at 80° C. for 4 hours. After cooling, the reaction mixture was added to a stirring solution of water (200.0 mL). The mixture was stirred at room temperature for 1 h then filtered to give the product compound 39 as light brown solid (2.6 g, 96% yield). $^1$H NMR (400 MHz, DMSO-d$_6$) δ 11.33 (s, 1H), 8.40 (s, 1H), 7.14 (d, 1H), 6.92 (t, 1H), 6.23 (s, 1H), 2.40 (s, 6H); ESI-MS: calcd for (C14H11ClFN3O) 291, found 292 [M+H]$^+$.

Example 40

(40)

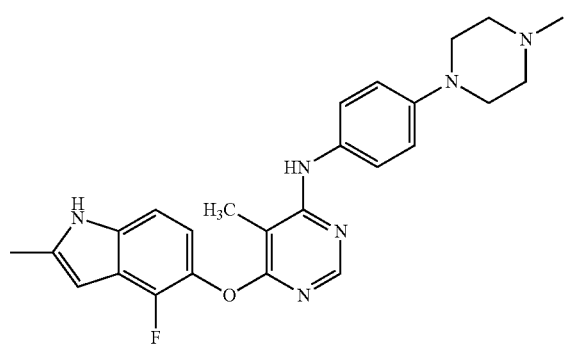

A mixture of compound 39 (200 mg, 0.69 mmol), 4-(4-methylpiperazin-1-yl)aniline (132 mg, 0.69 mmol), palladium(II) acetate (23 mg, 0.10 mmol), Xantphos (97 mg, 0.17 mmol) and K$_2$CO$_3$ (477 mg, 3.45 mmol) in 1,4-dioxane (2.0 ml) was purged with argon for 15 minutes. The mixture was heated with Biotage microwave initiator at 120° C. for 30 minutes. The reaction mixture was passed a pad of Celite, eluted with DCM/MeOH (1/1, 20 ml). The solution was concentrated and the cure product was purified by Teledyne-Isco flash system by using CH$_2$Cl$_2$/MeOH, 0 to 10% of methanol in dichloromethane to provide compound 40 as off white solid (30 mg, 10%). $^1$H NMR (400 MHz, DMSO-d$_6$) δ 11.22 (br, 1H), 8.34 (s, 1H), 7.95 (s, 1H), 7.39 (d, 2H), 7.07 (d, 1H), 6.92-6.80 (m, 3H), 6.18 (s, 1H), 3.07 (t, 4H), 2.45 (t, 4H), 2.39 (s, 3H), 2.23 (d, 3H); ESI-MS: calcd for (C25H27FN6O) 446, found 447 [M+H]$^+$. HPLC: retention time: 17.10 min. purity: 99%.

Example 41

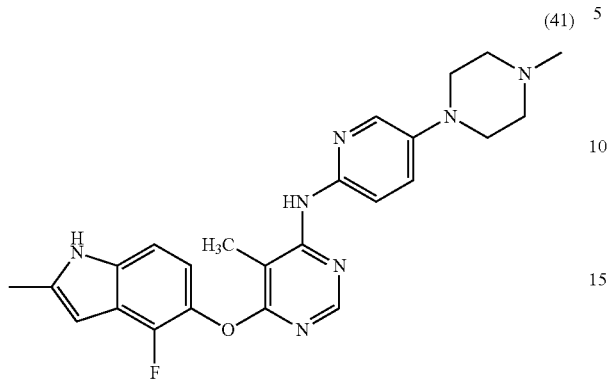

(41)

A mixture of compound 39 (200 mg, 0.69 mmol), 5-(4-methylpiperazin-1-yl)pyridin-2-amine (165 mg, 0.86 mmol), palladium(II) acetate (23 mg, 0.10 mmol), Xantphos (97 mg, 0.17 mmol) and $K_2CO_3$ (477 mg, 3.45 mmol) in 1,4-dioxane (2.0 ml) was purged with argon for 15 minutes. The mixture was heated with Biotage microwave initiator at 120° C. for 30 minutes. The reaction mixture was passed a pad of Celite, eluted with DCM/MeOH (1/1, 20 ml). The solution was concentrated and the cure product was purified by Teledyne-Isco flash system by using $CH_2Cl_2$/MeOH, 0 to 10% of methanol in dichloromethane to provide compound 41 as off white solid (180 mg, 59%). $^1$H NMR (400 MHz, DMSO-$d_6$) δ 11.25 (br, 1H), 8.72 (s, 1H), 8.07 (s, 1H), 8.01 (d, 1H), 7.83 (d, 1H), 7.42-7.39 (m, 1H), 7.08 (d, 1H), 6.85 (t, 1H), 6.20 (s, 1H), 3.14-3.12 (m, 4H), 2.48-2.45 (m, 4H), 2.40 (s, 3H), 2.27 (s, 3H), 2.23 (s, 3H); ESI-MS: calcd for (C24H26FN7O) 447, found 448 [M+H]$^+$. HPLC: retention time: 16.82 min. purity: 99.9%.

Example 42

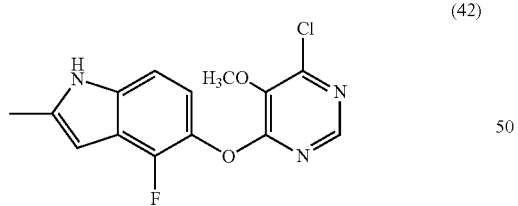

(42)

To a solution of 4,6-dichloro-5-methoxypyrimidine (1.5 g, 8.38 mmol) and 4-fluoro-2-methyl-1H-indol-5-ol (1.4 g, 8.38 mmol) in DMSO (15.0 mL) was added potassium carbonate (4.1 g, 29.33 mmol) and the mixture was stirred at 80° C. for 4 hours. After cooling, the reaction mixture was added to a stirring solution of water (200.0 mL). The mixture was stirred at room temperature for 1 h then filtered to give the product of compound 42 as light brown solid (2.5 g, 96% yield). $^1$H NMR (400 MHz, DMSO-$d_6$) δ 11.36 (s, 1H), 8.29 (s, 1H), 7.14 (d, 1H), 6.99 (t, 1H), 6.24 (s, 1H), 4.03 (s, 3H), 2.41 (s, 3H); ESI-MS: calcd for (C14H11ClFN3O2) 307, found 308 [M+H]$^+$.

Example 43

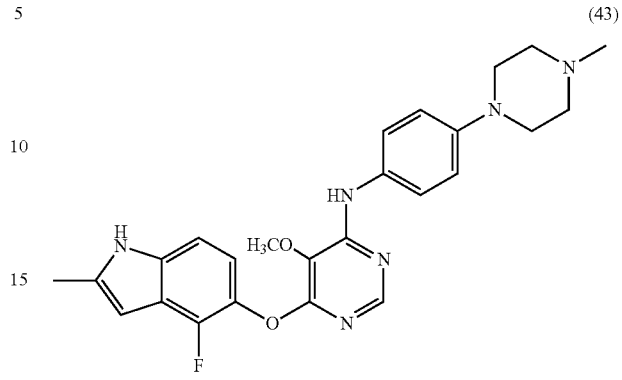

(43)

A mixture of compound 42 (200 mg, 0.65 mmol), 4-(4-methylpiperazin-1-yl)aniline (125 mg, 0.65 mmol), palladium(II) acetate (22 mg, 0.10 mmol), Xantphos (94 mg, 0.16 mmol) and $K_2CO_3$ (450 mg, 3.25 mmol) in 1,4-dioxane (2.0 ml) was purged with argon for 15 minutes. The mixture was heated with Biotage microwave initiator at 120° C. for 30 minutes. The reaction mixture was passed a pad of Celite, eluted with DCM/MeOH (1/1, 20 ml). The solution was concentrated and the cure product was purified by Teledyne-Isco flash system by using $CH_2Cl_2$/MeOH, 0 to 10% of methanol in dichloromethane to provide compound 43 as off white solid (100 mg, 30%). $^1$H NMR (400 MHz, DMSO-$d_6$) δ 11.26 (br, 1H), 8.84 (s, 1H), 7.86 (s, 1H), 7.55 (d, 2H), 7.09 (d, 1H), 6.92-6.88 (m, 3H), 6.21 (s, 1H), 3.93 (s, 3H), 3.08 (t, 4H), 2.45 (t, 4H), 2.40 (s, 3H), 2.22 (s, 3H); ESI-MS: calcd for (C25H27FN6O2) 462, found 463 [M+H]$^+$. HPLC: retention time: 17.43 min. purity: 99.4%.

Example 44

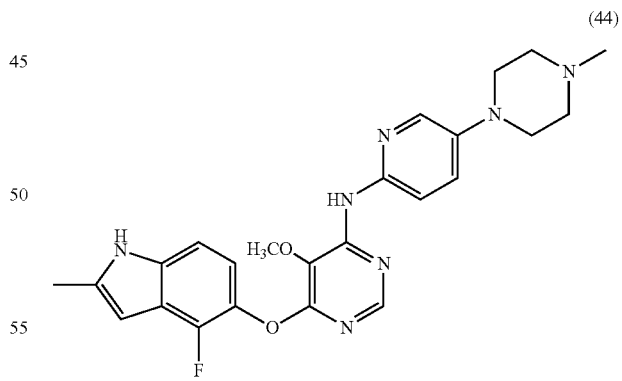

(44)

A mixture of compound 42 (200 mg, 0.65 mmol), 5-(4-methylpiperazin-1-yl)pyridin-2-amine (155 mg, 0.81 mmol), palladium(II) acetate (22 mg, 0.10 mmol), Xantphos (94 mg, 0.16 mmol) and $K_2CO_3$ (450 mg, 3.25 mmol) in 1,4-dioxane (2.0 ml) was purged with argon for 15 minutes. The mixture was heated with Biotage microwave initiator at 120° C. for 30 minutes. The reaction mixture was passed a pad of Celite, eluted with DCM/MeOH (1/1, 20 ml). The solution was concentrated and the cure product was purified by Teledyne-Isco flash system by using CH₂Cl₂/MeOH, 0 to 10% of methanol in dichloromethane to provide compound 44 as off white solid (170 mg, 56%). ¹H NMR (400 MHz, DMSO-d₆) δ 11.28 (br, 1H), 8.65 (s, 1H), 8.03-7.98 (s, 3H), 7.45-7.42 (m, 1H), 7.10 (d, 1H), 6.92 (t, 1H), 6.21 (s, 1H), 3.97 (s, 3H), 3.13 (t, 4H), 2.48 (t, 4H), 2.40 (s, 3H), 2.22 (s, 3H); ESI-MS: calcd for (C24H26FN7O2) 463, found 464 [M+H]⁺. HPLC: retention time: 8.74 min. purity: 99.9%.

Example 45

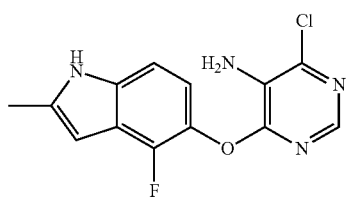

(45)

To a solution of 4,6-dichloropyrimidin-5-amine (1.5 g, 9.15 mmol) and 4-fluoro-2-methyl-1H-indol-5-ol (1.5 g, 9.15 mmol) in DMSO (15.0 mL) was added potassium carbonate (4.4 g, 32.01 mmol) and the mixture was stirred at 80° C. for 4 hours. After cooling, the reaction mixture was added to a stirring solution of water (200.0 mL). The mixture was stirred at room temperature for 1 h then filtered to give the product of compound 45 as light brown solid (2.5 g, 95% yield). ¹H NMR (400 MHz, DMSO-d₆) δ 11.31 (s, 1H), 7.75 (s, 1H), 7.13 (d, 1H), 6.92 (t, 1H), 6.22 (s, 1H), (5.80 (s, 2H), 2.40 (s, 3H); ESI-MS: calcd for (C13H10ClFN4O) 292, found 293 [M+H]⁺.

Example 46

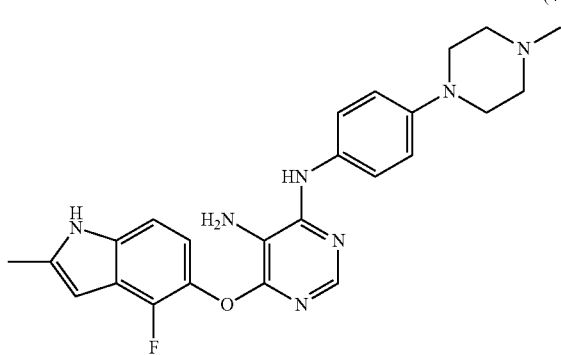

(46)

A mixture of compound 45 (200 mg, 0.68 mmol), 4-(4-methylpiperazin-1-yl)aniline (130 mg, 0.68 mmol), palladium(II) acetate (23 mg, 0.10 mmol), Xantphos (98 mg, 0.17 mmol) and K₂CO₃ (470 mg, 3.40 mmol) in 1,4-dioxane (2.0 ml) was purged with argon for 15 minutes. The mixture was heated with Biotage microwave initiator at 120° C. for 30 minutes. The reaction mixture was passed a pad of Celite, eluted with DCM/MeOH (1/1, 20 ml). The solution was concentrated and the cure product was purified by Teledyne-Isco flash system by using CH₂Cl₂/MeOH, 0 to 10% of methanol in dichloromethane to provide compound 46 as off white solid (5 mg, 2%). ¹H NMR (400 MHz, DMSO-d₆) δ 11.22 (br, 1H), 8.13 (bs, 1H), 7.60-7.48 (m, 3H), 7.17-6.91 (m, 4H), 6.20 (bs, 1H), 4.85 (bs, 2H), 3.07 (bs, 4H), 2.46 (bs, 4H), 2.40 (bs, 3H), 2.22 (bs, 3H); ESI-MS: calcd for (C24H26FN7O) 447, found 448 [M+H]⁺. HPLC: retention time: 12.68 min. purity: 87%.

Example 47

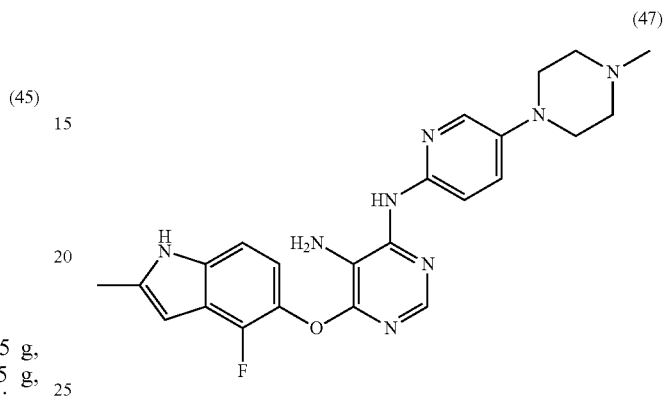

(47)

A mixture of compound 45 (200 mg, 0.68 mmol), 5-(4-methylpiperazin-1-yl)pyridin-2-amine (164 mg, 0.85 mmol), palladium(II) acetate (23 mg, 0.10 mmol), Xantphos (98 mg, 0.17 mmol) and K₂CO₃ (470 mg, 3.40 mmol) in 1,4-dioxane (2.0 ml) was purged with argon for 15 minutes. The mixture was heated with Biotage microwave initiator at 120° C. for 30 minutes. The reaction mixture was passed a pad of Celite, eluted with DCM/MeOH (1/1, 20 ml). The solution was concentrated and the cure product was purified by Teledyne-Isco flash system by using CH₂Cl₂/MeOH, 0 to 10% of methanol in dichloromethane to provide compound 47 as off white solid (100 mg, 33%). ¹H NMR (400 MHz, DMSO-d₆) δ 11.28 (br, 1H), 8.65 (s, 1H), 8.03-7.98 (s, 3H), 7.45-7.42 (m, 1H), 7.10 (d, 1H), 6.92 (t, 1H), 6.21 (s, 1H), 3.97 (s, 3H), 3.13 (t, 4H), 2.48 (t, 4H), 2.40 (s, 3H), 2.22 (s, 3H); ESI-MS: calcd for (C25H25FN8O) 448, found 449 [M+H]⁺. HPLC: retention time: 5.44 min. purity: 98%.

Example 48

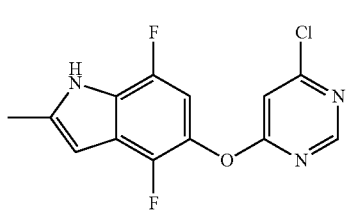

(48)

To a solution of 4,7-difluoro-2-methyl-1H-indol-5-ol, which was reported in WO2014145403 A1 (1.50 g, 8.19 mmol) and 4,6-dichloropyridine (1.28 g, 8.60 mmol) in DMSO (18 ml) was added potassium carbonate (4.07 g, 29.48 mmol) and the mixture was heated at 85° C. for 1.5 hours with Biotage Microwave initiator. The reaction mixture was added to a container with water (250 mL). The pH of the mixture was adjusted to 6 about with 2N HCl and the mixture was stirred at room temperature for 1 hour then stored at 4° C. overnight. The solids were collected by filtration and washed by water. Compound 48 was obtained as yellow solids (2.23 g, 92% yield). No further purification was performed and the product was used for the next step reaction. $^1$H NMR (400 MHz, DMSO-$d_6$) δ 11.85 (br, 1H), 8.65 (s, 1H), 7.50 (s, 1H), 6.97 (m, 1H), 6.34 (s, 1H), 2.41 (s, 3H); ESI-MS: calcd for (C13H8ClF2N3O) 295, found 296 (MH$^+$).

Example 49

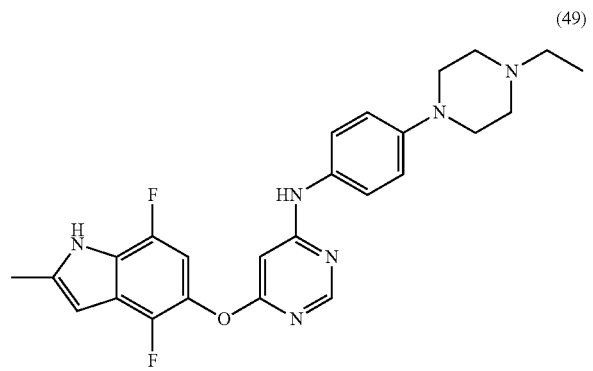 [SMILES: CCN1CCN(c2ccc(Nc3cc(Oc4cc(F)c5[nH]c(C)cc5c4F)ncn3)cc2)CC1]

(49)

A mixture of compound 48 (200 mg, 0.68 mmol), 4-(4-Ethylpiperazine-1-yl))aniline (139 mg, 0.68 mmol), and DIPEA (0.30 ml, 1.69 mmol) in DMSO (3.5 ml) was stirred at 100° C. for overnight. After cooled to room temperature, the mixture was added to water/sat. NH$_4$Cl (50 ml/50 ml) and stirred at room temperature for 30 min. The pH of the mixture was adjusted to 6~7 using 2N HCl. After stored at 4° C. for overnight, the solids were collected by filtration and washed by water to give the crude product. The crude product was purified by column chromatography (silica gel, 0-15% MeOH in DCM) to give compound 49 as brown solids (147 mg, 47% yield). $^1$H NMR (400 MHz, DMSO-$d_6$) δ 11.77 (br, 1H), 9.26 (s, 1H), 8.20 (s, 1H), 7.33 (d, J=8.8 Hz, 2H), 6.87 (m, 3H), 6.31 (s, 1H), 5.98 (s, 1H), 3.04 (m, 4H), 2.41 (m, 4H), 2.39 (br, 3H), 2.35 (q, J=7.2 Hz, 2H), 1.00 (t, J=7.2 Hz, 3H); ESI-MS: calcd for C25H26F2N6O) 464, found 465 (MH$^+$).

Example 50

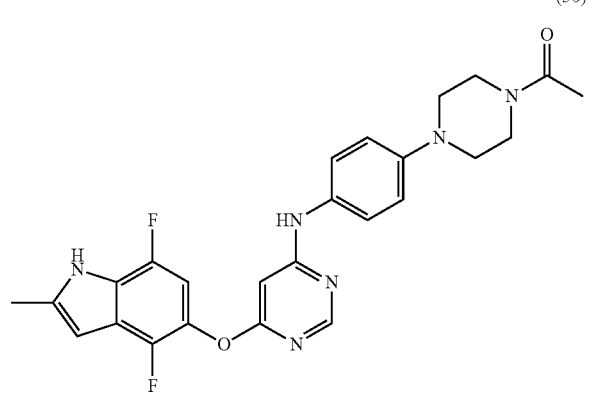

(50)

A mixture of compound 48 (200 mg, 0.68 mmol), 1-Actyl-4-(4-aminophenyl)piperazine (159 mg, 0.73 mmol), and DIPEA (0.30 ml, 1.69 mmol) in DMSO (3.5 ml) was stirred at 100° C. for overnight. After cooled to room temperature, the mixture was added to water/sat. NH$_4$Cl (50 ml/50 ml) and stirred at room temperature for 30 min. The pH of the mixture was adjusted to 6~7 using 2N HCl. After stored at 4° C. for overnight, the solids were collected by filtration and washed by water to give the crude product. The crude product was purified by column chromatography (silica gel, 0-15% MeOH in DCM) to give compound 50 as brown solids (212 mg, 65% yield). $^1$H NMR (400 MHz, DMSO-$d_6$) δ 11.77 (br, 1H), 9.30 (s, 1H), 8.21 (s, 1H), 7.36 (d, J=8.8 Hz, 2H), 6.90 (m, 3H), 6.31 (s, 1H), 5.99 (s, 1H), 3.55 (m, 4H), 3.06 (m, 2H), 3.01 (m, 2H), 2.39 (br, 3H), 2.01 (s, 3H); ESI-MS: calcd for (C25H24F2N6O2) 478, found 479 (MH$^+$).

Example 51

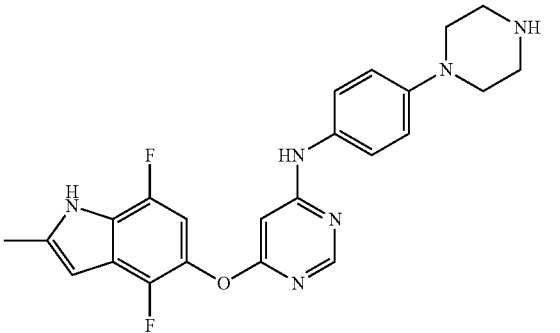

(51)

A mixture of compound 48 (200 mg, 0.68 mmol), tert-Butyl 4(4-aminophenyl)piperazine-1-carboxylate (187 mg, 0.68 mmol), and DIPEA (0.30 ml, 1.69 mmol) in DMSO (3.5 ml) was stirred at 100° C. for overnight. After cooled to room temperature, the mixture was added to water (100 ml) and stirred at room temperature for 30 min. After cooled with ice-bath, the solids were collected by filtration, washed by water. After air-drying at room temperature overnight, the solids were suspended into DCM/MeOH (10/1, 5 mL) and 1 ml of TFA was added. The mixture was stirred at room temperature for over night. After concentrated, the residue was dissolved into DCM/MeOH (8/2, 15 ml) and water was added. The pH of the mixture was adjusted to about 7 with aqueous solution of sat. sodium bicarbonate. The organic was dried over sodium sulfate and concentrated. The crude product was purified by column chromatography (silica gel, 0-15% MeOH in DCM) to give the compound 51 as yellow solids (60 mg, 20% yield). $^1$H NMR (400 MHz, DMSO-$d_6$) δ 11.80 (br, 1H), 9.31 (s, 1H), 8.22 (s, 1H), 7.38 (d, J=8.8 Hz, 2H), 6.88 (m, 3H), 6.33 (br, 1H), 6.01 (s, 1H), 3.04 (m, 4H), 2.91 (m, 4H), 2.41 (br, 3H); ESI-MS: calcd for C23H22F2N6O) 436, found 437 (MH$^+$).

Example 52

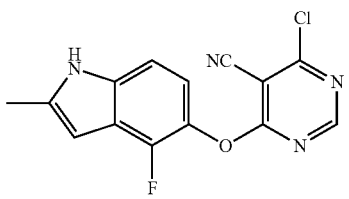

To a solution of 4,7-difluoro-2-methyl-1H-indol-5-ol (200 mg, 1.21 mmol) in a mixture of acetonitrile (4 mL) and N,N-dimethylformamide (1 mL) was added potassium carbonate (200 mg, 1.45 mmol). The reaction mixture was stirred for 1 h at room temperature before a suspension of 4,6-dichloropyrimidine-5-carbonitrile (221 mg, 1.27 mmol) in 3 mL of acetonitrile was added. This mixture was stirred at room temperature for 1 h. TLC was checked and the reaction was completed. The mixture was diluted with water and ethyl acetate. The layers were separated and the aqueous phase was extracted twice with ethyl acetate. The combined organic phases were washed once with water, then with brine, dried over sodium sulfate, filtered, and the filtrate was concentrated in vacuo to give compound 52 as brown solids (365 mg, 99% yield). $^1$H NMR (400 MHz, DMSO-$d_6$) δ 11.46 (br, 1H), 8.83 (s, 1H), 7.17 (d, J=8.8 Hz, 1H), 7.00 (t, J=7.6 Hz, 1H), 6.27 (s, 1H), 2.41 (s, 3H); ESI-MS: calcd for (C14H8ClFN4O) 302, found 303 (MH$^+$).

Example 53

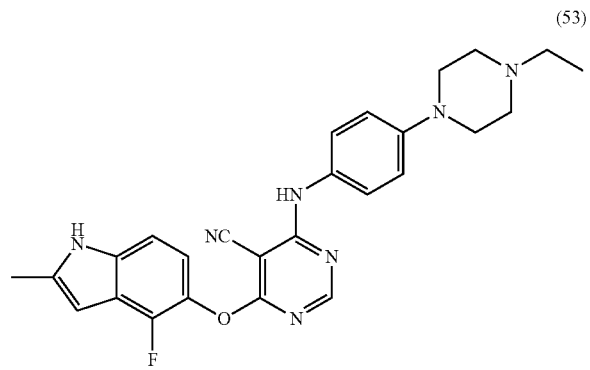 [SMILES: CCN1CCN(c2ccc(Nc3ncnc(Oc4ccc5[nH]c(C)cc5c4F)c3C#N)cc2)CC1]

A mixture of compound 52 (200 mg, 0.66 mmol), 4-(4-Ethylpiperazine-1-yl))aniline (135 mg, 0.66 mmol), and DIPEA (0.29 ml, 1.65 mmol) in DMSO (3.5 ml) was stirred at 80° C. for 3 hours. TLC was checked and the reaction was completed. After cooled to room temperature, the mixture was added to sat. NH$_4$Cl (100 ml) and stirred at room temperature for 30 min. The pH of the mixture was adjusted to 6~7 using 2N HCl. After stored at 4° C. for overnight and the solids were collected by filtration, washed by water to give the crude product. The crude product was purified by column chromatography (silica gel, 0-10% MeOH in DCM) to give compound 53 as brown solids (173 mg, 56% yield). $^1$H NMR (400 MHz, DMSO-$d_6$) δ 11.37 (br, 1H), 9.90 (s, 1H), 8.23 (s, 1H), 7.37 (d, J=8.8 Hz, 2H), 7.12 (d, J=8.8 Hz, 1H), 7.00 (d, J=8.8 Hz, 2H), 6.93 (t, J=7.6 Hz, 1H), 6.23 (s, 1H), 3.90-3.40 (m, 4H), 3.20-2.90 (m, 6H), 2.40 (s, 3H), 1.26 (br, 3H); ESI-MS: calcd for (C26H26FN7O) 471, found 472 (MH$^+$).

Example 54

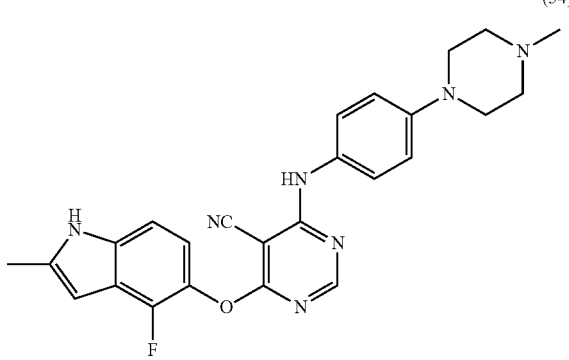

A mixture of compound 52 (100 mg, 0.66 mmol), 4-(4-methylpiperazin-1-yl)aniline (63 mg, 0.33 mmol), and DIPEA (0.15 ml, 0.82 mmol) in DMSO (5 ml) was stirred at 80° C. for 30 min. TLC was checked and the reaction was completed. After cooled to room temperature, the mixture was added to sat. NH$_4$Cl (100 ml) and stirred at room temperature for 30 min. The pH of the mixture was adjusted to 6~7 using 2N HCl. Aged at 4° C. for overnight and the solids were collected by filtration, washed by water to give the crude product. The crude product was purified by column on silica gel (0-10% MeOH in DCM) to give compound 54 as brown solids (52 mg, 34% yield). $^1$H NMR (400 MHz, DMSO-$d_6$) δ 11.34 (br, 1H), 9.84 (br, 1H), 8.21 (s, 1H), 7.32 (d, J=8.4 Hz, 2H), 7.13 (d, J=7.6 Hz, 1H), 6.95 (m, 3H), 6.23 (s, 1H), 3.12 (m, 4H), 3.20-2.90 (m, 6H), 2.45 (m, 4H), 2.40 (s, 3H), 2.20 (s, 3H); ESI-MS: calcd for (C$_{25}$H$_{24}$FN$_7$O) 457, found 458 (MH$^+$). HPLC: retention time: 7.71 min. purity: 99%.

Example 55

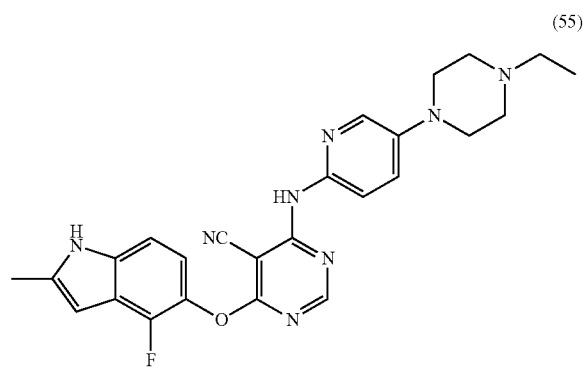 [SMILES: CCN1CCN(c2ccc(Nc3ncnc(Oc4ccc5[nH]c(C)cc5c4F)c3C#N)nc2)CC1]

A mixture of compound 52 (100 mg, 0.66 mmol), 5-(4-ethylpiperazin-1-yl)pyridin-2-amine (68 mg, 0.33 mmol), and DIPEA (0.15 ml, 0.82 mmol) in DMSO (5 ml) was stirred at 80° C. for 30 min. TLC was checked and the reaction was completed. After cooled to room temperature, the mixture was added to sat. NH₄Cl (100 ml) and stirred at room temperature for 30 min. The pH of the mixture was adjusted to 6~7 using 2N HCl. Aged at 4° C. for overnight and the solids were collected by filtration, washed by water to give the crude product. The crude product was purified by column on silica gel (0-10% MeOH in DCM) to give compound 55 as brown solids (28 mg, 18% yield). ¹H NMR (400 MHz, DMSO-$d_6$) δ 11.36 (m 1H, rotamer), 10.12 (br, 0.42H, rotamer), 9.61 (s, 0.58H, rotamer), 8.58 (m, 0.5H, rotamer), 8.50 (m, 0.5H, rotamer), 8.40 (m, 0.43H, rotamer), 8.10 (m, 0.5H, rotamer), 8.08 (m, 0.5H, rotamer), 7.4 (s, 0.3H, rotamer), 7.41 (s, 0.98H, rotamer), 7.16 (m, 0.5H, rotamer), 7.12 (m, 0.49H, rotamer), 7.03 (m, 0.49H, rotamer), 6.94 (m, 0.50H, rotamer), 6.24 (m, 1H, rotamer), 3.17 (m, 4H), 2.50 (m, 4H, barried in solvent), 2.39 (m, 5H), 1.01 (m, 3H); ESI-MS: calcd for ($C_{25}H_{25}FN_8O$) 472, found 473 (MH⁺). HPLC: retention time: 7.71 min. purity: 99%.

Example 56

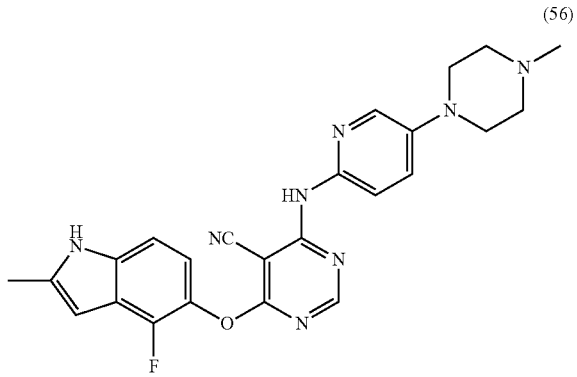

(56)

A mixture of compound 52 (100 mg, 0.66 mmol), 4-(4-methylpiperazin-1-yl)aniline (63 mg, 0.33 mmol), and DIPEA (0.15 ml, 0.82 mmol) in DMSO (5 ml) was stirred at 80° C. for 30 min. TLC was checked and the reaction was completed. After cooled to room temperature, the mixture was added to sat. NH₄Cl (100 ml) and stirred at room temperature for 30 min. The pH of the mixture was adjusted to 6~7 using 2N HCl. Aged at 4° C. for overnight and the solids were collected by filtration, washed by water to give the crude product. The crude product was purified by column on silica gel (0-10% MeOH in DCM) to give compound 56 as brown solids (32 mg, 22% yield); ¹H NMR (400 MHz, DMSO-$d_6$) δ 11.36 (m 1H, rotamer), 10.12 (br, 0.42H, rotamer), 9.61 (s, 0.58H, rotamer), 8.58 (m, 0.5H, rotamer), 8.50 (m, 0.5H, rotamer), 8.40 (m, 0.43H, rotamer), 8.10 (m, 0.5H, rotamer), 8.08 (m, 0.5H, rotamer), 7.4 (s, 0.3H, rotamer), 7.41 (s, 0.98H, rotamer), 7.16 (m, 0.5H, rotamer), 7.12 (m, 0.49H, rotamer), 7.03 (m, 0.49H, rotamer), 6.94 (m, 0.50H, rotamer), 6.24 (m, 1H, rotamer), 3.17 (m, 4H), 2.50 (m, 4H, barried in solvent), 2.39 (s, 3H), 2.25 (s, 3H); ESI-MS: calcd for ($C_{25}H_{25}FN_8O$) 472, found 473 (MH⁺). HPLC: retention time: 7.71 min. purity: 99%.

Example 57

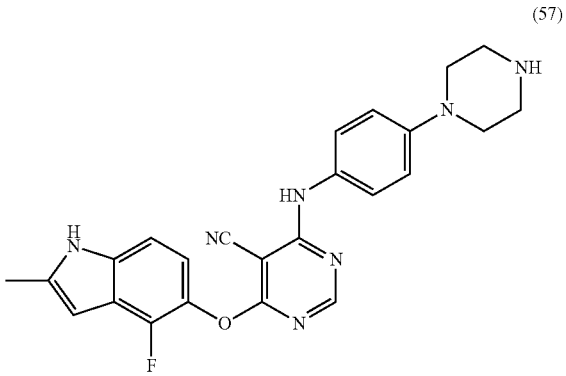 [SMILES: Cc1cc2c(F)c(Oc3ncnc(Nc4ccc(N5CCNCC5)cc4)c3C#N)ccc2[nH]1]

(57)

A mixture of compound 52 (100 mg, 0.33 mmol), QW811_1 (92 mg, 0.33 mmol, and DIPEA (0.15 ml, 0.82 mmol) in DMSO (3.5 ml) was stirred at 80° C. for 30 min. After cooled to room temperature, the mixture was added to water (100 ml) and stirred at room temperature for 30 min. After cooled with ice-bath, the solids were collected by filtration, washed by water. After air-drying at room temperature overnight, the solids were suspended into DCM/MeOH (10/1, 5 mL) and 1 ml of TFA was added. The mixture was stirred at room temperature for overnight. After concentrated, the residue was dissolved into DCM/MeOH (8/2, 15 ml) and sat. Sodium bicarbonate solution was added to pH about 7. The organic was dried over sodium sulfate and concentrated. The crude product was purified by column chromatography (silica gel, 0-15% MeOH in DCM) to give compound 57 as yellow solids (33 mg, 20% yield). ¹H NMR (400 MHz, DMSO-$d_6$) δ 11.36 (br, 1H), 9.91 (s, 1H), 8.25 (m, 1H), 7.36 (m, 2H), 7.18 (m, 1H), 6.95 (m, 3H), 6.29 (m, 1H), 6.01 (s, 1H), 4.30 (m, 1H), 3.15 (m, 4H), 2.91 (m, 4H), 2.55 br, 1H), 2.41 (br, 3H); ESI-MS: calcd for C24H22FN7O 443, found 444 (MH⁺). HPLC: retention time: 17.31 min. purity: 93%.

Example 58

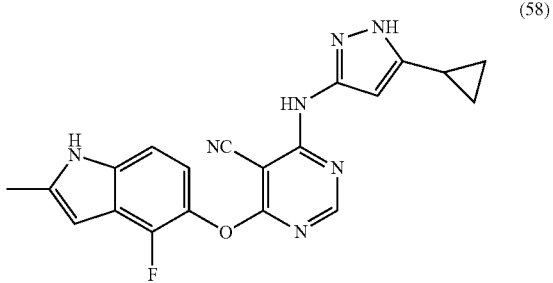 [SMILES: Cc1cc2c(F)c(Oc3ncnc(Nc4cc(C5CC5)[nH]n4)c3C#N)ccc2[nH]1]

(58)

A mixture of compound 52 (200 mg, 0.72 mmol), compound 30 (152.56 mg, 0.68 mmol), xantphos (4,5-diphenylphosphanyl-9,9'-dimethyl-9-H-xanthene, 99 mg, 0.17 mmol), K₂CO₃ (1.51 g, 10.93 mmol) and palladium(II) acetate (23 mg, 0.10 mmol) in 1,4-dioxane (12 ml) was purged with argon for 1 hour. The mixture was heated in microwave for 45 min at 120° C. TLC was checked and the starting material was almost consumed. After cooling to room temperature, the reaction mixture was diluted with DCM/MeOH 8/2) and passed a pad of Celite and concentrated. The crude product was purified by column chromatography (silica gel, 0-12% MeOH in DCM) and also purified by using the 5% 7N ammonia in dichloromethane. After removing the solvents, compound 58 was obtained (12 mg, 4% yield). $^1$H NMR (400 MHz, DMSO-d$_6$) δ 11.24 (br s, 1H), 8.69 (s, 1H), 7.39 (m, 2H), 7.09 (m, 2H), 6.83 (m, 3H), 6.21 (m, 3H), 5.21 (s, 1H), 3.04 (m, 4H), 2.49 (m, 4H), 2.39 (s, 3H), 2.36 (m, 2H), 1.02 (t, J=7.2 Hz, 3H), ESI-MS: calcd for (C25H28FN7O) 461, found 462 (MH$^+$). HPLC: retention time: 9.24 min. purity: 97%.

Example 59

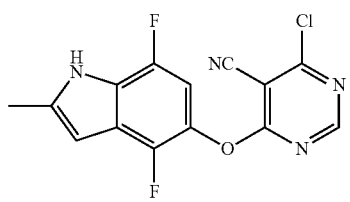

(59)

To a solution of 4,7-difluoro-2-methyl-1H-indol-5-ol (500 mg, 2.73 mmol) in a mixture of acetonitrile (9 mL) and N,N-dimethylformamide (1 mL) was added potassium carbonate (453 mg, 3.28 mmol). The reaction mixture was stirred for 30 min. at room temperature before a suspension of 2,4-dichloro5-cyanopyrimidine (499 mg, 2.87 mmol) in acetonitrile/DMF (2.5 mL/2.5 mL) was added. This mixture was stirred at 0° C. for 2 h. TLC was checked and the reaction was completed. The mixture was diluted with water/brine and ethyl acetate. The layers were separated and the aqueous phase was extracted twice with ethyl acetate. The combined organic phases were washed once with water/brine three times, dried over sodium sulfate, filtered, and the filtrate was concentrated in vacuo to give compound 59 as purple sticky solids (890 mg, 100% yield, contained some DMF). The product was used without further purification. $^1$H NMR (400 MHz, DMSO-d$_6$) δ 11.91 (br, 1H), 8.84 (s, 1H), 7.03 (dd, J=5.6 Hz, J=10.4 Hz, 1H), 6.35 (br, 1H), 2.39 (s, 3H); ESI-MS: calcd for (C14H7ClF2N4O) 320, found 321 (MH$^+$).

Example 60

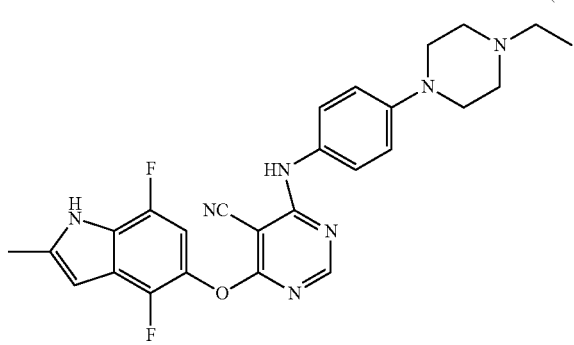

(60)

A mixture of compound 59 (crude, 195 mg, 0.61 mmol), 4-(4-Ethylpiperazine-1-yl))aniline (100 mg, 0.49 mmol), and DIPEA (0.21 ml, 1.22 mmol) in DMSO (2 ml) was stirred at room temperature for 2 hours. TLC was checked and the reaction was completed. DCM (30 ml) was added, followed by NH4Cl (30 mL). After separation, the aqueous was extracted with DCM/IPA (8/2, 15 ml×2). The combined organic was washed with brine, dried over Na$_2$SO$_4$ and concentrated. The crude product was purified by column on slica gel (0-10% MeOH in DCM) to give compound 60 as brown solids (128 mg, 53% yield). $^1$H NMR (400 MHz, DMSO-d$_6$) δ 11.80 (br, 1H), 9.85 (s, 1H), 8.21 (s, 1H), 7.28 (d, J=8.8 Hz, 2H), 6.97 (dd, J=5.6 Hz, J=10.4 Hz, 1H), 6.89 (d, J=8.8 Hz, 2H), 6.31 (s, 1H), 3.10 (m, 4H), 2.50 (m, 4H), 2.39 (s, 3H), 2.33 (q, J=6.8 Hz, 2H), 1.00 (t, J=7.2 Hz, 3H); ESI-MS: calcd for (C26H25F2N7O) 489, found 490 (MH$^+$).

Example 61

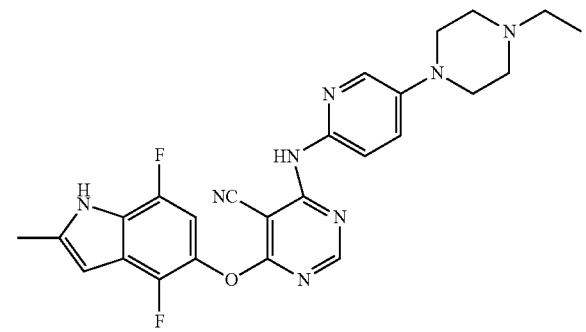

(61)

A mixture of compound 59 (179 mg, 0.56 mmol), QW817 (100 mg, 0.49 mmol), and DIPEA (0.21 ml, 1.22 mmol) in DMSO (2 ml) was stirred at 100° C. for overnight. TLC was checked and the reaction was completed. DCM (30 ml) was added, followed by NH4Cl (30 mL). After separation, the aqueous was extracted with DCM/IPA (8/2, 15 ml×2). The combined organic was washed with brine, dried over Na$_2$SO$_4$ and concentrated. The crude product was purified by column on silica gel (0-10% MeOH in DCM) to give compound 61 as brown solids (120 mg, 51% yield). (Two sets of NMR in the ratio of 1:1.35). Set 1: $^1$H NMR (400 MHz, DMSO-d$_6$) δ 11.82 (br, 1H, overlapped), 10.10 (br, 1H), 8.31 (s, 1H), 8.07 (m, 2H), 7.39 (s, 1H), 6.99 (dd, J=5.6 Hz, J=10.4 Hz, 1H), 6.32 (s, 1H, overlapped), 3.15 (m, 4H, overlapped), 2.50 (m, 4H, barried in solvent), 2.39 (s, 3H), 2.36 (m, 2H, overlapped), 1.01 (m, 3H, overlapped); Set 2: $^1$H NMR (400 MHz, DMSO-d$_6$) δ 11.82 (br, 1H, overlapped), 9.56 (s, 1H), 8.54 (s, 1H), 8.50 (s, 1H), 7.42 (m, 2H), 7.06 (dd, J=5.6 Hz, J=10.4 Hz, 1H), 6.32 (s, 1H, overlapped), 3.15 (m, 4H, overlapped), 2.53 (m, 4H, overlapped), 2.40 (s, 3H), 2.36 (m, 2H, overlapped), 1.01 (m, 3H, overlapped); ESI-MS: calcd for (C25H24F2N8O) 490, found 491 (MH$^+$).

Example 62

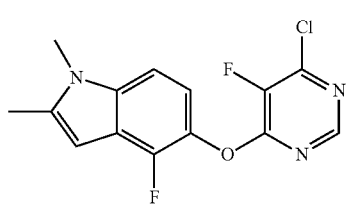
(62)

To a cold (0° C.) suspension of sodium hydride (60%, 81 mg, 2.03 mmol) in DMF (5 mL) was added slowly a solution of compound 23 (300 mg, 1.01 mmol) and iodomethane (0.13 mL, 2.03 mmol) in DMF (3.5 mL). The reaction mixture was stirred at 0° C. for 1 hours. TLC was checked and the starting material was consumed. Aqueous NH$_4$Cl and EtOAc/Hexane (20 mL/10 mL) was added and the mixture was stirred at room temperature for 1 h. The organic was separated and the aqueous layer was extracted with EtOAc/Hexane (50/50, 10 ml×2). The combined organic was washed with brine, dried (Na$_2$SO$_4$), and concentrated to give compound 62 as brown solids (325 mg, 100% yield). No further purification was conducted. $^1$H NMR (400 MHz, DMSO-d$_6$) δ 8.39 (s, 1H), 7.26 (d, J=8.8 Hz, 1H), 7.05 (t, J=7.6 Hz, 1H) 6.32 (s, 1H), 3.68 (s, 3H), 2.40 (s, 3H); ESI-MS: calcd for (C14H10ClF2N3O) 309, found 310 (MH$^+$).

Example 63

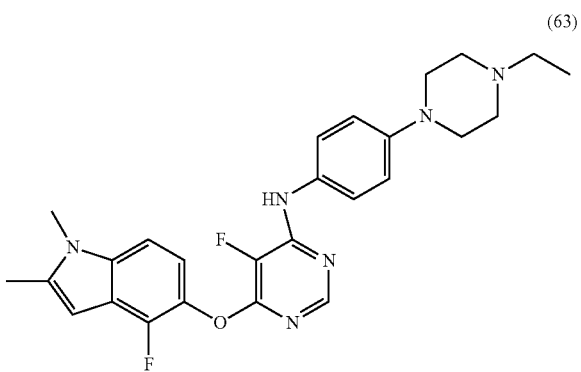 [SMILES: CCN1CCN(c2ccc(Nc3ncnc(Oc4ccc5c(cc(C)n5C)c4F)c3F)cc2)CC1]
(63)

A mixture of compound 62 (crude, 188 mg, 0.61 mmol), 4-(4-Ethylpiperazine-1-yl))aniline (100 mg, 0.49 mmol), and DIPEA (0.21 ml, 1.22 mmol) in DMSO (2 ml) was stirred at 100° C. for overnight. TLC was checked and the reaction was completed. DCM (30 ml) was added, followed by NH4Cl (30 mL), After separation, the aqueous was extracted with DCM/IPA (8/2, 15 ml×2). The combined organic was washed with brine, dried over Na$_2$SO$_4$ and concentrated. The crude product was purified by column on silica gel (0-10% MeOH in DCM) to give compound 63 as brown solids (108 mg, 46% yield). $^1$H NMR (400 MHz, DMSO-d$_6$) δ 9.35 (br, 1H), 7.89 (s, 1H), 7.45 (d, J=8.8 Hz, 2H), 7.22 (d, J=8.8 Hz, 1H), 6.99 (t, J=7.6 Hz, 1H), 6.88 (d, J=8.8 Hz, 2H), 6.29 (s, 1H), 3.67 (s, 3H), 3.06 (m, 4H), 2.50 (m, 4H), 2.39 (s, 3H), 2.33 (q, J=7.2 Hz, 2H), 1.00 (t, J=7.2 Hz, 3H); ESI-MS: calcd for (C26H28F2N6O) 478, found 479 (MH$^+$).

Example 64

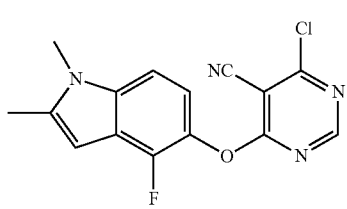
(64)

To a cold (0° C.) suspension of sodium hydride (60%, 66 mg, 1.65 mmol) in DMF (3 mL) was added slowly a solution of compound 52 (250 mg, 0.83 mmol) and iodomethane (0.13 mL, 2.06 mmol) in DMF (3 mL). The reaction mixture was stirred at 0° C. for 1.5 hours. TLC was checked and the starting material was consumed. Aqueous NH$_4$Cl and EtOAc (20 mL) was added and the mixture was stirred at room temperature for 15 min. The organic was separated and the aqueous layer was extracted with EtOAc (10 ml×2). The combined organic was washed with brine, dried (Na$_2$SO$_4$), and concentrated. The crude product was purified on column (silica gel, 0-10% MeOH in DCM) to give the product of compound 64 as yellow solids (70 mg, 27% yield). $^1$H NMR (400 MHz, DMSO-d$_6$) δ 8.81 (s, 1H), 7.31 (m, 1H), 7.08 (m, 1H) 6.34 (s, 1H), 3.69 (s, 3H), 2.41 (s, 3H); ESI-MS: calcd for (C25H10ClFN4O) 316, found 317 (MH$^+$).

Example 65

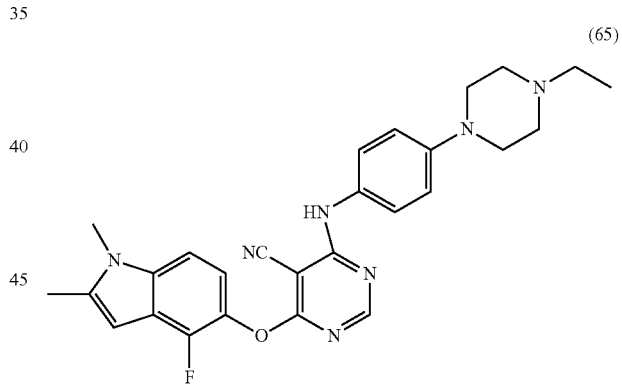
(65)

A mixture of compound 64 (55 mg, 0.18 mmol), 4-(4-Ethylpiperazine-1-yl))aniline (36 mg, 0.18 mmol), and DIPEA (0.1 ml, 0.44 mmol) in DMSO (2 ml) was stirred at room temperature for overnight. TLC was checked and the reaction was completed. DCM (15 ml) was added, followed by NH4Cl (15 mL), After separation, the aqueous was extracted with DCM/IPA (8/2, 10 ml×2). The combined organic was washed with brine, dried over Na$_2$SO$_4$ and concentrated. The crude product was purified by column on silica gel (0-10% MeOH in DCM) to give compound 65 as brown solids (23 mg, 27% yield). $^1$H NMR (400 MHz, DMSO-d$_6$) δ 9.82 (br, 1H), 8.18 (s, 1H), 7.29 (d, J=8.8 Hz, 2H), 7.24 (d, J=8.8 Hz, 1H), 7.00 (t, J=7.6 Hz, 1H), 76.90 (d, J=8.8 Hz, 2H), 6.30 (s, 1H), 3.67 (s, 3H), 3.10 (m, 4H), 2.50 (m, 4H), 2.40 (s, 3H), 2.34 (q, J=7.2 Hz, 2H), 1.01 (t, J=7.2 Hz, 3H); ESI-MS: calcd for (C27H28FN7O) 485, found 486 (MH$^+$).

Example 66

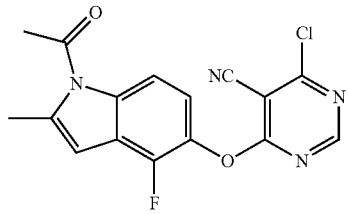

(66)

To the solution of compound 52 (250 mg, 0.83 mmol) in DMF (3 mL) was added DIPEA (0.43 ml, 2.48 mmol) at room temperature. Acetyl chloride (0.5 ml, 7.07 mmol) was added at room temperature and the mixture was stirred at 70° C. for overnight. TLC was checked and the starting material was consumed. The reaction mixture was poured into dilute sodium bicarbonate in water (~1%) and extracted with EtOAc/Hexane (8/2, 15 ml×3). The combined organic was washed by water (15 ml×3), brine, dried over sodium sulfate and concentrated The crude product was purified with column (silica gel, 10-60% EtOAc in Hexanes) to give compound 66 as yellow solids (43 mg, 15% yield). $^1$H NMR (400 MHz, DMSO-$d_6$) δ 8.83 (s, 1H), 8.00 (d, J=9.2 Hz, 1H), 7.26 (t, J=8.8 Hz, 1H), 6.66 (s, 1H), 2.72 (s, 3H), 2.64 (s, 3H); ESI-MS: calcd for (C16H10ClFN4O2) 344, found 345 (MH$^+$).

Example 67

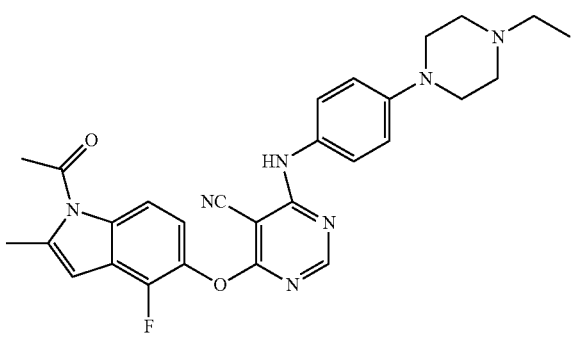

(67)

A mixture of compound 66 (38.6 mg, 0.11 mmol), 4-(4-Ethylpiperazine-1-yl))aniline (23.0 mg, 0.11 mmol), and DIPEA (0.05 ml, 0.28 mmol) in DMSO (2 ml) was stirred at room temperature for over night. TLC was checked and the reaction was completed. NH4Cl/water (9 ml/9 ml) was added and the mixture was stirred at room temperature for 30 min, then cooled to ° C. The solids were collected by filtration, washed by aq. NH4Cl and water to give compound 67 as off-white solids (42 mg, 72% yield). $^1$H NMR (400 MHz, DMSO-$d_6$) δ 9.91 (s, 1H), 8.21 (s, 1H), 7.97 (d, J=9.2 Hz, 1H), 7.31 (d, J=8.8 Hz, 2H), 7.21 (t, J=8.8 Hz, 1H), 6.93 (d, J=8.8 Hz, 2H), 6.63 (s, 1H), 3.60-3.10 (m, 4H), 3.20-2.50 (m, 6H), 2.71 (s, 3H), 2.63 (s, 3H), 1.08 (br, 3H); ESI-MS: calcd for (C28H28FN7O2) 513, found 514 (MH$^+$).

Example 68

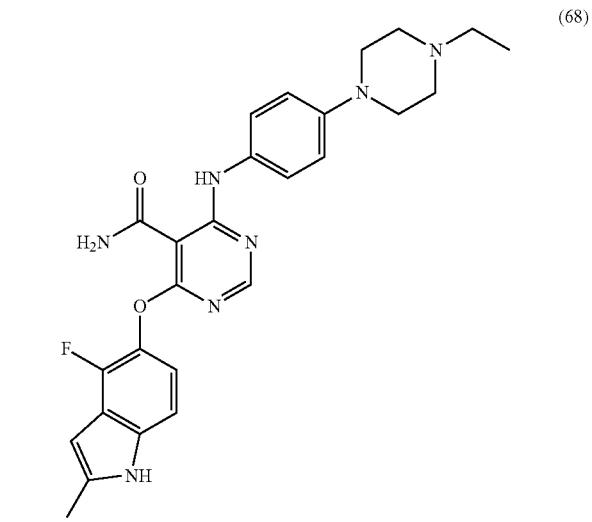 [SMILES: CCN1CCN(c2ccc(Nc3ncnc(Oc4ccc5[nH]c(C)cc5c4F)c3C(N)=O)cc2)CC1]

(68)

To a solution of compound 53 (100 mg, 0.21 mmol), in DMSO (2 ml) was added potassium carbonate (103 mg, 0.74 mmol) followed by hydrogen peroxide (35% w/w aq solution) (0.19 ml, 1.98 mmol) at room temperature. The mixture was stirred at room temperature for 6 hours. TLC was checked and the reaction was completed. Water was added and the mixture was extracted with DCM/IPA (8/2, 5 ml×3). The combined organic was dried (Na$_2$SO$_4$) and concentrated. The crude product was purified by column on silica gel (0-10% MeOH in DCM) to give the product of compound 68 as yellow solids (65 mg, 63% yield). $^1$H NMR (400 MHz, DMSO-$d_6$) δ 11.46 (br, 1H), 11.27 (br, 1H), 8.10 (s, 1H), 8.02 (s, 1H), 7.90 (s, 1H), 7.39 (d, J=8.8 Hz, 2H), 7.08 (d, J=8.8 Hz, 1H), 6.96 (t, J=7.6 Hz, 1H), 6.90 (d, J=8.8 Hz, 2H), 6.19 (s, 1H), 3.15-3.06 (m, 8H), 2.38-2.28 (m, 5H), 1.01 (t, J=7.2 Hz, 3H); ESI-MS: calcd for (C26H28FN7O2) 489, found 490 (MH$^+$).

Example 69

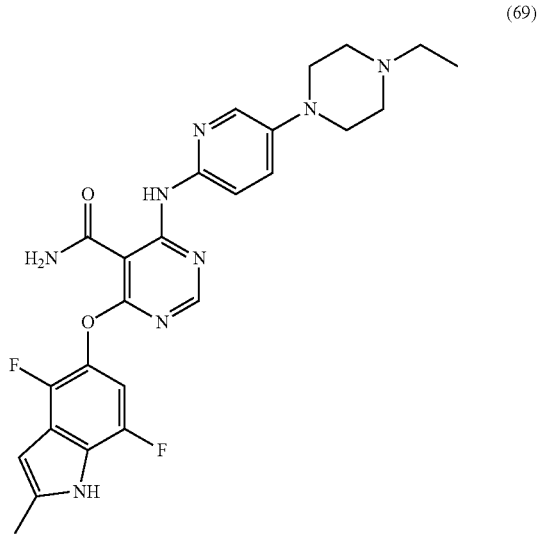 [SMILES: CCN1CCN(c2ccc(Nc3ncnc(Oc4cc(F)c5[nH]c(C)cc5c4F)c3C(N)=O)nc2)CC1]

(69)

To a solution of compound 61 (60 mg, 0.12 mmol), in DMSO (2.5 ml) was added potassium carbonate (108 mg, 0.75 mmol) followed by hydrogen peroxide (35% w/w aq solution) (0.3 ml, 2.97 mmol) at room temperature. The mixture was stirred at room temperature for 6 hours. TLC was checked and the reaction was completed. Water was added and the mixture was extracted with DCM/IPA (8/2, 5 ml×3). The combined organic was dried ($Na_2SO_4$) and concentrated. The crude product was purified by column on silica gel (0-15% MeOH in DCM) to give the product of compound 69 as yellow solids (14 mg, 21% yield). $^1$H NMR (400 MHz, DMSO-$d_6$) δ 11.75 (br, 1H), 11.73 (br, 1H), 8.27 (s, 1H), 8.16 (br, 2H), 8.00 (d, J=3.2 Hz, 1H), 7.93 (br, 1H), 7.40 (dd, J=2.8 Hz, J=9.2 Hz, 1H), 7.03 (dd, J=5.2 Hz, J=10.8 Hz, 1H), 6.30 (s, 1H), 3.12 (m, 4H), 2.50-2.30 (m, overlapped, 4H), 2.39-2.25 (m, 5H), 1.01 (t, J=7.6 Hz, 3H); ESI-MS: calcd for (C25H26F2N8O2) 508, found 509 (MH$^+$).

Example 70

The KinaseProfiler™ Service Assay Protocols (Millipore) were used to test the kinase inhibiting activity of novel compounds from this invention. To do this, the buffer composition was as: 20 mM MOPS, 1 mM EDTA, 0.01% Brij-35, 5% Glycerol, 0.1% β-mercaptoethanol, 1 mg/mL BSA. Test compounds were initially dissolved in DMSO at the desired concentration, then serially diluted to the kinase assay buffer. In a final reaction volume of 25 μL, Aurora-A(h) (5-10 mU) is incubated with 8 mM MOPS pH 7.0, 0.2 mM EDTA, 200 μM LRRASLG (Kemptide), 10 mM magnesium acetate and [γ$^{33}$P-ATP]. The reaction was initiated by the addition of the MgATP mix. After incubation for 40 minute at room temperature, the reaction was stopped by addition of 5 μL of a 3% phosphoric acid solution. 10 μL of the reaction was then spotted onto a P30 filtermat and washed three times for 5 minutes in 50 mM phosphoric acid and once in methanol prior to drying and scintillation counting. Wells containing substrate but no kinase and wells containing a phosphopeptide control were used to set 0% and 100% phosphorylation value, respectively.

Table 1 shows representative data for the inhibition of Abl kinase, Alk kinase, c-Src kinase, FGFR1 kinase, KDR kinase, Ret kinase and Ret Kinase by the compounds of this invention at a concentration of 1 μM.

TABLE 1

| Example No. | % Inhibition @1 μM | | | | | | |
|---|---|---|---|---|---|---|---|
| | Abl | Alk | cSrc | FGFR1 | KDR | Ret | Tie2 |
| 2 | 45 | 3 | 47 | 102 | 97 | 75 | 58 |
| 3 | 47 | -2 | 46 | 102 | 97 | 75 | 61 |
| 4 | 23 | 53 | 36 | 59 | 98 | 27 | 30 |
| 5 | 63 | -10 | 65 | 93 | 97 | 77 | 45 |
| 6 | 62 | 6 | 47 | 95 | 97 | 78 | 59 |
| 7 | 8 | 61 | 14 | 96 | 98 | -16 | 4 |
| 8 | 11 | 60 | 15 | 97 | 98 | 22 | 2 |
| 9 | 21 | 70 | 20 | 75 | 96 | 35 | 24 |
| 10 | 13 | 40 | 8 | -4 | 20 | -19 | -12 |
| 11 | 60 | 70 | 59 | 99 | 96 | 67 | 92 |
| 12 | 18 | 60 | 30 | 89 | 98 | 21 | 20 |
| 13 | 41 | 60 | 32 | 98 | 98 | 61 | 70 |
| 14 | 32 | 53 | 35 | 97 | 97 | 48 | 31 |
| 15 | 84 | 32 | 78 | 100 | 97 | 79 | 82 |
| 16 | 64 | 2 | 54 | 92 | 90 | 79 | 75 |
| 17 | 42 | 2 | 21 | 95 | 90 | 73 | 37 |
| 18 | 45 | 15 | 21 | 87 | 92 | 68 | 48 |
| 19 | 18 | -5 | 8 | 59 | 89 | 48 | 13 |

TABLE 1-continued

| Example No. | % Inhibition @1 μM | | | | | | |
|---|---|---|---|---|---|---|---|
| | Abl | Alk | cSrc | FGFR1 | KDR | Ret | Tie2 |
| 20 | 36 | 3 | 24 | 92 | 88 | 78 | 47 |
| 22 | 19 | 15 | 9 | 98 | 96 | 25 | 18 |
| 24 | 0 | 38 | 11 | 97 | 96 | -12 | -6 |
| 25 | 7 | 69 | 11 | 96 | 95 | -11 | 0 |
| 26 | 7 | 68 | 16 | 46 | 96 | -17 | -11 |
| 27 | 4 | 35 | 11 | 85 | 79 | -46 | -2 |
| 28 | 12 | 62 | 17 | 96 | 97 | -15 | -7 |
| 29 | -7 | -48 | 15 | 92 | 70 | -29 | 33 |
| 32 | 0 | -21 | -7 | 40 | 54 | -33 | -9 |
| 34 | 19 | 15 | 9 | 98 | 96 | 25 | 18 |
| 35 | -15 | -43 | 2 | 96 | 20 | -22 | 19 |
| 40 | 2 | -23 | -2 | 91 | 12 | -46 | 13 |
| 41 | 2 | -41 | 8 | 41 | 5 | -35 | 12 |
| 43 | -10 | -32 | -4 | 48 | -7 | -28 | 21 |
| 44 | -6 | -18 | -11 | 16 | -1 | -12 | 11 |
| 46 | -13 | -34 | 12 | 54 | 5 | -43 | 14 |
| 47 | -6 | -31 | -6 | 34 | 1 | -30 | 11 |
| 49 | 68 | 69 | 74 | 99 | 96 | 53 | 69 |
| 50 | 36 | 63 | 58 | 89 | 97 | 36 | 48 |
| 51 | 73 | 54 | 70 | 101 | 97 | 74 | 82 |
| 53 | 11 | 49 | 10 | 100 | 98 | -25 | 5 |
| 54 | 3 | -30 | 8 | 101 | 97 | -30 | 21 |
| 55 | 2 | -23 | 10 | 99 | 91 | -48 | 31 |
| 56 | -3 | -47 | 6 | 100 | 92 | -31 | 29 |
| 57 | -6 | -40 | 12 | 99 | 94 | -26 | 30 |
| 58 | 18 | -24 | 10 | 0 | 11 | -26 | 65 |
| 60 | -7 | 3 | 3 | 100 | 93 | -42 | 24 |
| 61 | 3 | -41 | -9 | 100 | 51 | -13 | 23 |
| 63 | 3 | -3 | 1 | 91 | 10 | -41 | 13 |
| 65 | -1 | -28 | 13 | 98 | 8 | -19 | 37 |
| 68 | 67 | 46 | 85 | 100 | 96 | 97 | 94 |

A number of studies were performed to analyze the consequences of tyrosine kinase inhibition in cell lines. To do this, 1000 cells are seeded in 27 μl/well in 384-well microplates, which are then placed in a humidified $CO_2$ incubator at 37° C. overnight. The next day, 3 μl/well of 10× concentrated drug is added and the plates are returned to the incubator for 72 hr. After 72 hr incubation, plates are removed and 6/well CellTiterblue (Promega) viability reagent is added. Plates are returned to the incubator for 3 hr, after which it is fluorescence measurements are read on the Victor X3 plate reader (Perkin Elmer). Data are analyzed using Excel (Microsoft), and $GI_{50}$ values are determined using Prism (Graphpad).

For the phospho-FGFR, the following assay Protocol was used. 25,000 cells are seeded in 90 μl/well in 96-well microplates, which are then placed in a humidified $CO_2$ incubator at 37° C. overnight. 96-well ELISA plates (Mesoscale Discovery) are coated with capture antibody (R&D Systems Duo-Set) at 4 μg/ml, 30 μl/well. The next day, 10 μl/well of 10× concentrated drug is added and the plates are returned to the incubator for 20 min. ELISA plates are washed using an automated plate washer (BioTek Instruments). After 30 min, cells are inverted and gently tapped to remove excess medium, and immediately placed on ice. 30 μl mPer cell lysis reagent (Thermo Scientific) with protease and phosphatase inhibitors is added/well. After 15 min on ice, lysates are mixed and 30 μl transferred to the ELISA plate. Plates are incubated for 2 hr, washed, and 30 μl/well detection antibody is added. After 1 hr, plates are washed and 30 μl "SulfoTag" (MesoScale Discovery) detection reagent is added. After 1 hr, plates are washed and 150 μl/well read solution is added. Electrochemiluminescence is determined on the Mesoscale Discovery Sector Imager 2000. Data are analyzed using Excel (Microsoft), and $EC_{50}$ values are determined using Prism (Graphpad).

Table 2 shows representative GI50 data for the inhibition of selected cancer cell lines The EC50 of phospho-FGFR2 on Kato III cells was also included in table 2.

TABLE 2

| Example No. | GI50 (nM) | | | | | EC50 (nM) P-FGFR2, |
|---|---|---|---|---|---|---|
| | MDA-MB134 | AN3_CA | Kato III | KG1a | RT112 | Kato III cells |
| 2 | — | 490 | 165 | >100 | >100 | 88 |
| 3 | — | >500 | — | >100 | >100 | 93 |
| 4 | — | >500 | — | — | — | — |
| 5 | — | 211 | >500 | >100 | >100 | >100 |
| 6 | — | 573 | >500 | >100 | >100 | >100 |
| 7 | — | >500 | >500 | — | — | — |
| 8 | — | >500 | >500 | — | — | — |
| 9 | — | >500 | >500 | — | — | — |
| 10 | — | 33 | 142 | >100 | >100 | >100 |
| 11 | — | >500 | >500 | >100 | >100 | 96 |
| 12 | — | >500 | >500 | — | — | — |
| 13 | — | >500 | 170 | — | — | — |
| 14 | — | 483 | >500 | >100 | >100 | >100 |
| 15 | — | 332 | 290 | >100 | >100 | 36 |
| 16 | — | >500 | — | >100 | >100 | >100 |
| 17 | — | >500 | — | >100 | >100 | >100 |
| 18 | — | >500 | — | — | — | — |
| 19 | — | >500 | — | — | — | — |
| 20 | — | >500 | — | >100 | >100 | >100 |
| 22 | — | >500 | 229 | >100 | >100 | >100 |
| 24 | — | >500 | 386 | — | — | — |
| 25 | — | >500 | >500 | >100 | >100 | >100 |
| 26 | — | >500 | >500 | — | — | — |
| 27 | — | >500 | >500 | — | — | — |
| 28 | — | >500 | >500 | — | — | — |
| 29 | >500 | >500 | >500 | — | — | — |
| 32 | 138 | >500 | >500 | >500 | >500 | >500 |
| 34 | — | >500 | 229 | >100 | >100 | >100 |
| 35 | >500 | >500 | >500 | >500 | >500 | — |
| 40 | 430 | >500 | >500 | >500 | >500 | — |
| 41 | 241 | >500 | >500 | >500 | >500 | — |
| 43 | >500 | >500 | >500 | >500 | >500 | — |
| 44 | >500 | >500 | >500 | >500 | >500 | — |
| 46 | 254 | >500 | >500 | >500 | >500 | — |
| 47 | >500 | >500 | >500 | >500 | >500 | — |
| 49 | 56 | >500 | 207 | 60 | >500 | 75 |
| 50 | — | >500 | 348 | — | — | — |
| 51 | — | 406 | 169 | >100 | >100 | 38 |
| 53 | 5 | >500 | 34 | 10 | >500 | 18 |
| 54 | 20 | 214 | 12 | 4 | 103 | — |
| 55 | 78 | 98 | 319 | 7 | >500 | — |
| 56 | 450 | >500 | >500 | 76 | >500 | — |
| 57 | 8 | >500 | 51 | 4 | 33 | — |
| 58 | >500 | >500 | >500 | >500 | >500 | — |
| 60 | 18 | >500 | 26 | 5 | 47 | — |
| 61 | 28 | >500 | 77 | 4 | 11 | — |
| 63 | 282 | >500 | >500 | >500 | >500 | — |
| 65 | 461 | >500 | >500 | >500 | >500 | — |
| 68 | 111 | 79 | 23 | 32 | 11 | — |

What is claimed is:

1. A compound of the formula

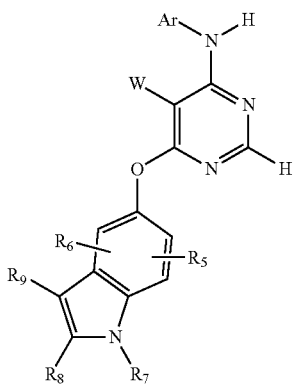

or a pharmaceutically acceptable salt thereof, wherein:

W is selected from the group consisting of: Cl, Br, I, CN, and $CONH_2$;

Ar represents heteroaryl or aryl, each of which is substituted with from 0 to 4 substituents independently chosen from the group consisting of:

(1) halogen, hydroxy, amino, amide, cyano, —COOH, —$SO_2NH_2$, oxo, nitro or alkoxycarbonyl;

(2) $NR_1$; and (3) groups of the formula

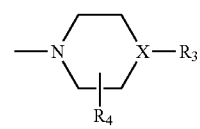

(Ia)

wherein:

$R_1$ represents hydrogen, alkyl, cycloalkyl, alkenyl, alkynyl, alkylthio, aryl, or arylalkyl;

$R_4$ represents hydrogen, $C_1$-$C_4$ alkyl, or oxo;

X—$R_3$ is CH; or X—$R_3$ is O; or X is N, and $R_3$ represents hydrogen, $C_1$-$C_6$ alkyl, $C_2$-$C_6$ alkenyl, $C_2$-$C_6$ alkynyl, $C_3$-$C_{10}$ aryl or heteroaryl, ($C_3$-$C_7$ cycloalkyl)$C_1$-$C_4$ alkyl, $C_1$-$C_6$ haloalkyl, $C_1$-$C_6$ alkoxy, $C_1$-$C_6$ alkylthio, $C_2$-$C_6$ alkanoyl, $C_1$-$C_6$ alkoxycarbonyl, $C_2$-$C_6$ alkanoyloxy, mono- and di-($C_3$-$C_8$ cycloalkyl)amino$C_0$-$C_4$alkyl, (4- to 7-membered heterocycle)$C_0$-$C_4$alkyl, $C_1$-$C_6$ alkylsulfonyl, mono- and di-($C_1$-$C_6$ alkyl) sulfonamido, and mono- and di-($C_1$-$C_6$ alkyl)aminocarbonyl, each of which is substituted with from 0 to 4 substituents independently chosen from halogen, hydroxy, cyano, amino, —COOH or oxo;

$R_5$ and $R_6$ are independently selected from the group consisting of: hydrogen, F, Cl, and Br; and $R_7$, $R_8$ and $R_9$ are independently selected from the group consisting of: hydrogen and $CH_3$.

2. A pharmaceutical composition comprising at least one compound of claim 1 or its pharmaceutically acceptable salts, hydrates, solvates, crystal forms salts and individual diastereomers thereof, and a pharmaceutically acceptable carrier.

3. The compound or the pharmaceutically acceptable salt thereof according to claim 1, wherein W is CN.

4. The compound or the pharmaceutically acceptable salt thereof according to claim 1, wherein $R_5$ and $R_6$ are each F.

5. The compound or the pharmaceutically acceptable salt thereof according to claim 3, wherein $R_5$ and $R_6$ are each F.

6. The compound or the pharmaceutically acceptable salt thereof according to claim 1, wherein $R_8$ is $CH_3$.

7. The compound or the pharmaceutically acceptable salt thereof according to claim 5, wherein $R_8$ is $CH_3$.

8. The compound or the pharmaceutically acceptable salt thereof according to claim 1, wherein $R_7$ and $R_9$ are each H.

9. The compound or the pharmaceutically acceptable salt thereof according to claim 7, wherein $R_7$ and $R_9$ are each H.

* * * * *